US012611303B2

(12) United States Patent
Lane et al.

(10) Patent No.: US 12,611,303 B2
(45) Date of Patent: Apr. 28, 2026

(54) TRANSCATHETER MITRAL VALVE PROSTHESIS

(71) Applicants: Neovasc Tiara Inc., Richmond (CA); Edwards Lifesciences CardiAQ LLC, Irvine, CA (US)

(72) Inventors: Randy Matthew Lane, Langley (CA); Colin A. Nyuli, Vancouver (CA); Jeremy Brent Ratz, Winchester, MA (US); Arshad Quadri, West Hartford, CT (US)

(73) Assignees: NEOVASC TIARA INC., Toronto (CA); EDWARDS LIFESCIENCES CARDIAQ LLC, Irvine, CA (US)

( * ) Notice: Subject to any disclaimer, the term of this patent is extended or adjusted under 35 U.S.C. 154(b) by 841 days.

(21) Appl. No.: 17/870,377

(22) Filed: Jul. 21, 2022

(65) Prior Publication Data

US 2023/0149163 A1 May 18, 2023

Related U.S. Application Data

(60) Continuation of application No. 16/559,191, filed on Sep. 3, 2019, now Pat. No. 11,419,720, which is a
(Continued)

(51) Int. Cl.
*A61F 2/24* (2006.01)
*A61F 2/95* (2013.01)

(52) U.S. Cl.
CPC .......... *A61F 2/2427* (2013.01); *A61F 2/2409* (2013.01); *A61F 2/2412* (2013.01);
(Continued)

(58) Field of Classification Search
CPC .... A61F 2/2427; A61F 2/2409; A61F 2/2412; A61F 2/2418; A61F 2/2436;
(Continued)

(56) References Cited

U.S. PATENT DOCUMENTS

| | | | |
|---|---|---|---|
| 2,967,856 A | 1/1961 | Coover, Jr. et al. | |
| 3,409,013 A | 11/1968 | Henry | |

(Continued)

FOREIGN PATENT DOCUMENTS

| | | |
|---|---|---|
| AU | 2011250606 B2 | 3/2014 |
| AU | 2014203064 A1 | 7/2014 |

(Continued)

OTHER PUBLICATIONS

US 8,062,357 B2, 11/2011, Salahieh et al. (withdrawn)
(Continued)

*Primary Examiner* — Suzette J Gherbi
(74) *Attorney, Agent, or Firm* — Morrison & Foerster LLP

(57) ABSTRACT

A prosthetic cardiac valve comprises an anchor having an atrial skirt, an annular region, and a ventricular skirt. The prosthetic valve also has a plurality of prosthetic valve leaflets each having a first end and a free end. The first end is coupled with the anchor and the free end is opposite the first end. The prosthetic cardiac valve has an open configuration in which the free ends of the prosthetic valve leaflets are disposed away from one another to allow antegrade blood flow therepast, and a closed configuration in which the free ends of the prosthetic valve leaflets engage one another and substantially prevent retrograde blood flow therepast. The anchor has a collapsed configuration for delivery to the heart and an expanded configuration for anchoring the prosthetic cardiac valve to a patient's heart.

21 Claims, 43 Drawing Sheets

Related U.S. Application Data continuation of application No. 15/682,890, filed on Aug. 22, 2017, now Pat. No. 10,449,042, which is a continuation of application No. 14/046,606, filed on Oct. 4, 2013, now Pat. No. 9,770,329, which is a division of application No. 13/096,572, filed on Apr. 28, 2011, now Pat. No. 8,579,964.

(60) Provisional application No. 61/414,879, filed on Nov. 17, 2010, provisional application No. 61/393,860, filed on Oct. 15, 2010, provisional application No. 61/331,799, filed on May 5, 2010.

(52) U.S. Cl.
CPC .......... *A61F 2/2418* (2013.01); *A61F 2/2436* (2013.01); *A61F 2002/9505* (2013.01); *A61F 2/9517* (2020.05); *A61F 2220/0008* (2013.01); *A61F 2220/0016* (2013.01); *A61F 2230/0034* (2013.01); *A61F 2230/005* (2013.01); *A61F 2230/0054* (2013.01); *A61F 2250/0039* (2013.01); *A61F 2250/0067* (2013.01); *A61F 2250/0098* (2013.01)

(58) Field of Classification Search
CPC ............ A61F 2/9517; A61F 2002/9505; A61F 2220/0008; A61F 2220/0016; A61F 2230/0034; A61F 2230/005; A61F 2230/0054; A61F 2250/0039; A61F 2250/0067; A61F 2250/0098
See application file for complete search history.

(56) References Cited

U.S. PATENT DOCUMENTS

| | | |
|---|---|---|
| 3,472,230 A | 10/1969 | Thomas |
| 3,548,417 A | 12/1970 | Ronnie et al. |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Goodenough et al. |
| 3,739,402 A | 6/1973 | Cooley et al. |
| 3,755,823 A | 9/1973 | Hancock |
| 4,011,947 A | 3/1977 | Sawyer |
| 4,035,849 A | 7/1977 | Angell et al. |
| 4,056,854 A | 11/1977 | Boretos et al. |
| 4,079,468 A | 3/1978 | Liotta et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,477,930 A | 10/1984 | Totten et al. |
| 4,490,859 A | 1/1985 | Black et al. |
| 4,535,483 A | 8/1985 | Klawitter et al. |
| 4,553,545 A | 11/1985 | Maass et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmar |
| 4,759,758 A | 7/1988 | Gabbay |
| 4,762,128 A | 8/1988 | Rosenbluth |
| 4,776,337 A | 10/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,865,600 A | 9/1989 | Carpentier et al. |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,950,227 A | 8/1990 | Savin et al. |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,067,957 A | 11/1991 | Jervis |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,197,978 A | 3/1993 | Hess |
| 5,232,446 A | 8/1993 | Arney |
| 5,266,073 A | 11/1993 | Wall |
| 5,282,847 A | 2/1994 | Trescony et al. |
| 5,326,371 A | 7/1994 | Love et al. |
| 5,332,402 A | 7/1994 | Teitelbaum |
| 5,344,427 A | 9/1994 | Cottenceau et al. |
| 5,360,444 A | 11/1994 | Kusuhara |
| 5,370,685 A | 12/1994 | Stevens |
| 5,397,351 A | 3/1995 | Pavcnik et al. |
| 5,397,355 A | 3/1995 | Marin et al. |
| 5,411,055 A | 5/1995 | Kane |
| 5,411,522 A | 5/1995 | Trott |
| 5,411,552 A | 5/1995 | Andersen et al. |
| 5,415,667 A | 5/1995 | Frater |
| 5,439,446 A | 8/1995 | Barry |
| 5,474,563 A | 12/1995 | Myler et al. |
| 5,480,424 A | 1/1996 | Cox |
| 5,500,014 A | 3/1996 | Quijano et al. |
| 5,509,930 A | 4/1996 | Love |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,575,818 A | 11/1996 | Pinchuk |
| 5,591,185 A | 1/1997 | Kilmer et al. |
| 5,599,305 A | 2/1997 | Hermann et al. |
| 5,607,444 A | 3/1997 | Lam |
| 5,607,464 A | 3/1997 | Trescony et al. |
| 5,607,469 A | 3/1997 | Frey |
| 5,609,626 A | 3/1997 | Quijano et al. |
| 5,639,274 A | 6/1997 | Fischell et al. |
| 5,665,115 A | 9/1997 | Cragg |
| 5,669,919 A | 9/1997 | Sanders et al. |
| 5,697,382 A | 12/1997 | Love et al. |
| D390,957 S | 2/1998 | Fontaine |
| 5,713,952 A | 2/1998 | Vanney et al. |
| 5,716,417 A | 2/1998 | Girard et al. |
| 5,725,519 A | 3/1998 | Penner et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,807,398 A | 9/1998 | Shaknovich |

(56)     References Cited

U.S. PATENT DOCUMENTS

| | | | |
|---|---|---|---|
| 5,810,873 A | 9/1998 | Morales |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,868,777 A | 2/1999 | Lam |
| 5,868,782 A | 2/1999 | Frantzen |
| 5,876,437 A | 3/1999 | Vanney et al. |
| 5,879,381 A | 3/1999 | Moriuchi et al. |
| 5,902,334 A | 5/1999 | Dwyer et al. |
| 5,906,619 A | 5/1999 | Olson et al. |
| 5,925,063 A | 7/1999 | Khosravi |
| 5,928,281 A | 7/1999 | Huynh et al. |
| 5,935,108 A | 8/1999 | Katoh |
| 5,954,764 A | 9/1999 | Parodi |
| 5,957,949 A | 9/1999 | Leonhardt et al. |
| 5,968,068 A | 10/1999 | Dehdashtian et al. |
| 5,992,000 A | 11/1999 | Humphrey et al. |
| 6,004,328 A | 12/1999 | Solar et al. |
| 6,015,431 A | 1/2000 | Thornton et al. |
| 6,027,525 A | 2/2000 | Suh et al. |
| 6,042,606 A | 3/2000 | Frantzen |
| 6,042,607 A | 3/2000 | Williamson, IV et al. |
| 6,053,940 A | 4/2000 | Wijay |
| 6,074,417 A | 6/2000 | Peredo |
| 6,086,612 A | 7/2000 | Jansen |
| 6,113,612 A | 9/2000 | Swanson et al. |
| 6,113,631 A | 9/2000 | Jansen |
| 6,132,458 A | 10/2000 | Staehle et al. |
| 6,132,473 A | 10/2000 | Williams et al. |
| 6,152,937 A | 11/2000 | Peterson et al. |
| 6,159,237 A | 12/2000 | Alt et al. |
| 6,168,614 B1 | 1/2001 | Andersen |
| 6,168,616 B1 | 1/2001 | Brown, III |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen et al. |
| 6,245,102 B1 | 6/2001 | Jayaraman |
| 6,251,093 B1 | 6/2001 | Valley et al. |
| 6,280,466 B1 | 8/2001 | Kugler et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,306,141 B1 | 10/2001 | Jervis |
| 6,312,465 B1 | 11/2001 | Griffin et al. |
| 6,336,938 B1 | 1/2002 | Kavteladze et al. |
| 6,338,740 B1 | 1/2002 | Carpentier |
| 6,350,277 B1 | 2/2002 | Kocur |
| 6,352,543 B1 | 3/2002 | Cole |
| 6,358,277 B1 | 3/2002 | Duran |
| 6,425,916 B1 | 7/2002 | Garrison et al. |
| 6,440,164 B1 | 8/2002 | Dimatteo et al. |
| 6,458,153 B1 | 10/2002 | Bailey et al. |
| 6,461,382 B1 | 10/2002 | Cao |
| 6,468,660 B2 | 10/2002 | Ogle et al. |
| 6,475,237 B2 | 11/2002 | Drasler et al. |
| 6,482,228 B1 | 11/2002 | Norred |
| 6,488,704 B1 | 12/2002 | Connelly et al. |
| 6,511,491 B2 | 1/2003 | Grudem et al. |
| 6,517,573 B1 | 2/2003 | Pollock et al. |
| 6,527,800 B1 | 3/2003 | McGuckin, Jr. et al. |
| 6,527,979 B2 | 3/2003 | Constantz et al. |
| 6,540,782 B1 | 4/2003 | Snyders |
| 6,551,303 B1 | 4/2003 | Van et al. |
| 6,575,959 B1 | 6/2003 | Sarge et al. |
| 6,582,462 B1 | 6/2003 | Andersen et al. |
| 6,602,281 B1 | 8/2003 | Klein |
| 6,605,112 B1 | 8/2003 | Moll et al. |
| 6,610,088 B1 | 8/2003 | Gabbay |
| 6,629,534 B1 | 10/2003 | St. Goar et al. |
| 6,641,606 B2 | 11/2003 | Ouriel et al. |
| 6,652,578 B2 | 11/2003 | Bailey et al. |
| D484,979 S | 1/2004 | Fontaine |
| 6,676,698 B2 | 1/2004 | McGuckin, Jr. et al. |
| 6,682,537 B2 | 1/2004 | Ouriel et al. |
| 6,695,878 B2 | 2/2004 | Mcguckin, Jr. et al. |
| 6,702,843 B1 | 3/2004 | Brown et al. |
| 6,712,836 B1 | 3/2004 | Berg et al. |
| 6,716,207 B2 | 4/2004 | Farnholtz |
| 6,723,123 B1 | 4/2004 | Kazatchkov et al. |
| 6,729,356 B1 | 5/2004 | Baker et al. |
| 6,730,118 B2 | 5/2004 | Spenser et al. |
| 6,733,523 B2 | 5/2004 | Shaolian et al. |
| 6,733,525 B2 | 5/2004 | Yang et al. |
| 6,746,422 B1 | 6/2004 | Noriega et al. |
| 6,749,560 B1 | 6/2004 | Konstorum et al. |
| 6,764,505 B1 | 7/2004 | Hossainy et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,858,034 B1 | 2/2005 | Hijlkema et al. |
| 6,875,231 B2 | 4/2005 | Anduiza et al. |
| 6,893,460 B2 | 5/2005 | Spenser et al. |
| 6,908,477 B2 | 6/2005 | Mcguckin, Jr. et al. |
| 6,908,481 B2 | 6/2005 | Cribier |
| 6,926,732 B2 | 8/2005 | Derus et al. |
| 6,929,660 B1 | 8/2005 | Ainsworth et al. |
| 6,936,058 B2 | 8/2005 | Forde et al. |
| 6,979,350 B2 | 12/2005 | Moll et al. |
| 7,014,653 B2 | 3/2006 | Ouriel et al. |
| 7,018,401 B1 | 3/2006 | Hyodoh et al. |
| 7,018,406 B2 | 3/2006 | Seguin et al. |
| 7,025,780 B2 | 4/2006 | Gabbay |
| 7,044,962 B2 | 5/2006 | Elliott |
| 7,044,966 B2 | 5/2006 | Svanidze et al. |
| 7,087,088 B2 | 8/2006 | Berg et al. |
| 7,147,660 B2 | 12/2006 | Chobotov et al. |
| 7,147,661 B2 | 12/2006 | Chobotov et al. |
| 7,147,663 B1 | 12/2006 | Berg et al. |
| 7,153,322 B2 | 12/2006 | Alt |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal |
| 7,252,682 B2 | 8/2007 | Seguin |
| D553,747 S | 10/2007 | Fliedner |
| 7,276,078 B2 | 10/2007 | Spenser et al. |
| 7,276,084 B2 | 10/2007 | Yang et al. |
| 7,318,278 B2 | 1/2008 | Zhang et al. |
| 7,329,278 B2 | 2/2008 | Seguin et al. |
| 7,338,520 B2 | 3/2008 | Bailey et al. |
| 7,374,571 B2 | 5/2008 | Pease et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,435,257 B2 | 10/2008 | Lashinski et al. |
| 7,442,204 B2 | 10/2008 | Schwammenthal et al. |
| 7,445,631 B2 | 11/2008 | Salahieh et al. |
| 7,455,689 B2 | 11/2008 | Johnson |
| 7,462,191 B2 | 12/2008 | Spenser et al. |
| 7,510,575 B2 | 3/2009 | Spenser et al. |
| 7,524,330 B2 | 4/2009 | Berreklouw |
| 7,527,646 B2 | 5/2009 | Rahdert et al. |
| 7,530,253 B2 | 5/2009 | Spenser et al. |
| 7,553,324 B2 | 6/2009 | Andreas et al. |
| 7,579,381 B2 | 8/2009 | Dove |
| 7,585,321 B2 | 9/2009 | Cribier |
| 7,608,114 B2 | 10/2009 | Levine et al. |
| 7,615,072 B2 | 11/2009 | Rust et al. |
| 7,618,446 B2 | 11/2009 | Andersen et al. |
| 7,618,447 B2 | 11/2009 | Case et al. |
| 7,628,805 B2 | 12/2009 | Spenser et al. |
| 7,632,298 B2 | 12/2009 | Hijlkema |
| 7,637,945 B2 | 12/2009 | Solem et al. |
| 7,637,946 B2 | 12/2009 | Solem et al. |
| 7,682,390 B2 | 3/2010 | Seguin |
| 7,704,222 B2 | 4/2010 | Wilk et al. |

(56)　　　　　References Cited

U.S. PATENT DOCUMENTS

| 7,708,775 | B2 | 5/2010 | Rowe et al. |
| 7,712,606 | B2 | 5/2010 | Salahieh et al. |
| 7,736,327 | B2 | 6/2010 | Wilk et al. |
| 7,748,389 | B2 | 7/2010 | Salahieh et al. |
| 7,753,949 | B2 | 7/2010 | Lamphere et al. |
| D622,387 | S | 8/2010 | Igaki |
| D622,388 | S | 8/2010 | Igaki |
| 7,771,463 | B2 | 8/2010 | Ton et al. |
| 7,771,472 | B2 | 8/2010 | Hendricksen et al. |
| 7,780,725 | B2 | 8/2010 | Haug et al. |
| 7,785,360 | B2 | 8/2010 | Freitag |
| 7,799,072 | B2 | 9/2010 | Greenberg |
| 7,803,185 | B2 | 9/2010 | Gabbay et al. |
| 7,806,917 | B2 | 10/2010 | Xiao |
| 7,806,919 | B2 | 10/2010 | Bloom et al. |
| 7,815,589 | B2 | 10/2010 | Meade et al. |
| 7,815,673 | B2 | 10/2010 | Bloom et al. |
| 7,824,443 | B2 | 11/2010 | Salahieh et al. |
| 7,837,727 | B2 | 11/2010 | Goetz et al. |
| 7,846,203 | B2 | 12/2010 | Cribier |
| 7,871,435 | B2 | 1/2011 | Carpentier et al. |
| 7,892,281 | B2 | 2/2011 | Seguin et al. |
| D635,261 | S | 3/2011 | Rossi |
| D635,262 | S | 3/2011 | Rossi |
| 7,896,915 | B2 | 3/2011 | Guyenot et al. |
| 7,914,569 | B2 | 3/2011 | Nguyen et al. |
| 7,914,575 | B2 | 3/2011 | Guyenot et al. |
| 7,919,112 | B2 | 4/2011 | Pathak et al. |
| 7,947,075 | B2 | 5/2011 | Goetz et al. |
| 7,959,672 | B2 | 6/2011 | Salahieh et al. |
| 7,967,853 | B2 | 6/2011 | Eidenschink et al. |
| 7,972,377 | B2 | 7/2011 | Lane |
| 7,972,378 | B2 | 7/2011 | Tabor et al. |
| 7,981,151 | B2 | 7/2011 | Rowe |
| 7,993,392 | B2 | 8/2011 | Righini et al. |
| 7,993,394 | B2 | 8/2011 | Hariton et al. |
| 7,993,395 | B2 | 8/2011 | Vanermen et al. |
| 7,998,196 | B2 | 8/2011 | Mathison |
| 8,007,992 | B2 | 8/2011 | Tian et al. |
| 8,009,887 | B2 | 8/2011 | Ionasec et al. |
| 8,016,870 | B2 | 9/2011 | Chew et al. |
| 8,016,877 | B2 | 9/2011 | Seguin et al. |
| 8,029,556 | B2 | 10/2011 | Rowe |
| 8,029,564 | B2 | 10/2011 | Johnson et al. |
| 8,048,153 | B2 | 11/2011 | Salahieh et al. |
| 8,052,747 | B2 | 11/2011 | Melnikov et al. |
| 8,052,750 | B2 | 11/2011 | Tuval et al. |
| 8,057,538 | B2 | 11/2011 | Bergin et al. |
| 8,057,539 | B2 | 11/2011 | Ghione et al. |
| 8,057,540 | B2 | 11/2011 | Letac et al. |
| 8,062,350 | B2 | 11/2011 | Gale et al. |
| 8,062,359 | B2 | 11/2011 | Marquez et al. |
| 8,066,763 | B2 | 11/2011 | Alt |
| 8,070,799 | B2 | 12/2011 | Righini et al. |
| 8,070,800 | B2 | 12/2011 | Lock et al. |
| 8,070,801 | B2 | 12/2011 | Cohn |
| 8,070,802 | B2 | 12/2011 | Lamphere et al. |
| 8,075,611 | B2 | 12/2011 | Millwee et al. |
| 8,075,615 | B2 | 12/2011 | Eberhardt et al. |
| 8,078,279 | B2 | 12/2011 | Dennis et al. |
| 8,080,054 | B2 | 12/2011 | Rowe |
| 8,083,793 | B2 | 12/2011 | Lane et al. |
| 8,088,158 | B2 | 1/2012 | Brodeur |
| 8,088,404 | B2 | 1/2012 | Udipi et al. |
| 8,092,520 | B2 | 1/2012 | Quadri |
| 8,092,521 | B2 | 1/2012 | Figulla et al. |
| 8,100,964 | B2 | 1/2012 | Spence |
| 8,105,375 | B2 | 1/2012 | Navia et al. |
| 8,105,377 | B2 | 1/2012 | Liddicoat |
| 8,109,995 | B2 | 2/2012 | Paniagua et al. |
| 8,109,996 | B2 | 2/2012 | Stacchino et al. |
| 8,114,154 | B2 | 2/2012 | Righini et al. |
| 8,118,866 | B2 | 2/2012 | Herrmann et al. |
| 8,119,704 | B2 | 2/2012 | Wang et al. |
| 8,123,801 | B2 | 2/2012 | Milo |
| 8,128,681 | B2 | 3/2012 | Shoemaker et al. |
| 8,128,688 | B2 | 3/2012 | Ding et al. |
| 8,136,218 | B2 | 3/2012 | Millwee et al. |
| 8,137,398 | B2 | 3/2012 | Tuval et al. |
| 8,137,687 | B2 | 3/2012 | Chen et al. |
| 8,142,492 | B2 | 3/2012 | Forster et al. |
| 8,142,494 | B2 | 3/2012 | Rahdert et al. |
| 8,147,504 | B2 | 4/2012 | Ino et al. |
| 8,155,754 | B2 | 4/2012 | Nygren et al. |
| 8,157,852 | B2 | 4/2012 | Bloom et al. |
| 8,157,853 | B2 | 4/2012 | Laske et al. |
| 8,158,187 | B2 | 4/2012 | Chen et al. |
| 8,163,014 | B2 | 4/2012 | Lane et al. |
| 8,167,926 | B2 | 5/2012 | Hartley et al. |
| 8,167,932 | B2 | 5/2012 | Bourang et al. |
| 8,167,934 | B2 | 5/2012 | Styrc et al. |
| 8,168,275 | B2 | 5/2012 | Lee et al. |
| 8,170,645 | B2 | 5/2012 | Solar et al. |
| 8,177,799 | B2 | 5/2012 | Orban, III |
| 8,177,836 | B2 | 5/2012 | Lee et al. |
| 8,180,428 | B2 | 5/2012 | Kaiser et al. |
| 8,182,528 | B2 | 5/2012 | Salahieh et al. |
| 8,182,530 | B2 | 5/2012 | Huber |
| 8,182,829 | B2 | 5/2012 | Kleiner et al. |
| 8,187,851 | B2 | 5/2012 | Shah et al. |
| 8,195,293 | B2 | 6/2012 | Limousin et al. |
| 8,202,529 | B2 | 6/2012 | Hossainy et al. |
| 8,211,169 | B2 | 7/2012 | Lane et al. |
| 8,216,174 | B2 | 7/2012 | Wilk et al. |
| 8,216,261 | B2 | 7/2012 | Solem |
| 8,216,301 | B2 | 7/2012 | Bonhoeffer et al. |
| 8,219,229 | B2 | 7/2012 | Cao et al. |
| 8,220,121 | B2 | 7/2012 | Hendriksen et al. |
| 8,221,482 | B2 | 7/2012 | Cottone et al. |
| 8,221,493 | B2 | 7/2012 | Boyle et al. |
| 8,226,710 | B2 | 7/2012 | Nguyen et al. |
| 8,231,930 | B2 | 7/2012 | Castro et al. |
| D665,079 | S | 8/2012 | Zago |
| D665,080 | S | 8/2012 | Zago |
| 8,236,045 | B2 | 8/2012 | Benichou et al. |
| 8,236,241 | B2 | 8/2012 | Carpentier et al. |
| 8,241,274 | B2 | 8/2012 | Keogh et al. |
| 8,246,675 | B2 | 8/2012 | Zegdi |
| 8,246,677 | B2 | 8/2012 | Ryan |
| 8,246,678 | B2 | 8/2012 | Salahieh et al. |
| 8,252,051 | B2 | 8/2012 | Chau et al. |
| 8,252,052 | B2 | 8/2012 | Salahieh et al. |
| 8,257,724 | B2 | 9/2012 | Cromack et al. |
| 8,257,725 | B2 | 9/2012 | Cromack et al. |
| 8,262,724 | B2 | 9/2012 | Seguin et al. |
| 8,273,118 | B2 | 9/2012 | Bergin |
| 8,273,120 | B2 | 9/2012 | Dolan |
| 8,276,533 | B2 | 10/2012 | Chambers et al. |
| 8,287,584 | B2 | 10/2012 | Salahieh et al. |
| 8,287,591 | B2 | 10/2012 | Keidar et al. |
| 8,303,653 | B2 | 11/2012 | Bonhoeffer et al. |
| 8,308,798 | B2 | 11/2012 | Pintor et al. |
| 8,313,520 | B2 | 11/2012 | Barbut et al. |
| 8,313,525 | B2 | 11/2012 | Tuval et al. |
| 8,317,854 | B1 | 11/2012 | Ryan et al. |
| 8,317,858 | B2 | 11/2012 | Straubinger et al. |
| 8,323,335 | B2 | 12/2012 | Rowe et al. |
| 8,323,336 | B2 | 12/2012 | Hill et al. |
| 8,337,541 | B2 | 12/2012 | Quadri et al. |
| 8,348,995 | B2 | 1/2013 | Tuval et al. |
| 8,349,001 | B2 | 1/2013 | Mensah et al. |
| 8,349,003 | B2 | 1/2013 | Shu et al. |
| 8,353,921 | B2 | 1/2013 | Schaller et al. |
| 8,353,948 | B2 | 1/2013 | Besselink et al. |
| 8,353,953 | B2 | 1/2013 | Giannetti et al. |
| 8,357,387 | B2 | 1/2013 | Dove et al. |
| 8,361,137 | B2 | 1/2013 | Perouse |
| 8,361,537 | B2 | 1/2013 | Shanley |
| 8,366,769 | B2 | 2/2013 | Huynh et al. |
| 8,377,116 | B2 | 2/2013 | Hsu et al. |
| 8,377,499 | B2 | 2/2013 | Kleiner et al. |
| 8,382,816 | B2 | 2/2013 | Pollock et al. |
| RE44,075 | E | 3/2013 | Williamson et al. |
| 8,398,704 | B2 | 3/2013 | Straubinger et al. |

(56)                    References Cited

U.S. PATENT DOCUMENTS

| | | | |
|---|---|---|---|
| 8,398,707 B2 | 3/2013 | Bergin |
| 8,398,708 B2 | 3/2013 | Meiri et al. |
| 8,403,983 B2 | 3/2013 | Quadri et al. |
| 8,408,214 B2 | 4/2013 | Spenser |
| 8,409,274 B2 | 4/2013 | Li et al. |
| 8,414,635 B2 | 4/2013 | Hyodoh et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,416,643 B2 | 4/2013 | Magee |
| 8,430,902 B2 | 4/2013 | Bergheim |
| 8,430,927 B2 | 4/2013 | Bonhoeffer |
| 8,444,689 B2 | 5/2013 | Zhang |
| 8,449,466 B2 | 5/2013 | Duhay et al. |
| 8,449,599 B2 | 5/2013 | Chau et al. |
| 8,449,625 B2 | 5/2013 | Campbell et al. |
| 8,454,684 B2 | 6/2013 | Bergin et al. |
| 8,454,685 B2 | 6/2013 | Hariton et al. |
| 8,460,335 B2 | 6/2013 | Carpenter |
| 8,460,365 B2 | 6/2013 | Haverkost et al. |
| 8,460,366 B2 | 6/2013 | Rowe |
| 8,460,368 B2 | 6/2013 | Taylor et al. |
| 8,460,370 B2 | 6/2013 | Zakay et al. |
| 8,460,373 B2 | 6/2013 | Fogarty et al. |
| 8,470,023 B2 | 6/2013 | Eidenschink et al. |
| 8,470,024 B2 | 6/2013 | Ghione et al. |
| 8,470,028 B2 | 6/2013 | Thornton et al. |
| 8,475,521 B2 | 7/2013 | Suri et al. |
| 8,475,522 B2 | 7/2013 | Jimenez et al. |
| 8,475,523 B2 | 7/2013 | Duffy |
| 8,479,380 B2 | 7/2013 | Malewicz et al. |
| 8,480,730 B2 | 7/2013 | Maurer et al. |
| 8,480,731 B2 | 7/2013 | Elizondo et al. |
| 8,486,137 B2 | 7/2013 | Suri et al. |
| 8,491,650 B2 | 7/2013 | Wiemeyer et al. |
| 8,500,688 B2 | 8/2013 | Engel et al. |
| 8,500,733 B2 | 8/2013 | Watson |
| 8,500,755 B2 | 8/2013 | Ino et al. |
| 8,500,798 B2 | 8/2013 | Rowe et al. |
| 8,500,801 B2 | 8/2013 | Eberhardt et al. |
| 8,500,802 B2 | 8/2013 | Lane et al. |
| 8,506,620 B2 | 8/2013 | Ryan |
| 8,506,625 B2 | 8/2013 | Johnson |
| 8,511,244 B2 | 8/2013 | Holecek et al. |
| 8,512,397 B2 | 8/2013 | Rolando et al. |
| 8,512,398 B2 | 8/2013 | Alkhatib |
| 8,512,399 B2 | 8/2013 | Lafontaine |
| 8,512,401 B2 | 8/2013 | Murray, III et al. |
| 8,518,096 B2 | 8/2013 | Nelson |
| 8,518,106 B2 | 8/2013 | Duffy et al. |
| 8,518,108 B2 | 8/2013 | Huynh et al. |
| 8,529,621 B2 | 9/2013 | Alfieri et al. |
| 8,535,368 B2 | 9/2013 | Headley, Jr. et al. |
| 8,539,662 B2 | 9/2013 | Stacchino et al. |
| 8,545,742 B2 | 10/2013 | Gada et al. |
| 8,551,162 B2 | 10/2013 | Fogarty et al. |
| 8,562,663 B2 | 10/2013 | Mearns et al. |
| 8,562,672 B2 | 10/2013 | Bonhoeffer et al. |
| 8,562,673 B2 | 10/2013 | Yeung et al. |
| 8,565,872 B2 | 10/2013 | Pederson |
| 8,568,472 B2 | 10/2013 | Marchand et al. |
| 8,579,963 B2 | 11/2013 | Tabor |
| 8,579,964 B2 | 11/2013 | Lane et al. |
| 8,579,965 B2 | 11/2013 | Bonhoeffer et al. |
| 8,584,849 B2 | 11/2013 | Mccaffrey |
| 8,585,749 B2 | 11/2013 | Shelso |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,591,574 B2 | 11/2013 | Lambrecht et al. |
| 8,597,348 B2 | 12/2013 | Rowe et al. |
| 8,603,154 B2 | 12/2013 | Strauss et al. |
| 8,603,160 B2 | 12/2013 | Salahieh et al. |
| 8,603,161 B2 | 12/2013 | Drews et al. |
| 8,608,648 B2 | 12/2013 | Banik et al. |
| 8,617,236 B2 | 12/2013 | Paul et al. |
| 8,623,074 B2 | 1/2014 | Ryan |
| 8,623,080 B2 | 1/2014 | Fogarty et al. |
| 8,628,566 B2 | 1/2014 | Eberhardt et al. |
| 8,632,586 B2 | 1/2014 | Spenser et al. |
| 8,632,608 B2 | 1/2014 | Carpentier et al. |
| 8,640,521 B2 | 2/2014 | Righini et al. |
| 8,641,639 B2 | 2/2014 | Manstrom et al. |
| 8,647,381 B2 | 2/2014 | Essinger et al. |
| 8,652,145 B2 | 2/2014 | Maimon et al. |
| 8,652,201 B2 | 2/2014 | Oberti et al. |
| 8,652,202 B2 | 2/2014 | Alon et al. |
| 8,652,203 B2 | 2/2014 | Quadri et al. |
| 8,653,632 B2 | 2/2014 | Pederson et al. |
| 8,663,318 B2 | 3/2014 | Ho |
| 8,663,319 B2 | 3/2014 | Ho |
| 8,668,730 B2 | 3/2014 | Mcguckin, Jr. et al. |
| 8,668,733 B2 | 3/2014 | Haug |
| 8,672,992 B2 | 3/2014 | Orr |
| 8,672,997 B2 | 3/2014 | Drasler et al. |
| 8,672,998 B2 | 3/2014 | Lichtenstein et al. |
| 8,672,999 B2 | 3/2014 | Cali et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,685,083 B2 | 4/2014 | Perier et al. |
| 8,685,086 B2 | 4/2014 | Navia et al. |
| 8,690,787 B2 | 4/2014 | Blomqvist et al. |
| 8,690,936 B2 | 4/2014 | Nguyen et al. |
| 8,696,742 B2 | 4/2014 | Pintor et al. |
| 8,707,957 B2 | 4/2014 | Callister et al. |
| 8,715,207 B2 | 5/2014 | Righini et al. |
| 8,715,337 B2 | 5/2014 | Chuter |
| 8,715,343 B2 | 5/2014 | Navia et al. |
| 8,721,707 B2 | 5/2014 | Boucher et al. |
| 8,721,708 B2 | 5/2014 | Seguin et al. |
| 8,721,713 B2 | 5/2014 | Tower et al. |
| 8,721,714 B2 | 5/2014 | Kelley |
| 8,728,154 B2 | 5/2014 | Alkhatib |
| 8,728,155 B2 | 5/2014 | Montorfano et al. |
| 8,731,658 B2 | 5/2014 | Hampton et al. |
| 8,734,484 B2 | 5/2014 | Ahlberg et al. |
| 8,740,930 B2 | 6/2014 | Goodwin |
| 8,740,974 B2 | 6/2014 | Lambrecht et al. |
| 8,740,975 B2 | 6/2014 | Yang et al. |
| 8,740,976 B2 | 6/2014 | Tran et al. |
| 8,747,458 B2 | 6/2014 | Tuval et al. |
| 8,747,459 B2 | 6/2014 | Nguyen et al. |
| 8,747,460 B2 | 6/2014 | Tuval et al. |
| 8,753,384 B2 | 6/2014 | Leanna |
| 8,758,432 B2 | 6/2014 | Solem |
| 8,764,814 B2 | 7/2014 | Solem |
| 8,764,818 B2 | 7/2014 | Gregg |
| 8,764,820 B2 | 7/2014 | Dehdashtian et al. |
| 8,771,302 B2 | 7/2014 | Woolfson et al. |
| 8,771,344 B2 | 7/2014 | Tran et al. |
| 8,771,345 B2 | 7/2014 | Tuval et al. |
| 8,771,346 B2 | 7/2014 | Tuval et al. |
| 8,777,975 B2 | 7/2014 | Kashkarov et al. |
| 8,778,018 B2 | 7/2014 | Iobbi |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,784,480 B2 | 7/2014 | Taylor et al. |
| 8,784,481 B2 | 7/2014 | Alkhatib et al. |
| 8,790,387 B2 | 7/2014 | Nguyen et al. |
| 8,790,395 B2 | 7/2014 | Straubinger et al. |
| 8,790,396 B2 | 7/2014 | Bergheim et al. |
| 8,791,171 B2 | 7/2014 | Pacetti |
| 8,795,356 B2 | 8/2014 | Quadri et al. |
| 8,801,776 B2 | 8/2014 | House et al. |
| 8,808,356 B2 | 8/2014 | Braido et al. |
| 8,808,366 B2 | 8/2014 | Braido et al. |
| 8,808,370 B2 | 8/2014 | Nitzan et al. |
| 8,821,569 B2 | 9/2014 | Gurskis et al. |
| 8,821,570 B2 | 9/2014 | Dumontelle et al. |
| 8,828,078 B2 | 9/2014 | Salahieh et al. |
| 8,828,079 B2 | 9/2014 | Thielen et al. |
| 8,834,561 B2 | 9/2014 | Figulla et al. |

(56) References Cited

U.S. PATENT DOCUMENTS

| | | | |
|---|---|---|---|
| 8,834,564 B2 | 9/2014 | Tuval et al. | |
| 8,840,661 B2 | 9/2014 | Manasse | |
| 8,845,718 B2 | 9/2014 | Tuval et al. | |
| 8,845,720 B2 | 9/2014 | Conklin | |
| 8,852,267 B2 | 10/2014 | Cattaneo | |
| 8,858,620 B2 | 10/2014 | Salahieh et al. | |
| 8,858,621 B2 | 10/2014 | Oba et al. | |
| 8,870,936 B2 | 10/2014 | Rowe | |
| 8,870,947 B2 | 10/2014 | Shaw | |
| 8,870,948 B1 | 10/2014 | Erzberger et al. | |
| 8,870,950 B2 | 10/2014 | Hacohen | |
| 8,876,712 B2 | 11/2014 | Yee et al. | |
| 8,876,883 B2 | 11/2014 | Rust | |
| 8,876,893 B2 | 11/2014 | Dwork et al. | |
| 8,876,894 B2 | 11/2014 | Tuval et al. | |
| 8,876,895 B2 | 11/2014 | Tuval et al. | |
| 8,882,831 B2 | 11/2014 | Alkhatib | |
| 8,894,702 B2 | 11/2014 | Quadri et al. | |
| 8,894,703 B2 | 11/2014 | Salahieh et al. | |
| 8,906,081 B2 | 12/2014 | Cully et al. | |
| 8,911,455 B2 | 12/2014 | Quadri et al. | |
| 8,911,844 B2 | 12/2014 | Ford | |
| 8,926,688 B2 | 1/2015 | Burkart et al. | |
| 8,926,693 B2 | 1/2015 | Duffy et al. | |
| 8,932,349 B2 | 1/2015 | Jenson et al. | |
| 8,939,960 B2 | 1/2015 | Rosenman et al. | |
| 8,940,887 B2 | 1/2015 | Chatterton et al. | |
| 8,945,208 B2 | 2/2015 | Jimenez et al. | |
| 8,945,209 B2 | 2/2015 | Bonyuet et al. | |
| 8,945,210 B2 | 2/2015 | Cartledge et al. | |
| 8,951,280 B2 | 2/2015 | Cohn et al. | |
| 8,951,299 B2 | 2/2015 | Paul et al. | |
| 8,961,583 B2 | 2/2015 | Hojeibane et al. | |
| 8,961,589 B2 | 2/2015 | Kleiner et al. | |
| 8,961,593 B2 | 2/2015 | Bonhoeffer et al. | |
| 8,961,595 B2 | 2/2015 | Alkhatib | |
| 8,968,393 B2 | 3/2015 | Rothstein | |
| 8,968,395 B2 | 3/2015 | Hauser et al. | |
| 8,974,524 B2 | 3/2015 | Yeung et al. | |
| 8,979,922 B2 | 3/2015 | Jayasinghe et al. | |
| 8,986,372 B2 | 3/2015 | Murry et al. | |
| 8,986,375 B2 | 3/2015 | Garde et al. | |
| 8,986,713 B2 | 3/2015 | Cleek et al. | |
| 8,992,608 B2 | 3/2015 | Haug et al. | |
| 8,998,978 B2 | 4/2015 | Wang | |
| 8,998,979 B2 | 4/2015 | Seguin et al. | |
| 8,998,980 B2 | 4/2015 | Shipley et al. | |
| 8,998,981 B2 | 4/2015 | Tuval et al. | |
| 8,999,369 B2 | 4/2015 | Gale et al. | |
| 9,005,273 B2 | 4/2015 | Salahieh et al. | |
| 9,005,277 B2 | 4/2015 | Pintor et al. | |
| 9,011,521 B2 | 4/2015 | Haug et al. | |
| 9,011,523 B2 | 4/2015 | Seguin | |
| 9,011,524 B2 | 4/2015 | Eberhardt | |
| 9,011,528 B2 | 4/2015 | Ryan et al. | |
| 9,023,100 B2 | 5/2015 | Quadri et al. | |
| 9,028,545 B2 | 5/2015 | Taylor | |
| 9,029,418 B2 | 5/2015 | Dove et al. | |
| 9,034,033 B2 | 5/2015 | Mclean et al. | |
| 9,055,937 B2 | 6/2015 | Rowe et al. | |
| 9,078,749 B2 | 7/2015 | Lutter et al. | |
| 9,078,751 B2 | 7/2015 | Naor | |
| 9,084,676 B2 | 7/2015 | Chau et al. | |
| 9,125,738 B2 | 9/2015 | Figulla et al. | |
| 9,138,312 B2 | 9/2015 | Tuval et al. | |
| 9,161,834 B2 | 10/2015 | Taylor et al. | |
| 9,186,249 B2 | 11/2015 | Rolando et al. | |
| 9,241,790 B2 | 1/2016 | Lane et al. | |
| 9,248,014 B2 | 2/2016 | Lane et al. | |
| 9,277,990 B2 | 3/2016 | Klima et al. | |
| 9,277,993 B2 | 3/2016 | Gamarra et al. | |
| D755,384 S | 5/2016 | Pesce et al. | |
| 9,333,074 B2 | 5/2016 | Quadri et al. | |
| 9,445,897 B2 | 9/2016 | Bishop et al. | |
| 9,456,877 B2 | 10/2016 | Weitzner et al. | |
| 9,554,897 B2 | 1/2017 | Lane et al. | |
| 9,681,968 B2 | 6/2017 | Goetz et al. | |
| 9,700,329 B2 | 7/2017 | Metzger et al. | |
| 9,700,411 B2 | 7/2017 | Klima et al. | |
| 9,770,329 B2 | 9/2017 | Lane et al. | |
| 9,795,479 B2 | 10/2017 | Lim et al. | |
| 9,833,313 B2 | 12/2017 | Board et al. | |
| 9,861,476 B2 | 1/2018 | Salahieh et al. | |
| 9,861,477 B2 | 1/2018 | Backus et al. | |
| 9,867,698 B2 | 1/2018 | Kovalsky et al. | |
| 9,877,830 B2 | 1/2018 | Lim et al. | |
| 9,889,029 B2 | 2/2018 | Yu et al. | |
| 9,895,225 B2 | 2/2018 | Rolando et al. | |
| 9,925,045 B2 | 3/2018 | Creaven et al. | |
| 10,350,066 B2 | 7/2019 | Cooper et al. | |
| 10,376,363 B2 | 8/2019 | Quadri et al. | |
| 10,449,042 B2 | 10/2019 | Lane et al. | |
| 10,575,951 B2 | 3/2020 | Johnson et al. | |
| 10,583,000 B2 * | 3/2020 | Ratz | A61F 2/2418 |
| 10,583,002 B2 * | 3/2020 | Lane | A61F 2/2436 |
| 10,695,177 B2 | 6/2020 | Hariton et al. | |
| 10,758,344 B2 | 9/2020 | Hariton et al. | |
| 10,856,984 B2 * | 12/2020 | Lane | A61F 2/2445 |
| 11,406,499 B2 | 8/2022 | Zhang et al. | |
| 11,419,720 B2 | 8/2022 | Lane et al. | |
| 11,432,924 B2 | 9/2022 | Lane et al. | |
| 11,464,631 B2 * | 10/2022 | Kerr | A61M 29/02 |
| 11,672,658 B2 | 6/2023 | Hariton et al. | |
| 11,903,829 B1 | 2/2024 | Ma et al. | |
| 12,295,839 B2 | 5/2025 | Becerra et al. | |
| 2001/0007956 A1 | 7/2001 | Letac et al. | |
| 2001/0021872 A1 | 9/2001 | Bailey et al. | |
| 2001/0047180 A1 | 11/2001 | Grudem et al. | |
| 2001/0047200 A1 | 11/2001 | White et al. | |
| 2002/0016623 A1 | 2/2002 | Kula et al. | |
| 2002/0022853 A1 | 2/2002 | Swanson et al. | |
| 2002/0032481 A1 | 3/2002 | Gabbay | |
| 2002/0045929 A1 | 4/2002 | Diaz | |
| 2002/0052644 A1 | 5/2002 | Shaolian et al. | |
| 2002/0055772 A1 | 5/2002 | Mcguckin et al. | |
| 2002/0107565 A1 | 8/2002 | Greenhalgh | |
| 2002/0111619 A1 | 8/2002 | Keast et al. | |
| 2002/0123802 A1 | 9/2002 | Snyders | |
| 2002/0173842 A1 | 11/2002 | Buchanan | |
| 2002/0183827 A1 | 12/2002 | Derus et al. | |
| 2003/0040792 A1 | 2/2003 | Gabbay | |
| 2003/0050694 A1 | 3/2003 | Yang et al. | |
| 2003/0100939 A1 | 5/2003 | Yodfat et al. | |
| 2003/0105517 A1 | 6/2003 | White et al. | |
| 2003/0114913 A1 | 6/2003 | Spenser et al. | |
| 2003/0120263 A1 | 6/2003 | Ouriel et al. | |
| 2003/0120330 A1 | 6/2003 | Ouriel et al. | |
| 2003/0120333 A1 | 6/2003 | Ouriel et al. | |
| 2003/0125797 A1 | 7/2003 | Chobotov et al. | |
| 2003/0130729 A1 | 7/2003 | Paniagua et al. | |
| 2003/0158597 A1 | 8/2003 | Quiachon et al. | |
| 2003/0176914 A1 | 9/2003 | Rabkin et al. | |
| 2003/0199971 A1 | 10/2003 | Tower et al. | |
| 2003/0212454 A1 | 11/2003 | Scott | |
| 2003/0220683 A1 | 11/2003 | Minasian et al. | |
| 2004/0039436 A1 | 2/2004 | Spenser et al. | |
| 2004/0087900 A1 | 5/2004 | Thompson et al. | |
| 2004/0092858 A1 | 5/2004 | Wilson et al. | |
| 2004/0093058 A1 | 5/2004 | Cottone et al. | |
| 2004/0093060 A1 | 5/2004 | Seguin et al. | |
| 2004/0093075 A1 | 5/2004 | Kuehne | |
| 2004/0102842 A1 | 5/2004 | Jansen | |
| 2004/0117009 A1 | 6/2004 | Cali et al. | |
| 2004/0133263 A1 | 7/2004 | Dusbabek et al. | |
| 2004/0133273 A1 | 7/2004 | Cox | |
| 2004/0181238 A1 | 9/2004 | Zarbatany et al. | |
| 2004/0186561 A1 | 9/2004 | Mcguckin et al. | |
| 2004/0193261 A1 | 9/2004 | Berreklouw | |
| 2004/0199176 A1 | 10/2004 | Berreklouw | |
| 2004/0210304 A1 | 10/2004 | Seguin et al. | |
| 2004/0210307 A1 | 10/2004 | Khairkhahan | |
| 2004/0215325 A1 | 10/2004 | Penn et al. | |
| 2004/0225353 A1 | 11/2004 | James, Jr. et al. | |
| 2004/0236411 A1 | 11/2004 | Sarac et al. | |

(56) References Cited

U.S. PATENT DOCUMENTS

| | | |
|---|---|---|
| 2004/0243230 A1 | 12/2004 | Navia et al. |
| 2004/0249433 A1 | 12/2004 | Freitag |
| 2004/0260389 A1 | 12/2004 | Case et al. |
| 2004/0260390 A1 | 12/2004 | Sarac et al. |
| 2005/0033398 A1 | 2/2005 | Seguin |
| 2005/0038470 A1 | 2/2005 | Van Der Burg et al. |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0125020 A1 | 6/2005 | Meade et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137691 A1 | 6/2005 | Salahieh et al. |
| 2005/0137693 A1 | 6/2005 | Haug |
| 2005/0137695 A1 | 6/2005 | Salahieh et al. |
| 2005/0137698 A1 | 6/2005 | Salahieh et al. |
| 2005/0137701 A1 | 6/2005 | Salahieh et al. |
| 2005/0143809 A1* | 6/2005 | Salahieh ............ A61F 2/2418 |
| | | 623/2.11 |
| 2005/0154444 A1 | 7/2005 | Quadri |
| 2005/0159811 A1 | 7/2005 | Lane |
| 2005/0182483 A1 | 8/2005 | Osborne et al. |
| 2005/0182486 A1 | 8/2005 | Gabbay |
| 2005/0203614 A1 | 9/2005 | Forster et al. |
| 2005/0203616 A1 | 9/2005 | Cribier |
| 2005/0203617 A1 | 9/2005 | Forster et al. |
| 2005/0216079 A1 | 9/2005 | Macoviak |
| 2005/0234546 A1 | 10/2005 | Nugent et al. |
| 2005/0283231 A1 | 12/2005 | Haug et al. |
| 2005/0288766 A1 | 12/2005 | Plain et al. |
| 2006/0020247 A1 | 1/2006 | Kagan et al. |
| 2006/0020327 A1 | 1/2006 | Lashinski et al. |
| 2006/0020334 A1 | 1/2006 | Lashinski et al. |
| 2006/0052802 A1 | 3/2006 | Sterman et al. |
| 2006/0052867 A1 | 3/2006 | Revuelta et al. |
| 2006/0058872 A1 | 3/2006 | Salahieh et al. |
| 2006/0064120 A1 | 3/2006 | Levine et al. |
| 2006/0095115 A1 | 5/2006 | Bladillah et al. |
| 2006/0106454 A1 | 5/2006 | Osborne et al. |
| 2006/0116625 A1 | 6/2006 | Renati et al. |
| 2006/0129235 A1 | 6/2006 | Seguin et al. |
| 2006/0142837 A1 | 6/2006 | Haverkost et al. |
| 2006/0149350 A1 | 7/2006 | Patel et al. |
| 2006/0149360 A1 | 7/2006 | Schwammenthal et al. |
| 2006/0161249 A1 | 7/2006 | Realyvasquez et al. |
| 2006/0161265 A1 | 7/2006 | Levine et al. |
| 2006/0173537 A1 | 8/2006 | Yang et al. |
| 2006/0195134 A1 | 8/2006 | Crittenden |
| 2006/0195183 A1 | 8/2006 | Navia et al. |
| 2006/0212110 A1 | 9/2006 | Osborne et al. |
| 2006/0224232 A1 | 10/2006 | Chobotov |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1* | 11/2006 | Nguyen ............ A61F 2/2412 |
| | | 623/2.18 |
| 2006/0259137 A1 | 11/2006 | Artof et al. |
| 2006/0265056 A1 | 11/2006 | Nguyen et al. |
| 2006/0276874 A1 | 12/2006 | Wilson et al. |
| 2006/0287717 A1 | 12/2006 | Rowe et al. |
| 2006/0287719 A1 | 12/2006 | Rowe et al. |
| 2006/0293698 A1 | 12/2006 | Douk |
| 2006/0293745 A1 | 12/2006 | Carpentier et al. |
| 2007/0010876 A1 | 1/2007 | Salahieh |
| 2007/0010877 A1 | 1/2007 | Salahieh et al. |
| 2007/0016286 A1 | 1/2007 | Herrmann et al. |
| 2007/0043435 A1 | 2/2007 | Seguin et al. |
| 2007/0050020 A1 | 3/2007 | Spence |
| 2007/0050021 A1 | 3/2007 | Johnson |
| 2007/0066863 A1 | 3/2007 | Rafiee et al. |
| 2007/0067016 A1 | 3/2007 | Jung |
| 2007/0088431 A1 | 4/2007 | Bourang et al. |
| 2007/0100432 A1 | 5/2007 | Case et al. |
| 2007/0100439 A1 | 5/2007 | Cangialosi et al. |
| 2007/0112422 A1 | 5/2007 | Dehdashtian et al. |
| 2007/0118206 A1 | 5/2007 | Colgan et al. |
| 2007/0118207 A1 | 5/2007 | Amplatz et al. |
| 2007/0129794 A1 | 6/2007 | Realyvasquez |
| 2007/0142906 A1 | 6/2007 | Figulla et al. |
| 2007/0156224 A1 | 7/2007 | Cioanta et al. |
| 2007/0162107 A1 | 7/2007 | Haug et al. |
| 2007/0185559 A1 | 8/2007 | Shelso |
| 2007/0203575 A1 | 8/2007 | Forster et al. |
| 2007/0213813 A1 | 9/2007 | Von Segesser et al. |
| 2007/0219620 A1 | 9/2007 | Eells et al. |
| 2007/0233228 A1 | 10/2007 | Eberhardt et al. |
| 2007/0250151 A1 | 10/2007 | Pereira |
| 2007/0255391 A1 | 11/2007 | Hojeibane et al. |
| 2007/0255394 A1 | 11/2007 | Ryan |
| 2007/0265656 A1 | 11/2007 | Amplatz et al. |
| 2007/0270932 A1 | 11/2007 | Headley et al. |
| 2007/0270937 A1 | 11/2007 | Leanna |
| 2007/0270943 A1 | 11/2007 | Solem et al. |
| 2007/0293940 A1 | 12/2007 | Schaeffer et al. |
| 2008/0009934 A1 | 1/2008 | Schneider et al. |
| 2008/0021546 A1 | 1/2008 | Patz et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0087581 A1 | 4/2008 | Eisenhut et al. |
| 2008/0097571 A1 | 4/2008 | Denison et al. |
| 2008/0097581 A1 | 4/2008 | Shanley |
| 2008/0114441 A1 | 5/2008 | Rust et al. |
| 2008/0114442 A1 | 5/2008 | Mitchell et al. |
| 2008/0125853 A1 | 5/2008 | Bailey et al. |
| 2008/0125859 A1 | 5/2008 | Salahieh et al. |
| 2008/0133003 A1 | 6/2008 | Seguin et al. |
| 2008/0140175 A1 | 6/2008 | Boucher et al. |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154358 A1 | 6/2008 | Tansley et al. |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208307 A1 | 8/2008 | Ben-muvhar et al. |
| 2008/0208328 A1 | 8/2008 | Antocci et al. |
| 2008/0208332 A1 | 8/2008 | Lamphere et al. |
| 2008/0221672 A1 | 9/2008 | Lamphere |
| 2008/0228201 A1 | 9/2008 | Zarbatany et al. |
| 2008/0228254 A1 | 9/2008 | Ryan |
| 2008/0243233 A1 | 10/2008 | Ben-muvhar et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0262596 A1 | 10/2008 | Xiao |
| 2008/0262603 A1 | 10/2008 | Giaquinta et al. |
| 2008/0269878 A1 | 10/2008 | Lobbi |
| 2008/0275549 A1 | 11/2008 | Rowe |
| 2008/0281411 A1 | 11/2008 | Berreklouw |
| 2008/0288062 A1 | 11/2008 | Andrieu et al. |
| 2008/0319526 A1 | 12/2008 | Hill et al. |
| 2009/0005863 A1 | 1/2009 | Goetz et al. |
| 2009/0012602 A1 | 1/2009 | Quadri |
| 2009/0054974 A1 | 2/2009 | McGuckin, Jr. et al. |
| 2009/0054976 A1 | 2/2009 | Tuval et al. |
| 2009/0062908 A1 | 3/2009 | Bonhoeffer et al. |
| 2009/0076531 A1 | 3/2009 | Richardson et al. |
| 2009/0076585 A1 | 3/2009 | Hendriksen et al. |
| 2009/0076598 A1 | 3/2009 | Salahieh et al. |
| 2009/0082844 A1 | 3/2009 | Zacharias et al. |
| 2009/0082847 A1 | 3/2009 | Zacharias et al. |
| 2009/0088832 A1 | 4/2009 | Chew et al. |
| 2009/0112309 A1 | 4/2009 | Jaramillo et al. |

(56)          References Cited

U.S. PATENT DOCUMENTS

| | | |
|---|---|---|
| 2009/0118744 A1 | 5/2009 | Wells et al. |
| 2009/0118824 A1 | 5/2009 | Samkov |
| 2009/0118826 A1 | 5/2009 | Khaghani |
| 2009/0125096 A1 | 5/2009 | Chu et al. |
| 2009/0132035 A1 | 5/2009 | Roth et al. |
| 2009/0138079 A1 | 5/2009 | Tuval et al. |
| 2009/0149946 A1 | 6/2009 | Dixon |
| 2009/0157175 A1 | 6/2009 | Benichou |
| 2009/0163934 A1 | 6/2009 | Raschdorf, Jr. et al. |
| 2009/0171438 A1 | 7/2009 | Chuter et al. |
| 2009/0171447 A1 | 7/2009 | Von Segesser et al. |
| 2009/0171456 A1 | 7/2009 | Kveen |
| 2009/0177262 A1 | 7/2009 | Oberti et al. |
| 2009/0182407 A1 | 7/2009 | Leanna et al. |
| 2009/0182413 A1 | 7/2009 | Burkart et al. |
| 2009/0188964 A1 | 7/2009 | Orlov |
| 2009/0192601 A1 | 7/2009 | Rafiee et al. |
| 2009/0216310 A1 | 8/2009 | Straubinger et al. |
| 2009/0216313 A1 | 8/2009 | Straubinger et al. |
| 2009/0216314 A1 | 8/2009 | Quadri |
| 2009/0216317 A1 | 8/2009 | Cromack et al. |
| 2009/0216322 A1 | 8/2009 | Le et al. |
| 2009/0222076 A1 | 9/2009 | Figulla et al. |
| 2009/0227992 A1 | 9/2009 | Nir et al. |
| 2009/0234443 A1 | 9/2009 | Ottma et al. |
| 2009/0248132 A1 | 10/2009 | Bloom et al. |
| 2009/0248133 A1 | 10/2009 | Bloom et al. |
| 2009/0258958 A1 | 10/2009 | Ford |
| 2009/0259306 A1 | 10/2009 | Rowe |
| 2009/0264989 A1 | 10/2009 | Bonhoeffer et al. |
| 2009/0264997 A1 | 10/2009 | Salahieh |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0281619 A1 | 11/2009 | Le et al. |
| 2009/0287296 A1 | 11/2009 | Manasse |
| 2009/0287299 A1 | 11/2009 | Tabor et al. |
| 2009/0292350 A1 | 11/2009 | Eberhardt et al. |
| 2009/0306768 A1 | 12/2009 | Quadri |
| 2009/0318871 A1 | 12/2009 | Zarbatany et al. |
| 2010/0004740 A1 | 1/2010 | Seguin et al. |
| 2010/0016958 A1 | 1/2010 | St. Goar et al. |
| 2010/0024818 A1 | 2/2010 | Stenzler et al. |
| 2010/0036479 A1 | 2/2010 | Hill et al. |
| 2010/0049306 A1 | 2/2010 | House et al. |
| 2010/0082089 A1 | 4/2010 | Quadri et al. |
| 2010/0082094 A1 | 4/2010 | Quadri et al. |
| 2010/0094411 A1 | 4/2010 | Tuval et al. |
| 2010/0100167 A1* | 4/2010 | Bortlein .................. A61F 2/95 |
| | | 623/1.11 |
| 2010/0114299 A1 | 5/2010 | Ben Muvhar et al. |
| 2010/0114305 A1 | 5/2010 | Kang et al. |
| 2010/0121461 A1 | 5/2010 | Sobrino-Serrano et al. |
| 2010/0131054 A1 | 5/2010 | Tuval et al. |
| 2010/0145438 A1 | 6/2010 | Barone |
| 2010/0161027 A1 | 6/2010 | Orr |
| 2010/0168839 A1 | 7/2010 | Braido et al. |
| 2010/0179633 A1 | 7/2010 | Solem |
| 2010/0179647 A1 | 7/2010 | Carpenter et al. |
| 2010/0191326 A1 | 7/2010 | Alkhatib |
| 2010/0204781 A1 | 8/2010 | Alkhatib |
| 2010/0217382 A1 | 8/2010 | Chau et al. |
| 2010/0249894 A1 | 9/2010 | Oba et al. |
| 2010/0249908 A1 | 9/2010 | Chau et al. |
| 2010/0249911 A1 | 9/2010 | Alkhatib |
| 2010/0256723 A1 | 10/2010 | Murray |
| 2010/0262157 A1 | 10/2010 | Silver et al. |
| 2010/0262231 A1 | 10/2010 | Tuval et al. |
| 2010/0268332 A1 | 10/2010 | Tuval et al. |
| 2010/0274345 A1 | 10/2010 | Rust |
| 2010/0280606 A1 | 11/2010 | Naor |
| 2010/0298931 A1 | 11/2010 | Quadri et al. |
| 2010/0305685 A1 | 12/2010 | Millwee et al. |
| 2010/0312333 A1 | 12/2010 | Navia et al. |
| 2011/0004296 A1 | 1/2011 | Lutter et al. |
| 2011/0004299 A1 | 1/2011 | Navia et al. |
| 2011/0015616 A1 | 1/2011 | Straubinger et al. |
| 2011/0015729 A1 | 1/2011 | Jimenez et al. |
| 2011/0015731 A1 | 1/2011 | Carpentier et al. |
| 2011/0022157 A1 | 1/2011 | Essinger et al. |
| 2011/0022165 A1 | 1/2011 | Oba et al. |
| 2011/0029067 A1 | 2/2011 | Mcguckin, Jr. et al. |
| 2011/0029072 A1 | 2/2011 | Gabbay |
| 2011/0137397 A1 | 6/2011 | Chau et al. |
| 2011/0166644 A1 | 7/2011 | Keeble et al. |
| 2011/0178597 A9 | 7/2011 | Navia et al. |
| 2011/0202128 A1 | 8/2011 | Duffy |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0218619 A1 | 9/2011 | Benichou et al. |
| 2011/0224785 A1 | 9/2011 | Hacohen |
| 2011/0238159 A1 | 9/2011 | Guyenot et al. |
| 2011/0264196 A1 | 10/2011 | Savage et al. |
| 2011/0264198 A1 | 10/2011 | Murray, III et al. |
| 2011/0282438 A1 | 11/2011 | Drews et al. |
| 2011/0301704 A1 | 12/2011 | Alfieri et al. |
| 2011/0313515 A1 | 12/2011 | Quadri et al. |
| 2011/0319981 A1 | 12/2011 | Hill et al. |
| 2011/0319989 A1 | 12/2011 | Lane et al. |
| 2012/0012487 A1 | 1/2012 | Tian et al. |
| 2012/0016342 A1 | 1/2012 | Brecker |
| 2012/0016411 A1 | 1/2012 | Tuval |
| 2012/0022605 A1 | 1/2012 | Jahns et al. |
| 2012/0022639 A1 | 1/2012 | Hacohen et al. |
| 2012/0022642 A1 | 1/2012 | Haug et al. |
| 2012/0029627 A1 | 2/2012 | Salahieh et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041550 A1 | 2/2012 | Salahieh et al. |
| 2012/0041551 A1 | 2/2012 | Spenser et al. |
| 2012/0053681 A1 | 3/2012 | Alkhatib et al. |
| 2012/0059452 A1 | 3/2012 | Boucher et al. |
| 2012/0059454 A1 | 3/2012 | Millwee et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0179051 A1 | 7/2012 | Pfeiffer et al. |
| 2012/0179239 A1 | 7/2012 | Quadri |
| 2012/0179243 A1 | 7/2012 | Yang et al. |
| 2012/0185033 A1 | 7/2012 | Ryan |
| 2012/0215303 A1 | 8/2012 | Quadri et al. |
| 2012/0259405 A1 | 10/2012 | Weber et al. |
| 2012/0259409 A1 | 10/2012 | Nguyen et al. |
| 2012/0271398 A1 | 10/2012 | Essinger et al. |
| 2012/0283820 A1 | 11/2012 | Tseng et al. |
| 2012/0283824 A1 | 11/2012 | Lutter et al. |
| 2012/0290062 A1 | 11/2012 | Mcnamara et al. |
| 2012/0296418 A1 | 11/2012 | Bonyuet et al. |
| 2012/0303116 A1 | 11/2012 | Gorman, III et al. |
| 2012/0310328 A1 | 12/2012 | Olson et al. |
| 2012/0323316 A1 | 12/2012 | Chau et al. |
| 2012/0330409 A1 | 12/2012 | Haug et al. |
| 2013/0006294 A1 | 1/2013 | Kashkarov et al. |
| 2013/0018458 A1 | 1/2013 | Yohanan et al. |
| 2013/0030418 A1 | 1/2013 | Taft et al. |
| 2013/0030523 A1 | 1/2013 | Padala et al. |
| 2013/0035759 A1 | 2/2013 | Gross et al. |
| 2013/0046378 A1 | 2/2013 | Millwee et al. |
| 2013/0053949 A1 | 2/2013 | Pintor et al. |
| 2013/0053950 A1 | 2/2013 | Rowe et al. |
| 2013/0075215 A1 | 3/2013 | Saito et al. |
| 2013/0079869 A1 | 3/2013 | Straubinger et al. |
| 2013/0095264 A1 | 4/2013 | Sowinski et al. |
| 2013/0096671 A1 | 4/2013 | Iobbi |
| 2013/0110226 A1 | 5/2013 | Gurskis |
| 2013/0110227 A1 | 5/2013 | Quadri et al. |
| 2013/0110230 A1 | 5/2013 | Solem |
| 2013/0116777 A1 | 5/2013 | Pintor et al. |
| 2013/0131788 A1 | 5/2013 | Quadri et al. |

(56)　　　　　References Cited

U.S. PATENT DOCUMENTS

| | | |
|---|---|---|
| 2013/0131793 A1 | 5/2013 | Quadri et al. |
| 2013/0138203 A1 | 5/2013 | Quadri |
| 2013/0138207 A1 | 5/2013 | Quadri et al. |
| 2013/0144375 A1 | 6/2013 | Giasolli et al. |
| 2013/0144378 A1 | 6/2013 | Quadri et al. |
| 2013/0144380 A1 | 6/2013 | Quadri et al. |
| 2013/0144381 A1 | 6/2013 | Quadri et al. |
| 2013/0150956 A1 | 6/2013 | Yohanan et al. |
| 2013/0166024 A1 | 6/2013 | Drews et al. |
| 2013/0172983 A1 | 7/2013 | Clerc et al. |
| 2013/0172992 A1 | 7/2013 | Gross et al. |
| 2013/0184813 A1 | 7/2013 | Quadri et al. |
| 2013/0184814 A1 | 7/2013 | Huynh et al. |
| 2013/0190861 A1 | 7/2013 | Chau et al. |
| 2013/0190862 A1 | 7/2013 | Pintor et al. |
| 2013/0197622 A1 | 8/2013 | Mitra et al. |
| 2013/0211508 A1 | 8/2013 | Lane et al. |
| 2013/0236889 A1 | 9/2013 | Kishimoto et al. |
| 2013/0238087 A1 | 9/2013 | Taylor |
| 2013/0245615 A1 | 9/2013 | Koltz |
| 2013/0245736 A1 | 9/2013 | Alexander et al. |
| 2013/0253635 A1 | 9/2013 | Straubinger et al. |
| 2013/0253637 A1 | 9/2013 | Wang et al. |
| 2013/0253639 A1 | 9/2013 | Alkhatib |
| 2013/0253641 A1 | 9/2013 | Lattouf |
| 2013/0253642 A1 | 9/2013 | Brecker |
| 2013/0261737 A1 | 10/2013 | Costello |
| 2013/0261738 A1 | 10/2013 | Clague et al. |
| 2013/0268069 A1 | 10/2013 | Zakai et al. |
| 2013/0289695 A1 | 10/2013 | Tian et al. |
| 2013/0304200 A1 | 11/2013 | Mclean et al. |
| 2013/0310928 A1 | 11/2013 | Morriss et al. |
| 2013/0325098 A1 | 12/2013 | Desai et al. |
| 2013/0325121 A1 | 12/2013 | Whatley et al. |
| 2013/0331714 A1 | 12/2013 | Manstrom et al. |
| 2013/0331929 A1 | 12/2013 | Mitra et al. |
| 2013/0338764 A1 | 12/2013 | Thornton et al. |
| 2013/0338765 A1 | 12/2013 | Braido et al. |
| 2013/0338766 A1 | 12/2013 | Hastings et al. |
| 2013/0345786 A1 | 12/2013 | Behan |
| 2013/0345803 A1 | 12/2013 | Bergheim, III |
| 2014/0018912 A1 | 1/2014 | Delaloye et al. |
| 2014/0025163 A1 | 1/2014 | Padala et al. |
| 2014/0031930 A1 | 1/2014 | Keidar et al. |
| 2014/0039611 A1 | 2/2014 | Lane et al. |
| 2014/0039612 A1 | 2/2014 | Dolan |
| 2014/0039614 A1 | 2/2014 | Delaloye et al. |
| 2014/0044689 A1 | 2/2014 | Liu et al. |
| 2014/0046219 A1 | 2/2014 | Sauter et al. |
| 2014/0046427 A1 | 2/2014 | Michalak |
| 2014/0052237 A1 | 2/2014 | Lane et al. |
| 2014/0052242 A1 | 2/2014 | Revuelta et al. |
| 2014/0081393 A1 | 3/2014 | Hasenkam et al. |
| 2014/0086934 A1 | 3/2014 | Shams |
| 2014/0088685 A1 | 3/2014 | Yevzlin et al. |
| 2014/0088694 A1 | 3/2014 | Rowe et al. |
| 2014/0100420 A1 | 4/2014 | Mortier et al. |
| 2014/0100651 A1 | 4/2014 | Kheradvar et al. |
| 2014/0100653 A1 | 4/2014 | Savage et al. |
| 2014/0107761 A1 | 4/2014 | Gale et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0172085 A1 | 6/2014 | Quadri et al. |
| 2014/0172086 A1 | 6/2014 | Quadri et al. |
| 2014/0186417 A1 | 7/2014 | Trollsas et al. |
| 2014/0194978 A1 | 7/2014 | Seguin et al. |
| 2014/0194981 A1 | 7/2014 | Menk et al. |
| 2014/0194982 A1 | 7/2014 | Kovalsky et al. |
| 2014/0194983 A1 | 7/2014 | Kovalsky et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214157 A1 | 7/2014 | Bortlein |
| 2014/0214160 A1 | 7/2014 | Naor |
| 2014/0215791 A1 | 8/2014 | Soundararajan et al. |
| 2014/0221823 A1 | 8/2014 | Keogh et al. |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0222144 A1 | 8/2014 | Eberhardt et al. |
| 2014/0230515 A1 | 8/2014 | Tuval et al. |
| 2014/0236288 A1 | 8/2014 | Lambrecht et al. |
| 2014/0243966 A1 | 8/2014 | Garde et al. |
| 2014/0249622 A1 | 9/2014 | Carmi et al. |
| 2014/0256035 A1 | 9/2014 | Strasly et al. |
| 2014/0257467 A1 | 9/2014 | Lane et al. |
| 2014/0257475 A1 | 9/2014 | Gross et al. |
| 2014/0257476 A1 | 9/2014 | Montorfano et al. |
| 2014/0277390 A1 | 9/2014 | Ratz et al. |
| 2014/0277402 A1 | 9/2014 | Essinger et al. |
| 2014/0277403 A1 | 9/2014 | Peter |
| 2014/0277412 A1 | 9/2014 | Bortlein |
| 2014/0277422 A1 | 9/2014 | Ratz et al. |
| 2014/0277423 A1 | 9/2014 | Alkhatib et al. |
| 2014/0277426 A1 | 9/2014 | Dakin |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309731 A1 | 10/2014 | Quadri et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0350565 A1 | 11/2014 | Yacoby et al. |
| 2014/0350666 A1 | 11/2014 | Righini |
| 2014/0350668 A1 | 11/2014 | Delaloye et al. |
| 2014/0356519 A1 | 12/2014 | Hossainy et al. |
| 2014/0358223 A1 | 12/2014 | Rafiee et al. |
| 2014/0364404 A1 | 12/2014 | Cleek et al. |
| 2014/0364939 A1 | 12/2014 | Deshmukh |
| 2014/0364944 A1 | 12/2014 | Lutter et al. |
| 2014/0370071 A1 | 12/2014 | Chen et al. |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018940 A1* | 1/2015 | Quill .................... A61F 2/2442 623/2.11 |
| 2015/0018944 A1 | 1/2015 | O'connell et al. |
| 2015/0032153 A1 | 1/2015 | Quadri et al. |
| 2015/0039083 A1 | 2/2015 | Rafiee |
| 2015/0045881 A1 | 2/2015 | Lim |
| 2015/0066140 A1 | 3/2015 | Quadri et al. |
| 2015/0081009 A1 | 3/2015 | Quadri et al. |
| 2015/0086603 A1 | 3/2015 | Hossainy et al. |
| 2015/0088252 A1 | 3/2015 | Jenson et al. |
| 2015/0105856 A1 | 4/2015 | Rowe et al. |
| 2015/0142100 A1 | 5/2015 | Morriss et al. |
| 2015/0142103 A1 | 5/2015 | Vidlund |
| 2015/0148731 A1 | 5/2015 | Mcnamara et al. |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209137 A1 | 7/2015 | Quadri et al. |
| 2015/0209141 A1 | 7/2015 | Braido et al. |
| 2015/0216653 A1 | 8/2015 | Freudenthal |
| 2015/0216655 A1 | 8/2015 | Lane et al. |

(56) References Cited

U.S. PATENT DOCUMENTS

| | | | |
|---|---|---|---|
| 2015/0238315 A1 | 8/2015 | Rabito et al. |
| 2015/0257878 A1 | 9/2015 | Lane et al. |
| 2015/0272737 A1 | 10/2015 | Dale et al. |
| 2015/0297346 A1 | 10/2015 | Duffy et al. |
| 2015/0305864 A1 | 10/2015 | Quadri et al. |
| 2015/0328000 A1 | 11/2015 | Ratz et al. |
| 2015/0335429 A1 | 11/2015 | Morriss et al. |
| 2015/0342736 A1 | 12/2015 | Rabito et al. |
| 2015/0351903 A1 | 12/2015 | Morriss et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0038280 A1 | 2/2016 | Morriss et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0278923 A1 | 9/2016 | Krans et al. |
| 2016/0279386 A1 | 9/2016 | Dale et al. |
| 2016/0310267 A1 | 10/2016 | Zeng et al. |
| 2017/0042678 A1 | 2/2017 | Ganesan et al. |
| 2017/0079785 A1 | 3/2017 | Li |
| 2017/0128209 A1 | 5/2017 | Morriss et al. |
| 2017/0165064 A1 | 6/2017 | Nyuli et al. |
| 2017/0216023 A1 | 8/2017 | Lane et al. |
| 2017/0216575 A1 | 8/2017 | Asleson et al. |
| 2017/0257902 A1 | 9/2017 | Xing et al. |
| 2017/0258614 A1 | 9/2017 | Griffin |
| 2017/0325945 A1 | 11/2017 | Dale et al. |
| 2017/0325954 A1 | 11/2017 | Perszyk |
| 2017/0333186 A1 | 11/2017 | Spargias |
| 2017/0348096 A1 | 12/2017 | Anderson |
| 2017/0348100 A1 | 12/2017 | Lane et al. |
| 2017/0367821 A1 | 12/2017 | Landon et al. |
| 2017/0367823 A1 | 12/2017 | Hariton et al. |
| 2018/0014931 A1 | 1/2018 | Morriss et al. |
| 2018/0021129 A1 | 1/2018 | Peterson et al. |
| 2018/0055629 A1 | 3/2018 | Oba et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2018/0110622 A1 | 4/2018 | Gregg et al. |
| 2018/0116790 A1 | 5/2018 | Ratz et al. |
| 2018/0126119 A1 | 5/2018 | McNiven et al. |
| 2018/0296341 A1 | 10/2018 | Noe et al. |
| 2018/0344457 A1 | 12/2018 | Gross et al. |
| 2018/0344490 A1 | 12/2018 | Fox et al. |
| 2019/0008639 A1 | 1/2019 | Landon et al. |
| 2019/0060072 A1 | 2/2019 | Zeng |
| 2019/0262129 A1 | 8/2019 | Cooper et al. |
| 2020/0000579 A1 | 1/2020 | Manash et al. |
| 2020/0015965 A1 | 1/2020 | Lane et al. |
| 2020/0108225 A1 | 4/2020 | Jamal et al. |
| 2020/0138572 A1 | 5/2020 | Zhao et al. |
| 2020/0146814 A1 | 5/2020 | Fung et al. |
| 2020/0323668 A1 | 10/2020 | Diedering et al. |
| 2020/0345494 A1 | 11/2020 | Srinimukesh et al. |
| 2020/0352718 A1 | 11/2020 | Rowe et al. |
| 2021/0015615 A1 | 1/2021 | Groothuis et al. |
| 2021/0228354 A1 | 7/2021 | Rafiee et al. |
| 2021/0259835 A1 | 8/2021 | Tyler, II |
| 2021/0307900 A1 | 10/2021 | Hacohen |
| 2021/0378817 A1 | 12/2021 | Nia et al. |
| 2021/0386544 A1 | 12/2021 | Cooper et al. |
| 2022/0142777 A1 | 5/2022 | Scheinblum et al. |
| 2022/0287836 A1 | 9/2022 | Landon et al. |
| 2022/0346993 A1 | 11/2022 | Srinimukesh |
| 2023/0000624 A1 | 1/2023 | Manickam et al. |
| 2023/0149163 A1 | 5/2023 | Lane et al. |
| 2023/0200980 A1 | 6/2023 | Peterson et al. |
| 2023/0218391 A1 | 7/2023 | Dass et al. |
| 2023/0380963 A1 | 11/2023 | Kaufman et al. |
| 2023/0390052 A1 | 12/2023 | Okafor et al. |
| 2024/0008978 A1 | 1/2024 | Nawalakhe et al. |
| 2024/0091000 A1 | 3/2024 | King et al. |
| 2024/0122705 A1 | 4/2024 | Lane et al. |

FOREIGN PATENT DOCUMENTS

| | | | |
|---|---|---|---|
| AU | 2014203064 B2 | 6/2015 |
| CA | 2304325 A1 | 10/2000 |
| CA | 2797863 A1 | 11/2011 |
| CA | 2797863 C | 7/2019 |
| CA | 3043737 C | 5/2021 |
| CN | 101128168 A | 2/2008 |
| CN | 101262833 A | 9/2008 |
| CN | 101415379 A | 4/2009 |
| CN | 103079498 A | 5/2013 |
| CN | 103079498 B | 11/2015 |
| CN | 105287050 A | 2/2016 |
| CN | 105287050 B | 12/2017 |
| DE | 2246526 C3 | 7/1981 |
| DE | 3128704 A1 | 2/1983 |
| DE | 19532846 A1 | 3/1997 |
| DE | 19907646 A1 | 8/2000 |
| DE | 10103955 B4 | 11/2001 |
| DE | 10033858 B4 | 1/2002 |
| DE | 10049813 C1 | 4/2002 |
| DE | 19546692 C2 | 11/2002 |
| DE | 19857887 B4 | 5/2005 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 103546 B1 | 5/1988 |
| EP | 0657147 A2 | 6/1995 |
| EP | 850607 A1 | 7/1998 |
| EP | 1057460 A1 | 12/2000 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1472996 A1 | 11/2004 |

(56) References Cited

FOREIGN PATENT DOCUMENTS

| | | | |
|----|----------|----|---------|
| EP | 1107710 | B1 | 12/2004 |
| EP | 1121070 | B1 | 12/2004 |
| EP | 1217966 | B1 | 12/2004 |
| EP | 1233731 | B1 | 12/2004 |
| EP | 1294318 | B1 | 12/2004 |
| EP | 1237510 | B1 | 1/2005 |
| EP | 1034753 | B1 | 2/2005 |
| EP | 1259194 | B1 | 2/2005 |
| EP | 1121069 | B1 | 3/2005 |
| EP | 1143879 | B1 | 3/2005 |
| EP | 1339356 | B1 | 4/2005 |
| EP | 1214022 | B1 | 5/2005 |
| EP | 1088529 | B1 | 6/2005 |
| EP | 1171060 | B1 | 6/2005 |
| EP | 1251803 | B1 | 6/2005 |
| EP | 1259776 | B1 | 6/2005 |
| EP | 1272123 | B1 | 6/2005 |
| EP | 1049422 | B1 | 7/2005 |
| EP | 1230901 | B1 | 8/2005 |
| EP | 1335683 | B1 | 8/2005 |
| EP | 1307246 | B1 | 9/2005 |
| EP | 1267753 | B1 | 10/2005 |
| EP | 1284688 | B1 | 10/2005 |
| EP | 1343536 | B1 | 10/2005 |
| EP | 1027020 | B1 | 11/2005 |
| EP | 1152780 | B1 | 11/2005 |
| EP | 1171059 | B1 | 11/2005 |
| EP | 1237508 | B1 | 11/2005 |
| EP | 1303234 | B1 | 11/2005 |
| EP | 1328215 | B1 | 11/2005 |
| EP | 1341487 | B1 | 11/2005 |
| EP | 1392197 | B1 | 11/2005 |
| EP | 1469797 | B1 | 11/2005 |
| EP | 1255505 | B1 | 12/2005 |
| EP | 1360942 | B1 | 12/2005 |
| EP | 1322260 | B1 | 1/2006 |
| EP | 1359870 | B1 | 1/2006 |
| EP | 1237586 | B1 | 2/2006 |
| EP | 1112043 | B1 | 4/2006 |
| EP | 1309360 | B1 | 4/2006 |
| EP | 1322259 | B1 | 5/2006 |
| EP | 1124592 | B1 | 6/2006 |
| EP | 1237516 | B1 | 6/2006 |
| EP | 1098673 | B1 | 7/2006 |
| EP | 1124591 | B1 | 7/2006 |
| EP | 1083845 | B1 | 8/2006 |
| EP | 1155666 | B1 | 8/2006 |
| EP | 1463462 | B1 | 8/2006 |
| EP | 1684671 | A1 | 8/2006 |
| EP | 1519695 | B1 | 9/2006 |
| EP | 1444993 | B1 | 10/2006 |
| EP | 1117350 | B1 | 11/2006 |
| EP | 1212011 | B1 | 11/2006 |
| EP | 1261294 | B1 | 11/2006 |
| EP | 1318775 | B1 | 11/2006 |
| EP | 1429690 | B1 | 11/2006 |
| EP | 1173111 | B1 | 12/2006 |
| EP | 1239795 | B1 | 12/2006 |
| EP | 1299049 | B1 | 12/2006 |
| EP | 1487382 | B1 | 12/2006 |
| EP | 1112044 | B1 | 1/2007 |
| EP | 1482997 | B1 | 1/2007 |
| EP | 1117352 | B1 | 2/2007 |
| EP | 1128849 | B1 | 2/2007 |
| EP | 1392666 | B1 | 2/2007 |
| EP | 1474077 | B1 | 2/2007 |
| EP | 1251805 | B1 | 3/2007 |
| EP | 1117334 | B1 | 4/2007 |
| EP | 1255510 | B1 | 4/2007 |
| EP | 1263484 | B1 | 5/2007 |
| EP | 1313410 | B1 | 5/2007 |
| EP | 1318774 | B1 | 5/2007 |
| EP | 1370200 | B1 | 5/2007 |
| EP | 1560526 | B1 | 6/2007 |
| EP | 1173117 | B1 | 7/2007 |
| EP | 1434615 | B1 | 7/2007 |
| EP | 1465546 | B1 | 7/2007 |
| EP | 1499366 | B1 | 7/2007 |
| EP | 1225948 | B1 | 8/2007 |
| EP | 1819304 | A2 | 8/2007 |
| EP | 1519962 | B1 | 9/2007 |
| EP | 1239901 | B1 | 10/2007 |
| EP | 1337285 | B1 | 10/2007 |
| EP | 1849440 | A1 | 10/2007 |
| EP | 1112042 | B1 | 11/2007 |
| EP | 1148821 | B1 | 11/2007 |
| EP | 1143882 | B1 | 12/2007 |
| EP | 1330189 | B1 | 12/2007 |
| EP | 1489996 | B1 | 12/2007 |
| EP | 1296618 | B1 | 1/2008 |
| EP | 1401356 | B1 | 1/2008 |
| EP | 1629795 | B1 | 1/2008 |
| EP | 1128786 | B1 | 2/2008 |
| EP | 1616532 | B1 | 2/2008 |
| EP | 1289447 | B1 | 3/2008 |
| EP | 1895942 | A2 | 3/2008 |
| EP | 1115353 | B1 | 5/2008 |
| EP | 1330190 | B1 | 5/2008 |
| EP | 1383448 | B1 | 6/2008 |
| EP | 1251804 | B1 | 7/2008 |
| EP | 1294310 | B1 | 7/2008 |
| EP | 1313409 | B1 | 7/2008 |
| EP | 1395202 | B1 | 7/2008 |
| EP | 1395204 | B1 | 7/2008 |
| EP | 1395205 | B1 | 7/2008 |
| EP | 1423066 | B1 | 7/2008 |
| EP | 1560545 | B1 | 7/2008 |
| EP | 1605871 | B1 | 7/2008 |
| EP | 1671608 | B1 | 7/2008 |
| EP | 1690515 | B1 | 7/2008 |
| EP | 1180987 | B1 | 8/2008 |
| EP | 1337386 | B1 | 8/2008 |
| EP | 1492579 | B1 | 9/2008 |
| EP | 1524942 | B1 | 9/2008 |
| EP | 1627091 | B1 | 9/2008 |
| EP | 1827577 | B1 | 9/2008 |
| EP | 1259195 | B1 | 10/2008 |
| EP | 1704834 | B1 | 10/2008 |
| EP | 1146835 | B1 | 11/2008 |
| EP | 1498086 | B1 | 11/2008 |
| EP | 1622548 | B1 | 11/2008 |
| EP | 1235537 | B1 | 12/2008 |
| EP | 1237509 | B1 | 12/2008 |
| EP | 1355590 | B1 | 12/2008 |
| EP | 1455680 | B1 | 12/2008 |
| EP | 1472995 | B1 | 12/2008 |
| EP | 1513474 | B1 | 12/2008 |
| EP | 1562522 | B1 | 12/2008 |
| EP | 1620042 | B1 | 12/2008 |
| EP | 1690514 | B1 | 12/2008 |
| EP | 1258232 | B1 | 1/2009 |
| EP | 1420723 | B1 | 1/2009 |
| EP | 1570809 | B1 | 1/2009 |
| EP | 1395182 | B1 | 2/2009 |
| EP | 1408882 | B1 | 2/2009 |
| EP | 1482868 | B1 | 2/2009 |
| EP | 1255510 | B3 | 3/2009 |
| EP | 1330213 | B1 | 3/2009 |
| EP | 1429651 | B1 | 3/2009 |
| EP | 1610727 | B1 | 4/2009 |
| EP | 1617788 | B1 | 4/2009 |
| EP | 1634547 | B1 | 4/2009 |
| EP | 1790318 | B1 | 4/2009 |
| EP | 2040645 | A1 | 4/2009 |
| EP | 1250165 | B1 | 5/2009 |
| EP | 1842508 | B1 | 6/2009 |
| EP | 1968482 | B1 | 6/2009 |
| EP | 2072027 | A1 | 6/2009 |
| EP | 1343438 | B1 | 7/2009 |
| EP | 1406608 | B1 | 7/2009 |
| EP | 1509256 | B1 | 7/2009 |
| EP | 1626681 | B1 | 7/2009 |
| EP | 1723935 | B1 | 7/2009 |
| EP | 1803420 | B1 | 7/2009 |

(56)        References Cited

FOREIGN PATENT DOCUMENTS

| | | | |
|----|---------|----|---------|
| EP | 2073755 | A2 | 7/2009 |
| EP | 1401359 | B1 | 8/2009 |
| EP | 1411865 | B1 | 8/2009 |
| EP | 1485033 | B1 | 8/2009 |
| EP | 1581120 | B1 | 8/2009 |
| EP | 1620040 | B1 | 8/2009 |
| EP | 1684667 | B1 | 8/2009 |
| EP | 1872743 | B1 | 8/2009 |
| EP | 1100378 | B1 | 9/2009 |
| EP | 1198203 | B1 | 9/2009 |
| EP | 1370201 | B1 | 9/2009 |
| EP | 1408850 | B1 | 9/2009 |
| EP | 1472996 | B1 | 9/2009 |
| EP | 1478364 | B1 | 9/2009 |
| EP | 1653888 | B1 | 9/2009 |
| EP | 1785154 | B1 | 9/2009 |
| EP | 1881804 | B1 | 9/2009 |
| EP | 1903991 | B1 | 9/2009 |
| EP | 1418865 | B1 | 10/2009 |
| EP | 1561437 | B1 | 10/2009 |
| EP | 1615595 | B1 | 10/2009 |
| EP | 1353612 | B1 | 11/2009 |
| EP | 1348406 | B1 | 12/2009 |
| EP | 1370202 | B1 | 12/2009 |
| EP | 1603492 | B1 | 12/2009 |
| EP | 1670364 | B1 | 12/2009 |
| EP | 1759663 | B1 | 12/2009 |
| EP | 1994887 | B1 | 12/2009 |
| EP | 1615593 | B1 | 1/2010 |
| EP | 1643938 | B1 | 1/2010 |
| EP | 1863402 | B1 | 1/2010 |
| EP | 1943942 | B1 | 1/2010 |
| EP | 2010101 | B1 | 1/2010 |
| EP | 2081518 | B1 | 1/2010 |
| EP | 1703865 | B1 | 2/2010 |
| EP | 1276437 | B1 | 3/2010 |
| EP | 1276439 | B1 | 3/2010 |
| EP | 1411867 | B1 | 3/2010 |
| EP | 1458313 | B1 | 3/2010 |
| EP | 1520519 | B1 | 3/2010 |
| EP | 1648340 | B1 | 3/2010 |
| EP | 1682048 | B1 | 3/2010 |
| EP | 1773239 | B1 | 3/2010 |
| EP | 1935377 | B1 | 3/2010 |
| EP | 1994912 | B1 | 3/2010 |
| EP | 1154738 | B1 | 4/2010 |
| EP | 1531762 | B1 | 4/2010 |
| EP | 1600178 | B1 | 4/2010 |
| EP | 1626682 | B1 | 4/2010 |
| EP | 1511445 | B1 | 5/2010 |
| EP | 1198213 | B1 | 6/2010 |
| EP | 1250097 | B1 | 6/2010 |
| EP | 1272249 | B1 | 6/2010 |
| EP | 1978895 | B1 | 6/2010 |
| EP | 1572033 | B1 | 7/2010 |
| EP | 1968491 | B1 | 7/2010 |
| EP | 2019652 | B1 | 7/2010 |
| EP | 1610722 | B1 | 8/2010 |
| EP | 1682047 | B1 | 8/2010 |
| EP | 1952772 | B1 | 8/2010 |
| EP | 1427356 | B1 | 9/2010 |
| EP | 1631218 | B1 | 9/2010 |
| EP | 1765224 | B1 | 9/2010 |
| EP | 1871290 | B1 | 9/2010 |
| EP | 1895288 | B1 | 9/2010 |
| EP | 1895913 | B1 | 9/2010 |
| EP | 2014257 | B1 | 9/2010 |
| EP | 1176913 | B1 | 10/2010 |
| EP | 1178758 | B1 | 10/2010 |
| EP | 1248579 | B1 | 10/2010 |
| EP | 1913899 | B1 | 10/2010 |
| EP | 1259193 | B1 | 11/2010 |
| EP | 1928357 | B1 | 11/2010 |
| EP | 1968660 | B1 | 11/2010 |
| EP | 2249711 | A2 | 11/2010 |
| EP | 1408895 | B1 | 12/2010 |
| EP | 1465554 | B1 | 12/2010 |
| EP | 1732473 | B1 | 12/2010 |
| EP | 1768610 | B1 | 12/2010 |
| EP | 1827314 | B1 | 12/2010 |
| EP | 1940321 | B1 | 12/2010 |
| EP | 1964532 | B1 | 12/2010 |
| EP | 2078498 | B1 | 12/2010 |
| EP | 1600182 | B1 | 1/2011 |
| EP | 1617789 | B1 | 1/2011 |
| EP | 1663332 | B1 | 1/2011 |
| EP | 2147659 | B1 | 1/2011 |
| EP | 2268231 | A2 | 1/2011 |
| EP | 2273951 | A1 | 1/2011 |
| EP | 1187582 | B1 | 2/2011 |
| EP | 1450733 | B1 | 2/2011 |
| EP | 1803421 | B1 | 2/2011 |
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |
| EP | 2299938 | A2 | 3/2011 |
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2349095 | A1 | 8/2011 |
| EP | 2349097 | A1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |
| EP | 2055266 | B1 | 2/2012 |
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |

(56) References Cited

FOREIGN PATENT DOCUMENTS

| | | | |
|----|---------|----|--------|
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A1 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2520249 | A1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |
| EP | 2079400 | B1 | 1/2013 |
| EP | 2238947 | B1 | 1/2013 |
| EP | 2241287 | B1 | 1/2013 |
| EP | 2359774 | B1 | 1/2013 |
| EP | 2538878 | A1 | 1/2013 |
| EP | 2538883 | A1 | 1/2013 |
| EP | 1512383 | B1 | 2/2013 |
| EP | 1578474 | B1 | 2/2013 |
| EP | 1648339 | B1 | 2/2013 |
| EP | 1750622 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2566416 | A1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |
| EP | 1977719 | B1 | 7/2013 |
| EP | 2111337 | B1 | 7/2013 |
| EP | 2298237 | B1 | 7/2013 |
| EP | 2309949 | B1 | 7/2013 |
| EP | 2608741 | A2 | 7/2013 |
| EP | 2611388 | A2 | 7/2013 |
| EP | 2611389 | A2 | 7/2013 |
| EP | 2618781 | A2 | 7/2013 |
| EP | 1599151 | B1 | 8/2013 |
| EP | 1761211 | B1 | 8/2013 |
| EP | 2047871 | B1 | 8/2013 |
| EP | 2142144 | B1 | 8/2013 |
| EP | 2150206 | B1 | 8/2013 |
| EP | 2319459 | B1 | 8/2013 |
| EP | 2397108 | B1 | 8/2013 |
| EP | 2623068 | A1 | 8/2013 |
| EP | 1758523 | B1 | 9/2013 |
| EP | 1545392 | B1 | 10/2013 |
| EP | 1638627 | B1 | 10/2013 |
| EP | 1779868 | B1 | 10/2013 |
| EP | 2073756 | B1 | 10/2013 |
| EP | 2111190 | B1 | 10/2013 |
| EP | 1848375 | B1 | 11/2013 |
| EP | 1928356 | B1 | 11/2013 |
| EP | 1933766 | B1 | 11/2013 |
| EP | 2109417 | B1 | 11/2013 |
| EP | 2194925 | B1 | 11/2013 |
| EP | 2387977 | B1 | 11/2013 |
| EP | 2476394 | B1 | 11/2013 |
| EP | 2529701 | B1 | 11/2013 |
| EP | 1945142 | B1 | 12/2013 |
| EP | 2387972 | B1 | 12/2013 |
| EP | 2477555 | B1 | 12/2013 |
| EP | 2670349 | A2 | 12/2013 |
| EP | 2117476 | B1 | 1/2014 |
| EP | 2526895 | B1 | 1/2014 |
| EP | 2526899 | B1 | 1/2014 |
| EP | 2529696 | B1 | 1/2014 |
| EP | 2529697 | B1 | 1/2014 |
| EP | 2529698 | B1 | 1/2014 |
| EP | 2529699 | B1 | 1/2014 |
| EP | 2679198 | A1 | 1/2014 |
| EP | 1395214 | B1 | 2/2014 |
| EP | 1499266 | B1 | 2/2014 |
| EP | 1838241 | B1 | 2/2014 |
| EP | 2520250 | B1 | 2/2014 |
| EP | 2526977 | B1 | 2/2014 |
| EP | 2693985 | A1 | 2/2014 |
| EP | 2698129 | A1 | 2/2014 |
| EP | 2699302 | A2 | 2/2014 |
| EP | 1629794 | B1 | 3/2014 |
| EP | 1919398 | B1 | 3/2014 |
| EP | 2099508 | B1 | 3/2014 |
| EP | 2399549 | B1 | 3/2014 |
| EP | 2422823 | B1 | 3/2014 |
| EP | 2706958 | A1 | 3/2014 |
| EP | 1369098 | B1 | 4/2014 |
| EP | 1804860 | B1 | 4/2014 |
| EP | 1926455 | B1 | 4/2014 |
| EP | 2081519 | B1 | 4/2014 |

(56)         References Cited

FOREIGN PATENT DOCUMENTS

| | | | |
|---|---|---|---|
| EP | 2117477 | B1 | 4/2014 |
| EP | 2405966 | B1 | 4/2014 |
| EP | 2420205 | B1 | 4/2014 |
| EP | 2593048 | B1 | 4/2014 |
| EP | 2713894 | A2 | 4/2014 |
| EP | 2713955 | A2 | 4/2014 |
| EP | 2723273 | A2 | 4/2014 |
| EP | 1499265 | B1 | 5/2014 |
| EP | 1594569 | B1 | 5/2014 |
| EP | 2029056 | B1 | 5/2014 |
| EP | 2257243 | B1 | 5/2014 |
| EP | 1791500 | B1 | 6/2014 |
| EP | 2073753 | B1 | 6/2014 |
| EP | 2306933 | B1 | 6/2014 |
| EP | 2331017 | B1 | 6/2014 |
| EP | 2337522 | B1 | 6/2014 |
| EP | 2389897 | B1 | 6/2014 |
| EP | 2606723 | B1 | 6/2014 |
| EP | 2739250 | A1 | 6/2014 |
| EP | 1487350 | B1 | 7/2014 |
| EP | 1977718 | B1 | 7/2014 |
| EP | 2117469 | B1 | 7/2014 |
| EP | 2124826 | B1 | 7/2014 |
| EP | 2258316 | B1 | 7/2014 |
| EP | 2747708 | A1 | 7/2014 |
| EP | 2750630 | A1 | 7/2014 |
| EP | 2750631 | A1 | 7/2014 |
| EP | 1667604 | B1 | 8/2014 |
| EP | 1786368 | B1 | 8/2014 |
| EP | 2211779 | B1 | 8/2014 |
| EP | 2217174 | B1 | 8/2014 |
| EP | 2293740 | B1 | 8/2014 |
| EP | 2367504 | B1 | 8/2014 |
| EP | 2453942 | B1 | 8/2014 |
| EP | 2475328 | B1 | 8/2014 |
| EP | 2545884 | B1 | 8/2014 |
| EP | 2571460 | B1 | 8/2014 |
| EP | 2763708 | A2 | 8/2014 |
| EP | 2765954 | A1 | 8/2014 |
| EP | 1935378 | B1 | 9/2014 |
| EP | 2246011 | B1 | 9/2014 |
| EP | 2422749 | B1 | 9/2014 |
| EP | 2531139 | B1 | 9/2014 |
| EP | 2609893 | B1 | 9/2014 |
| EP | 2777616 | A1 | 9/2014 |
| EP | 2779945 | A1 | 9/2014 |
| EP | 1853199 | B1 | 10/2014 |
| EP | 2133039 | B1 | 10/2014 |
| EP | 2549955 | B1 | 10/2014 |
| EP | 2549956 | B1 | 10/2014 |
| EP | 2651335 | B1 | 10/2014 |
| EP | 2785281 | A1 | 10/2014 |
| EP | 2793743 | A1 | 10/2014 |
| EP | 2793749 | A1 | 10/2014 |
| EP | 2793752 | A1 | 10/2014 |
| EP | 2049721 | B1 | 11/2014 |
| EP | 2142143 | B1 | 11/2014 |
| EP | 2229921 | B1 | 11/2014 |
| EP | 2288403 | B1 | 11/2014 |
| EP | 2415421 | B1 | 11/2014 |
| EP | 1551274 | B1 | 12/2014 |
| EP | 1768735 | B1 | 12/2014 |
| EP | 1959865 | B1 | 12/2014 |
| EP | 2077718 | B1 | 12/2014 |
| EP | 2303185 | B1 | 12/2014 |
| EP | 2334857 | B1 | 12/2014 |
| EP | 2365840 | B1 | 12/2014 |
| EP | 2420207 | B1 | 12/2014 |
| EP | 2422750 | B1 | 12/2014 |
| EP | 2707073 | B1 | 12/2014 |
| EP | 1768630 | B1 | 1/2015 |
| EP | 2254515 | B1 | 1/2015 |
| EP | 2641569 | B1 | 1/2015 |
| EP | 2709559 | B1 | 1/2015 |
| EP | 2825203 | A1 | 1/2015 |
| EP | 1903990 | B1 | 2/2015 |
| EP | 2255753 | B1 | 2/2015 |
| EP | 2335649 | B1 | 2/2015 |
| EP | 2522308 | B1 | 2/2015 |
| EP | 2591754 | B1 | 2/2015 |
| EP | 2835112 | A1 | 2/2015 |
| EP | 1861045 | B1 | 3/2015 |
| EP | 2029057 | B1 | 3/2015 |
| EP | 2193761 | B1 | 3/2015 |
| EP | 2379010 | B1 | 3/2015 |
| EP | 2416737 | B1 | 3/2015 |
| EP | 1023879 | B1 | 4/2015 |
| EP | 1791495 | B1 | 4/2015 |
| EP | 2298252 | B1 | 4/2015 |
| EP | 2536359 | B1 | 4/2015 |
| EP | 2538879 | B1 | 4/2015 |
| EP | 2609894 | B1 | 4/2015 |
| EP | 2693984 | B1 | 4/2015 |
| EP | 2712633 | B1 | 4/2015 |
| EP | 2747707 | B1 | 4/2015 |
| EP | 2862546 | A1 | 4/2015 |
| EP | 2863842 | A1 | 4/2015 |
| EP | 1465555 | B1 | 5/2015 |
| EP | 1924224 | B1 | 5/2015 |
| EP | 1992369 | B1 | 5/2015 |
| EP | 2410947 | B1 | 5/2015 |
| EP | 2484311 | B1 | 5/2015 |
| EP | 2654616 | B1 | 5/2015 |
| EP | 2866741 | A1 | 5/2015 |
| EP | 1646332 | B1 | 6/2015 |
| EP | 2745805 | B1 | 6/2015 |
| EP | 2749254 | B1 | 6/2015 |
| EP | 2877123 | A2 | 6/2015 |
| EP | 2882374 | A1 | 6/2015 |
| EP | 2884906 | A1 | 6/2015 |
| EP | 1729685 | B1 | 7/2015 |
| EP | 1976439 | B1 | 7/2015 |
| EP | 2068767 | B1 | 7/2015 |
| EP | 2068769 | B1 | 7/2015 |
| EP | 2444031 | B1 | 7/2015 |
| EP | 2455041 | B1 | 7/2015 |
| EP | 2498719 | B1 | 7/2015 |
| EP | 2558030 | B1 | 7/2015 |
| EP | 2752209 | B1 | 7/2015 |
| EP | 2892467 | A1 | 7/2015 |
| EP | 1702247 | B1 | 8/2015 |
| EP | 1729688 | B1 | 8/2015 |
| EP | 1887979 | B1 | 8/2015 |
| EP | 2032079 | B1 | 8/2015 |
| EP | 2219558 | B1 | 8/2015 |
| EP | 2234657 | B1 | 8/2015 |
| EP | 2250976 | B1 | 8/2015 |
| EP | 2262447 | B1 | 8/2015 |
| EP | 2303384 | B1 | 8/2015 |
| EP | 2387365 | B1 | 8/2015 |
| EP | 2560579 | B1 | 8/2015 |
| EP | 2575621 | B1 | 8/2015 |
| EP | 2590595 | B1 | 8/2015 |
| EP | 2709560 | B1 | 8/2015 |
| EP | 2755603 | B1 | 8/2015 |
| EP | 2906147 | A1 | 8/2015 |
| EP | 1534185 | B1 | 9/2015 |
| EP | 1765225 | B1 | 9/2015 |
| EP | 1778127 | B1 | 9/2015 |
| EP | 2094194 | B1 | 9/2015 |
| EP | 2201911 | B1 | 9/2015 |
| EP | 2306934 | B1 | 9/2015 |
| EP | 2397113 | B1 | 9/2015 |
| EP | 2453843 | B1 | 9/2015 |
| EP | 2459127 | B1 | 9/2015 |
| EP | 2675396 | B1 | 9/2015 |
| EP | 2675397 | B1 | 9/2015 |
| EP | 2736454 | B1 | 9/2015 |
| EP | 2754414 | A4 | 9/2015 |
| EP | 2790609 | B1 | 9/2015 |
| EP | 2805693 | B1 | 9/2015 |
| EP | 2916781 | A2 | 9/2015 |
| EP | 2919712 | A1 | 9/2015 |
| EP | 1734903 | B1 | 10/2015 |

(56) References Cited

FOREIGN PATENT DOCUMENTS

| | | | |
|---|---|---|---|
| EP | 1863546 | B1 | 10/2015 |
| EP | 1900343 | B1 | 10/2015 |
| EP | 2081515 | B1 | 10/2015 |
| EP | 2191792 | B1 | 10/2015 |
| EP | 2254513 | B1 | 10/2015 |
| EP | 2381896 | B1 | 10/2015 |
| EP | 2450008 | B1 | 10/2015 |
| EP | 2544626 | B1 | 10/2015 |
| EP | 2561830 | B1 | 10/2015 |
| EP | 2600798 | B1 | 10/2015 |
| EP | 2626039 | B1 | 10/2015 |
| EP | 2647354 | B1 | 10/2015 |
| EP | 2729093 | B1 | 10/2015 |
| EP | 2836165 | B1 | 10/2015 |
| EP | 1863545 | B1 | 11/2015 |
| EP | 2303395 | B1 | 11/2015 |
| EP | 2497446 | B1 | 11/2015 |
| EP | 2772228 | B1 | 11/2015 |
| EP | 1482869 | B1 | 12/2015 |
| EP | 1551473 | B1 | 12/2015 |
| EP | 1748745 | B1 | 12/2015 |
| EP | 1755459 | B1 | 12/2015 |
| EP | 1850796 | B1 | 12/2015 |
| EP | 1920030 | B1 | 12/2015 |
| EP | 1954212 | B1 | 12/2015 |
| EP | 2424472 | B1 | 12/2015 |
| EP | 2470120 | B1 | 12/2015 |
| EP | 2542179 | B1 | 12/2015 |
| EP | 2948100 | A1 | 12/2015 |
| EP | 2948103 | A2 | 12/2015 |
| EP | 2959866 | A1 | 12/2015 |
| EP | 1991168 | B1 | 1/2016 |
| EP | 2254512 | B1 | 1/2016 |
| EP | 2422748 | B1 | 1/2016 |
| EP | 2967700 | A1 | 1/2016 |
| EP | 2967807 | A2 | 1/2016 |
| EP | 2967834 | A1 | 1/2016 |
| EP | 2967856 | A1 | 1/2016 |
| EP | 2967858 | A2 | 1/2016 |
| EP | 2967860 | A1 | 1/2016 |
| EP | 2967866 | A2 | 1/2016 |
| EP | 2977026 | A1 | 1/2016 |
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2621409 | A4 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2991588 | A1 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996641 | A1 | 3/2016 |
| EP | 2999435 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |
| EP | 2563236 | B1 | 6/2016 |
| EP | 2572675 | B1 | 6/2016 |
| EP | 2626040 | B1 | 6/2016 |
| EP | 2704668 | B1 | 6/2016 |
| EP | 2777611 | B1 | 6/2016 |
| EP | 2815724 | B1 | 6/2016 |
| EP | 2854710 | B1 | 6/2016 |
| EP | 2901966 | B1 | 6/2016 |
| EP | 3024527 | A2 | 6/2016 |
| EP | 1605866 | B1 | 7/2016 |
| EP | 1933756 | B1 | 7/2016 |
| EP | 2393452 | B1 | 7/2016 |
| EP | 2410948 | B1 | 7/2016 |
| EP | 2412397 | B1 | 7/2016 |
| EP | 2724690 | B1 | 7/2016 |
| EP | 2815723 | B1 | 7/2016 |
| EP | 2870945 | B1 | 7/2016 |
| EP | 3040054 | A1 | 7/2016 |
| EP | 3042635 | A1 | 7/2016 |
| EP | 3043745 | A1 | 7/2016 |
| EP | 3043747 | A1 | 7/2016 |
| EP | 3043755 | A1 | 7/2016 |
| EP | 1401358 | B1 | 8/2016 |
| EP | 1915105 | B1 | 8/2016 |
| EP | 1937186 | B1 | 8/2016 |
| EP | 2292186 | B1 | 8/2016 |
| EP | 2379012 | B1 | 8/2016 |
| EP | 2385809 | B1 | 8/2016 |
| EP | 2536345 | B1 | 8/2016 |
| EP | 2537490 | B1 | 8/2016 |
| EP | 2549954 | B1 | 8/2016 |
| EP | 2618779 | B1 | 8/2016 |
| EP | 2670352 | B1 | 8/2016 |
| EP | 2829235 | B1 | 8/2016 |

(56) References Cited

FOREIGN PATENT DOCUMENTS

| | | | |
|---|---|---|---|
| EP | 2853238 | B1 | 8/2016 |
| EP | 2866738 | B1 | 8/2016 |
| EP | 2906150 | B1 | 8/2016 |
| EP | 3052053 | A1 | 8/2016 |
| EP | 3052611 | A1 | 8/2016 |
| EP | 3060174 | A1 | 8/2016 |
| EP | 3061421 | A1 | 8/2016 |
| EP | 3061422 | A1 | 8/2016 |
| EP | 1156755 | B1 | 9/2016 |
| EP | 1492478 | B1 | 9/2016 |
| EP | 1912697 | B1 | 9/2016 |
| EP | 2393449 | B1 | 9/2016 |
| EP | 2670356 | B1 | 9/2016 |
| EP | 2793969 | B1 | 9/2016 |
| EP | 2809271 | B1 | 9/2016 |
| EP | 2896425 | B1 | 9/2016 |
| EP | 3068345 | A1 | 9/2016 |
| EP | 3068346 | A1 | 9/2016 |
| EP | 3071148 | A1 | 9/2016 |
| EP | 2023858 | B1 | 10/2016 |
| EP | 2112912 | B1 | 10/2016 |
| EP | 2640319 | B1 | 10/2016 |
| EP | 2663257 | B1 | 10/2016 |
| EP | 2727612 | B1 | 10/2016 |
| EP | 2760384 | B1 | 10/2016 |
| EP | 2806829 | B1 | 10/2016 |
| EP | 2858599 | B1 | 10/2016 |
| EP | 2918250 | B1 | 10/2016 |
| EP | 2922594 | A4 | 10/2016 |
| EP | 2934387 | B1 | 10/2016 |
| EP | 3076901 | A1 | 10/2016 |
| EP | 3079633 | A1 | 10/2016 |
| EP | 1539047 | B1 | 11/2016 |
| EP | 2282700 | B1 | 11/2016 |
| EP | 2400926 | B1 | 11/2016 |
| EP | 2467104 | B1 | 11/2016 |
| EP | 2525743 | B1 | 11/2016 |
| EP | 2549953 | B1 | 11/2016 |
| EP | 2575696 | B1 | 11/2016 |
| EP | 2598045 | B1 | 11/2016 |
| EP | 2670355 | B1 | 11/2016 |
| EP | 2676640 | B1 | 11/2016 |
| EP | 2680792 | B1 | 11/2016 |
| EP | 2707053 | B1 | 11/2016 |
| EP | 2717803 | B1 | 11/2016 |
| EP | 2773297 | B1 | 11/2016 |
| EP | 2801387 | B1 | 11/2016 |
| EP | 2844192 | B1 | 11/2016 |
| EP | 2849679 | B1 | 11/2016 |
| EP | 2877122 | B1 | 11/2016 |
| EP | 2908778 | B1 | 11/2016 |
| EP | 2922500 | B1 | 11/2016 |
| EP | 2922501 | B1 | 11/2016 |
| EP | 2967854 | B1 | 11/2016 |
| EP | 3020365 | B1 | 11/2016 |
| EP | 3090703 | A1 | 11/2016 |
| EP | 1645244 | B1 | 12/2016 |
| EP | 1667614 | B1 | 12/2016 |
| EP | 1684656 | B1 | 12/2016 |
| EP | 1684670 | B1 | 12/2016 |
| EP | 1750592 | B1 | 12/2016 |
| EP | 1883375 | B1 | 12/2016 |
| EP | 2293739 | B1 | 12/2016 |
| EP | 2339988 | B1 | 12/2016 |
| EP | 2512375 | B1 | 12/2016 |
| EP | 2754417 | B1 | 12/2016 |
| EP | 2754418 | B1 | 12/2016 |
| EP | 2755562 | B1 | 12/2016 |
| EP | 2889019 | B1 | 12/2016 |
| EP | 3010442 | B1 | 12/2016 |
| EP | 3099271 | A1 | 12/2016 |
| EP | 3102150 | A1 | 12/2016 |
| EP | 3107495 | A1 | 12/2016 |
| EP | 3107498 | A2 | 12/2016 |
| EP | 3107500 | A1 | 12/2016 |
| EP | 1893127 | B1 | 1/2017 |
| EP | 1951352 | B1 | 1/2017 |
| EP | 2109419 | B1 | 1/2017 |
| EP | 2185107 | B1 | 1/2017 |
| EP | 2266503 | B1 | 1/2017 |
| EP | 2340055 | B1 | 1/2017 |
| EP | 2395941 | B1 | 1/2017 |
| EP | 2400923 | B1 | 1/2017 |
| EP | 2629699 | B1 | 1/2017 |
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 3158975 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |

(56)          References Cited

FOREIGN PATENT DOCUMENTS

| | | | |
|----|---------|----|--------|
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3175823 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |
| EP | 2676638 | B1 | 7/2017 |
| EP | 2774630 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |
| EP | 2849681 | B1 | 8/2017 |
| EP | 2858600 | B1 | 8/2017 |
| EP | 2897556 | B1 | 8/2017 |
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 3206631 | A2 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 1945141 | B1 | 10/2017 |
| EP | 2313737 | B1 | 10/2017 |
| EP | 2317956 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |

(56)        References Cited

FOREIGN PATENT DOCUMENTS

| | | | |
|----|---------|----|---------|
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |
| EP | 3253332 | A2 | 12/2017 |
| EP | 3256073 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2446915 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3057541 | B1 | 1/2018 |
| EP | 3078350 | B1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277221 | A1 | 2/2018 |
| EP | 3277222 | A1 | 2/2018 |
| EP | 3280358 | A1 | 2/2018 |
| EP | 3281608 | A1 | 2/2018 |
| EP | 3283009 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288491 | A1 | 3/2018 |
| EP | 3288494 | A1 | 3/2018 |
| EP | 3288497 | A2 | 3/2018 |
| EP | 3288498 | A1 | 3/2018 |
| EP | 3288499 | A1 | 3/2018 |
| EP | 3290004 | A1 | 3/2018 |
| EP | 3290007 | A1 | 3/2018 |
| EP | 3294214 | A1 | 3/2018 |
| EP | 3294215 | A1 | 3/2018 |
| EP | 3294218 | A1 | 3/2018 |
| EP | 3298970 | A1 | 3/2018 |
| EP | 3298987 | A1 | 3/2018 |
| EP | 2209440 | A1 | 4/2018 |
| EP | 2536357 | B1 | 4/2018 |
| EP | 2536358 | B1 | 4/2018 |
| EP | 2605725 | B1 | 4/2018 |
| EP | 2608743 | B1 | 4/2018 |
| EP | 2709561 | B1 | 4/2018 |
| EP | 2787925 | B1 | 4/2018 |
| EP | 2789314 | B1 | 4/2018 |
| EP | 2900150 | B1 | 4/2018 |
| EP | 2908779 | B1 | 4/2018 |
| EP | 2922502 | B1 | 4/2018 |
| EP | 2964441 | B1 | 4/2018 |
| EP | 2967868 | B1 | 4/2018 |
| EP | 2979665 | B1 | 4/2018 |
| EP | 2994073 | A1 | 4/2018 |
| EP | 3095394 | B1 | 4/2018 |
| EP | 3128927 | A4 | 4/2018 |
| EP | 3134033 | B1 | 4/2018 |
| EP | 3137146 | A4 | 4/2018 |
| EP | 3280482 | A4 | 4/2018 |
| EP | 3302297 | A2 | 4/2018 |
| EP | 3302362 | A1 | 4/2018 |
| EP | 3302367 | A1 | 4/2018 |
| EP | 3307208 | A1 | 4/2018 |
| EP | 3308745 | A1 | 4/2018 |
| EP | 3310301 | A1 | 4/2018 |
| EP | 3311774 | A1 | 4/2018 |
| EP | 3311775 | A1 | 4/2018 |
| EP | 3311783 | A1 | 4/2018 |
| EP | 1945112 | B1 | 5/2018 |
| EP | 2007313 | B1 | 5/2018 |
| EP | 2316381 | B2 | 5/2018 |
| EP | 2377469 | B1 | 5/2018 |
| EP | 2531115 | B1 | 5/2018 |
| EP | 2561831 | B1 | 5/2018 |
| EP | 2605724 | B1 | 5/2018 |
| EP | 2723277 | B1 | 5/2018 |
| EP | 2741711 | B1 | 5/2018 |
| EP | 2755573 | B1 | 5/2018 |
| EP | 2768429 | B1 | 5/2018 |
| EP | 2819618 | B1 | 5/2018 |
| EP | 2833836 | B1 | 5/2018 |
| EP | 2886083 | B1 | 5/2018 |
| EP | 2926840 | B1 | 5/2018 |
| EP | 2943157 | B1 | 5/2018 |
| EP | 2948099 | B1 | 5/2018 |
| EP | 3000437 | B1 | 5/2018 |
| EP | 3145448 | B1 | 5/2018 |
| EP | 3154475 | B1 | 5/2018 |
| EP | 3316819 | A1 | 5/2018 |
| EP | 3316821 | A1 | 5/2018 |
| EP | 3322381 | A1 | 5/2018 |
| EP | 3322383 | A1 | 5/2018 |
| EP | 3323353 | A1 | 5/2018 |
| EP | 3323439 | A1 | 5/2018 |
| EP | 3324892 | A1 | 5/2018 |
| EP | 3326584 | A1 | 5/2018 |
| EP | 2150312 | B1 | 6/2018 |
| EP | 2379322 | B1 | 6/2018 |
| EP | 2400925 | B1 | 6/2018 |
| EP | 2552355 | B1 | 6/2018 |
| EP | 2560589 | B1 | 6/2018 |
| EP | 2563277 | B1 | 6/2018 |
| EP | 2661305 | B1 | 6/2018 |
| EP | 2736456 | B1 | 6/2018 |
| EP | 2782523 | B1 | 6/2018 |
| EP | 3056170 | B1 | 6/2018 |
| EP | 3062745 | B1 | 6/2018 |
| EP | 3130320 | B1 | 6/2018 |
| EP | 3187150 | B1 | 6/2018 |
| EP | 3334378 | A1 | 6/2018 |
| EP | 3334380 | A1 | 6/2018 |
| EP | 3334381 | A1 | 6/2018 |

(56) References Cited

FOREIGN PATENT DOCUMENTS

| EP | 3335670 A1 | 6/2018 |
|----|-----------|--------|
| EP | 3337424 A1 | 6/2018 |
| EP | 2478872 B1 | 7/2018 |
| EP | 2563278 B1 | 7/2018 |
| EP | 2616004 B1 | 7/2018 |
| EP | 2779943 B1 | 7/2018 |
| EP | 2802290 B1 | 7/2018 |
| EP | 2816980 B1 | 7/2018 |
| EP | 2938293 B1 | 7/2018 |
| EP | 3107496 B1 | 7/2018 |
| EP | 3178450 B1 | 7/2018 |
| EP | 3212097 B1 | 7/2018 |
| EP | 3340923 A1 | 7/2018 |
| EP | 3340932 A1 | 7/2018 |
| EP | 3340934 A1 | 7/2018 |
| EP | 3340936 A1 | 7/2018 |
| EP | 3340945 A1 | 7/2018 |
| EP | 3342355 A1 | 7/2018 |
| EP | 3342377 A1 | 7/2018 |
| EP | 3344158 A1 | 7/2018 |
| EP | 3346952 A1 | 7/2018 |
| EP | 3348235 A1 | 7/2018 |
| EP | 3349693 A1 | 7/2018 |
| EP | 2536354 B1 | 8/2018 |
| EP | 2616006 B1 | 8/2018 |
| EP | 2797556 B1 | 8/2018 |
| EP | 2822473 B1 | 8/2018 |
| EP | 2854711 B1 | 8/2018 |
| EP | 2866847 B1 | 8/2018 |
| EP | 2918246 B1 | 8/2018 |
| EP | 2967845 B1 | 8/2018 |
| EP | 2999436 B1 | 8/2018 |
| EP | 3013281 B1 | 8/2018 |
| EP | 3060170 B1 | 8/2018 |
| EP | 3104811 B1 | 8/2018 |
| EP | 3143944 B1 | 8/2018 |
| EP | 3157467 B1 | 8/2018 |
| EP | 3193791 B1 | 8/2018 |
| EP | 3241526 B1 | 8/2018 |
| EP | 3355800 A1 | 8/2018 |
| EP | 3360513 A1 | 8/2018 |
| EP | 3360514 A1 | 8/2018 |
| EP | 3361988 A1 | 8/2018 |
| EP | 3361991 A1 | 8/2018 |
| EP | 2114305 B1 | 9/2018 |
| EP | 2155115 B1 | 9/2018 |
| EP | 2601910 B1 | 9/2018 |
| EP | 2617390 B1 | 9/2018 |
| EP | 2734157 B1 | 9/2018 |
| EP | 2968674 B1 | 9/2018 |
| EP | 2999415 B1 | 9/2018 |
| EP | 3106130 B1 | 9/2018 |
| EP | 3151763 B1 | 9/2018 |
| EP | 3213717 B1 | 9/2018 |
| EP | 3245985 B1 | 9/2018 |
| EP | 3367979 A1 | 9/2018 |
| EP | 3370649 A1 | 9/2018 |
| EP | 3370650 A1 | 9/2018 |
| EP | 1827256 B1 | 10/2018 |
| EP | 1850790 B1 | 10/2018 |
| EP | 2063823 B1 | 10/2018 |
| EP | 2124825 B1 | 10/2018 |
| EP | 2249746 B1 | 10/2018 |
| EP | 2254514 B1 | 10/2018 |
| EP | 2285309 B1 | 10/2018 |
| EP | 2455042 B1 | 10/2018 |
| EP | 2571561 B1 | 10/2018 |
| EP | 2616008 B1 | 10/2018 |
| EP | 2647393 B1 | 10/2018 |
| EP | 2739214 B1 | 10/2018 |
| EP | 2739247 B1 | 10/2018 |
| EP | 2776114 B1 | 10/2018 |
| EP | 2836171 B1 | 10/2018 |
| EP | 2842581 B1 | 10/2018 |
| EP | 2870946 B1 | 10/2018 |
| EP | 2923665 B1 | 10/2018 |
| EP | 2964277 B1 | 10/2018 |
| EP | 3001978 B1 | 10/2018 |
| EP | 3010562 B1 | 10/2018 |
| EP | 3072475 B1 | 10/2018 |
| EP | 3081161 B1 | 10/2018 |
| EP | 3081195 B1 | 10/2018 |
| EP | 3099345 B1 | 10/2018 |
| EP | 3120809 B1 | 10/2018 |
| EP | 3238663 B1 | 10/2018 |
| EP | 3275404 A4 | 10/2018 |
| EP | 3384879 A1 | 10/2018 |
| EP | 3388027 A1 | 10/2018 |
| EP | 3390706 A1 | 10/2018 |
| EP | 1708650 B1 | 11/2018 |
| EP | 1945143 B1 | 11/2018 |
| EP | 2205183 B1 | 11/2018 |
| EP | 2663258 B1 | 11/2018 |
| EP | 2790615 B1 | 11/2018 |
| EP | 2854709 B1 | 11/2018 |
| EP | 2898859 B1 | 11/2018 |
| EP | 2921139 B1 | 11/2018 |
| EP | 2928538 B1 | 11/2018 |
| EP | 3075354 B1 | 11/2018 |
| EP | 3082949 B1 | 11/2018 |
| EP | 3145452 B1 | 11/2018 |
| EP | 3216424 B1 | 11/2018 |
| EP | 3260084 B1 | 11/2018 |
| EP | 3397206 A1 | 11/2018 |
| EP | 3398562 A1 | 11/2018 |
| EP | 3400908 A1 | 11/2018 |
| EP | 3405139 A1 | 11/2018 |
| EP | 1858450 B1 | 12/2018 |
| EP | 2150208 B1 | 12/2018 |
| EP | 2326261 B1 | 12/2018 |
| EP | 2344075 B1 | 12/2018 |
| EP | 2370028 B1 | 12/2018 |
| EP | 2555709 B1 | 12/2018 |
| EP | 2564812 B1 | 12/2018 |
| EP | 2777618 B1 | 12/2018 |
| EP | 2814427 B1 | 12/2018 |
| EP | 2829240 B1 | 12/2018 |
| EP | 2911594 B1 | 12/2018 |
| EP | 2911729 B1 | 12/2018 |
| EP | 2954876 B1 | 12/2018 |
| EP | 2958520 B1 | 12/2018 |
| EP | 2958605 B1 | 12/2018 |
| EP | 3010446 B1 | 12/2018 |
| EP | 3064174 B1 | 12/2018 |
| EP | 3206628 B1 | 12/2018 |
| EP | 3242629 B1 | 12/2018 |
| EP | 3260085 B1 | 12/2018 |
| EP | 3266416 B1 | 12/2018 |
| EP | 3326583 B1 | 12/2018 |
| EP | 3410984 A1 | 12/2018 |
| EP | 3410987 A1 | 12/2018 |
| EP | 3415120 A1 | 12/2018 |
| EP | 3417813 A1 | 12/2018 |
| EP | 2129332 B1 | 1/2019 |
| EP | 2196159 B1 | 1/2019 |
| EP | 2370025 B1 | 1/2019 |
| EP | 2549957 B1 | 1/2019 |
| EP | 2819619 B1 | 1/2019 |
| EP | 2849680 B1 | 1/2019 |
| EP | 2856972 B1 | 1/2019 |
| EP | 2866742 B1 | 1/2019 |
| EP | 2884946 B1 | 1/2019 |
| EP | 2948102 B1 | 1/2019 |
| EP | 2979664 B1 | 1/2019 |
| EP | 3043748 B1 | 1/2019 |
| EP | 3145449 B1 | 1/2019 |
| EP | 3288491 A4 | 1/2019 |
| EP | 3332743 B1 | 1/2019 |
| EP | 3427695 A1 | 1/2019 |
| EP | 3429507 A1 | 1/2019 |
| EP | 3432832 A1 | 1/2019 |
| EP | 3432834 A1 | 1/2019 |
| EP | 1895943 B1 | 2/2019 |
| EP | 2070490 B1 | 2/2019 |

(56) References Cited

FOREIGN PATENT DOCUMENTS

| | | | |
|---|---|---|---|
| EP | 2308425 | B1 | 2/2019 |
| EP | 2379009 | B1 | 2/2019 |
| EP | 2575685 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3409454 | A4 | 2/2019 |
| EP | 3435919 | A1 | 2/2019 |
| EP | 3441045 | A1 | 2/2019 |
| EP | 3442469 | A1 | 2/2019 |
| EP | 3443937 | A1 | 2/2019 |
| EP | 3445290 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3448314 | A1 | 3/2019 |
| EP | 3448315 | A1 | 3/2019 |
| EP | 3449969 | A1 | 3/2019 |
| EP | 3454785 | A1 | 3/2019 |
| EP | 3454786 | A1 | 3/2019 |
| EP | 3454789 | A1 | 3/2019 |
| EP | 3454794 | A1 | 3/2019 |
| EP | 3454795 | A1 | 3/2019 |
| EP | 3457987 | A1 | 3/2019 |
| EP | 3457988 | A1 | 3/2019 |
| EP | 3457990 | A1 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3471662 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3478224 | A1 | 5/2019 |
| EP | 3479797 | A1 | 5/2019 |
| EP | 3481335 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3487451 | A1 | 5/2019 |
| EP | 3487452 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3490500 | A1 | 6/2019 |
| EP | 3490657 | A1 | 6/2019 |
| EP | 3490659 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |

(56)  References Cited

FOREIGN PATENT DOCUMENTS

| | | | |
|---|---|---|---|
| EP | 2640431 | B1 | 7/2019 |
| EP | 2641572 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |
| EP | 3503848 | A1 | 7/2019 |
| EP | 3505077 | A1 | 7/2019 |
| EP | 3512465 | A1 | 7/2019 |
| EP | 3515365 | A1 | 7/2019 |
| EP | 3517075 | A1 | 7/2019 |
| EP | 1861043 | B1 | 8/2019 |
| EP | 2303190 | B1 | 8/2019 |
| EP | 2593171 | B1 | 8/2019 |
| EP | 2632393 | B1 | 8/2019 |
| EP | 2663355 | B1 | 8/2019 |
| EP | 2665509 | B1 | 8/2019 |
| EP | 2688525 | B1 | 8/2019 |
| EP | 2699201 | B1 | 8/2019 |
| EP | 2755564 | B1 | 8/2019 |
| EP | 2769681 | B1 | 8/2019 |
| EP | 2793751 | B1 | 8/2019 |
| EP | 2900177 | B1 | 8/2019 |
| EP | 2967536 | B1 | 8/2019 |
| EP | 3050541 | B1 | 8/2019 |
| EP | 3102152 | B1 | 8/2019 |
| EP | 3157607 | B1 | 8/2019 |
| EP | 3231392 | B1 | 8/2019 |
| EP | 3284411 | B1 | 8/2019 |
| EP | 3328318 | B1 | 8/2019 |
| EP | 3366262 | B1 | 8/2019 |
| EP | 3448233 | B1 | 8/2019 |
| EP | 3527170 | A1 | 8/2019 |
| EP | 3530236 | A1 | 8/2019 |
| EP | 2358297 | B1 | 9/2019 |
| EP | 2368525 | B1 | 9/2019 |
| EP | 2542186 | B1 | 9/2019 |
| EP | 2656863 | B1 | 9/2019 |
| EP | 3003221 | B1 | 9/2019 |
| EP | 3003452 | B1 | 9/2019 |
| EP | 3220971 | B1 | 9/2019 |
| EP | 3223874 | B1 | 9/2019 |
| EP | 3288495 | B1 | 9/2019 |
| EP | 3311776 | B1 | 9/2019 |
| EP | 3334379 | B1 | 9/2019 |
| EP | 3531975 | A1 | 9/2019 |
| EP | 3534840 | A1 | 9/2019 |
| EP | 3534845 | A2 | 9/2019 |
| EP | 3535010 | A1 | 9/2019 |
| EP | 3538026 | A1 | 9/2019 |
| EP | 3538027 | A1 | 9/2019 |
| EP | 3539508 | A1 | 9/2019 |
| EP | 3539509 | A1 | 9/2019 |
| EP | 3541325 | A1 | 9/2019 |
| EP | 3542758 | A1 | 9/2019 |
| EP | 1740265 | B1 | 10/2019 |
| EP | 2039756 | B1 | 10/2019 |
| EP | 2456506 | B1 | 10/2019 |
| EP | 2470122 | B1 | 10/2019 |
| EP | 2613738 | B1 | 10/2019 |
| EP | 2637607 | B1 | 10/2019 |
| EP | 2674174 | B1 | 10/2019 |
| EP | 2811923 | B1 | 10/2019 |
| EP | 2901967 | B1 | 10/2019 |
| EP | 3010431 | B1 | 10/2019 |
| EP | 3019091 | B1 | 10/2019 |
| EP | 3019123 | B1 | 10/2019 |
| EP | 3057522 | B1 | 10/2019 |
| EP | 3067075 | B1 | 10/2019 |
| EP | 3146937 | B1 | 10/2019 |
| EP | 3238777 | B1 | 10/2019 |
| EP | 3359211 | B1 | 10/2019 |
| EP | 3388026 | B1 | 10/2019 |
| EP | 3432806 | B1 | 10/2019 |
| EP | 3496626 | A4 | 10/2019 |
| EP | 3544548 | A1 | 10/2019 |
| EP | 3545905 | A1 | 10/2019 |
| EP | 3547936 | A1 | 10/2019 |
| EP | 3547966 | A1 | 10/2019 |
| EP | 3549555 | A1 | 10/2019 |
| EP | 3549556 | A1 | 10/2019 |
| EP | 3552585 | A1 | 10/2019 |
| EP | 3556323 | A1 | 10/2019 |
| EP | 3558165 | A1 | 10/2019 |
| EP | 3558168 | A1 | 10/2019 |
| EP | 3558169 | A2 | 10/2019 |
| EP | 2043559 | B1 | 11/2019 |
| EP | 2358308 | B1 | 11/2019 |
| EP | 2405863 | B1 | 11/2019 |
| EP | 2701633 | B1 | 11/2019 |
| EP | 2898857 | B1 | 11/2019 |
| EP | 2967853 | B1 | 11/2019 |
| EP | 3009104 | B1 | 11/2019 |
| EP | 3021792 | B1 | 11/2019 |
| EP | 3076900 | B1 | 11/2019 |
| EP | 3111889 | B1 | 11/2019 |
| EP | 3142607 | B1 | 11/2019 |
| EP | 3167850 | B1 | 11/2019 |
| EP | 3397205 | B1 | 11/2019 |
| EP | 3563799 | A1 | 11/2019 |
| EP | 3563806 | A1 | 11/2019 |
| EP | 3570779 | A1 | 11/2019 |
| EP | 3572045 | A1 | 11/2019 |
| EP | 3572117 | A1 | 11/2019 |
| EP | 3479800 | A4 | 12/2019 |
| EP | 3576677 | A1 | 12/2019 |
| EP | 3579761 | A2 | 12/2019 |
| EP | 3582697 | A1 | 12/2019 |
| EP | 3583922 | A1 | 12/2019 |
| EP | 3445443 | A4 | 1/2020 |
| EP | 3590471 | A1 | 1/2020 |
| EP | 3590472 | A1 | 1/2020 |
| EP | 3592284 | A1 | 1/2020 |
| EP | 3592288 | A1 | 1/2020 |
| EP | 3592289 | A1 | 1/2020 |
| EP | 3593763 | A1 | 1/2020 |
| EP | 3600159 | A1 | 2/2020 |
| EP | 3606443 | A1 | 2/2020 |
| EP | 3606472 | A1 | 2/2020 |
| EP | 3660156 | A1 | 2/2020 |
| EP | 2241287 | B2 | 3/2020 |
| EP | 2376013 | B1 | 3/2020 |
| EP | 2911593 | B1 | 3/2020 |
| EP | 2995279 | B1 | 3/2020 |
| EP | 3009103 | B1 | 3/2020 |
| EP | 3038664 | B1 | 3/2020 |
| EP | 3167848 | B1 | 3/2020 |
| EP | 3175822 | B1 | 3/2020 |
| EP | 3179960 | B1 | 3/2020 |
| EP | 3280479 | B1 | 3/2020 |
| EP | 3616651 | A1 | 3/2020 |
| EP | 3619136 | A1 | 3/2020 |
| EP | 3626208 | A1 | 3/2020 |
| EP | 1667614 | B2 | 4/2020 |
| EP | 2119417 | B2 | 4/2020 |
| EP | 2155114 | B1 | 4/2020 |
| EP | 2299937 | B1 | 4/2020 |
| EP | 2331016 | B1 | 4/2020 |
| EP | 2376013 | B8 | 4/2020 |
| EP | 2413843 | B1 | 4/2020 |
| EP | 2854705 | B1 | 4/2020 |

(56)            References Cited

FOREIGN PATENT DOCUMENTS

| | | | |
|---|---|---|---|
| EP | 2918249 | B1 | 4/2020 |
| EP | 2922593 | B1 | 4/2020 |
| EP | 2950753 | B1 | 4/2020 |
| EP | 2967810 | B1 | 4/2020 |
| EP | 3110367 | B1 | 4/2020 |
| EP | 3111888 | B1 | 4/2020 |
| EP | 3128927 | B1 | 4/2020 |
| EP | 3134032 | B1 | 4/2020 |
| EP | 3142606 | B1 | 4/2020 |
| EP | 3270825 | B1 | 4/2020 |
| EP | 3300696 | B1 | 4/2020 |
| EP | 3316823 | B1 | 4/2020 |
| EP | 3334487 | B1 | 4/2020 |
| EP | 3342355 | B1 | 4/2020 |
| EP | 3373863 | B1 | 4/2020 |
| EP | 3459498 | B1 | 4/2020 |
| EP | 3470105 | B1 | 4/2020 |
| EP | 3628239 | A1 | 4/2020 |
| EP | 3632338 | A1 | 4/2020 |
| EP | 3636312 | A1 | 4/2020 |
| EP | 3639792 | A1 | 4/2020 |
| EP | 3639888 | A1 | 4/2020 |
| EP | 3643273 | A1 | 4/2020 |
| EP | 1895942 | B1 | 5/2020 |
| EP | 2120821 | B1 | 5/2020 |
| EP | 2437688 | B1 | 5/2020 |
| EP | 2785281 | B1 | 5/2020 |
| EP | 2852354 | B1 | 5/2020 |
| EP | 2884906 | B1 | 5/2020 |
| EP | 2999412 | B1 | 5/2020 |
| EP | 3060174 | B1 | 5/2020 |
| EP | 3071147 | B1 | 5/2020 |
| EP | 3104812 | B1 | 5/2020 |
| EP | 3139861 | B1 | 5/2020 |
| EP | 3232989 | B1 | 5/2020 |
| EP | 3294219 | B1 | 5/2020 |
| EP | 3298970 | B1 | 5/2020 |
| EP | 3302366 | B1 | 5/2020 |
| EP | 3323389 | B1 | 5/2020 |
| EP | 3332744 | B1 | 5/2020 |
| EP | 3402440 | B1 | 5/2020 |
| EP | 3417813 | B1 | 5/2020 |
| EP | 3417831 | B1 | 5/2020 |
| EP | 3457987 | B1 | 5/2020 |
| EP | 3484413 | B1 | 5/2020 |
| EP | 3531975 | B1 | 5/2020 |
| EP | 3644866 | A1 | 5/2020 |
| EP | 3646822 | A1 | 5/2020 |
| EP | 3646824 | A1 | 5/2020 |
| EP | 3646825 | A1 | 5/2020 |
| EP | 3648706 | A1 | 5/2020 |
| EP | 3656354 | A1 | 5/2020 |
| EP | 1648339 | B2 | 6/2020 |
| EP | 2072027 | B1 | 6/2020 |
| EP | 2331016 | B8 | 6/2020 |
| EP | 2616007 | B1 | 6/2020 |
| EP | 2967856 | B1 | 6/2020 |
| EP | 3042635 | B1 | 6/2020 |
| EP | 3060165 | B1 | 6/2020 |
| EP | 3280338 | B1 | 6/2020 |
| EP | 3283010 | B1 | 6/2020 |
| EP | 3400908 | B1 | 6/2020 |
| EP | 3494928 | B1 | 6/2020 |
| EP | 3498225 | B1 | 6/2020 |
| EP | 3583920 | B1 | 6/2020 |
| EP | 3659553 | A1 | 6/2020 |
| EP | 3661429 | A1 | 6/2020 |
| EP | 3668450 | A1 | 6/2020 |
| EP | 3668452 | A1 | 6/2020 |
| EP | 3669828 | A1 | 6/2020 |
| EP | 3669829 | A1 | 6/2020 |
| EP | 2291145 | B1 | 7/2020 |
| EP | 2512952 | B1 | 7/2020 |
| EP | 2558029 | B1 | 7/2020 |
| EP | 2693985 | B1 | 7/2020 |
| EP | 2858708 | B1 | 7/2020 |
| EP | 2862546 | B1 | 7/2020 |
| EP | 2967807 | B1 | 7/2020 |
| EP | 2967866 | B1 | 7/2020 |
| EP | 3061421 | B1 | 7/2020 |
| EP | 3107497 | B1 | 7/2020 |
| EP | 3139862 | B1 | 7/2020 |
| EP | 3423000 | B1 | 7/2020 |
| EP | 3441045 | B1 | 7/2020 |
| EP | 3451972 | B1 | 7/2020 |
| EP | 3501454 | B1 | 7/2020 |
| EP | 3512466 | B1 | 7/2020 |
| EP | 3616652 | B1 | 7/2020 |
| EP | 3672528 | A1 | 7/2020 |
| EP | 3672529 | A1 | 7/2020 |
| EP | 3673925 | A1 | 7/2020 |
| EP | 3679894 | A1 | 7/2020 |
| EP | 3681439 | A1 | 7/2020 |
| EP | 3681441 | A1 | 7/2020 |
| EP | 3682852 | A1 | 7/2020 |
| EP | 3682854 | A1 | 7/2020 |
| EP | 3685802 | A1 | 7/2020 |
| EP | 2367505 | B1 | 8/2020 |
| EP | 2497445 | B1 | 8/2020 |
| EP | 2537486 | B1 | 8/2020 |
| EP | 2777616 | B1 | 8/2020 |
| EP | 3007651 | B1 | 8/2020 |
| EP | 3052053 | B1 | 8/2020 |
| EP | 3237033 | B1 | 8/2020 |
| EP | 3388005 | B1 | 8/2020 |
| EP | 3410986 | B1 | 8/2020 |
| EP | 3451974 | B1 | 8/2020 |
| EP | 3463192 | B1 | 8/2020 |
| EP | 3554423 | B1 | 8/2020 |
| EP | 3568089 | A1 | 8/2020 |
| EP | 3573544 | B1 | 8/2020 |
| EP | 3634255 | B1 | 8/2020 |
| EP | 3689299 | A1 | 8/2020 |
| EP | 3691567 | A1 | 8/2020 |
| EP | 3697346 | A1 | 8/2020 |
| EP | 2485795 | B1 | 9/2020 |
| EP | 3125777 | B1 | 9/2020 |
| EP | 3182930 | B1 | 9/2020 |
| EP | 3285690 | B1 | 9/2020 |
| EP | 3459500 | B1 | 9/2020 |
| EP | 3570782 | B1 | 9/2020 |
| EP | 3700467 | A1 | 9/2020 |
| EP | 3711711 | A1 | 9/2020 |
| EP | 3714936 | A1 | 9/2020 |
| EP | 2979667 | B2 | 10/2020 |
| EP | 3193783 | B1 | 10/2020 |
| EP | 3490501 | B1 | 10/2020 |
| EP | 3720363 | A1 | 10/2020 |
| EP | 2387973 | B1 | 11/2020 |
| EP | 2427144 | B1 | 11/2020 |
| EP | 2506777 | B1 | 11/2020 |
| EP | 2793743 | B1 | 11/2020 |
| EP | 2825203 | B1 | 11/2020 |
| EP | 2863842 | B1 | 11/2020 |
| EP | 2967700 | B1 | 11/2020 |
| EP | 2977026 | B1 | 11/2020 |
| EP | 3139864 | B1 | 11/2020 |
| EP | 3145451 | B1 | 11/2020 |
| EP | 3156007 | B1 | 11/2020 |
| EP | 3244834 | B1 | 11/2020 |
| EP | 3298987 | B1 | 11/2020 |
| EP | 3302362 | B1 | 11/2020 |
| EP | 3311777 | B1 | 11/2020 |
| EP | 3316819 | B1 | 11/2020 |
| EP | 3361988 | B1 | 11/2020 |
| EP | 3503813 | B1 | 11/2020 |
| EP | 3527170 | B1 | 11/2020 |
| EP | 3530236 | B1 | 11/2020 |
| EP | 3590471 | B1 | 11/2020 |
| EP | 3593762 | B1 | 11/2020 |
| EP | 3737336 | A1 | 11/2020 |
| EP | 3740162 | A1 | 11/2020 |
| EP | 2370138 | B1 | 12/2020 |
| EP | 2445450 | B1 | 12/2020 |

(56) References Cited

FOREIGN PATENT DOCUMENTS

| | | | |
|---|---|---|---|
| EP | 2739250 | B1 | 12/2020 |
| EP | 2877123 | B1 | 12/2020 |
| EP | 2967834 | B1 | 12/2020 |
| EP | 2996632 | B1 | 12/2020 |
| EP | 3090703 | B1 | 12/2020 |
| EP | 3191025 | B1 | 12/2020 |
| EP | 3202371 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3538028 | B1 | 12/2020 |
| EP | 3539510 | B1 | 12/2020 |
| EP | 3544548 | B1 | 12/2020 |
| EP | 3545906 | B1 | 12/2020 |
| EP | 3572117 | B1 | 12/2020 |
| EP | 3593763 | B1 | 12/2020 |
| EP | 3744291 | A1 | 12/2020 |
| EP | 3749254 | A1 | 12/2020 |
| EP | 3753535 | A1 | 12/2020 |
| EP | 1906883 | B1 | 1/2021 |
| EP | 2334261 | B1 | 1/2021 |
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 2835112 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |
| EP | 3758651 | A1 | 1/2021 |
| EP | 3760164 | A1 | 1/2021 |
| EP | 3763331 | A1 | 1/2021 |
| EP | 2273951 | B1 | 2/2021 |
| EP | 2379008 | B1 | 2/2021 |
| EP | 2996641 | B1 | 2/2021 |
| EP | 3043747 | B1 | 2/2021 |
| EP | 3340936 | B1 | 2/2021 |
| EP | 3457985 | B1 | 2/2021 |
| EP | 3503847 | B1 | 2/2021 |
| EP | 3538027 | B1 | 2/2021 |
| EP | 3558168 | B1 | 2/2021 |
| EP | 3581232 | B1 | 2/2021 |
| EP | 3656354 | B1 | 2/2021 |
| EP | 3697324 | B1 | 2/2021 |
| EP | 3773329 | A1 | 2/2021 |
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3787561 | A1 | 3/2021 |
| EP | 3791795 | A1 | 3/2021 |
| EP | 3791828 | A1 | 3/2021 |
| EP | 3796875 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3454794 | B1 | 4/2021 |
| EP | 3487420 | B1 | 4/2021 |
| EP | 3558165 | B1 | 4/2021 |
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B1 | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 3834879 | A1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 2558032 | B1 | 8/2021 |
| EP | 2992857 | B1 | 8/2021 |
| EP | 2994075 | B1 | 8/2021 |
| EP | 3038539 | B1 | 8/2021 |
| EP | 3287099 | B1 | 8/2021 |
| EP | 3348235 | B1 | 8/2021 |
| EP | 3643273 | B1 | 8/2021 |

(56) References Cited

FOREIGN PATENT DOCUMENTS

| | | | |
|---|---|---|---|
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 3863567 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 3833302 | A4 | 9/2021 |
| EP | 3870110 | A1 | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 3886762 | A1 | 10/2021 |
| EP | 3892240 | A1 | 10/2021 |
| EP | 3900679 | A1 | 10/2021 |
| EP | 3914191 | B1 | 10/2021 |
| EP | 38886763 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3912595 | A1 | 11/2021 |
| EP | 3912596 | A1 | 11/2021 |
| EP | 277608 | B1 | 12/2021 |
| EP | 2358307 | B1 | 12/2021 |
| EP | 2765954 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3624705 | B1 | 12/2021 |
| EP | 3749254 | B1 | 12/2021 |
| EP | 3914191 | A1 | 12/2021 |
| EP | 2400922 | B1 | 1/2022 |
| EP | 2545885 | B1 | 1/2022 |
| EP | 2747708 | B1 | 1/2022 |
| EP | 2763708 | B1 | 1/2022 |
| EP | 2994072 | B1 | 1/2022 |
| EP | 3220856 | B1 | 1/2022 |
| EP | 3288498 | B1 | 1/2022 |
| EP | 3534840 | B1 | 1/2022 |
| EP | 3558169 | B1 | 1/2022 |
| EP | 3668452 | B1 | 1/2022 |
| EP | 3682854 | B1 | 1/2022 |
| EP | 3697346 | B1 | 1/2022 |
| EP | 3700467 | B1 | 1/2022 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | B1 | 2/2022 |
| EP | 3962415 | A1 | 3/2022 |
| EP | 2538893 | B1 | 6/2022 |
| EP | 2575681 | B1 | 6/2022 |
| EP | 2583640 | B1 | 6/2022 |
| EP | 3071149 | B1 | 6/2022 |
| EP | 3253332 | B1 | 6/2022 |
| EP | 3283009 | B1 | 6/2022 |
| EP | 3296979 | B1 | 6/2022 |
| EP | 3298988 | B1 | 6/2022 |
| EP | 3342377 | B1 | 6/2022 |
| EP | 3365349 | B1 | 6/2022 |
| EP | 3397206 | B1 | 6/2022 |
| EP | 3426194 | B1 | 6/2022 |
| EP | 3595588 | B1 | 6/2022 |
| EP | 3636312 | B1 | 6/2022 |
| EP | 3661436 | B1 | 6/2022 |
| EP | 3790501 | B1 | 6/2022 |
| EP | 3846740 | B1 | 6/2022 |
| EP | 3849472 | B1 | 6/2022 |
| EP | 3897454 | B1 | 6/2022 |
| EP | 4014928 | A1 | 6/2022 |
| EP | 2271284 | B1 | 7/2022 |
| EP | 2621409 | B1 | 7/2022 |
| EP | 2787926 | B1 | 7/2022 |
| EP | 2838473 | B1 | 7/2022 |
| EP | 2950752 | B1 | 7/2022 |
| EP | 3060171 | B1 | 7/2022 |
| EP | 3206631 | B1 | 7/2022 |
| EP | 3245980 | B1 | 7/2022 |
| EP | 3256073 | B1 | 7/2022 |
| EP | 3311783 | B1 | 7/2022 |
| EP | 3347182 | B1 | 7/2022 |
| EP | 3389557 | B1 | 7/2022 |
| EP | 3463120 | B1 | 7/2022 |
| EP | 3579788 | B1 | 7/2022 |
| EP | 3756623 | B1 | 7/2022 |
| EP | 3796872 | B1 | 7/2022 |
| EP | 3796876 | B1 | 7/2022 |
| EP | 2313152 | B1 | 8/2022 |
| EP | 2688516 | B1 | 8/2022 |
| EP | 2849678 | B1 | 8/2022 |
| EP | 2950751 | B1 | 8/2022 |
| EP | 2964153 | B1 | 8/2022 |
| EP | 3019092 | B1 | 8/2022 |
| EP | 3184082 | B1 | 8/2022 |
| EP | 3231395 | B1 | 8/2022 |
| EP | 3266417 | B1 | 8/2022 |
| EP | 3407834 | B1 | 8/2022 |
| EP | 3458136 | B1 | 8/2022 |
| EP | 3459499 | B1 | 8/2022 |

(56) References Cited

FOREIGN PATENT DOCUMENTS

| | | | |
|---|---|---|---|
| EP | 3471662 | B1 | 8/2022 |
| EP | 3484412 | B1 | 8/2022 |
| EP | 3534841 | B1 | 8/2022 |
| EP | 3541328 | B1 | 8/2022 |
| EP | 3672532 | B1 | 8/2022 |
| EP | 3718509 | B1 | 8/2022 |
| EP | 3769721 | B1 | 8/2022 |
| EP | 3789077 | B1 | 8/2022 |
| EP | 3908228 | B1 | 8/2022 |
| EP | 3915493 | B1 | 8/2022 |
| EP | 3967274 | B1 | 8/2022 |
| EP | 2670351 | B1 | 9/2022 |
| EP | 2777617 | B1 | 9/2022 |
| EP | 2810620 | B1 | 9/2022 |
| EP | 2922592 | B1 | 9/2022 |
| EP | 3038567 | B1 | 9/2022 |
| EP | 3096713 | B1 | 9/2022 |
| EP | 3220857 | B1 | 9/2022 |
| EP | 3448315 | B1 | 9/2022 |
| EP | 3481335 | B1 | 9/2022 |
| EP | 3520715 | B1 | 9/2022 |
| EP | 3645065 | B1 | 9/2022 |
| EP | 3737336 | B1 | 9/2022 |
| EP | 2104470 | B1 | 10/2022 |
| EP | 2536353 | B1 | 10/2022 |
| EP | 2991588 | B1 | 10/2022 |
| EP | 3043755 | B1 | 10/2022 |
| EP | 3288491 | B1 | 10/2022 |
| EP | 3466373 | B1 | 10/2022 |
| EP | 3552585 | B1 | 10/2022 |
| EP | 3791828 | B1 | 10/2022 |
| EP | 2538882 | B1 | 11/2022 |
| EP | 2698129 | B1 | 11/2022 |
| EP | 2959866 | B1 | 11/2022 |
| EP | 3175823 | B1 | 11/2022 |
| EP | 3280358 | B1 | 11/2022 |
| EP | 3340923 | B1 | 11/2022 |
| EP | 3478224 | B1 | 11/2022 |
| EP | 3490659 | B1 | 11/2022 |
| EP | 3744291 | B1 | 11/2022 |
| FR | 1264471 | A | 6/1961 |
| FR | 2788217 | A1 | 7/2000 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920664 | B1 | 9/2010 |
| FR | 2932376 | B1 | 4/2011 |
| FR | 2947716 | B1 | 9/2011 |
| FR | 2945440 | B1 | 12/2012 |
| FR | 2951549 | B1 | 8/2013 |
| FR | 2964855 | B1 | 10/2013 |
| FR | 2977792 | B1 | 10/2013 |
| FR | 2980968 | B1 | 12/2013 |
| FR | 2986149 | B1 | 12/2014 |
| FR | 2997288 | B1 | 1/2015 |
| FR | 2998167 | B1 | 1/2015 |
| FR | 2996747 | B1 | 2/2015 |
| FR | 2996748 | B1 | 2/2015 |
| FR | 3004638 | B1 | 5/2015 |
| FR | 2982763 | B1 | 7/2015 |
| FR | 2991162 | B1 | 7/2015 |
| FR | 3006582 | B1 | 7/2015 |
| FR | 3001121 | B1 | 1/2016 |
| FR | 2998166 | B1 | 2/2016 |
| FR | 3021862 | B1 | 5/2016 |
| FR | 3004917 | B1 | 6/2016 |
| FR | 3006884 | B1 | 6/2016 |
| FR | 3023704 | B1 | 8/2016 |
| FR | 3008885 | B1 | 12/2016 |
| FR | 3033494 | B1 | 3/2017 |
| FR | 3057154 | B1 | 10/2018 |
| FR | 3058631 | B1 | 1/2019 |
| FR | 3058632 | B1 | 1/2019 |
| FR | 3060292 | B1 | 1/2019 |
| FR | 3063631 | B1 | 3/2019 |
| FR | 3020265 | B1 | 9/2019 |
| FR | 3072013 | B1 | 9/2019 |
| GB | 243370 | A | 8/1926 |
| GB | 1264471 | A | 2/1972 |
| GB | 1315844 | A | 5/1973 |
| GB | 2245495 | A | 1/1992 |
| GB | 2398245 | A | 8/2004 |
| GB | 2407146 | B | 4/2006 |
| GB | 2398245 | B | 3/2007 |
| GB | 2433700 | B | 12/2007 |
| GB | 2478498 | B | 7/2012 |
| GB | 2530487 | B | 12/2016 |
| GB | 2517609 | B | 5/2017 |
| GB | 2538749 | B | 8/2017 |
| GB | 2538072 | B | 11/2017 |
| GB | 2536538 | B | 7/2018 |
| GB | 2548891 | B | 7/2018 |
| JP | 2002540889 | A | 12/2002 |
| JP | 2008539985 | A | 11/2008 |
| JP | 2008541865 | A | 11/2008 |
| JP | 2013525039 | A | 6/2013 |
| JP | 6010530 | B2 | 9/2016 |
| JP | 2016185404 | A | 10/2016 |
| JP | 6463706 | B2 | 1/2019 |
| JP | 2019069241 | A | 5/2019 |
| JP | 6811262 | B2 | 12/2020 |
| JP | 2021037423 | A | 3/2021 |
| JP | 7204724 | B2 | 1/2023 |
| JP | 2023026533 | | 2/2023 |
| SU | 1271508 | A1 | 11/1986 |
| WO | WO-1991017720 | A1 | 11/1991 |
| WO | WO-1992017118 | A1 | 10/1992 |
| WO | WO-1993001768 | A1 | 2/1993 |
| WO | WO-1997024080 | A1 | 7/1997 |
| WO | WO-9749355 | A1 | 12/1997 |
| WO | WO-1999033414 | A1 | 7/1999 |
| WO | WO-1999040964 | A1 | 8/1999 |
| WO | WO-1999047075 | A1 | 9/1999 |
| WO | WO-2000018333 | A1 | 4/2000 |
| WO | WO-2000041652 | A1 | 7/2000 |
| WO | WO-2000047139 | A1 | 8/2000 |
| WO | WO-0053104 | A1 | 9/2000 |
| WO | WO-0061034 | A1 | 10/2000 |
| WO | WO-2001028459 | A1 | 4/2001 |
| WO | WO-0135861 | A1 | 5/2001 |
| WO | WO-0135870 | A1 | 5/2001 |
| WO | WO-2001035878 | A2 | 5/2001 |
| WO | WO-2001049213 | A2 | 7/2001 |
| WO | WO-2001054624 | A1 | 8/2001 |
| WO | WO-2001054625 | A1 | 8/2001 |
| WO | WO-2001064137 | A1 | 9/2001 |
| WO | WO-0172239 | A2 | 10/2001 |
| WO | WO-2001076510 | A1 | 10/2001 |
| WO | WO-0236048 | A1 | 5/2002 |
| WO | WO-0238084 | A2 | 5/2002 |
| WO | WO-2002041789 | A2 | 5/2002 |
| WO | WO-03028522 | A2 | 4/2003 |
| WO | WO-2003047468 | A1 | 6/2003 |
| WO | WO-03092554 | A1 | 11/2003 |
| WO | WO-2004014257 | A1 | 2/2004 |

(56) References Cited

FOREIGN PATENT DOCUMENTS

| | | | |
|---|---|---|---|
| WO | WO-2004014474 A1 | 2/2004 |
| WO | WO-2004030569 A2 | 4/2004 |
| WO | WO-2004058097 A2 | 7/2004 |
| WO | WO-2005011534 A1 | 2/2005 |
| WO | WO-2005034812 A1 | 4/2005 |
| WO | WO-2005041810 A2 | 5/2005 |
| WO | WO-2005062980 A2 | 7/2005 |
| WO | WO-2005087140 A1 | 9/2005 |
| WO | WO-2005102015 A2 | 11/2005 |
| WO | WO-2006014233 A2 | 2/2006 |
| WO | WO-2006034008 A2 | 3/2006 |
| WO | WO-2006070372 A2 | 7/2006 |
| WO | WO-2006085225 A1 | 8/2006 |
| WO | WO-2006085304 A2 | 8/2006 |
| WO | WO-2006089236 A1 | 8/2006 |
| WO | WO-2006097931 A2 | 9/2006 |
| WO | WO-2006108090 A2 | 10/2006 |
| WO | WO-2006113906 A1 | 10/2006 |
| WO | WO-2006127765 A1 | 11/2006 |
| WO | WO-2006138173 A2 | 12/2006 |
| WO | WO-2007025028 A1 | 3/2007 |
| WO | WO-2007034488 A2 | 3/2007 |
| WO | WO-2007058857 A2 | 5/2007 |
| WO | WO-2006097931 A3 | 7/2007 |
| WO | WO-2007097983 A2 | 8/2007 |
| WO | WO-2007122459 A2 | 11/2007 |
| WO | WO-2007123658 A1 | 11/2007 |
| WO | WO-2007134290 A2 | 11/2007 |
| WO | WO-2007122459 A3 | 1/2008 |
| WO | WO-2008005405 A2 | 1/2008 |
| WO | WO-2008005535 A2 | 1/2008 |
| WO | WO-2008013915 A2 | 1/2008 |
| WO | WO-2007097983 A3 | 3/2008 |
| WO | WO-2008070797 A2 | 6/2008 |
| WO | WO-2008013915 A3 | 7/2008 |
| WO | WO-2008091515 A2 | 7/2008 |
| WO | WO-2008103722 A2 | 8/2008 |
| WO | WO-2008103722 A3 | 10/2008 |
| WO | WO-2008125153 A1 | 10/2008 |
| WO | WO-2008147964 A1 | 12/2008 |
| WO | WO-2008150529 A1 | 12/2008 |
| WO | WO-2009024859 A2 | 2/2009 |
| WO | WO-2009026563 A2 | 2/2009 |
| WO | WO-2009033469 A1 | 3/2009 |
| WO | WO-2009042196 A2 | 4/2009 |
| WO | WO-2009045331 A1 | 4/2009 |
| WO | WO-2009052188 A1 | 4/2009 |
| WO | WO-2009053497 A1 | 4/2009 |
| WO | WO-200909450 A1 | 7/2009 |
| WO | WO-2009091509 A1 | 7/2009 |
| WO | WO-2009106545 A1 | 9/2009 |
| WO | WO-2009108615 A1 | 9/2009 |
| WO | WO-2009116041 A2 | 9/2009 |
| WO | WO-2009134701 A2 | 11/2009 |
| WO | WO-2009137359 A1 | 11/2009 |
| WO | WO-2009149462 A2 | 12/2009 |
| WO | WO-2009155561 A2 | 12/2009 |
| WO | WO-2010004546 A1 | 1/2010 |
| WO | WO-2010005524 A2 | 1/2010 |
| WO | WO-2010008549 A1 | 1/2010 |
| WO | WO-2009134701 A3 | 2/2010 |
| WO | WO-2010037141 A1 | 4/2010 |
| WO | WO-2010040009 A1 | 4/2010 |
| WO | WO-2010057262 A1 | 5/2010 |
| WO | WO-2010098857 A1 | 9/2010 |
| WO | WO-2010121076 A2 | 10/2010 |
| WO | WO-2010138853 A2 | 12/2010 |
| WO | WO-2011025945 A1 | 3/2011 |
| WO | WO-201107284 A2 | 6/2011 |
| WO | WO-2011081997 A1 | 7/2011 |
| WO | WO-2011109813 A2 | 9/2011 |
| WO | WO-2011137531 A1 | 11/2011 |
| WO | WO-2011137531 A9 | 11/2011 |
| WO | WO-2012032187 A1 | 3/2012 |
| WO | WO-2012035279 A1 | 3/2012 |
| WO | WO-2012095455 A2 | 7/2012 |
| WO | WO-2012162228 A1 | 11/2012 |
| WO | WO-2012177942 A2 | 12/2012 |
| WO | WO-2013028387 A2 | 2/2013 |
| WO | WO-2013075215 A1 | 5/2013 |
| WO | WO-2013106585 A1 | 7/2013 |
| WO | WO-2014018432 A2 | 1/2014 |
| WO | WO-2014079291 A1 | 5/2014 |
| WO | WO-2014145338 A1 | 9/2014 |
| WO | WO-2014149865 A1 | 9/2014 |
| WO | WO-2014163706 A1 | 10/2014 |
| WO | WO-2014194178 A1 | 12/2014 |
| WO | WO-2015057407 A1 | 4/2015 |
| WO | WO-2015077274 A1 | 5/2015 |
| WO | WO-2016016899 A1 | 2/2016 |
| WO | WO-2017035487 A1 | 3/2017 |
| WO | WO-2018213209 A1 | 11/2018 |
| WO | WO-2020093172 A1 | 5/2020 |
| WO | WO-2023076103 A1 | 5/2023 |
| WO | WO-2023081236 A1 | 5/2023 |
| WO | WO-2023091769 A1 | 5/2023 |
| WO | WO-2023096804 A1 | 6/2023 |
| WO | WO-2023154250 A1 | 8/2023 |
| WO | WO-2023196150 A1 | 10/2023 |
| WO | WO-2023244454 A1 | 12/2023 |
| WO | WO-2023244767 A1 | 12/2023 |
| WO | WO-2023250114 A1 | 12/2023 |
| WO | WO-2024009540 A1 | 1/2024 |
| WO | WO-2024010739 A1 | 1/2024 |
| WO | WO-2024030520 A1 | 2/2024 |

OTHER PUBLICATIONS

US 8,221,315 B2, 07/2012, Lambrecht et al. (withdrawn)
"50 Early-to Late-Stage Medical Device Companies Seeking Investment and Partnering Opportunities to Present in 3 Weeks at Investment in Innovation (In3) Medical Device Summit", [Online] Retrieved from the internet: <Businesswire.com>, (May 27, 2008), 3 pgs.
"U.S. Appl. No. 13/096,572, Examiner Interview Summary mailed Sep. 6, 2013", 3 pgs.
"U.S. Appl. No. 13/096,572, Non Final Office Action mailed Jun. 4, 2013", 11 pgs.
"U.S. Appl. No. 13/096,572, Notice of Allowance mailed Sep. 26, 2013", 8 pgs.
"U.S. Appl. No. 13/096,572, Preliminary Amendment filed Sep. 9, 2011", 15 pgs.
"U.S. Appl. No. 13/096,572, Response filed Mar. 25, 2013 to Restriction Requirement mailed Mar. 4, 2018", 2 pgs.
"U.S. Appl. No. 13/096,572, Response filed Aug. 30, 2013 to Non Final Office Action mailed Jun. 4, 2013", 11 pgs.
"U.S. Appl. No. 13/096,572, Restriction Requirement mailed Mar. 4, 2013", 10 pgs.
"U.S. Appl. No. 14/046,606, 312 Amendment filed Aug. 14, 2017", 11 pgs.
"U.S. Appl. No. 14/046,606, Advisory Action mailed Oct. 12, 2016", 2 pgs.
"U.S. Appl. No. 14/046,606, Applicant's Summary of Examiner Interview filed Apr. 28, 2017", 3 pgs.
"U.S. Appl. No. 14/046,606, Examiner Interview Summary mailed Feb. 16, 2016", 3 pgs.
"U.S. Appl. No. 14/046,606, Examiner Interview Summary mailed Apr. 27, 2017", 3 pgs.
"U.S. Appl. No. 14/046,606, Examiner Interview Summary mailed Aug. 16, 2017", 3 pgs.
"U.S. Appl. No. 14/046,606, Examiner Interview Summary mailed Sep. 20, 2016", 3 pgs.
"U.S. Appl. No. 14/046,606, Final Office Action mailed Apr. 22, 2016", 11 pgs.
"U.S. Appl. No. 14/046,606, Non Final Office Action mailed Sep. 18, 2015", 11 pgs.
"U.S. Appl. No. 14/046,606, Non Final Office Action mailed Dec. 27, 2016", 10 pgs.
"U.S. Appl. No. 14/046,606, Notice of Allowance mailed May 24, 2017", 8 pgs.

(56) References Cited

OTHER PUBLICATIONS

"U.S. Appl. No. 14/046,606, PTO Response to Rule 312 Communication mailed Aug. 24, 2017", 2 pgs.
"U.S. Appl. No. 14/046,606, Response filed Apr. 20, 2017 to Non Final Office Action mailed Dec. 27, 2016", 8 pgs.
"U.S. Appl. No. 14/046,606, Response filed Aug. 26, 2015 to Restriction Requirement mailed Jun. 1, 2015", 2 pgs.
"U.S. Appl. No. 14/046,606, Response filed Sep. 22, 2016 to Final Office Action mailed Apr. 22, 2016", 8 pgs.
"U.S. Appl. No. 14/046,606, Response filed Dec. 18, 2015 to Non Final Office Action mailed Sep. 18, 2015", 7 pgs.
"U.S. Appl. No. 14/046,606, Restriction Requirement mailed Jun. 1, 2015", 7 pgs.
"U.S. Appl. No. 14/046,606, Supplemental Amendment filed Feb. 12, 2016", 8 pgs.
"U.S. Appl. No. 14/685,418, Examiner Interview Summary mailed Nov. 2, 2015", 3 pgs.
"U.S. Appl. No. 14/685,418, Non Final Office Action mailed Aug. 12, 2015", 16 pgs.
"U.S. Appl. No. 14/685,418, Notice of Allowance mailed Dec. 2, 2015", 7 pgs.
"U.S. Appl. No. 14/685,418, Response filed Oct. 22, 2015 to Non Final Office Action mailed Aug. 12, 2015", 12 pgs.
"U.S. Appl. No. 14/692,605, Examiner Interview Summary mailed Oct. 30, 2015", 3 pgs.
"U.S. Appl. No. 14/692,605, Non Final Office Action mailed Aug. 14, 2015", 13 pgs.
"U.S. Appl. No. 14/692,605, Notice of allowance mailed Nov. 5, 2015", 7 pgs.
"U.S. Appl. No. 14/692,605, Response filed Oct. 22, 2015 to Non Final Office Action mailed Aug. 14, 2015", 13 pgs.
"U.S. Appl. No. 15/682,890, Corrected Notice of Allowability mailed Aug. 8, 2019", 2 pgs.
"U.S. Appl. No. 15/682,890, Non Final Office Action mailed Nov. 5, 2018", 7 pgs.
"U.S. Appl. No. 15/682,890, Notice of Allowance mailed Jun. 5, 2019", 9 pgs.
"U.S. Appl. No. 15/682,890, Preliminary Amendment filed Feb. 27, 2018", 6 pgs.
"U.S. Appl. No. 15/682,890, Response filed May 6, 2009 to Non Final Office Action mailed Nov. 5, 2018", 5 pgs.
"U.S. Appl. No. 16/559,191 Preliminary Amendment filed Sep. 3, 2019", 6 pgs.
"U.S. Appl. No. 16/559,191, Corrected Notice of Allowability mailed Jul. 21, 2022", 2 pgs.
"U.S. Appl. No. 16/559,191, Non Final Office Action mailed Dec. 10, 2021", 7 pgs.
"U.S. Appl. No. 16/559,191, Notice of Allowance mailed Apr. 14, 2022", 8 pgs.
"U.S. Appl. No. 16/559,191, Response filed Mar. 10, 2022 to Non Final Office Action mailed Dec. 10, 2021", 6 pgs.
"Australian Application Serial No. 2011250606, First Examination Report mailed Sep. 20, 2013", 4 pgs.
"Australian Application Serial No. 2011250606, Response filed Feb. 13, 2014 to First Examination Report mailed Sep. 20, 2013", 14 pgs.
"Australian Application Serial No. 2014203064, First Examination Report mailed Jan. 23, 2015", 5 pgs.
"Australian Application Serial No. 2014203064, Response filed May 6, 2015 to First Examination Report mailed Jan. 23, 2015", 16 pgs.
"Canadian Application Serial No. 2,797,863, Office Action mailed Mar. 3, 2017", 4 pgs.
"Canadian Application Serial No. 2,797,863, Response filed Aug. 29, 2018 to Office Action mailed Mar. 3, 2017", 28 pgs.
"Canadian Application Serial No. 3,043,737, Office Action mailed May 11, 2020", 4 pgs.
"Canadian Application Serial No. 3,043,737, Response filed Sep. 8, 2020 to Office Action mailed May 11, 2020", 12 pgs.

"Canadian Application Serial No. 3112399, Office Action mailed Jun. 6, 2022", 3 pgs.
"CardiAQ Valve Technologies", Medical Devices Today, [Online]. Retrieved from the Internet: <http://www.medicaldevicestoday.com/2009/07/medical-device-start-up-cardiaq-valve-technologies-percutaneous-mitral-valve-replacement.html> Accessed: Mar. 8, 2012, (Jul. 17, 2009), 2 pgs.
"CardiAQ Valve Technologies ("CVT") to disclose data during 'EuroPCR 2010' about the world's first successful in vivo transcatheter delivery of a mitral heart valve implant", Irvine, California, Businesswire.com, (May 20, 2010), 2 pgs.
"CardiAQ Valve Technologies to pursue first-in-man studies of its transcatheter mitral valve system", Cardiac Interventions Today, (Jan. 12, 2010), 2 pgs.
"*CardiAQ Valve Technologies v NeoVasc*", Case 1:14-cv-12405-NMG. Document 01-1, (Jun. 6, 2014), 1 pg.
"*CardiAQ Valve Technologies v NeoVasc*", Case 1:14-cv-12405-NMG. Document 01-2, (Jun. 6, 2014), 1 pg.
"*CardiAQ Valve Technologies v NeoVasc*", Case 1:14-cv-12405-NMG. Document 01-main, (Jun. 6, 2014), 20 pgs.
"*CardiAQ Valve Technologies v NeoVasc*", Case 1:14-cv-12405-NMG. Document 02-main, (Jun. 6, 2014), 2 pgs.
"*CardiAQ Valve Technologies v NeoVasc*", Case 1:14-cv-12405-NMG. Document 03-1, (Jun. 6, 2014), 1 pg.
"*CardiAQ Valve Technologies v NeoVasc*", Case 1:14-cv-12405-NMG. Document 03-2, (Jun. 6, 2014), 3 pgs.
"*CardiAQ Valve Technologies v NeoVasc*", Case 1:14-cv-12405-NMG. Document 03-3, (Jun. 6, 2014), 1 pg.
"*CardiAQ Valve Technologies v NeoVasc*", Case 1:14-cv-12405-NMG. Document 03-4, (Jun. 6, 2014), 1 pg.
"*CardiAQ Valve Technologies v NeoVasc*", Case 1:14-cv-12405-NMG. Document 03-5, (Jun. 6, 2014), 2 pgs.
"*CardiAQ Valve Technologies v NeoVasc*", Case 1:14-cv-12405-NMG. Document 03-main, (Jun. 6, 2014), 20 pgs.
"*CardiAQ Valve Technologies v NeoVasc*", Case 1:14-cv-12405-NMG. Document 05-main, (Jun. 6, 2014), 2 pgs.
"*CardiAQ Valve Technologies v NeoVasc*", Case 1:14-cv-12405-NMG. Document 06-main, (Jul. 21, 2014), 3 pgs.
"*CardiAQ Valve Technologies v NeoVasc*", Case 1:14-cv-12405-NMG. Document 07-main, (Jul. 21, 2014), 3 pgs.
"*CardiAQ Valve Technologies v NeoVasc*", Case 1:14-cv-12405-NMG. Document 08-1, (Jul. 25, 2014), 3 pgs.
"*CardiAQ Valve Technologies v NeoVasc*", Case 1:14-cv-12405-NMG. Document 08-main, (Jul. 25, 2014), 2 pgs.
"*CardiAQ Valve Technologies v NeoVasc*", Case 1:14-cv-12405-NMG. Document 09-1, (Jul. 25, 2014), 3 pgs.
"*CardiAQ Valve Technologies v NeoVasc*", Case 1:14-cv-12405-NMG. Document 09-main, (Jul. 25, 2014), 2 pgs.
"*CardiAQ Valve Technologies v NeoVasc*", Case 1:14-cv-12405-NMG. Document 11-1, (Jul. 28, 2014), 3 pgs.
"*CardiAQ Valve Technologies v NeoVasc*", Case 1:14-cv-12405-NMG. Document 11-main, (Jul. 28, 2014), 2 pgs.
"*CardiAQ Valve Technologies v NeoVasc*", Case 1:14-cv-12405-NMG. Document 13-1, (Jul. 29, 2014), 3 pgs.
"*CardiAQ Valve Technologies v NeoVasc*", Case 1:14-cv-12405-NMG. Document 13-2, (Jul. 29, 2014), 1 pg.
"*CardiAQ Valve Technologies v NeoVasc*", Case 1:14-cv-12405-NMG. Document 13-main, (Jul. 29, 2014), 3 pgs.
"*CardiAQ Valve Technologies v NeoVasc*", Case 1:14-cv-12405-NMG. Document 14-1, (Jul. 29, 2014), 3 pgs.
"*CardiAQ Valve Technologies v NeoVasc*", Case 1:14-cv-12405-NMG. Document 14-2, (Jul. 29, 2014), 1 pg.
"*CardiAQ Valve Technologies v NeoVasc*", Case 1:14-cv-12405-NMG. Document 14-main, (Jul. 29, 2014), 3 pgs.
"*CardiAQ Valve Technologies v NeoVasc*", Case 1:14-cv-12405-NMG. Document 15-1, (Jul. 29, 2014), 3 pgs.
"*CardiAQ Valve Technologies v NeoVasc*", Case 1:14-cv-12405-NMG. Document 15-2, (Jul. 29, 2014), 2 pgs.
"*CardiAQ Valve Technologies v NeoVasc*", Case 1:14-cv-12405-NMG. Document 15-main, (Jul. 29, 2014), 3 pgs.
"*CardiAQ Valve Technologies v NeoVasc*", Case 1:14-cv-12405-NMG. Document 16-1, (Jul. 29, 2014), 4 pgs.

(56)            References Cited

OTHER PUBLICATIONS

"*CardiAQ Valve Technologies* v *NeoVasc*", Case 1:14-cv-12405-NMG. Document 16-2, (Jul. 29, 2014), 1 pg.
"*CardiAQ Valve Technologies* v *NeoVasc*", Case 1:14-cv-12405-NMG. Document 16-main, (Jul. 29, 2014), 3 pgs.
"*CardiAQ Valve Technologies* v *NeoVasc*", Case 1:14-cv-12405-NMG. Document 17-1, (Jul. 29, 2014), 3 pg.
"*CardiAQ Valve Technologies* v *NeoVasc*", Case 1:14-cv-12405-NMG. Document 17-main, (Jul. 29, 2014), 2 pgs.
"*CardiAQ Valve Technologies* v *NeoVasc*", Case 1:14-cv-12405-NMG. Document 18-main, (Jul. 29, 2014), 27 pgs.
"*CardiAQ Valve Technologies* v *NeoVasc*", Case 1:14-cv-12405-NMG. Document 19-1, (Jul. 29, 2014), 1 pg.
"*CardiAQ Valve Technologies* v *NeoVasc*", Case 1:14-cv-12405-NMG. Document 19-main, (Jul. 29, 2014), 2 pgs.
"*CardiAQ Valve Technologies* v *NeoVasc*", Case 1:14-cv-12405-NMG. Document 20-main, (Jul. 29, 2014), 25 pgs.
"*CardiAQ Valve Technologies* v *NeoVasc*", Case 1:14-cv-12405-NMG. Document 21-main, (Jul. 29, 2014), 5 pgs.
"*CardiAQ Valve Technologies* v *NeoVasc*", Case 1:14-cv-12405-NMG. Document 22-1, (Jul. 29, 2014), 89 pgs.
"*CardiAQ Valve Technologies* v *NeoVasc*", Case 1:14-cv-12405-NMG. Document 22-main, (Jul. 29, 2014), 4 pgs.
"*CardiAQ Valve Technologies* v *NeoVasc*", Case 1:14-cv-12405-NMG. Document 24-1, (Aug. 12, 2014), 17 pgs.
"*CardiAQ Valve Technologies* v *NeoVasc*", Case 1:14-cv-12405-NMG. Document 24-2, (Aug. 12, 2014), 4 pgs.
"*CardiAQ Valve Technologies* v *NeoVasc*", Case 1:14-cv-12405-NMG. Document 24-3, (Aug. 12, 2014), 2 pgs.
"*CardiAQ Valve Technologies* v *NeoVasc*", Case 1:14-cv-12405-NMG. Document 24-4, (Aug. 12, 2014), 2 pgs.
"*CardiAQ Valve Technologies* v *NeoVasc*", Case 1:14-cv-12405-NMG. Document 24-5, (Aug. 12, 2014), 3 pgs.
"*CardiAQ Valve Technologies* v *NeoVasc*", Case 1:14-cv-12405-NMG. Document 24-main, (Aug. 12, 2014), 21 pgs.
"*CardiAQ Valve Technologies* v *NeoVasc*", Case 1:14-cv-12405-NMG. Document 25-main, (Aug. 12, 2014), 15 pgs.
"*CardiAQ Valve Technologies* v *NeoVasc*", Case 1:14-cv-12405-NMG. Document 26-main, (Aug. 12, 2014), 4 pgs.
"*CardiAQ Valve Technologies* v *NeoVasc*", Case 1:14-cv-12405-NMG. Document 27-1, (Aug. 12, 2014), 28 pgs.
"*CardiAQ Valve Technologies* v *NeoVasc*", Case 1:14-cv-12405-NMG. Document 27-2, (Aug. 12, 2014), 51 pgs.
"*CardiAQ Valve Technologies* v *NeoVasc*", Case 1:14-cv-12405-NMG. Document 27-3, (Aug. 12, 2014), 3 pgs.
"*CardiAQ Valve Technologies* v *NeoVasc*", Case 1:14-cv-12405-NMG. Document 27-main, (Aug. 12, 2014), 4 pgs.
"*CardiAQ Valve Technologies* v *NeoVasc*", Case 1:14-cv-12405-NMG. Document 28-main, (Aug. 12, 2014), 16 pgs.
"*CardiAQ Valve Technologies* v *NeoVasc*", Case 1:14-cv-12405-NMG. Document 29-main, (Aug. 13, 2014), 2 pgs.
"*CardiAQ Valve Technologies* v *NeoVasc*", Case 1:14-cv-12405-NMG. Document 30-main, (Aug. 19, 2014), 2 pgs.
"*CardiAQ Valve Technologies* v *NeoVasc*", Case 1:14-cv-12405-NMG. Document 31-1, (Aug. 19, 2014), 6 pgs.
"*CardiAQ Valve Technologies* v *NeoVasc*", Case 1:14-cv-12405-NMG. Document 31-main, (Aug. 19, 2014), 3 pgs.
"*CardiAQ Valve Technologies* v *NeoVasc*", Case 1:14-cv-12405-NMG. Document 32-main, (Aug. 19, 2014), 4 pgs.
"*CardiAQ Valve Technologies* v *NeoVasc*", Case 1:14-cv-12405-NMG. Document 34-main, (Aug. 20, 2014), 3 pgs.
"*CardiAQ Valve Technologies* v *NeoVasc*", Case 1:14-cv-12405-NMG. Document 35-main, (Aug. 20, 2014), 6 pgs.
"*CardiAQ Valve Technologies* v *NeoVasc*", Case 1:14-cv-12405-NMG. Document 36-main, (Aug. 20, 2014), 2 pgs.
"*CardiAQ Valve Technologies* v *NeoVasc*", Case 1:14-cv-12405-NMG. Document 38-main, (Aug. 28, 2014), 3 pgs.
"*CardiAQ Valve Technologies* v *NeoVasc*", Case 1:14-cv-12405-NMG. Document 39-main, (Aug. 28, 2014), 28 pgs.

"*CardiAQ Valve Technologies* v *NeoVasc*", Case 1:14-cv-12405-NMG. Document 40-main, (Sep. 11, 2014), 4 pgs.
"*CardiAQ Valve Technologies* v *NeoVasc*", Case 1:14-cv-12405-NMG. Document 41-main, (Sep. 11, 2014), 17 pgs.
"*CardiAQ Valve Technologies* v *NeoVasc*", Case 1:14-cv-12405-NMG. Document 42-main, (Oct. 3, 2014), 6 pgs.
"*CardiAQ Valve Technologies* v *NeoVasc*", Case 1:14-cv-12405-NMG. Document 43-main, (Oct. 7, 2014), 1 pg.
"*CardiAQ Valve Technologies* v *NeoVasc*", Case 1 :14-cv-12405-ADB. Document 583, (Oct. 31, 16), 40 pgs.
"*CardiAQ Valve Technologies* v *NeoVasc*", Case 1:14-cv-12405-NMG. Document 31-2, (Aug. 19, 2014), 2 pgs.
"CardiAQ Valve Technologies: Percutaneous Mitral Valve Replacement", Start Up Windhover Review of Emerging Medical Ventures, vol. 14. No. 6, (Jun. 2009), 48-49.
"CardiAQ's Complaint and Jury Demand; U.S. District Court—District of Massachusetts", *CardiAQ Valve, Technologies Inc.* v. *Neovasc Inc. and Neovasc Tiara*, (Jun. 6, 2014), 22 pgs.
"CardiAQ's First Amended Complaint and Jury Demand", U.S. District Court—District of Massachusetts *CardiAQ Valve, Technologies Inc.* v. *Neovasc Inc. and Neovasc Tiara Inc*, (Aug. 12, 2014), 21 pgs.
"CardiAQ's Objection in Patent Vindication Action in regard to EP 2566416", Administrative Court of Munich; *CardiAQ Valve Technologies, Inc.*, v. *Neovasc Tiara Inc*, (Jun. 25, 2014), 22 pgs.
"CardiAQ's Second Amended Complaint and Jury Demand", U.S. District Court—District of Massachusetts; *CardiAQ Valve, Technologies Inc.* v. *Neovasc Inc. and Neovasc Tiara Inc*, (Jan. 15, 2015), 25 pgs.
"Chinese Application Serial No. 201180029086.5, Office Action mailed Oct. 28, 2014", W/English Translation, 20 pgs.
"Chinese Application Serial No. 201510607482.1, Office Action mailed Jan. 19, 2017", W/English Translation, 16 pgs.
"Company Fact Sheet—CardiAQ Valve Technologies", (2009), 1 pg.
"Company Overview—CardiAQ Valve Technologies", (Jun. 25, 2009), 17 pgs.
"CoreValve USA", An advanced TAVR design, Medtronic.com, Accessed Jan. 27, 2015, (Jan. 27, 2015), 2 pgs.
"Court's Memorandum & Order; U.S. District Court—District of Massachusetts", *CardiAQ Valve, Technologies Inc.* v. *Neovasc Inc. and Neovasc Tiara Inc*, (Nov. 6, 2014), 14 pgs.
"CVT's Transcatheter Mitral Valve Implanation (TMVI) platform might be the 'next big thing' in the cardiac cath lab", CardiAQ Valve Technologies (CVT) Elects Michael Mack, MD, to its Scientific Advisory Board, (Jun. 2, 2009), 4 pgs.
"Defendants Neovasc Inc.'s and Neovasc Tiara Inc.'s Answer to Plaintiffs First Amended Complaint", *CardiAQ Valve, Technologies Inc.* v. *Neovasc Inc. and Neovasc Tiara Inc*, (Nov. 20, 2014), 20 pgs.
"Defendants Neovasc Inc.'s and Neovasc Tiara Inc.'s Answer to Plaintiffs Second Amended Complaint", *CardiAQ Valve, Technologies Inc.* v. *Neovasc Inc. and Neovasc Tiara Inc.*, (Jan. 29, 2015), 22 pgs.
"Edwards Lifesciences 2005 Annual Report", (Jan. 27, 2015), 24 pgs.
"Edwards Lifesciences 2005 annual report", (Accessed Jan. 27, 2015), 24 pgs.
"*Edwards Lifesciences cardiaq LLC* v.", *Neovasc Inc.and Neovasc Tiara, Inc.*, (Mar. 23, 2017), 15 pgs.
"Engager system. Precise Valve positioning", TAVR, (Jan. 28, 2015), 2 pgs.
"European Application Serial No. 06827638, Extended European Search Report mailed Feb. 28, 2013", 6 pgs.
"European Application Serial No. 11777065.1, Extended European Search Report mailed Dec. 10, 2013", 6 pgs.
"European Application Serial No. 11777065.1, Grounds for Appeal filed May 28, 2021", 26 pgs.
"European Application Serial No. 11777065.1, Office Action mailed Dec. 10, 2013", 5 pgs.
"European Application Serial No. 11777065.1, Response filed Sep. 1, 2022 to Extended European Search Report mailed Dec. 10, 2013", 10 pgs.

(56)         References Cited

OTHER PUBLICATIONS

"European Application Serial No. 11798780, Extended European Search Report mailed Jan. 30, 2014", 7 pgs.
"European Application Serial No. 19189541.6, Office Action mailed Dec. 6, 2019", 4 pgs.
"European Application Serial No. 19189546.5, Office Action mailed Dec. 6, 2019", 3 pgs.
"European Application Serial No. 19189600.0, Office Action mailed Dec. 6, 2019", 4 pgs.
"Exhibits accompanying CardiAQ's Objection in Patent Vindication Action in regard to EP 2566416", (Jun. 25, 2014), 306 pgs.
"Exhibits accompanying Neovasc's Statement of Defense in Patent Vindication Action in regard to EP 2566416", (Dec. 9, 2014), 67 pgs.
"International Application Serial No. PCT/CA2011/000662, International Preliminary Report on Patentability mailed Nov. 15, 2012", 8 pgs.
"International Application Serial No. PCT/CA2011/000662, International Search Report mailed Sep. 27, 2011", 5 pgs.
"International Application Serial No. PCT/CA2011/000662, Written Opinion mailed Sep. 27, 2011", 6 pgs.
"International Application Serial No. PCT/US2006/043526, International Search Report mailed Jun. 25, 2018", 1 pg.
"International Application Serial No. PCT/US2006/043526, Written Opinion mailed Jun. 25, 2018", 3 pgs.
"International Application Serial No. PCT/US2007/016855, International Search Report mailed Mar. 26, 2018", 1 pg.
"International Application Serial No. PCT/US2007/016855, Written Opinion mailed Mar. 26, 2018", 3 pgs.
"International Application Serial No. PCT/US2009/058893, International Search Report mailed Dec. 11, 2009", 5 pgs.
"International Application Serial No. PCT/US2009/058893, Written Opinion mailed Dec. 11, 2009", 5 pgs.
"International Application Serial No. PCT/US2009/059299, International Search Report mailed Dec. 18, 2009", 5 pgs.
"International Application Serial No. PCT/US2009/059299, Written Opinion mailed Dec. 18, 2009", 8 pgs.
"International Application Serial No. PCT/US2010/031313, International Search Report mailed Dec. 22, 2010", 4 pgs.
"International Application Serial No. PCT/US2010/031313, Written Opinion mailed Dec. 22, 2010", 3 pgs.
"International Application Serial No. PCT/US2011/041306, International Search Report mailed Feb. 29, 2012", 8 pgs.
"International Application Serial No. PCT/US2011/041306, Written Opinion mailed Feb. 29, 2012", 5 pgs.
"Japanese Application Serial No. 2019-000320, Notification of Reasons for Rejection mailed Apr. 6, 2020", with English translation of claims, 7 pgs.
"Japanese Application Serial No. 2019-000320, Response filed Jul. 3, 2020 to Notification of Reasons for Rejection mailed Apr. 6, 2020", w/English Claims, 6 pgs.
"Japanese Application Serial No. 2019-000320, Voluntary Amendment filed Jan. 30, 2019", with English translation of claims, 17 pgs.
"Japanese Application Serial No. 2020-206854, Notification of Reasons for Refusal mailed Jul. 5, 2021", w/ English Translation, 2 pgs.
"Japanese Application Serial No. 2020-206854, Notification of Reasons for Rejection mailed Feb. 24, 2022", W/English Translation, 9 pgs.
"Japanese Application Serial No. 2020-206854, Response filed Jul. 19, 2022 to Notification of Reasons for Rejection mailed Feb. 24, 2022", w/ English Claims, 10 pgs.
"Japanese Application Serial No. 2020-206854, Response filed Sep. 30, 2021 to Notification of Reasons for Refusal mailed Jul. 5, 2021", w/ English Claims, 5 pgs.
"Neovasc corporate presentation", [Online]. Retrieved from the Internet: <http://www.neovasc.com/investors/documents/Neovasc-Corporate-Presentation-Oct.2009.pdf>, (Oct. 2009), 21 pgs.

"Neovasc Ostial Products Overview", [Online]. Retrieved from the Internet: <https://web.archive.org/web/20090930050359/https://www.neovasc.com/vascular-products/ostialproducts/default.php>, (Sep. 30, 2008), 1 pg.
"Neovasc Surgical Products: An Operating Division of Neovasc Inc", (Apr. 2009), 17 pgs.
"Neovasc's Statement of Defense in Patent Vindication Action in regard to EP 2566416; Administrative Court of Munich", *CardiAQ Valve Technologies, Inc.*, v. *Neovasc Tiara Inc*, (Dec. 9, 2014), 39 pgs.
"The Jena Valve—the prosthesis", Jena Valve Technology, (Jan. 28, 2015), 1 pg.
"United States Court of Appeals for the Federal Circuit: *Cardiaq Valve Technologies, Inc.* v. *Neovasc Inc.*", Neovasc Tiara Inc. 2017-1302, 2017-1513, (Sep. 1, 2017).
"Update—CardiAQ Valve Technologies", (Jun. 6, 2010), 12 pgs.
Al-Attar, "Next generation surgical aortic biological prostheses: sutureless valves", European Society of Cardiology, (Dec. 21, 2011), 3 pgs.
Banai, et al., "Tiara: a novel catheter-based mitral valve bioprosthesis: initial experiments and short-term pre-clinical results", J Am Coll Cardiol, 60(15), (2012), 1430-1.
Bavaria, "CardiAQ Valve Technologies (CVT) discloses successful results of acute in vivo study of its novel transcatheter mitral valve implantation (TMVI) system", [Online]. Retrieved from the Internet: <http://eon.businesswire.com/news/eon/20090928005120/en/CardiAQ-Valve-Technologies/Heart/heart-failure>, (Sep. 28, 2009), 2 pgs.
Bavaria, "CardiAQ Valve Technologies. TCT Company Overview", Transcatheter Cardiovascular Therapeutics Conference. San Francisco, CA, (Sep. 21-25, 2009), 11 pgs.
Berreklouw, et al., "Sutureless mitral valve replacementattachment rings: feasibility in acute pig experiments", J Thorac Cardiovasc Surg, (Feb. 4, 2011), 390-5.
Boudjemline, et al., "Steps toward the percutaneous replacement of atrioventricular valves an experimental study", J Am Coll Cardiol, (2005), 360-5.
Brinkman, "Transcatheter cardiac valve interventions", Surg Clin North Am, (2009), 951-66.
Carpentier-Edwards, "Why compromise in the mitral position?", Edwards Lifesciences, (2004), 4 pgs.
Chiam, et al., "Percutaneous transcatheter aortic valve implantation: assessing results judging outcomes, and planning trials: the interventionalist perspective", JACC Cardiovasc Interv, (2008), 341-50.
Condado, et al., "Percutaneous treatment of heart valves", Rev Esp Cardiol, (2006), 1225-31.
De Backer, et al., "Percutaneous transcatheter mitral valve replacement: an overview of devices in preclinical and early clinical evaluation", Circ Cardiovasc Interv, (Jun. 2014), 400-9 pgs.
Fanning, et al., "Transcatheter aortic valve implantation (TAVI): valve design and evolution", Int J Cardiol, (Oct. 3, 2013), 1822-31.
Feldman, et al., "Prospects for percutaneous valve therapies", Circulation, (2007), 2866-77.
Fitzgerald, "Tomorrow's technology: percutaneous mitral valve replacement, chordal shortening and beyond", Transcatheter Valve Therapies (TVT) Conference. Seattle, WA, (Jun. 7, 2010), 8 pgs.
Gillespie, et al., "Sutureless mitral valve replacement: initial steps toward a percutaneous procedure", Ann Thorac Surg 96(2), (2013), 4 pgs.
Grube, et al., "Percutaneous aortic valve replacement forpatients using the second- and current third-generationprosthesis: device success and 30-day clinical outcome", J Am Coll Cardiol, (Jun. 6 2007), 69-76 pgs.
Grube, et al., "Percutaneous implantation of the Core Valve self-expanding valve prosthesis in high-risk patients with aortic valve disease: the Siegburg first-in-man study", Circulation, (Oct. 2, 2006), 1616-24.
Harmon, et al., "Effect of acute myocardial infarction on the angle between the mitral and aortic valve plane", Am J Cardiol, 84(3), (Aug. 1999), 342-4.
Herrman, "Trancatheter mitral valve implantation", Cardiac Interventions Today, (Aug./Sep. 2009), 82-85.

(56)                  References Cited

OTHER PUBLICATIONS

Horvath, et al., "Transapical aortic valve replacement under real-time magnetic resonance imaging guidance: experimental results with balloon-expandable and self-expanding stents", Eur J Cardiothorac Surg, (Jun. 2011), 822-8 pgs.
Ionasec, "Personalized modeling and assessment of the aortic-mitral coupling from 4D TEE and CT", Med Image Comput Comput Assist Interv, (2009), 767-75 pgs.
Karimi, et al., "Percutaneous Valve Therapies", Chapter 11, (2007), 11 pgs.
Kronemyer, "CardiAQ Valve Technologies: Percutaneous Mitral Valve Replacement", Windhover Review of Emerging Medical Ventures, vol. 14, No. 6, (Jun. 2009), 48-49 pgs.
Kumar, et al., "Design considerations and quantitative assessment for the development of percutaneous mitral valve stent", Med Eng Phys, (Apr. 16, 2014), 882-8.
Lane, Matthew, et al., "Transcatheter Mitral Valve Prosthesis", Co-pending U.S. Appl. No. 15/161,020, filed May 20, 2016, 92 pgs.
Lane, Matthew, et al., "Transcatheter Mitral Valve Prosthesis", Co-pending U.S. Appl. No. 14/685,418, filed Apr. 13, 2015, 87 pgs.
Lane, Matthew, "Transcatheter Mitral Valve Prosthesis", Co-pending U.S. Appl. No. 14/692,605, filed Apr. 21, 2015, 87 pgs.
Lansac, et al., "Dynamic balance of the aortomitral junction", J Thorac Cardiovasc Surg, 123(5), (2002), 911-8 pgs.
Lauten, et al., "Experimental evaluation of the JenaClip transcatheter aortic valve", Catheter Cardiovasc Interv, 74(3), (Sep. 1, 2009), 514-19.
Leon, et al., "Transcatheter aortic valve replacement in patients with critical aortic stenosis: rationale, device descriptions, early clinical experiences, and perspectives", Semin Thorac Cardiovasc Surg, 18(2), (2006), 165-74.
Lozonschi, et al., "Transapical mitral valved stent implantation", Ann Thorac Surg, 86(3), (2008), 745-8.
Lutter, et al., "Off-pump transapical mitral valve replacement", Eur J Cardiothorac Surg, (2009), 124-8.
Lutter, et al., "Transapical mitral valve implantation: the Lutter valve", Heart Lung Vessel, (2013), 6 pgs.
Lutter, G, et al., "Transcatheter Mitral Valve Replacement—Early Animal Results", Universitatsklinikum, Schleswig-Holstein, (Aug. 28, 2012), 51 pgs.
Ma, et al., "Double-crowned valved stents for off-pump mitral valve replacement", Eur J Cardiothorac Surg, (Aug. 2005), 194-8.
Mack, "Advantages and limitations of surgical mitral valve replacement; lessons for the transcatheter approach", Texas Cardiovascular Innovative Ventures (TCIV) Conference. Dallas, TX, (Jun. 7, 2010), 32 pgs.
Mack, Michael, et al., "Antegrade Transcatheter Mitral valve Implantation: A Short-term Experience in Swine Model", Applicant believes this may have been presented, (May of 2011), 10 pgs.
Maisano, "Mitral transcatheter technologies", Rambam Maimonides Med J, 4(3), (Jul. 25, 2013), 12 pgs.
Masson, et al., "Percutaneous treatment of mitral regurgitation", Circ Cardiovasc Interv, (2009), 140-6 pgs.
Navia, et al., "Sutureless implantation a expandable mitral stent-valve prosthesis in acute animal model", TCT728. JACC vol. 58, No. 20, (Nov. 8, 2011), 1 pg.
Nkomo, et al., "Burden of valvular heart diseases: a population-based study", Lancet, 368(9540), (Sep. 16, 2006), 1005-11 pgs.
Ormiston, et al., "Size and motion of the mitral valve annulus in man", A two-dimensional echocardiographic method and findings in normal subjects. Circulation, (1981), 113-20 pgs.
Orton, "Mitralseal: hybrid trancatheter mitral valve replacement", Colorado State University, [Online] Retrieved from the internet: <https://www.acvs.org/files/proceedings/2011/data/papers/102.pdf.>, (2011), 311-312.
Ostrovsky, "Transcatheter mitral valve implantation technology from CardiAQ", [Online]. Retrieved from the Internet: <http://medgadget.com/2010/01/transcatheter_mitral_valveimplantation_technologyfrom_cardiaq.html>, Accessed Jun. 27, 2012 from, (Jan. 15, 2010), 2 pgs.

Ostrovsky, Gene, "A Trial of Zenith Fenestrated AAA Endovascular Graft Goes on", [Online] Retrieved from the internet <http://www.medgadget.com/2008/08/a_trial_of_zenith_fenestrated_aaa_endovascular_graft_goes_on.html.>, (Aug. 1, 2008), 9 pgs.
Otto, "Evaluation and management of chronic mitral regurgitation", Clinical practice N Engl J Med, (2001), 740-6 pgs.
Piazza, et al., "Anatomy of the aortic valvar complex and its implications for transcatheter implantation of the aortic valve", Circ Cardiovasc Interv, (Aug. 2008), 74-81.
Pluth, et al., "Aortic and mitral valve replacement with cloth-covered Braunwald-Cutter prosthesis", A three-year follow-up. Ann Thorac Surg, (Sep. 1975), 239-48.
Preston-Maher, et al., "A Technical Review of Minimally Invasive Mitral Valve Replacements", Cardiovasc Eng Technol, (Nov. 25, 2014), 11 pgs.
Quadri, et al., "CVT is developing a non-surgical apporach to replacing mitral valves that may be the alternative to open-chest surgery", CardiAQ Valve Technologies, (May 8, 2009), 1 pg.
Quadri, Arshad, "Transcatheter Mitral Valve Implantation (TMVI) (An Acute in Vivo Study", Applicant believes this may have been presented, (Sep. 22, 2010), 19 pgs.
Ratz, et al., "Any experiences making an expandable stent frame?", Forums: Modeling,Multiple forum postings, [Online] Retrieved from the internet: <http://www.arch-pub.com/Any-experiences-making-an-expandable-stent-frame_10601513.html.>, (Feb. 3, 2009), 5 pgs.
Ratz, "CardiAQ Valve Technologies. Innovations in heartvalve therapy", IN3 San Francisco PowerPoint presentation in 19 slides, (Jun. 18, 2008), 19 pgs.
Ratz, Brent J, et al., "Fabric, Skin, Cloth expansion . . . best approach'?", [Online]. Retrieved from the Internet: <http://forums.autodesk.com/t5/modeling/fabric-skin-cloth-expansion-best-approach/td-p/4062607>, (Feb. 18, 2009), 3 pgs.
Ratz, Brent J, et al., "Isolating Interpolation", Architecture Forums: Animation and Rigging, Forum, (Feb. 9, 2009), 2 pgs.
Ratz, Brent J, et al., "In3 Company Overview", (Jun. 24, 2009), 15 pgs.
Ratz, Brent J, "LSI EMT Spotlight", (May 15, 2009), 21 pgs.
Ribiero, "Balloon-expandable prostheses for transcatheter aortic valve replacement", Prog Cardiovasc Dis, (Mar. 1, 2014), 583-95.
Ross, "Renal Ostial Stent System with Progressi-flex Technology, Evasc Medical Systems", Applicant requests the Examiner to consider this reference to be prior art, (Jun. 2009), 1 pg.
Ruiz, "Overview of novel transcatheter valve technologies", Glimpse into the future. New transcatheter mitral valve treatment. Euro PCR. Paris, France, (May 27, 2010), 14 pgs.
Seidel, et al., "A mitral valve prosthesis and a study of thrombosis on heart valves in dogs", J Surg Res, (May 1962), 168-75.
Shuto, et al., "Percutaneous transvenous Melody valve-in-ring procedure for mitral valve replacement", J Am Coll Cardiol, (Dec. 2011), 2475-80.
Sondergaard, et al., "First-in-human CardiAQ transcatheter mitral valve implantation via transapical approach", TCT-811. JACC vol. 64, No. 11 Suppl B, (Sep. 13, 2014), 1 pg.
Spencer, et al., "Surgical treatment of valvular heart disease", Part V. Prosthetic replacement of the mitral valve. American Heart Journal, (Oct. 1968), 576-580.
Spillner, et al., "New sutureless 'atrial mitral-valve prosthesis' for minimally invasive mitral valve therapy", Textile Research Journal, (2010), 7 pgs.
Timek, et al., "Aorto-mitral annular dynamics", Ann Thorac Surg, (Dec. 2003), 1944-50.
Tsang, et al., "Changes in aortic-mitral coupling with severe aortic stenosis", JACC vol. 55. Issue 1A, (Mar. 9, 2010), 1 pg.
Van Mieghem, "Anatomy of the mitral valvular complex and its implications for transcatheter interventions for mitral regurgitation", J Am Coll Cardiol, (2010), 617-26 pgs.
Veronesi, "A study of functional anatomy of aortic-mitral valve coupling using 3D matrix transesophageal echocardiography", Circ Cardiovasc Imaging, (Dec. 2, 2008), 24-31 pgs.
Vu, et al., "Novel sutureless mitral valve implantation method involving a bayonet insertion and release mechanism: A proof of concept study in pigs", J Thorac Cardiovasc Surg, (2012), 985-8.

(56)  References Cited

OTHER PUBLICATIONS

Walther, Thomas, et al., "Transapical approach for sutureless stent-fixed aortic valve implantation: experimental results", European Journal of Cardio-thoracic Surgery, 29, (2006), 703-708.

Webb, J. G, et al., "Transcatheter aortic valve implantation: The evolution of prostheses, delivery systems and approaches", Archives of Cardiovascular Disease, 105(3), (2012), 153-159.

Yamada, et al., "The left ventricular ostium: an anatomic concept relevant to idiopathic ventricular arrhythmias", Circ Arrhythm Electrophysiol, (2009), 396-404 pgs.

"Japanese Application Serial No. 2022-211552, Notification of Reasons for Rejection mailed Oct. 2, 2023", W English Translation, 2 pgs.

"Canadian Application Serial No. 3,112,399, Examiners Rule 86(2) Report mailed Mar. 19, 2024", 5 pgs.

"Japanese Application Serial No. 2022-211552, Response filed Apr. 1, 2024 to Notification of Reasons for Rejection mailed Oct. 2, 2023", w current English claims, 7 pgs.

"European Application Serial No. 11777065.1, Communication Pursuant to Article 94(3) EPC mailed May 3, 2024", 3 pgs.

"Canadian Application Serial No. 3,112,399, Response filed Jul. 19, 2024 to Examiners Rule 86(2) Report mailed Mar. 19, 2024", 12 pgs.

Andersen H.R, et al., "Transluminal Implantation of Artificial Heart Valves. Description of a New Expandable Aortic Valve and initial Results with Implantation by Catheter Technique in Closed Chest Pigs," European Heart Journal, The European Society of Cardiology, Oxford I University Press, United Kingdom, May 1, 1992, vol. 13, No. 5, pp. 704-708.

Andersen, HR "History of Percutaneous Aortic Valve Prosthesis," Herz No. 34, pp. 343-346. 2009.

Bavaria, Joseph E, MD, "CardiAQ Valve Technologies Transcatheter Mitral Valve Implantation", 11 pages, 2009, CardiAQ Valve Technologies, Inc., Irvine, California.

Biospace: "CardiAQ Valve Technologies (CVT) Reports Cardiovascular Medicine Mllestone: First-In-Human Non-Surgical Percutaneous Implantation of a Bioprosthetic Mitra! Heart Valve," Jun. 14, 2012, p. 1 (3 Pages), [Retrieved on Mar. 1, 2016], Retrieved from URL: http://www.biospace.com/News/cardiaq-valve-technologies-cvt-reports/263900.

Biospace: "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, (3 Pages), [Retrieved on Feb. 5, 2016], Retrieved From URL: www.Biospace.com/News/cardiaq-valve-technologies-cvt-reports-first- in/382370.

CardiAQ Valve Technologies (CVT) Elects Michael Mack, MD, to its Scientific Advisory Board. "CVT's Transcatheter Mitral Valve implantation (TMVI) platform might be the 'next big thing' in the cardiac cath lab." BusinessWire. Dated Jun. 2, 2009. 4 pages.

Dotter C.T., et al., "Transluminal Treatment of Arteriosderotic Obstruction: Description of a New Technic and a Preliminary Report of Its Application," Circulation, Lippincott Williams & Wilkins, Philadelphia, PA, Nov. 1, 1964, vol. XXX, No. 30, pp. 654-670.

Fornell D., Transcatheter Mitral Valve Replacement Devices in Development, Diagnostic and interventional Cardiology, Dec. 30, 2014, p. 3 (5 Pages), [Retrieved on Feb. 5, 2016], Retrieved from URL: http://www.dicardiology.com/article/transcatheter-mitral-valvereplacement-devices-development.

Herrmann, Howard C., M.D., "Advances in Transseptal Transcatheter Mitral Valve Replacement," Cardiovascular Research Foundation, tct, Sep. 21-25, 2018, 10 Pages, San Diego, California.

Inoue K, et al "Clinical Application of Transvenous Mitral Commissurotomy by a New Balloon Catheter," The Journal of Thorade and Cardiovascular Surgery, Mar. 1984, vol. 87, No. 3, pp. 394-402 (10 Pages).

Mack, Michael M.D., "Antegrade Transcatheter Mitral Valve Implantation: A Short-term Experience in Swine Model". TVT, Sep. 2011, 10 pages, Washington D.C.

Mack. Michael M.D., "Antegrade Transcatheter Mitral Valve implantation: On-Going Experience in Swine Model," TVT, Sep. 2011, 16 Pages, Washington D.C.

Mal., et al., "Double-crowned Valved Stents for Off-pump Mitra! Valve Replacement," European Journal of Cardio-thoracic Surgery, 2005, vol. 28, No. 2, pp. 194-199, Discussion 198-9, (Aug. 2008).

Medical Devices Today. CardiAQ Valve Technologies. Start-Up-Jul. 17, 2009. Accessed: Mar. 8, 2012. http:/www.medicaldevicestoday.com/2009/07/medical-device-start-up-cardiaq-valve-technologies-percutaneous-mitral-valve-replacement.html, 3 pages.

Neaia, Todd, "Flushing TAVI Valves With Carbon Dioxide May Protect Against Brain Injury", News Conference News, EuroPCR 2023, TCTMD, May 16, 2023, Paris France, 2 pages.

Neovasc: Neovasc Corporate Presentation, Oct. 2009, 21 Pages, Retrieved from URL: http://www.neovasc.com/investors/documents/Neovasc-Corporate-Presentation-October-2009.

Notice of allowance dated May 24, 2017 for U.S. Appl. No. 14/046,606, 9 pages.

Notice of allowance dated Sep. 26, 2013 for U.S. Appl. No. 13/096,572, 8 pages.

Notice of allowance dated Nov. 5, 2015 for U.S. Appl. No. 14/692,605, 7 pages.

Notice of allowance dated Dec. 2, 2015 for U.S. Appl. No. 14/685,418, 7 pages.

Office action dated Apr. 22, 2016 for U.S. Appl. No. 14/046,606, 10 pages.

Office action dated Jun. 4, 2013 for U.S. Appl. No. 13/096,572, 9 pages.

Office action dated Aug. 12, 2015 for U.S. Appl. No. 14/685,418, 15 pages.

Office action dated Aug. 14, 2015 for U.S. Appl. No. 14/692,605, 13 pages.

Office action dated Sep. 18, 2015 for U.S. Appl. No. 14/046,606, 9 pages.

Office Action dated Dec. 27, 2016 for U.S. Appl. No. 14/046,606, 10 pages.

Orton. Mitralseal: hybrid transcatheter mitral valve replacement. Colorado State University. 2011; 311-312. https://www.acvs.org/files/proceedings/2011/data/papers/102.pdf.

Pavcnik D., et al., "Development and Initial Experimental Evaluation of a Prosthetic Aortic Valve for Transcatheter Placement," Cardiovascular Radiology, Apr. 1, 1992, vol. 183, No. 1, pp. 151-154.

Rosch J., et al., "The Birth, Early Years and Future of interventional Radiology," Journal of Vascular and interventional Radiology, Jul. 2003, vol. 14. No. 7, pp. 841-853.

Ross, "Aortic Valve Surgery," Surgery of the Aortic Valves, Guy's Hospital, London, At a meeting of the Council on Aug. 4, 1966, pp. 192-197.

Ruiz et al, "Glimpse into the Future New Transcatheter Mitral Valve Treatment, Overview of Novel Transcatheter Valve Technologies," May 25-28, 2010, 14 pages, EuroPCR 2010, Paris, France.

Sabbah et al, "Mechanical Factors in the Degeneration of Porcine Bioprosthetic Valves: An Overview", Journal of Cardiac Surgery, vol. 4, No. 4, pp. 302-309, Dec. 1989.

Sondergaard L., et al., "Transcatheter Mitral Valve Implantation: CardiAQ(TM)," Cardiovascular Research Foundation, 2013, 16 Pages, Applicant believes this may have been presented at TCT.

Sondergaard, Lars, "CardiAQ TMVR FIH—Generation 2," Cardiovascular Research Foundation, Jun. 2014, 23 pages, TVT, Vancouver, BC.

Taramasso M., et al, "New Devices for TAVI: Technologies and Initial Clinical Experiences," Nature Reviews Cardiology, Mar. 2014, vol. 11, pp. 157-167, [Retrieved on Jan. 21, 2014], Retrieved from URL http://www. nature.comlnrcardio/journal/v11 /n3/fu11/nrcardio.2013221.Htmlmessageglobal=remove#access.

Tavr. Engager system. Precise Valve positioning. Accessed Jan. 28, 2015, 4 pages.

Transcatheter Aortic Valve Delivery Catheter System Compression Loading System, Medtronic CoreValveSystem, Medtronic Inc, 2014, 61 pages, Santa Ana, California.

Treede H., et al., "Transapical Transcatheter Aortic Valve Implantation Using the JenaValve(TM) System: Acute and 30-Day Results

(56)        References Cited

OTHER PUBLICATIONS of the Multicenter CE-Mark Study," European Journal of Cardio-Thoracic Surgery, Apr. 16, 2012, vol. 41, pp. e131-e138, Retrieved From URL: http://ejcts.oxfordjournals.org/content/141/6/e131. long.

U.S. Appl. No. 15/400,908, filed Jan. 6, 2017, titled "Transcatheter Mitral Valve Prosthesis,".

U.S. Appl. No. 15/679,011, filed Aug. 16, 2017, titled "Transcatheter Mitral Valve Prosthesis,".

U.S. Appl. No. 15/955,286, filed Apr. 17, 2018, titled "Transcatheter Mitral Valve Prosthesis,".

U.S. Appl. No. 16/211,708, filed Dec. 6, 2018, titled "Transcatheter Mitral Valve Prosthesis,".

Wayback Machine: "Transcatheter Mitral, Stent/Valve Prosthetic," Cleveland Clinic Lerner Research Institute, archived on Aug. 31, 2013, 2 Pages, [Retrieved on Jun. 23, 2016], Retrieved from URL: https://web.archive.org/web/20130831094624/http://mds.clevelandclinic. org/Portfolio.aspx?n=331.

Wheatley D.J, "Valve Prostheses," Operative Surgery, 4th edition, 1986, pp. 415-424.

Extended European Search Report and Written Opinion received for European Patent Application No. 25155359.0 mailed on May 7, 2025, 7 pages.

* cited by examiner

NATIVE LEAFLET BARBS
823

VENTRICULAR SKIRT
828

800

813

828

812

813

LOADING
ANCHOR
812

821

813
COMMISSURE
STRUCTURE

810
VEN-
TRICULAR
REGION

830

830

824

824
TRIGONAL
TAB

821

820

808
ANNULAR
REGION

806
ATRIAL
SKIRT
REGION

816

804
POSTERIOR

814a
RADIOPAQUE
MARKERS

802
FLAT ANTERIOR
REGION

814

804
POSTERIOR

DETAIL A

DETAIL A

1157

DETAIL A

A

1144

DETAIL A

1144

TRANSCATHETER MITRAL VALVE PROSTHESIS

CROSS-REFERENCE TO RELATED APPLICATIONS

This application is a continuation of U.S. patent application Ser. No. 16/559,191 (U.S. Pat. No. 11,419,720), filed Sep. 3, 2019; which application is a continuation of U.S. patent application Ser. No. 15/682,890 (U.S. Pat. No. 10,449,042), filed Aug. 22, 2017; which application is a continuation of U.S. patent application Ser. No. 14/046,606 (U.S. Pat. No. 9,770,329), filed Oct. 4, 2013; which is a divisional of U.S. patent application Ser. No. 13/096,572 (U.S. Pat. No. 8,579,964), filed Apr. 28, 2011; which claims the benefit of U.S. Provisional Patent Applications Nos. 61/414,879 filed Nov. 17, 2010; 61/393,860 filed Oct. 15, 2010; and 61/331,799 filed May 5, 2010; the entire contents of which are incorporated herein by reference.

BACKGROUND OF THE INVENTION

Field of the Invention

The present invention generally relates to medical devices and methods, and more particularly relates to the treatment of valve insufficiency, such as mitral insufficiency, also referred to as mitral regurgitation. The use of prosthetic valves delivered by traditional surgical implantation methods, or by less invasive percutaneous catheter or minimally invasive transapical methods are one possible treatment for valvar insufficiency.

The heart of vertebrate animals is divided into four chambers, and is equipped with four valves (the mitral, aortic, pulmonary and tricuspid valves) that ensure that blood pumped by the heart flows in a forward direction through the cardiovascular system. The mitral valve of a healthy heart prevents the backflow of blood from the left ventricle into the left atrium of the heart, and comprises two flexible leaflets (anterior and posterior) that close when the left ventricle contracts. The leaflets are attached to a fibrous annulus, and their free edges are tethered by subvalvular chordae tendineae to papillary muscles in the left ventricle to prevent them from prolapsing into the left atrium during the contraction of the left ventricle.

Various cardiac diseases or degenerative changes may cause dysfunction in any of these portions of the mitral valve apparatus, causing the mitral valve to become abnormally narrowed or dilated, or to allow blood to leak (i.e. regurgitate) from the left ventricle back into the left atrium. Any such impairments compromise cardiac sufficiency, and can be debilitating or life threatening.

Numerous surgical methods and devices have accordingly been developed to treat mitral valve dysfunction, including open-heart surgical techniques for replacing, repairing or reshaping the native mitral valve apparatus, and the surgical implantation of various prosthetic devices such as annuloplasty rings to modify the anatomy of the native mitral valve. More recently, less invasive transcatheter techniques for the delivery of replacement mitral valve assemblies have been developed. In such techniques, a prosthetic valve is generally mounted in a crimped state on the end of a flexible catheter and advanced through a blood vessel or the body of the patient until the valve reaches the implantation site. The prosthetic valve is then expanded to its functional size at the site of the defective native valve.

While these devices and methods are promising treatments for valvar insufficiency, they can be difficult to deliver, expensive to manufacture, or may not be indicated for all patients. Therefore, it would be desirable to provide improved devices and methods for the treatment of valvar insufficiency such as mitral insufficiency. At least some of these objectives will be met by the devices and methods disclosed below.

Description of the Background Art

By way of example, PCT international patent number PCT/US2008/054410 (published as PCT international publication no. WO2008/103722), the disclosure of which is hereby incorporated by reference, describes a transcatheter mitral valve prosthesis that comprises a resilient ring, a plurality of leaflet membranes mounted with respect to the ring so as to permit blood flow therethrough in one direction, and a plurality of tissue-engaging positioning elements movably mounted with respect to the ring and dimensioned to grip the anatomical structure of the heart valve annulus, heart valve leaflets, and/or heart wall. Each of the positioning elements defines respective proximal, intermediate, and distal tissue engaging regions cooperatively configured and dimensioned to simultaneously engage separate corresponding areas of the tissue of an anatomical structure, and may include respective first, second, and third elongate tissue-piercing elements. The valve prosthesis may also include a skirt mounted with respect to the resilient ring for sealing a periphery of the valve prosthesis against a reverse flow of blood around the valve prosthesis.

PCT international patent number PCT/US2009/041754 (published as PCT international publication no. WO2009/134701), the disclosure of which is hereby incorporated by reference, describes a prosthetic mitral valve assembly that comprises an anchor or outer support frame with a flared upper end and a tapered portion to fit the contours of the native mitral valve, and a tissue-based one-way valve mounted therein. The assembly is adapted to expand radially outwardly and into contact with the native heart tissue to create a pressure fit, and further includes tension members anchoring the leaflets of the valve assembly to a suitable location on the heart to function as prosthetic chordae tendineae.

Also known in the prior art are prosthetic mitral valve assemblies that utilize a claw structure for attachment of the prosthesis to the heart (see, for example, U.S. patent application publication no. US2007/0016286 to Hermann et al., the disclosure of which is hereby incorporated by reference), as are prosthetic mitral valve assemblies that rely on the application of axial rather than radial clamping forces to facilitate the self-positioning and self-anchoring of the prosthesis with respect to the native anatomical structure.

Another method which has been proposed as a treatment of mitral valve regurgitation is the surgical bow tie method, which recently has been adapted into a minimally invasive catheter based treatment where an implant is used to clip the valve leaflets together. This procedure is more fully disclosed in the scientific and patent literature, such as in U.S. Pat. No. 6,629,534 to St. Goar et al., the entire contents of which are incorporated herein by reference.

Other relevant publications include U.S. Patent Publication No. 2011/0015731 to Carpentier et al.

BRIEF SUMMARY OF THE INVENTION

The present invention generally relates to medical devices and methods, and more particularly prosthetic valves used to treat mitral regurgitation. While the present disclosure focuses on the use of a prosthetic valve for treating mitral regurgitation, this is not intended to be limiting. The prosthetic valves disclosed herein may also be used to treat other body valves including other heart valves or venous valves. Exemplary heart valves include the aortic valve, the triscupsid valve, or the pulmonary valve.

In embodiments of the present subject matter, transcatheter mitral valve prostheses and transcatheter methods and systems of deploying the same are provided. In certain embodiments, fire mitral valve prosthesis comprises a tissue-type prosthetic one-way valve structure comprising a plurality of leaflets affixed within a self-expanding or expandable anchor (i.e. frame) portion having a geometry that expands into a low profile atrial skirt region, an annular region dimensioned to generally conform to a native mitral valve annulus, a ventricular skirt region that displaces the native mitral valve leaflets, and a plurality of leaflet commissures extending into the sub-annular ventricular space (i.e. in the direction of the outflow of blood through the prosthesis) and configured to optimize the efficiency of the prosthetic valve structure and the load distribution on the leaflets thereof. The anchor portion may also in preferred embodiments be asymmetrical along its longitudinal axis, with the atrial skirt region, the annular region and/or the ventricular skirt region having differently configured anterior and posterior aspects in order to facilitate close accommodation of the asymmetrical contours and features of a typical native mitral valve apparatus. This asymmetry may result inherently from the structural configuration of the anchor portion as discussed further below, and/or as a consequence of shaping or forming steps employed during the manufacturing process.

The prosthetic valve structure in preferred embodiments may comprise a bicuspid or tricuspid valve in order, in part, to simplify manufacture of the mitral valve prosthesis, but as would be readily apparent to those of skill in the art, other configurations are possible. The leaflets may be fabricated from a single piece or from multiple pieces of standard biologic prosthetic materials, such as cryo- or chemically-preserved pericardium (e.g. bovine, equine, porcine, caprine, kangaroo), or from standard suitable synthetic prosthetic materials (e.g. fiber-reinforced matrix materials) well known in the art, and may be sewn or otherwise adhered to the anchor to form the valve leaflets in any standard suitable manner.

To optimize prosthetic valve efficiency and the load distribution on the prosthetic leaflets, the commissures extend generally axially in a cantilevered fashion downstream into the sub-annular space, and are capable of flexing radially and laterally along their axial lengths to distribute the forces associated with blood flow through the prosthetic valve structure. In some embodiments, the commissures define (when the mitral valve prosthesis is in an expended state) a somewhat frustoconical aperture that narrows along the forward direction of blood flow in order to aid in the closure of the prosthetic valve structure during contraction of the ventricle. To further optimize efficiency and load distribution on the leaflets, the commissures may be shaped and dimensioned so as to provide for the attachment of the leaflets along arcuate seams, and may also be made selectively flexible at different points or zones along their axial length through, for example, the addition or deletion of reinforcing struts, or through variation of the thickness of the commissures in selected regions.

The anchor portion of the mitral valve prosthesis is preferably fabricated from a single piece of metallic material that has been cut so as to permit the mitral valve prosthesis to be compressed into a compact, generally tubular delivery configuration, and expanded into the deployment configuration further described herein. In self-expanding embodiments, the anchor portion of the mitral valve prosthesis may be fabricated from a shape memory alloy (SMA) such as the nickel-titanium alloy nitinol, and in expandable embodiments, the anchor portion may be fabricated from any metallic material, such as chromium alloy or stainless steel, that is suitable for implantation into the body. In some embodiments, the metallic material may be of a single thickness throughout entirety of the anchor portion, and in others may vary in thickness so as to facilitate variations in the radial force that is exerted by the anchor portion in specific regions thereof, to increase or decrease the flexibility of the anchor portion in certain regions, and/or to control the process of compression in preparation for deployment and the process of expansion during deployment.

When deployed, the atrial skirt region of the mitral valve prosthesis extends generally radially outwards so as to lie flat against and cover the atrial surface of the native mitral valve annulus, and to anchor the mitral valve prosthesis against at least a portion of the adjoining atrial surface of the heart. The atrial skirt region has a low axial profile (extending only slightly into the atrium of the heart) in order to minimize potentially thrombogenic turbulence in blood flow, and in preferred embodiments, may be covered with standard biologic or synthetic prosthetic materials of the sort described above in order to seal the atrial skirt region against the atrial surface and to facilitate the funnelling of atrial blood through the mitral valve prosthesis. In some embodiments, the atrial skirt region further comprises atrial barbs or prongs to further facilitate the anchoring of the deployed prosthesis to the atrial heart surface. To facilitate the orientation and alignment of the mitral valve prosthesis within the native mitral valve upon deployment, particularly in embodiments where the anchor portion is longitudinally asymmetrical, the atrial skirt region of the anchor portion of the mitral valve prosthesis may preferably further comprise an alignment structure that may be differentiated (such as by angiography, computed tomography, etc.) from the remainder of the atrial skirt region and thereby used as an orientation guide during deployment. Most preferably, the alignment structure may comprise an elongation of the anterior aspect of the atrial skirt region configured to expand radially to accommodate the aortic root portion of the atrial surface.

The annular region of the mitral valve prosthesis is dimensioned, as noted above, to generally conform to and anchor against a native mitral valve annulus when deployed. In preferred embodiments, the deployed annular region may define a generally D-shaped annulus suitable for fitting the contours of a typical native mitral valve, and may be covered with standard biologic or synthetic prosthetic materials of the sort previously described to seal the annular region against the native mitral valve annulus.

The ventricular skirt region expands when deployed in the ventricular space generally radially outwards against the native mitral valve, but not so far as to obstruct the left ventricular outflow tract, nor to contact the ventricular wall. To anchor the mitral valve prosthesis against the displaced native leaflets in the ventricular space, the maximal radial displacement of the fully deployed ventricular skirt region is selected to be slightly greater than the circumference of the native mitral valve. In preferred embodiments, the ventricular skirt region also comprises ventricular and/or native leaflet barbs or prongs to further anchor the deployed prosthesis thereto. Most preferably, the ventricular skirt region is asymmetrical and the prongs thereof comprise two trigonal anchoring tabs located in the anterior aspect of the ventricular skirt region for anchoring against the fibrous trigones on either side of the anterior leaflet of the native mitral valve, and one posterior ventricular anchoring tab located in the posterior aspect of the ventricular skirt region for anchoring over the posterior leaflet of the native mitral valve. Associated with these tabs are deployment control regions as described in further detail below.

The ventricular skirt region may also in some embodiments be covered with standard biologic or synthetic prosthetic materials of the sort previously described in order to seal the ventricular skirt region against the displaced native leaflets, and thereby to funnel ventricular blood (during contraction of the ventricle) towards the prosthetic valve structure to assist in the closure thereof during contraction of the ventricle.

The combined 3-zone anchoring of the mitral valve prosthesis against the atrial surface, the native valve annulus, and the displaced native leaflets (supplemented, in preferred embodiments by a fourth zone of anchoring from the trigonal and posterior ventricular anchoring) in the ventricular space prevents the prosthesis from migrating or dislodging from within the native valve annulus during the contraction of the atrium or the ventricle, and lessens the anchoring pressure that is required to be applied in any given anchoring zone as compared to a prosthesis that is anchored in only a single anchoring zone, or in any combination of these four anchoring zones. The consequent reduction in radial force required to be exerted against the native structures in each zone minimizes the risk of obstruction or impingement of the nearby aortic valve or aortic root caused by the displacement of the native mitral valve apparatus. The combined 3 or 4-zone anchoring of the mitral valve prosthesis also facilitates the positioning and/or re-positioning of the mitral valve prosthesis as described below.

To deploy the mitral valve prosthesis within the native mitral valve apparatus, the prosthesis is first compacted and loaded into a suitably-adapted conventional catheter delivery system of the sort well known to those of skill in the art. Preferably, to facilitate later deployment, the commissures and associated prosthetic valve structure of the prosthesis are captured within an inner lumen of the catheter delivery system, and the remaining portions of the anchor region are captured within a secondary outer lumen of the catheter delivery system. The loaded mitral valve prosthesis may then be delivered (typically either transseptally or transapically) in its compacted form into the left atrium of the heart using a conventional catheter delivery system. The prosthesis is releasably attached to the catheter delivery system via its commissures, and shielded by the (preferably dual-lumen) delivery sheath thereof during transit into the atrial space. Once the prosthesis has been guided into the left atrium, the delivery sheath of the catheter delivery system is retracted as described below in order to permit expansion of the various regions of the prosthesis to proceed. Of course, in self-expanding embodiments, expansion of the prosthesis will occur spontaneously upon retraction of the delivery sheath, and in expandable embodiments, a catheter inflation structure such as a balloon is required to effect the expansion.

Deployment of the mitral valve prosthesis may proceed differently depending upon the features of the particular embodiment of the prosthesis being deployed. For example, in asymmetrical embodiments that comprise trigonal anchoring tabs and a posterior ventricular anchoring tab in the ventricular skirt region (as well as, preferably, an alignment structure in the atrial region), these tabs may preferably be deployed before deployment of the remaining portions of the ventricular skirt regions in order to facilitate the anchoring of these tabs against the native fibrous trigones and posterior leaflet, respectively.

In the first general deployment step, the atrial skirt region of the mitral valve prosthesis is permitted to expand by retracting the corresponding portion of the catheter delivery sheath (or is balloon-expanded following the retraction of the corresponding portion of the delivery sheath) within the left atrium of the heart, and the expanded atrial skirt region is then positioned over the atrial surface of the native mitral valve and anchored against at least a portion of the adjoining atrial surface of the heart. In preferred embodiments where the atrial skirt region comprises an alignment structure, this first general deployment step may be further broken down into two sub-steps, wherein the catheter delivery sheath is first retracted only so far as to permit expansion of the alignment structure (so that it may be visualized to facilitate manipulation of the delivery system in such a way as to orient the mitral valve prosthesis into a desired position), and then, once initial alignment of the prosthesis appears to be satisfactory, further retracted to permit the expansion, positioning and anchoring of the remaining portions of the atrial skirt region. In embodiments where the alignment structure comprises an elongation of the anterior aspect of the atrial skirt region, such initial alignment comprises the rotation and/or alignment of the alignment structure so that it is situated adjacent the aortic root and between the fibrous trigones of the native anterior leaflet.

Next, the annular region of the prosthesis is permitted to expand by further retraction of the catheter delivery sheath so as to engage the native mitral valve annulus (i.e. to contact the native valve annulus throughout at least a majority thereof) in order to create a second anchoring zone and to create a suitable opening for blood flow through the prosthetic valve structure.

Then, in embodiments that comprise trigonal anchoring tabs and a posterior ventricular anchoring tab in the ventricular skirt region, the catheter delivery sheath is further retracted so far as to permit the tabs to expand while the remainder of the ventricular skirt region of the prosthesis, including the deployment control regions of the tabs, remain sheathed. With the deployment control regions still retained within the delivery system and the atrial skirt region anchored against the atrial surface, the tabs project radially outward to facilitate engagement with the corresponding features of the native mitral valve. The posterior ventricular anchoring tab is aligned in the middle of the posterior leaflet of the mitral valve where there is an absence of chordae attachments to the posterior leaflet, and passed over the posterior leaflet to seat between the posterior leaflet and the ventricular wall. The two trigonal anchoring tabs are positioned on either side of the anterior leaflet with their heads positioned at the fibrous trigones. Slight rotation and realignment of the prosthesis can occur at this time.

Once the assembly has been satisfactorily positioned and the tabs aligned, the catheter delivery sheath may be further retracted to permit expansion of the remaining portions of the ventricular skirt region to secure the prosthesis within the mitral apparatus and seal the mitral annulus. Complete retraction of the outer catheter delivery sheath releases the ventricular skirt region and allows the anchoring tabs to proximate their anchoring location. As the prosthesis expands, the trigonal tabs anchor against the fibrous trigones, capturing the native anterior leaflet and chordae between the tabs and the anterior surface of the prosthetic valve assembly, and the posterior ventricular tab anchors between the ventricular wall and the posterior leaflet, capturing the posterior leaflet between the posterior anchoring tab and the posterior surface of the prosthetic valve assembly. The remaining portions of the ventricular skirt region expand out against the native mitral valve leaflets and adjacent anatomy, thereby creating a sealing funnel within the native leaflets and displacing the native leaflets from the prosthetic commissures to avoid obstruction of the prosthetic valve function. With the commissures of the prosthesis still captured within the delivery system, very minor adjustments may still made to ensure accurate positioning, anchoring and sealing.

In embodiments that do not comprise trigonal anchoring tabs and a posterior ventricular anchoring tab in the ventricular skirt region, the retraction of the catheter delivery sheath from the ventricular skirt region may, of course, be performed in one step after the atrial skirt and annular regions of the prosthesis have been initially anchored, to permit the ventricular skirt region of the prosthesis to expand against the native mitral valve, and to additionally anchor the prosthesis against the displaced native leaflets in the ventricular space. Optionally, the mitral valve prosthesis, which is still at this point releasably attached to the catheter delivery system via its commissures, may be driven slightly further downstream into ventricular space to create a greater seating force as between the atrial skirt region and atrial surface of the heart, and to provide additional purchase for any ventricular and/or native leaflet barbs or prongs that may be present in the ventricular skirt region. In embodiments where one or more of the atrial skirt region, the annular region and the ventricular skirt region are covered with a suitable biologic or synthetic prosthetic material, a seal may also be formed between the respective regions of the prosthesis and the associated zone of the native mitral valve apparatus.

Finally, once satisfactory positioning of the prosthesis has been achieved, the commissures are released from the catheter delivery system, allowing the catheter delivery system to be withdrawn, and leaving the mitral valve prosthesis in place as a functional replacement for the native mitral valve apparatus. Upon release of the commissures, the prosthesis may further undergo a final stage of foreshortening and seating as any remaining pressure exerted by the delivery system is released. The atrial skirt region may recoil slightly from this release in pressure, pulling the prosthesis slightly further up in to the left atrium, and thereby further seating the ventricular skirt region, including any associated barbs, prongs or tabs. In embodiments that comprise trigonal anchoring tabs, the seating thereof pulls the captured anterior leaflet tightly against the prosthesis, thereby avoiding or minimizing obstruction of the Left Ventricular Outflow Tract (LVOT), and firmly seats the ventricular skirt region in the annulus to prevent paravalvular leakage. Once final deployment is complete, the delivery system is retracted and removed.

In a first aspect of the present invention, a method of anchoring a prosthetic valve in a patient's heart comprises providing the prosthetic valve, wherein the prosthetic valve comprises an anchor having an atrial skirt, an annular region, a ventricular skirt, and a plurality of valve leaflets, wherein the anchor has a collapsed configuration for delivery to the heart and an expanded configuration for anchoring with the heart, and positioning the prosthetic valve in the patient's heart. The method also comprises expanding the atrial skirt radially outward so as to lie over a superior surface of the patient's native mitral valve, anchoring the atrial skirt against a portion of the atrium, and radially expanding the annular region of the anchor to conform with and to engage the native mitral valve annulus. The method also comprises radially expanding the ventricular skirt thereby displacing the native mitral valve leaflets radially outward.

At least a portion of the prosthetic valve may be covered with tissue or a synthetic material. Positioning the prosthetic valve may comprise transseptally delivering the prosthetic valve from the right atrium to the left atrium of the heart, or transapically delivering the prosthetic valve from a region outside the heart to the left ventricle of the heart.

Expanding the atrial skirt may comprise slidably moving a restraining sheath away from the atrial skirt thereby allowing radial expansion thereof. The atrial skirt may self-expand when the restraining sheath is removed therefrom. The method may further comprise applying a force on the prosthetic valve to ensure that the atrial skirt engages the superior surface of the mitral valve. The atrial skirt may comprise a plurality of barbs, and expanding the atrial skirt may comprise anchoring the barbs into the superior surface of the mitral valve. Expanding the atrial skirt may comprise sealing the atrial skirt against the superior surface of the native mitral valve.

Radially expanding the annular region may comprise slidably moving a restraining sheath away from the annular region thereby allowing radial expansion thereof. The annular region may self-expand when the restraining sheath is removed therefrom. Radially expanding the annular region may comprise asymmetrically expanding the annular region such that an anterior portion of the annular region is substantially flat, and a posterior portion of the annular region is cylindrically shaped.

The ventricular skirt may further comprise a trigonal anchoring tab on an anterior portion of the ventricular skirt, and radially expanding the ventricular skirt may comprise anchoring the trigonal anchoring tab against a first fibrous trigon on a first side of the anterior leaflet of the native mitral valve. The native anterior leaflet and adjacent chordae tendineae may be captured between the trigonal anchoring tab and an anterior surface of the anchor. The ventricular skirt may further comprise a second trigonal anchoring tab on the anterior portion of the ventricular skirt, and wherein radially expanding the ventricular skirt may comprise anchoring the second trigonal anchoring tab against a second fibrous trigon opposite the first fibrous trigon. The native anterior leaflet and adjacent chordae tendineae may be captured between the second trigonal anchoring tab and an anterior surface of the anchor. The ventricular skirt may further comprise a posterior ventricular anchoring tab on a posterior portion of the ventricular skirt. Radially expanding the ventricular skirt may comprise anchoring the posterior ventricular anchoring tab over a posterior leaflet of the native mitral valve to seat between the posterior leaflet and a ventricular wall of the heart. Radially expanding the ventricular skirt may comprise slidably moving a restraining sheath away from the ventricular skirt thereby allowing radial expansion thereof. The ventricular skirt may self-expand when the restraining sheath is removed therefrom.

The ventricular skirt may comprise a plurality of barbs, and expanding the ventricular skirt may comprise anchoring the barbs into heart tissue. The prosthetic valve may comprise a plurality of prosthetic valve leaflets, and radially expanding the ventricular skirt may comprise displacing the native mitral valve leaflets radially outward thereby preventing interference of the native mitral valve leaflets with the prosthetic valve leaflets. Radially expanding the ventricular skirt may comprise displacing the native mitral valve leaflets radially outward without contacting a ventricular wall, and without obstructing a left ventricular outflow tract. Radially expanding the ventricular skirt may comprise asymmetrically expanding the ventricular skirt such that an anterior portion of the ventricular skirt is substantially flat, and a posterior portion of the ventricular skirt is cylindrically shaped.

The atrial skirt may comprise an alignment element, and the method may comprise aligning the alignment element relative to the patient's valve. The valve may comprise a mitral valve, and aligning may comprise aligning the alignment element with an aortic root and disposing the alignment between two fibrous trigones of an anterior leaflet of the mitral valve. Aligning may comprise rotating the prosthetic valve. The prosthetic valve may comprise a plurality of prosthetic leaflets coupled to one or more commissures, and the method may comprise releasing the commissures from a delivery catheter. The prosthetic valve may comprise a tricuspid leaflet configuration.

The prosthetic valve may have an open configuration in which the prosthetic valve leaflets are disposed away from one another, and a closed configuration in which the prosthetic valve leaflets engage one another. Blood flows freely through the prosthetic valve in the open configuration, and retrograde blood flow across the prosthetic valve is substantially prevented in the closed configuration. The method may comprise reducing or eliminating mitral regurgitation. The prosthetic valve may comprise a therapeutic agent, and the method may comprise eluting the therapeutic agent from the prosthetic valve into adjacent tissue.

In another aspect of the present invention, a prosthetic cardiac valve comprises an anchor having an atrial skirt, an annular region, and a ventricular skirt. The anchor has a collapsed configuration for delivery to the heart and an expanded configuration for anchoring the prosthetic cardiac valve to a patient's heart. The prosthetic valve also comprises a plurality of prosthetic valve leaflets, each of the leaflets having a first end and a free end, wherein the first end is coupled with the anchor and the free end is opposite of the first end. The prosthetic cardiac valve has an open configuration in which the free ends of the prosthetic valve leaflets are disposed away from one another to allow antegrade blood-flow therepast, and a closed configuration in which the free ends of the prosthetic valve leaflets engage one another and substantially prevent retrograde bloodflow therepast.

At least a portion of the atrial skirt may be covered with tissue or a synthetic material. The atrial skirt may further comprise a plurality of barbs coupled thereto, the plurality of barbs adapted to anchor the atrial skirt into a superior surface of the patient's mitral valve. The atrial skirt may comprise a collapsed configuration and an expanded configuration. The collapsed configuration may be adapted for delivery to the patient's heart, and the expanded configuration may be radially expanded relative to the collapsed configuration and adapted to lie over a superior surface of the patient's native mitral valve, thereby anchoring the atrial skirt against a portion of the atrium. The atrial skirt may self-expand from the collapsed configuration to the radially expanded configuration when unconstrained. The atrial skirt may comprise one more radiopaque markers. The atrial skirt may comprise a plurality of axially oriented struts connected together with a connector element thereby forming a series of peaks and valleys. Some of the peaks and valleys may extend axially outward further than the rest of the atrial skirt, thereby forming an alignment element.

At least a portion of the annular region may be covered with tissue or a synthetic material. The annular region may have a collapsed configuration and an expanded configuration. The collapsed configuration may be adapted for delivery to the patient's heart, and the expanded configuration may be radially expanded relative to the collapsed configuration and adapted to conform with and to engage the native mitral valve annulus. The annular region may self-expand from the collapsed configuration to the expanded configuration when unconstrained. The annular region may comprise an asymmetrically D-shaped cross-section having a substantially flat anterior portion, and a cylindrically shaped posterior portion. The annular region may comprise a plurality of axially oriented struts connected together with a connector element thereby forming a series of peaks and valleys. One or more of the axially oriented struts may comprise one or more suture holes extending therethrough, the suture holes sized to receive a suture.

At least a portion of the ventricular skirt may be covered with tissue or a synthetic material. The ventricular skirt may comprise an asymmetrically D-shaped cross-section having a substantially flat anterior portion, and a cylindrically shaped posterior portion. The ventricular skirt may have a collapsed configuration and an expanded configuration. The collapsed configuration may be adapted for delivery to the patient's heart, and the expanded configuration may be radially expanded relative to the collapsed configuration and adapted to displace the native mitral valve leaflets radially outward. The ventricular skirt may self-expand from the collapsed configuration to the expanded configuration when unconstrained.

The ventricular skirt may further comprise a trigonal anchoring tab disposed on an anterior portion of the ventricular skirt. The trigonal anchoring tab may be adapted to being anchored against a first fibrous trigon on a first side of an anterior leaflet of the patient's mitral valve. Thus, the anterior leaflet and adjacent chordae tendineae may be captured between the trigonal anchoring tab and an anterior surface of the anchor. The ventricular skirt may further comprise a second trigonal anchoring tab that may be disposed on the anterior portion of the ventricular skirt. The second trigonal anchoring tab may be adapted to being anchored against a second fibrous trigon opposite the first fibrous trigon, such that the anterior leaflet and adjacent chordae tendineae are captured between the second trigonal anchoring tab and the anterior surface of the anchor. The ventricular skirt may further comprise a posterior ventricular anchoring tab disposed on a posterior portion of the ventricular skirt. The posterior ventricular anchoring tab may be adapted to being anchored over a posterior leaflet of the patient's mitral valve, such that the posterior ventricular anchoring tab is seated between the posterior leaflet and a ventricular wall of the patient's heart. The ventricular skirt may further comprise a plurality of barbs coupled thereto, and that may be adapted to anchor the ventricular skirt into heart tissue. The ventricular skirt may comprise a plurality of struts connected together with a connector element thereby forming a series of peaks and valleys. The one or more struts may comprise one or more suture holes extending therethrough, and that may be sized to receive a suture.

The plurality of prosthetic valve leaflets may comprise a tricuspid leaflet configuration. At least a portion of the one or more prosthetic valve leaflets may comprise tissue or a synthetic material. One or more of the plurality of prosthetic valve leaflets may be disposed over one or more commissure posts or struts that are radially biased inward relative to the ventricular skirt. The one or more commissure posts or struts may comprise one or more suture holes extending therethrough and that may be sized to receive a suture. The one or more prosthetic valve leaflets may be coupled to a commissure post or strut having a commissure tab adapted to releasably engage the commissure post or strut with a delivery device.

The prosthetic cardiac valve may further comprise an alignment element coupled to an anterior portion of the anchor. The alignment element may be adapted to be aligned with an aortic root of the patient's heart and disposed between two fibrous trigones of an anterior leaflet of the patient's mitral valve. The alignment element may be coupled with the atrial skirt. The prosthetic cardiac valve may further comprise a therapeutic agent coupled thereto, and adapted to being controllably eluted therefrom.

In still another aspect of the present invention, a delivery system for delivering a prosthetic cardiac valve to a patient's heart comprises an inner guidewire shaft having a lumen extending therethrough and adapted to slidably receive a guidewire, and a hub shaft concentrically disposed over the inner guidewire shaft. The delivery system also comprises a bell shaft slidably and concentrically disposed over the hub shaft, a sheath slidably and concentrically disposed over the bell shaft, and a handle near a proximal end of the delivery system. The handle comprises an actuator mechanism adapted to advance and retract the bell shaft and the sheath.

The system may further comprise the prosthetic cardiac valve which may be housed in the sheath in a radially collapsed configuration. The prosthetic cardiac valve may comprise an anchor having an atrial skirt, an annular region, and a ventricular skirt. The prosthetic valve may also comprise a plurality of prosthetic valve leaflets. Each of the leaflets may have a first end and a free end. The first end may be coupled with the anchor and the free end may be opposite of the first end. The prosthetic cardiac valve may have an open configuration in which the free ends of the prosthetic valve leaflets are disposed away from one another to allow antegrade bloodflow therepast. The valve may have a closed configuration in which the free ends of the prosthetic valve leaflets engage one another and substantially prevent retrograde blood flow therepast.

Proximal retraction of the sheath relative to the bell shaft may remove a constraint from the prosthetic cardiac valve thereby allowing the prosthetic cardiac valve to self-expand into engagement with the patient's native heart tissue. The prosthetic cardiac valve may be releasably coupled with the hub shaft, and proximal retraction of the bell shaft relative to the hub shaft may release the prosthetic cardiac valve therefrom. The actuator mechanism may comprise a rotatable wheel. The system may further comprise a tissue penetrating distal tip coupled to the hub shaft. The tissue penetrating distal tip may be adapted to pass through and expand an incision in the patient's heart. The system may further comprise a pin lock mechanism releasably coupled with the handle. The pin lock mechanism may limit proximal retraction of the sheath.

These and other embodiments are described in further detail in the following description related to the appended drawing figures.

BRIEF DESCRIPTION OF THE DRAWINGS

In the drawings, like reference numerals designate like or similar steps or components.

DETAILED DESCRIPTION OF THE INVENTION

Specific embodiments of the disclosed device, delivery system, and method will now be described with reference to the drawings. Nothing in this detailed description is intended to imply that any particular component, feature, or step is essential to the invention.

Figure 1:
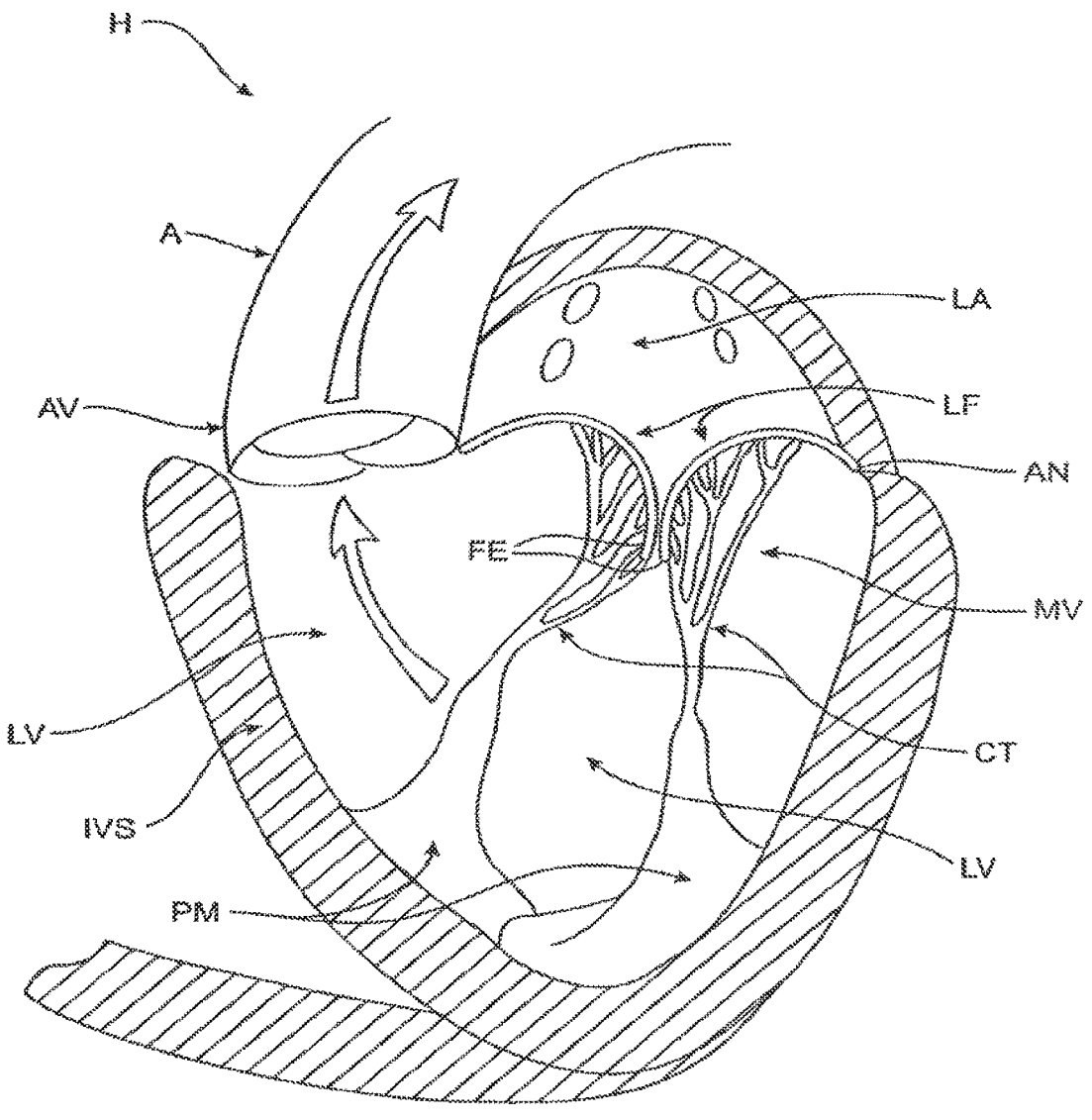
FIG. 1 is a schematic illustration of the left ventricle of a heart showing blood flow during systole with arrows.

Cardiac Anatomy. The left ventricle LV of a normal heart H in systole is illustrated in FIG. 1. The left ventricle LV is contracting and blood flows outwardly through the aortic valve AV, a tricuspid valve in the direction of the arrows. Bach flow of blood or "regurgitation" through the mitral valve MV is prevented since the mitral valve is configured as a "check valve" which prevents back flow when pressure in the left ventricle is higher than that in the left atrium LA, The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
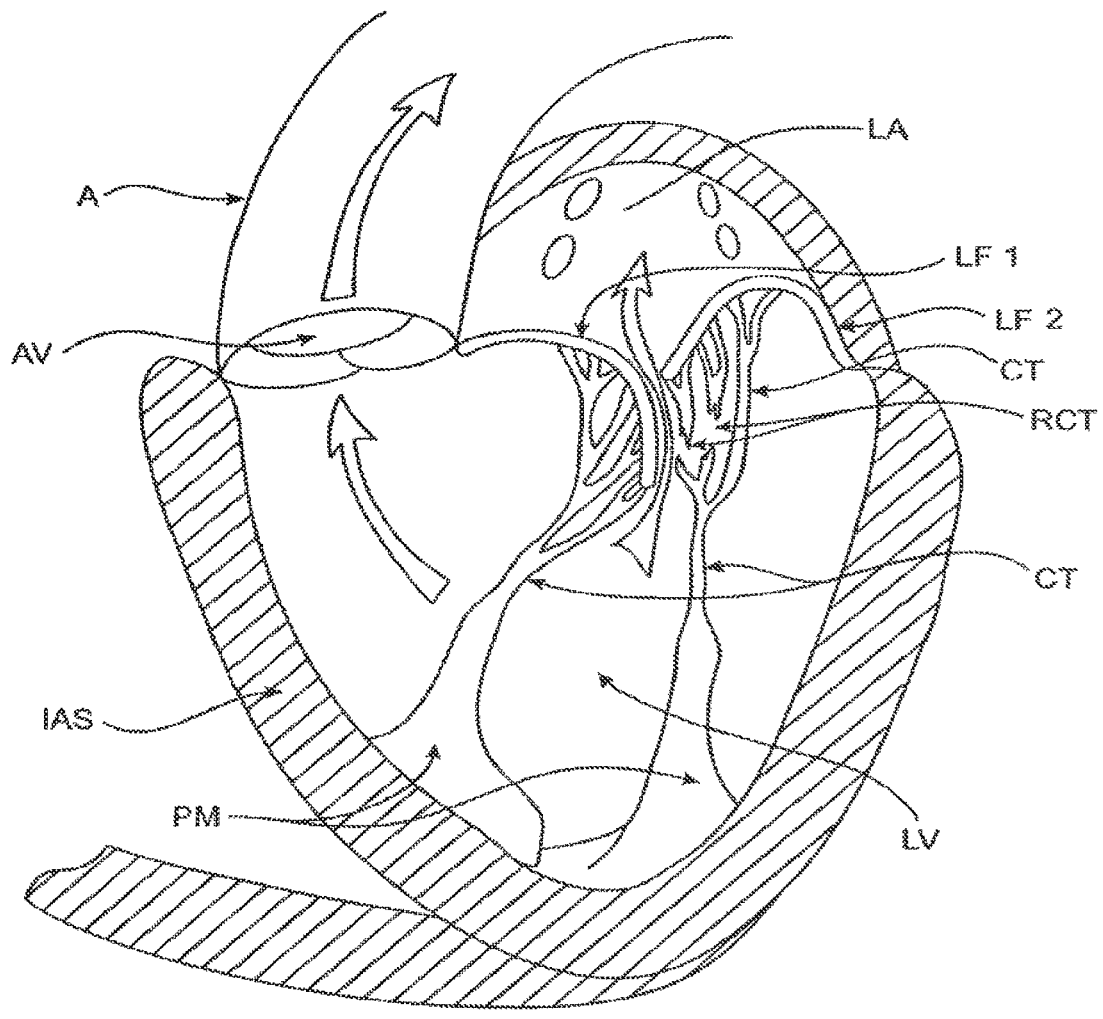
FIG. 2 is a schematic illustration of the left ventricle of a heart having prolapsed leaflets in the mitral valve.
Figure 3:
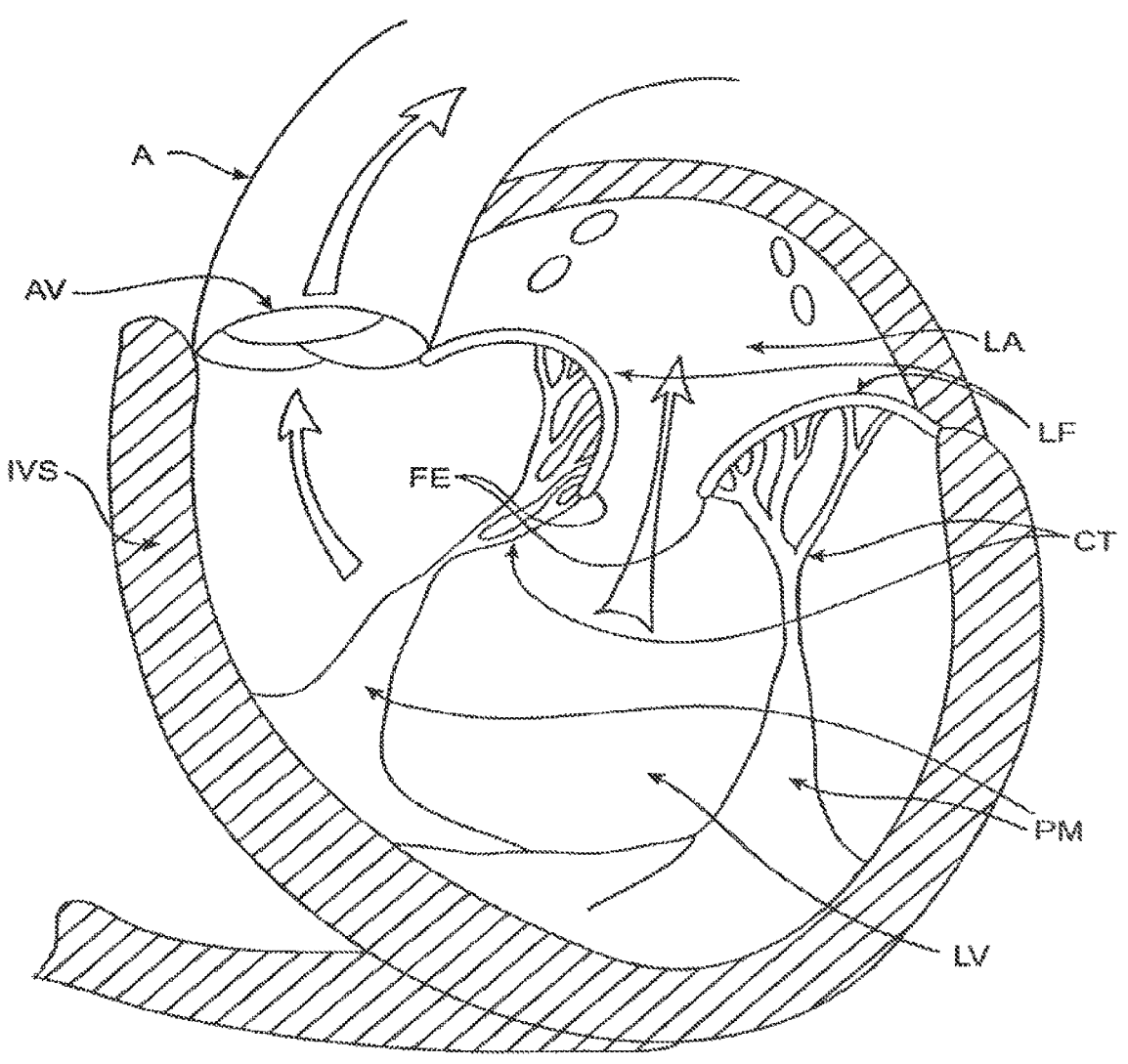
FIG. 3 is a schematic illustration of a heart in a patient suffering from cardiomyopathy where the heart is dilated and the leaflets do not meet.
Figure 4:
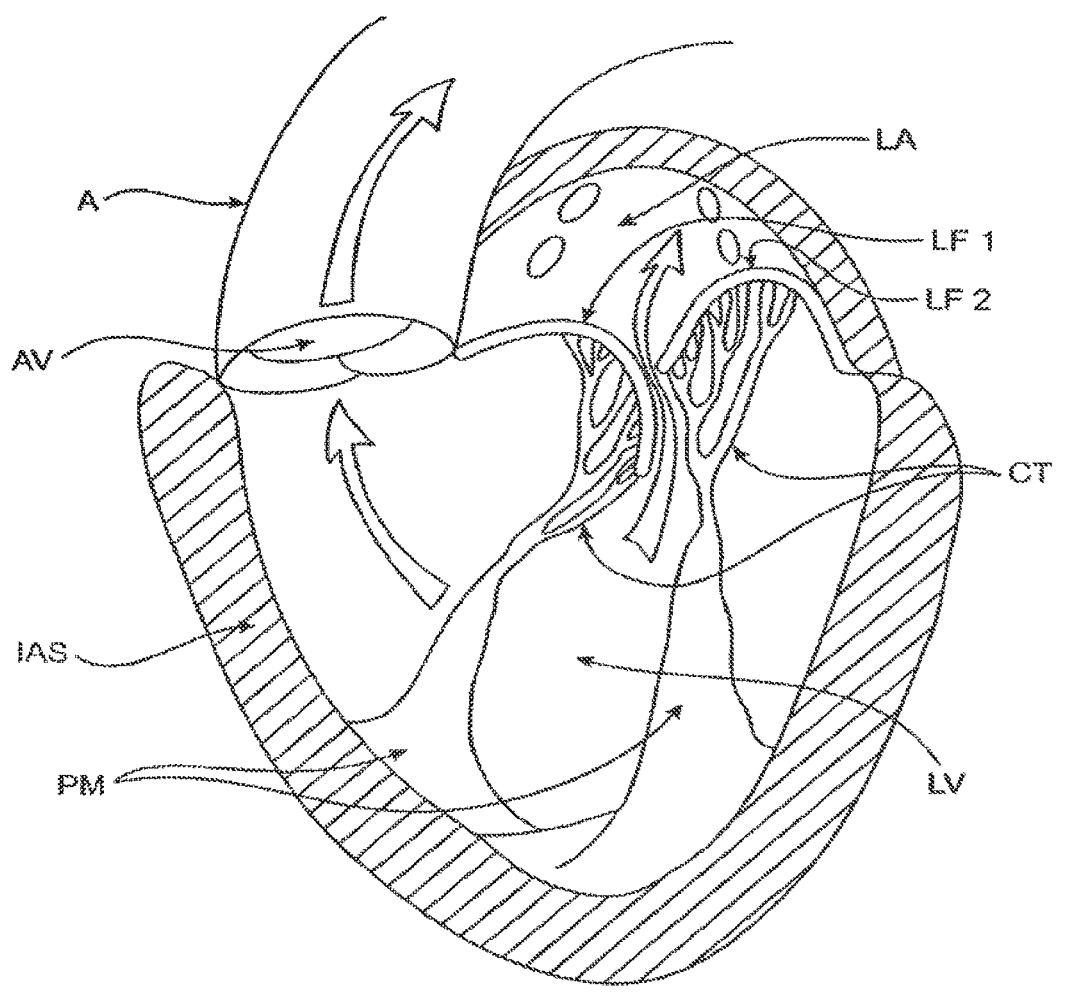
FIG. 4 illustrates mitral valve regurgitation in the left ventricle of a heart having impaired papillary muscles.

Referring now to FIGS. 2-4, a number of structural defects in the heart can cause mitral prolapse since inadequate tension is transmitted to the leaflet via the chordae. While the other leaflet maintains a normal profile, the two valve leaflets do not properly meet and leakage from the left ventricle LV into the left atrium LA will occur, as shown by the arrow.

Figure 3A:
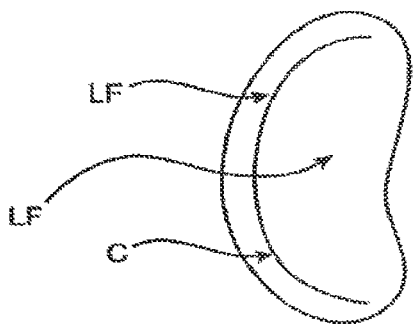
FIG. 3A shows, normal closure of the leaflets.
Figure 3B:
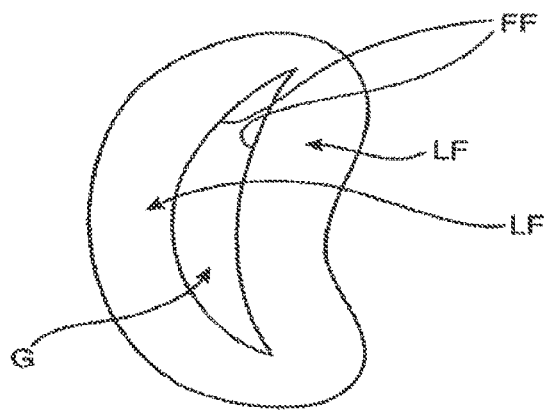
FIG. 3B shows abnormal closure in the dilated heart.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated, Leakage again occurs from the left ventricle LV to the left atrium LA, as shown by the arrow.

Figure 5A:
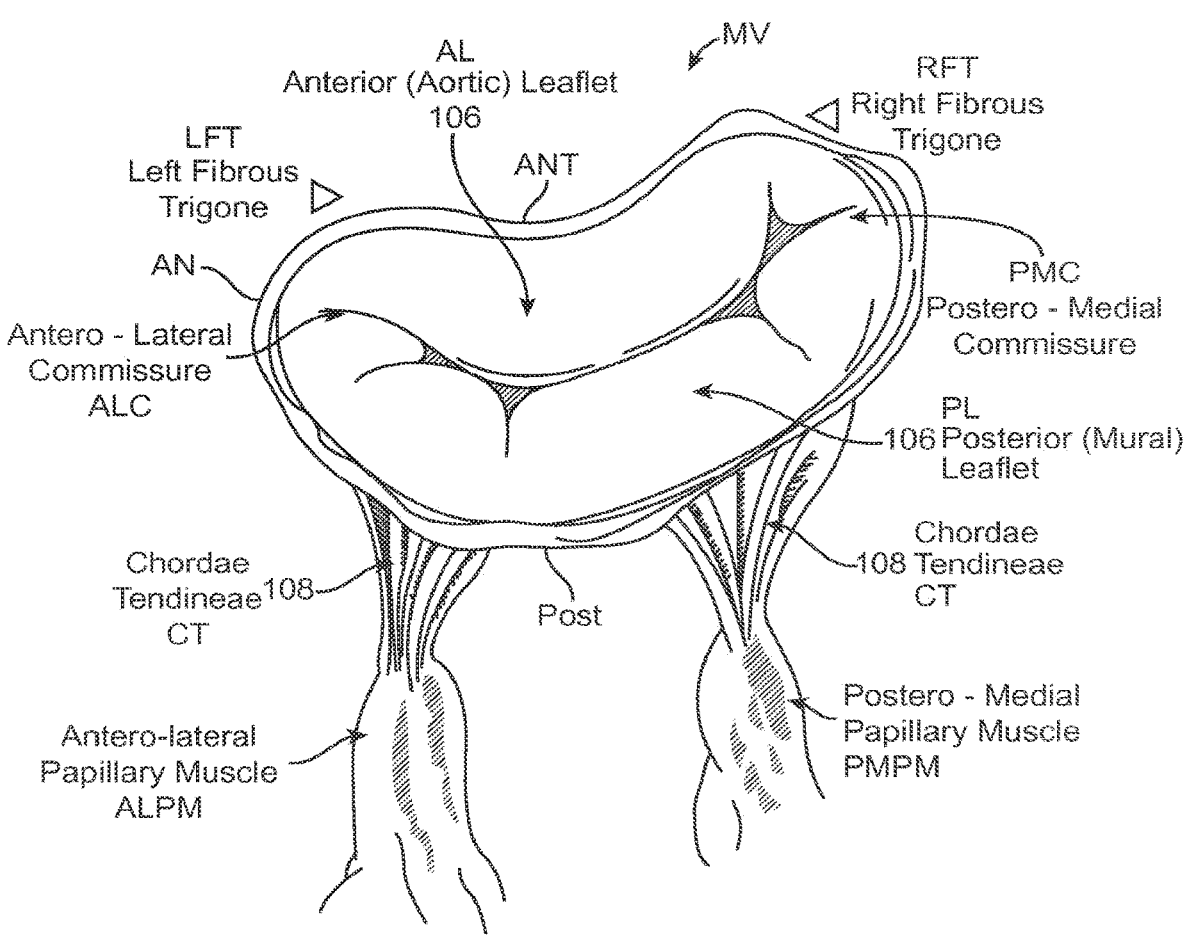
FIGS. 5A-5B illustrate the mitral valve.
Figure 5B:
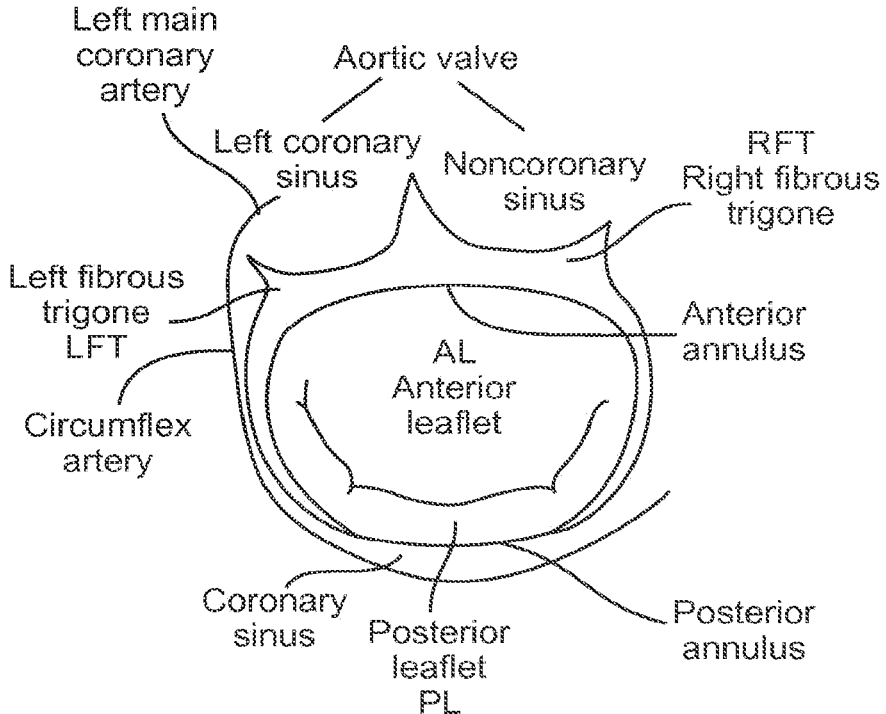

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted by generally by the solid triangles. FIG. 5B more clearly illustrates the left and right fibrous trigones, LFT, RFT.

While various surgical techniques as well as implantable devices have been proposed and appear to be promising treatments for mitral regurgitation, surgical approaches can require a lengthy recovery period, and implantable devices have varying clinical results. Therefore, there still is a need for improved devices and methods for treating mitral regurgitation. While the embodiments disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc, as well as other valves in the body such as venous valves.

Prosthetic Valve. Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the valve to the patients heart, and a valve mechanism, either a mechanical valve, a valve with animal tissue, or combinations thereof. The prosthetic valve once implanted, takes over for malfunctioning native valve, thereby reducing or eliminating valvar insufficiency. While some of these valves appear promising, there still is a need for improved valves. The following discloses exemplary embodiments of a prosthetic valve, a delivery system for the prosthetic valve, and methods of delivering the valve that overcome some of the challenges associated with existing prosthetic valves.

Figure 6:
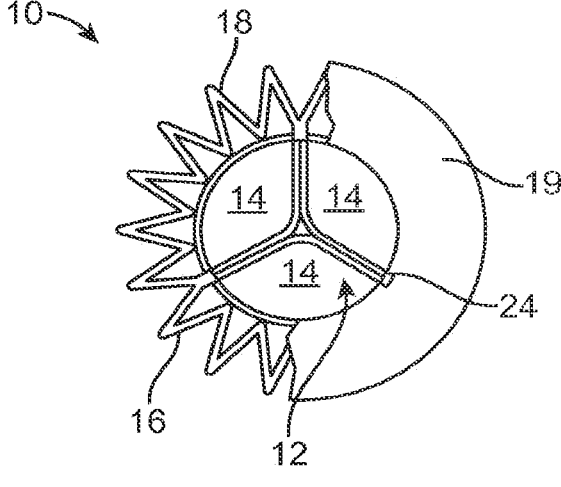
FIG. 6 illustrates a bottom, partial cross-sectional view of an exemplary prosthetic mitral valve.
Figure 7:
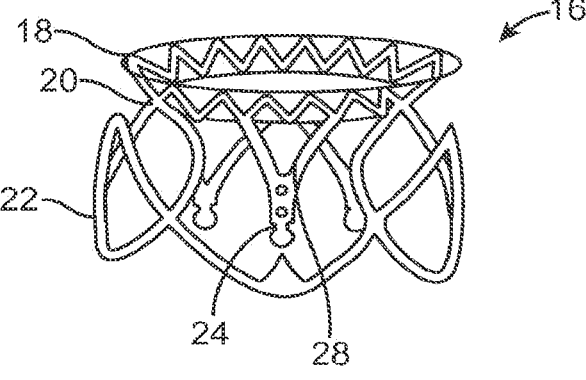
FIG. 7 is a perspective view of the anchor portion of the prosthetic mitral valve seen in FIG. 6.

Referring now to FIGS. 6-7, exemplary embodiments of a mitral valve prosthesis generally designated with reference numeral 10 comprise tricuspid tissue-type prosthetic one-way valve structure 12 comprising leaflets 14 affixed within self-expanding or expandable anchor portion 16 having a geometry that expands into low profile atrial skirt region 18, annular region 20, ventricular skirt region 22, and a plurality of leaflet commissures 24 (also referred to herein as commissure posts) extending axially in a cantilevered fashion downstream into the sub-annular space defined by ventricular skirt region 22. FIG. 6 shows a partial cross-section of the valve 10 from the patient's left ventricle looking upward toward the right atrium. The atrial skirt region 18 is anchored to a lower portion of the right atrium 19. The valve leaflets 14 have an open position (not illustrated) and a closed position illustrated in FIG. 6. In the open position, the leaflets 14 are displaced away from one another to allow blood flow therepast, and in the closed position, the leaflets 14 engage one another to close the valve and prevent retrograde blood flow therepast. The valve commissures 24 may be configured to optimize the efficiency of the prosthetic valve structure 12 and the load distribution on the leaflets 14 by providing for the attachment of the leaflets 14 along arcuate seams 28 (best seen in FIG. 7), and by being made selectively flexible at different points or zones along their axial length through the addition/deletion of reinforcing struts.

FIG. 7 shows a perspective view of the anchor portion 16 of the valve 10 which has been formed from a series of interconnected struts. The atrial skirt region 18 forms an annular flanged region on the anchor to help secure an upper portion of the prosthetic valve in the atrium, and the annular region 20 is a cylindrical region for anchoring the valve along the native valve annulus. The ventricular skirt region 22 similarly is cylindrically shaped and helps anchor a lower portion of the valve in the patients left ventricle. Any portion, or all of the anchor may be covered with tissue such as pericardium or other tissues disclosed herein, or a synthetic material such as Dacron or ePTFE may be used to cover the anchor. The covering helps to seal the anchor to the native valve, and this helps funnel blood into and through the prosthetic valve, rather than around the valve. In some embodiments, the anchor may remain uncovered. The prosthetic valve has an expanded configuration and a collapsed configuration. The collapsed configuration has a low profile cylindrical shape that is suitable for mounting on a delivery system and delivery is preferably made either transluminally on a catheter, or transapically through the heart wall. The expanded configuration (as illustrated) allow the prosthetic valve to be anchored into a desired position.

Figure 8A:
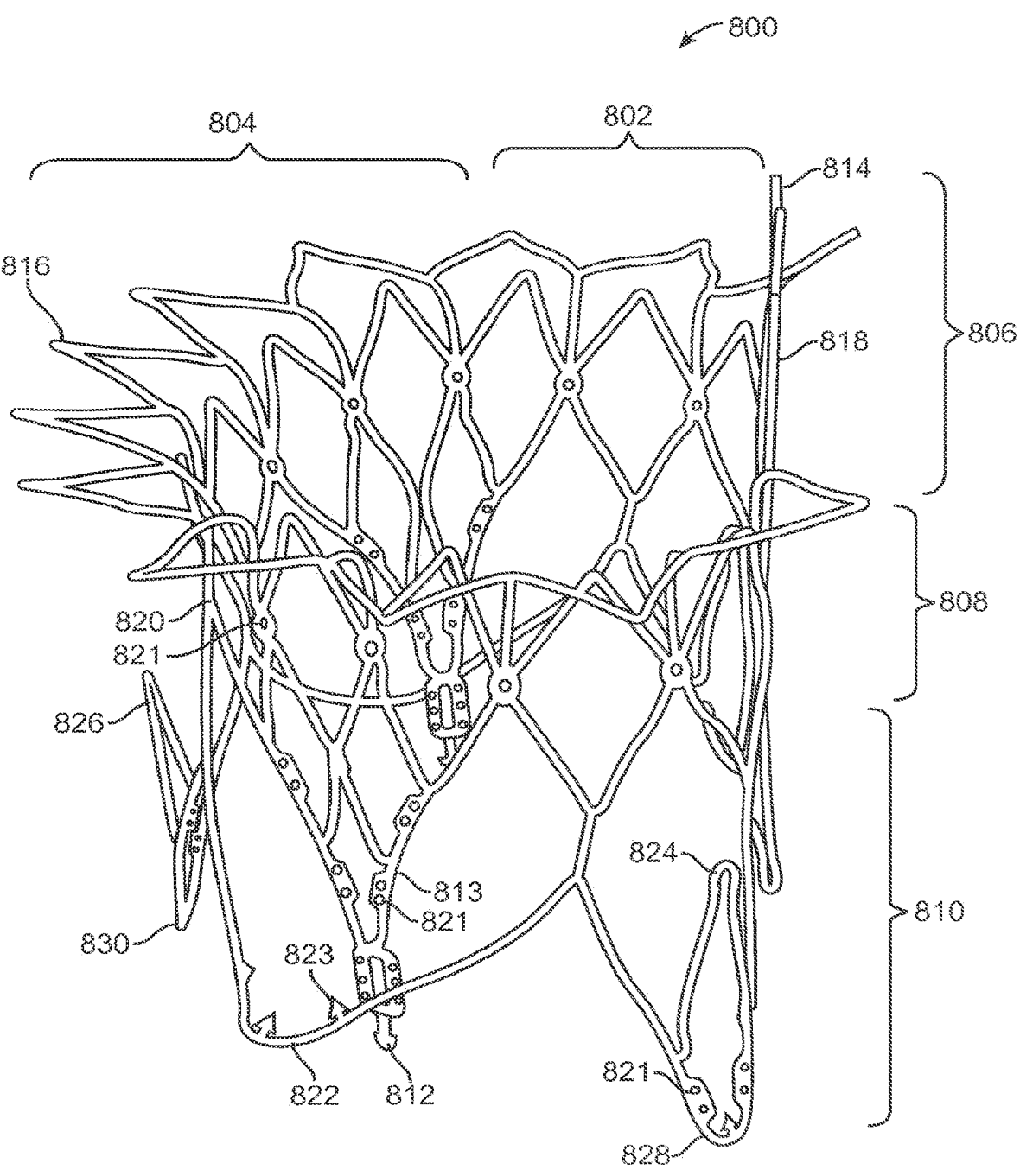
FIG. 8A is a perspective view of a prosthetic mitral valve.
Figure 8B:
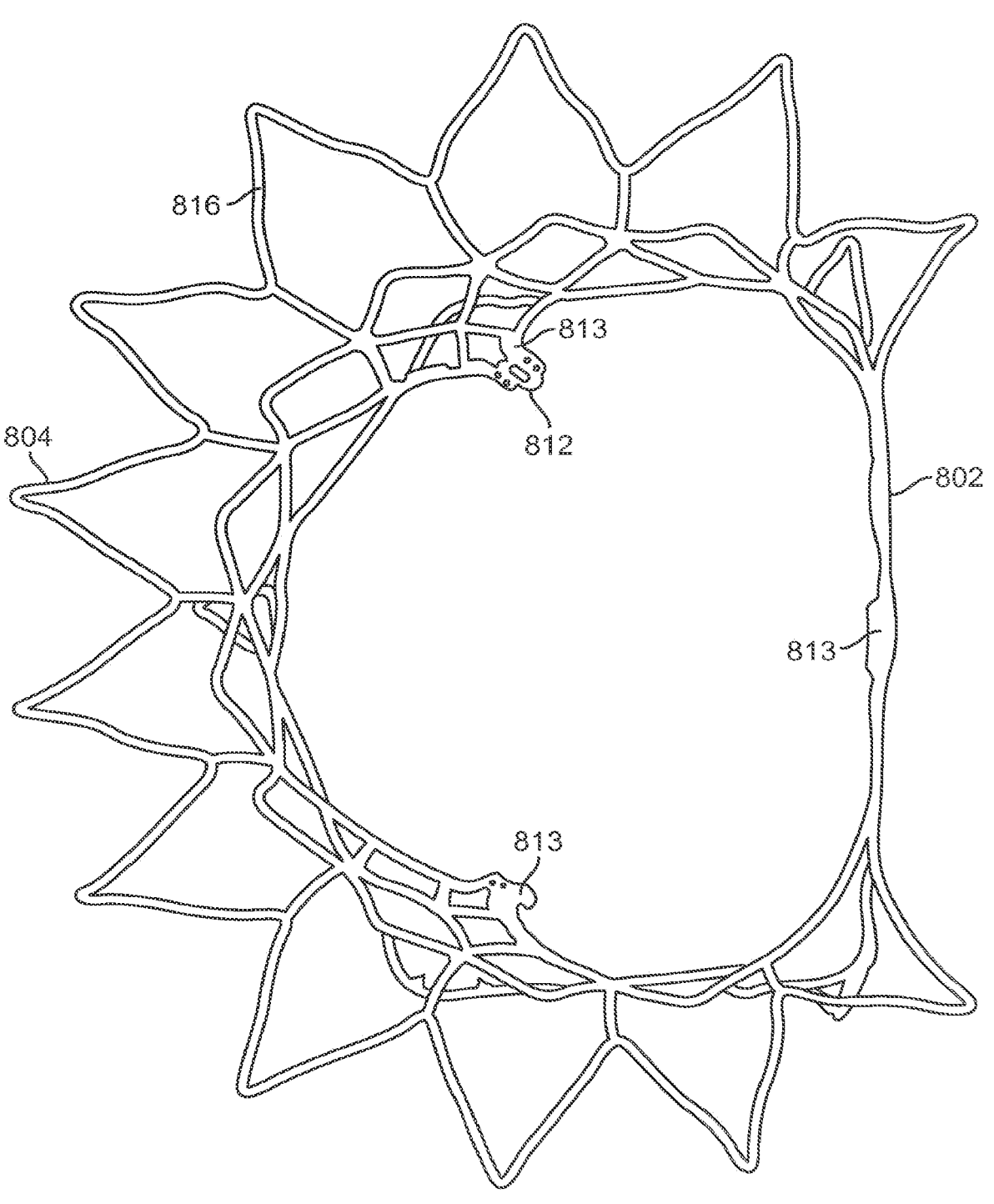
FIG. 8B is a top view from the atrium of the prosthetic valve in FIG. 8A.

FIG. 8A illustrates a perspective view of a preferred embodiment of a prosthetic mitral valve with optional coverings removed to allow visibility of the anchor struts. FIG. 8B illustrates a top view of the prosthetic valve in FIG. 8A from the atrium looking down into the ventricle. The valve 800 includes an asymmetrical expanded anchor portion having a D-shaped cross-section. As shown, the anchor portion generally comprises anterior 802 and posterior 804 aspects along the longitudinal axis thereof, as well as atrial 806, annular 808 and ventricular 810 regions that correspond generally to the atrial skirt 18, annular 20 and ventricular skirt 22 regions of the embodiment described above in FIGS. 6-7. Commissures (also referred to herein as commissure posts) 813 also correspond generally to the leaflets 14 of the embodiment in FIGS. 6-7. The prosthetic valve 800 has a collapsed configuration and an expanded configuration. The collapsed configuration is adapted to loading on a shaft such as a delivery catheter for transluminal delivery to the heart, or on a shaft for transapical delivery through the heart wall. The radially expanded configuration is adapted to anchor the valve to the patient's native heart adjacent the damaged valve. In order to allow the valve to expand from the collapsed configuration to the expanded configuration, the anchor portion of the valve may be fabricated from a self-expanding material such as a nickel titanium alloy like nitinol, or it may also be made from spring temper stainless steel, or a resilient polymer. In still other embodiments, the anchor may be expandable with an expandable member such as a balloon. In preferred embodiments, the anchor is fabricated by laser cutting, electrical discharge machining (EDM), or photochemically etching a tube. The anchor may also be fabricated by photochemically etching a flat sheet of material which is then rolled up with the opposing ends welded together.

The atrial skirt portion 816 forms a flanged region that helps to anchor the prosthetic valve to the atrium, above the mitral valve. The atrial skirt includes a plurality of triangular fingers which extend radially outward from the anchor to form the flange. The posterior 804 portion of the atrial skirt 816 is generally round or circular, while a portion of the anterior 802 part of the atrial skirt 816 is flat. Thus, the atrial skirt region preferably has a D-shaped cross-section. This allows the prosthetic valve to conform to the patient's cardiac anatomy without obstructing other portions of the heart, as will be discussed below. Each triangular finger is formed from a pair of interconnected struts. The triangular fingers of the atrial skirt generally are bent radially outward from the central axis of the prosthetic valve and lie in a plane that is transverse to the valve central axis. In some embodiments, the atrial skirt lies in a plane that is substantially perpendicular to the central axis of the valve. The anterior portion 802 of the atrial skirt 806 optionally includes an alignment element 814 which may be one or more struts which extend vertically upward and substantially parallel to the prosthetic valve. The alignment element 814 may include radiopaque markers (not illustrated) to facilitate visualization under fluoroscopy. The alignment element helps the physician to align the prosthetic valve with the native mitral valve anatomy, as will be discussed later.

Disposed under the atrial skirt region is the annular region 820 which also has a collapsed configuration for delivery, and an expanded configuration for anchoring the prosthetic valve along the native valve annulus. The annular region is also comprised of a plurality of interconnected struts that form a series of cells, preferably closed. Suture holes 821 in some of the struts allow tissue or other coverings (not illustrated) to be attached to the annular region. Covering all or a portion of the anchor with tissue or another covering helps seal the anchor against the heart valve and adjacent tissue, thereby ensuring that blood is funneled through the valve, and not around it. The annular region may be cylindrical, but in preferred embodiments has a posterior portion 804 which is circular, and an anterior portion 802 which is flat, thereby forming a D-shaped cross-section. This D-shaped cross-section conforms better to the native mitral valve anatomy without obstructing blood flow in other areas of the heart.

The lower portion of the prosthetic valve includes the ventricular skirt region 828. The ventricular skirt region also has a collapsed configuration for delivery, and an expanded configuration for anchoring. It is formed from a plurality of interconnected struts that form a series of cells, preferably closed, that can radially expand. The ventricular skirt in the expanded configuration anchors the prosthetic valve to the ventricle by expanding against the native mitral valve leaflets. Optional barbs 823 in the ventricular skirt may be used to further help anchor the prosthetic valve into the ventricular tissue, Barbs may optionally also be included in the atrial skirt portion as well as the annular region of the anchor. Additionally, optional suture holes 821 in the ventricular skirt may be used to help suture tissue or another material to the ventricular skirt region, similarly as discussed above. The anterior 802 portion of the ventricular skirt may be flat, and the posterior 804 portion of the ventricular skirt may be circular, similarly forming a D-shaped cross-section to anchor and conform to the native anatomy without obstructing other portions of the heart. Also, the lower portions of the ventricular skirt serve as deployment control regions since the lower portions can remain sheathed thereby constraining the ventricular skirt from radial expansion until after the optional ventricular trigonal tabs and posterior tab have expanded, as will be explained in greater detail below.

The ventricular skirt portion may optionally also include a pair of ventricular trigonal tabs 824 on the anterior portion of the anchor (only 1 visible in this view) for helping to anchor the prosthetic valve as will be discussed in greater detail below. The ventricular skirt may also optionally include a posterior tab 826 on a posterior portion 804 of the ventricular skirt for anchoring the prosthetic valve to a posterior portion of the annulus. The trigonal tabs 824 or the posterior tab 826 are tabs that extend radially outward from the anchor, and they are inclined upward in the upstream direction.

The actual valve mechanism is formed from three commissures posts (also referred to as commissures) 813 which extend radially inward toward the central axis of the anchor in a funnel or cone like shape. The commissures 813 are formed from a plurality of interconnected struts that create the triangular shaped commissures. The struts of the commissures may include one or more suture holes 821 that allow tissue or a synthetic material to be attached to the commissures. In this exemplary embodiment, the valve is a tricuspid valve, therefore it includes three commissures 813. The tips of the commissures may include a commissure tab 812 (also referred to as a tab) for engaging a delivery catheter. In this embodiment, the tabs have enlarged head regions connected to a narrower neck, forming a mushroom-like shape. The commissures may be biased in any position, but preferably angle inward slightly toward the central axis of the prosthetic valve so that retrograde blood flow forces the commissures into apposition with one another to close the valve, and antegrade blood flow pushes the commissures radially outward, to fully open the valve. FIG. 8B is a top view illustrating the prosthetic valve of FIG. 8A from the atrial side, and shows the preferred D-shaped cross-section.

Figure 9A:
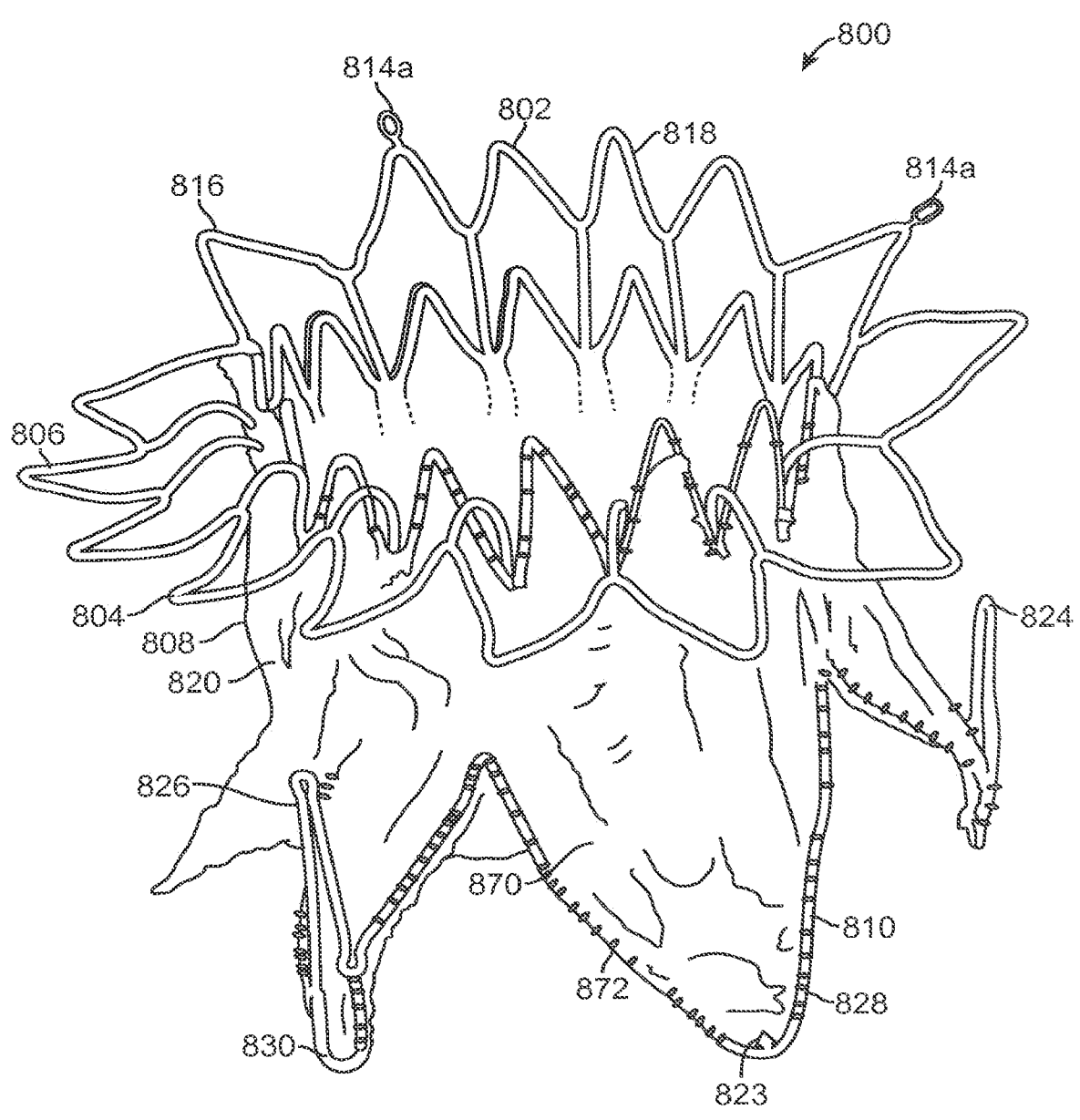
FIG. 9A illustrates a perspective view of the prosthetic valve in FIG. 8A from the atrium.

FIG. 9A illustrates the prosthetic mitral valve of FIGS. 8A-8B with a covering 870 coupled to portions of the anchor with suture 872. This view is taken from an atrial perspective. In this embodiment, the covering is preferably pericardium which may come from a number of sources as disclosed elsewhere in this specification. In alternative embodiments, the covering may be a polymer such as Dacron polyester, ePTFE, or another synthetic material. The covering is preferably disposed over the annular region 820 and the ventricular skirt region 828, and in some embodiments the anterior ventricular trigonal 824 tabs and the ventricular posterior tab 830 may also be covered with the same or a different material. The covering helps seal the anchor against the adjacent tissue so that blood funnels through the valve mechanism. In this embodiment, the atrial skirt is left uncovered, as well as tabs 824, 830. Additionally, radiopaque markers 814a form a portion of the alignment element and facilitate visualization of the prosthetic valve under fluoroscopy which is important during alignment of the valve.

Figure 9B:
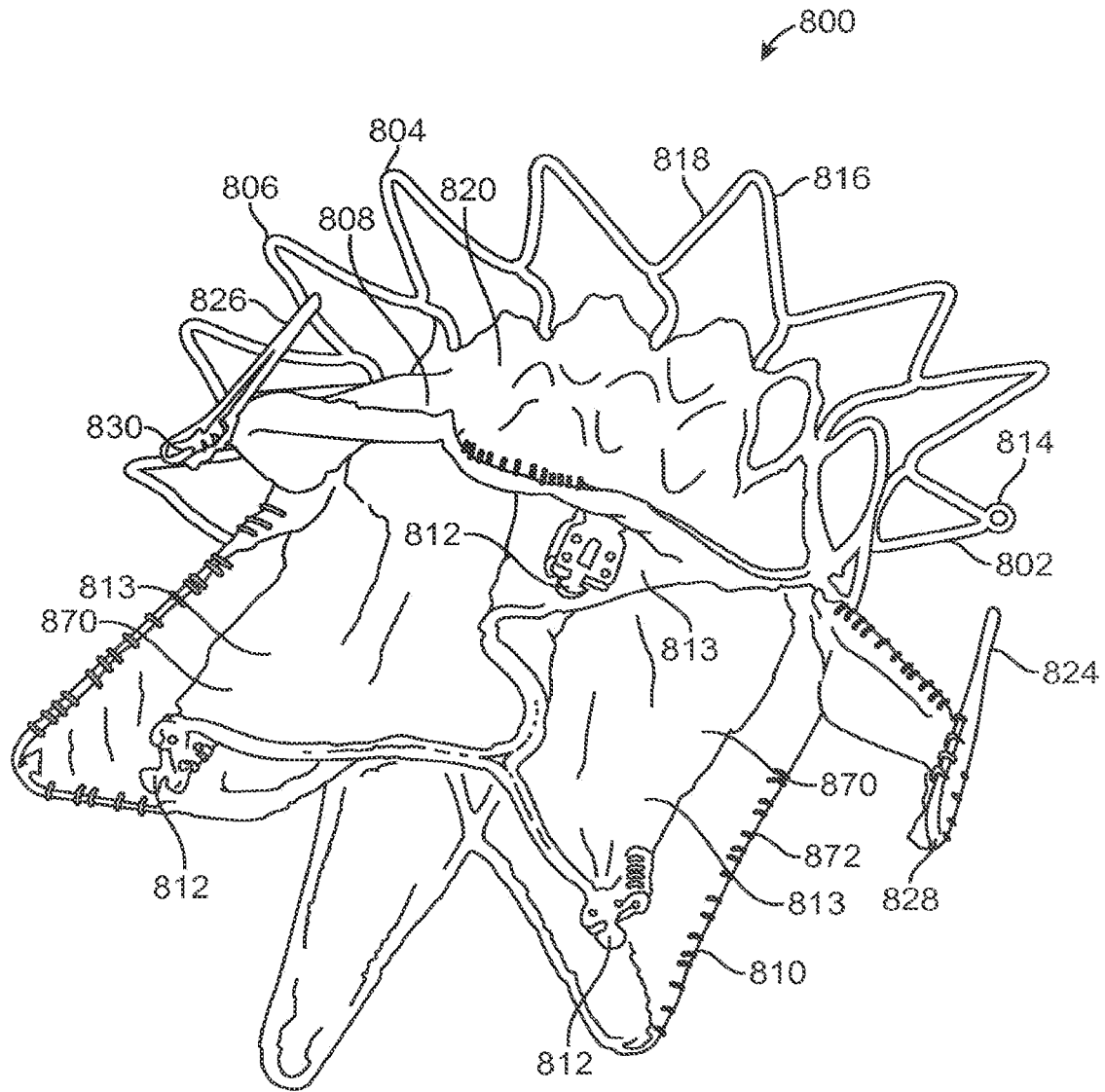
FIG. 9B illustrates a perspective view of the prosthetic valve in FIG. 8A from the ventricle.

FIG. 9B is a perspective view of the prosthetic mitral valve seen in FIG. 9A, as seen from the ventricle. The struts of the valve commissures are covered with the same material or a different material as the annular and ventricular regions as discussed above, thereby forming the tricuspid valve leaflets 813. FIG. 9B shows the valve in the closed configuration where the three leaflets are engaged with one another preventing retrograde blood flow. Commissure tabs 812 remain uncovered and allow the commissures to be coupled with a delivery device as will be explained below. The prosthetic valve in FIGS. 9A-9B may be sterilized so they are suitable for implantation in a patient using methods known in the art.

Figure 10:
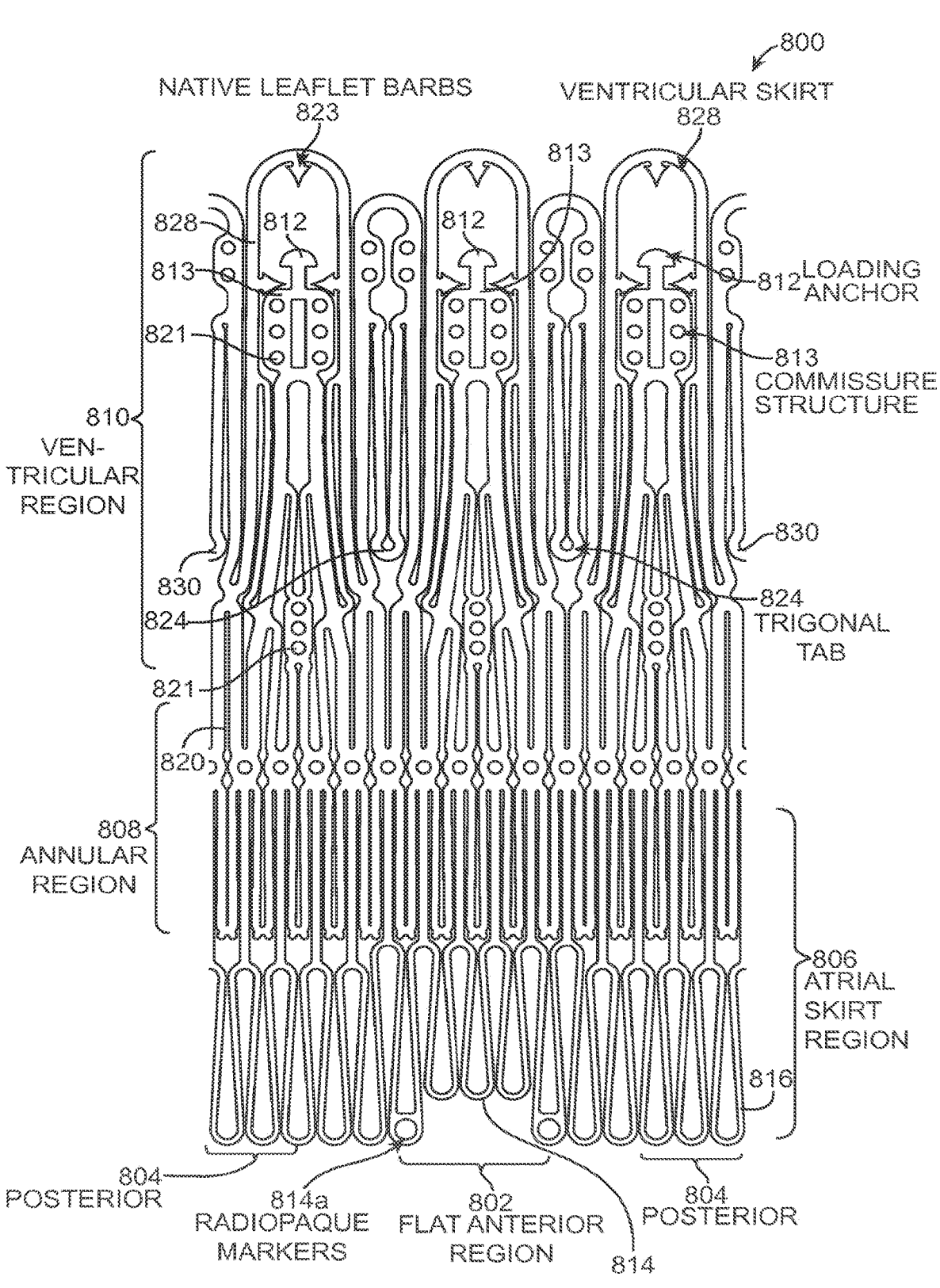
FIG. 10 illustrates the prosthetic valve of FIG. 8A uncovered and unrolled in a flat pattern.

FIG. 10 illustrates the prosthetic valve of FIG. 9A with the covering removed, and the remaining anchor unrolled and flattened out. The prosthetic valve 800 is formed from a plurality of interconnected struts. For example, the atrial skirt region 806 includes a plurality of interconnected struts that form a series of peaks and valleys. The flat anterior region 802 of the prosthetic valve has its peaks and valleys axially offset from those of the remaining portion of the atrial skirt, and this region becomes a part of the alignment element 814. Radiopaque markers 814a are disposed on either side of the offset peaks and valleys and help with visualization during implantation of the valve. An axially oriented connector joins the struts of the skirt region 806 with the struts of the annular region 808. The annular region is also comprised of a plurality of axially oriented and interconnected struts that form peaks and valleys. Connector struts couple struts of the annular region with the struts of the ventricular region 810. The ventricular region also includes a plurality of interconnected struts that form peaks and valleys. Additionally, the struts form the leaflet commissures 813, the ventricular skirt 828, as well as the trigonal and posterior tabs 824, 830. Suture holes 821 are disposed along the struts of the annular region as well as the ventricular region to allow attachment of a cover such as pericardium or a polymer such as Dacron or ePTFE. Barbs 823 are disposed along the ventricular skirt 828 to help anchor the prosthetic valve to adjacent tissue. Commissure tabs or tabs 812 are disposed on the tips of the commissures 813 and may be used to releasably couple the prosthetic valve with a delivery system as will be described below. One of skill in the art will appreciate that a number of strut geometries may be used, and additionally that strut dimensions such as length, width, thickness, etc. may be adjusted in order to provide the anchor with the desired mechanical properties such as stiffness, radial crush strength, commissure deflection, etc. Therefore, the illustrated geometry is not intended to be limiting.

Once the flat anchor pattern has been formed by EDM, laser cutting, photochemical etching, or other techniques known in the art, the anchor is radially expanded into a desired geometry. The anchor is then heat treated using known processes to set the shape. Thus, the anchor may be loaded onto a delivery catheter in a collapsed configuration and constrained in the collapsed configuration with a constraining sheath. Removal of the constraining sheath will allow the anchor to self-expand into its unbiased pre-set shape. In other embodiments, an expandable member such as a balloon may be used to radially expand the anchor into its preferred expanded configuration.

Delivery Systems. FIGS. 11-15C show a delivery apparatus 1124 fashioned to deliver a prosthetic mitral valve to the heart transapically. However, one of skill in the art will appreciate that the delivery system may be modified and relative motion of the various components adjusted to allow the device to be used to deliver a prosthetic mitral valve transseptally. The delivery apparatus is generally comprised of a handle 1101 that is the combination of a handle section 1102 and a handle section 1103 (best seen in FIG. 12), as well as a flexible tip 1110 that can smoothly penetrate the apex of the heart, and a sheath catheter 1109 which houses several additional catheters that are designed to translate axially and will be described in detail below.

The handle 1101 includes a female threaded leer adaptor 1113 which connects to a Tuohy Borst adaptor 1114 in order to provide a hemostatic seal with a 0.035" diameter guide wire (not shown). The female threaded leer adaptor 1113 is in threaded contact with the proximal section of the handle 1101 through a threaded port 1131 (best seen in FIG. 12).

Figure 11:
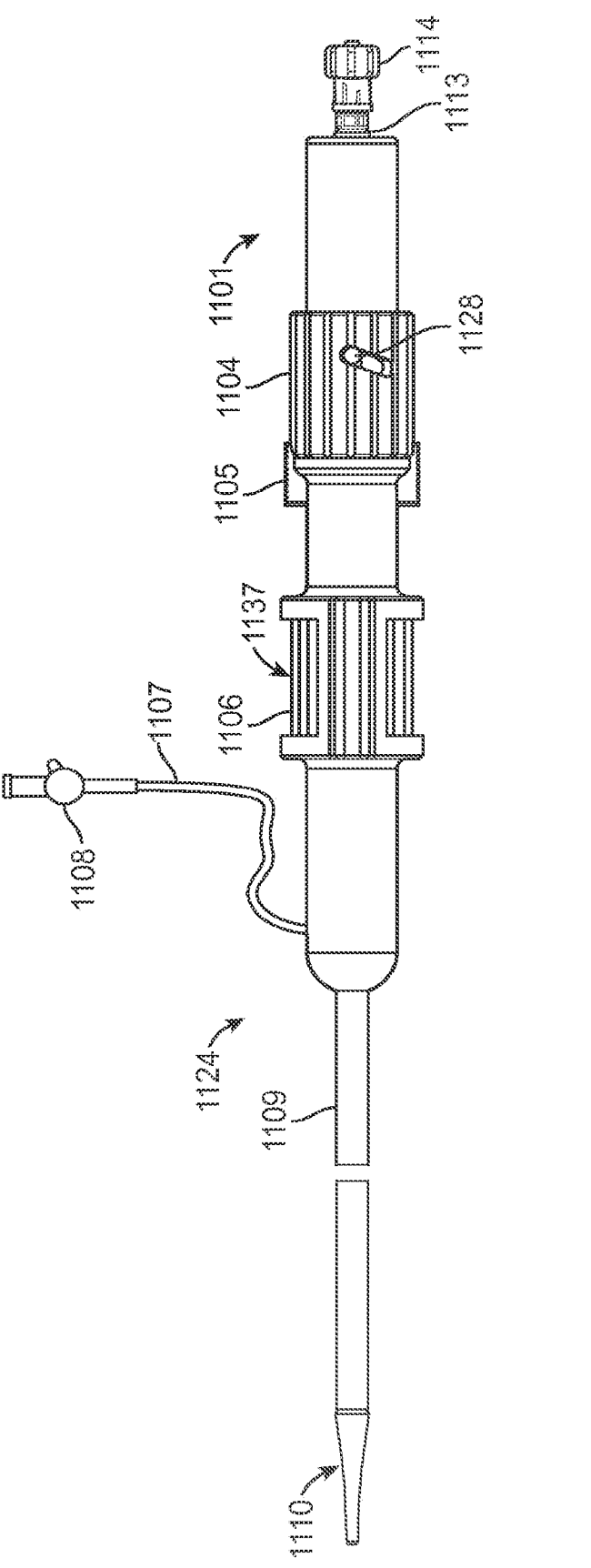
FIG. 11 is a side view of a delivery device for implantation of a prosthetic valve.

As can be seen in FIG. 11, the handle 1101 provides location for the control mechanisms used to position and deploy a prosthetic mitral valve. The handle 1101 provides housing for a thumbwheel 1106 that can be accessed through a window 1137 that appears on both the top and bottom of the handle 1101. The thumbwheel 1106 internally mates with a threaded insert 1115 (best seen in FIG. 12) that actuates the sheath catheter 1109, and the mechanics of this interaction will be explained in detail below.

FIG. 11 also shows a deployment thumbwheel 1104 that provides linear translation to a deployment catheter 1120 (best seen in FIG. 12) when turned, since the turning motion of the deployment thumbwheel 1104 acts as a power screw, pushing the peg 1128 forward and distally from the user. The mechanics behind the peg 1128 will be further detailed below. The thumbwheel lock 1105 provides a security measure against unwanted rotation of the deployment thumbwheel 1104 by acting as a physical barrier to rotation. In order to turn the deployment thumbwheel 1104 the user must push forward the thumbwheel lock 1105, disengaging it from two slots 1147 (seen in FIG. 12) in the deployment thumbwheel 1105.

As can also be seen in FIG. 11, a bleed valve 1108 and fluid line 1107 are connected to an internal mechanism in the distal portion of the handle 1101, which provides a hemostatic seal for the sheath catheter 1109. The details of this connection will be described below.

Figure 12:
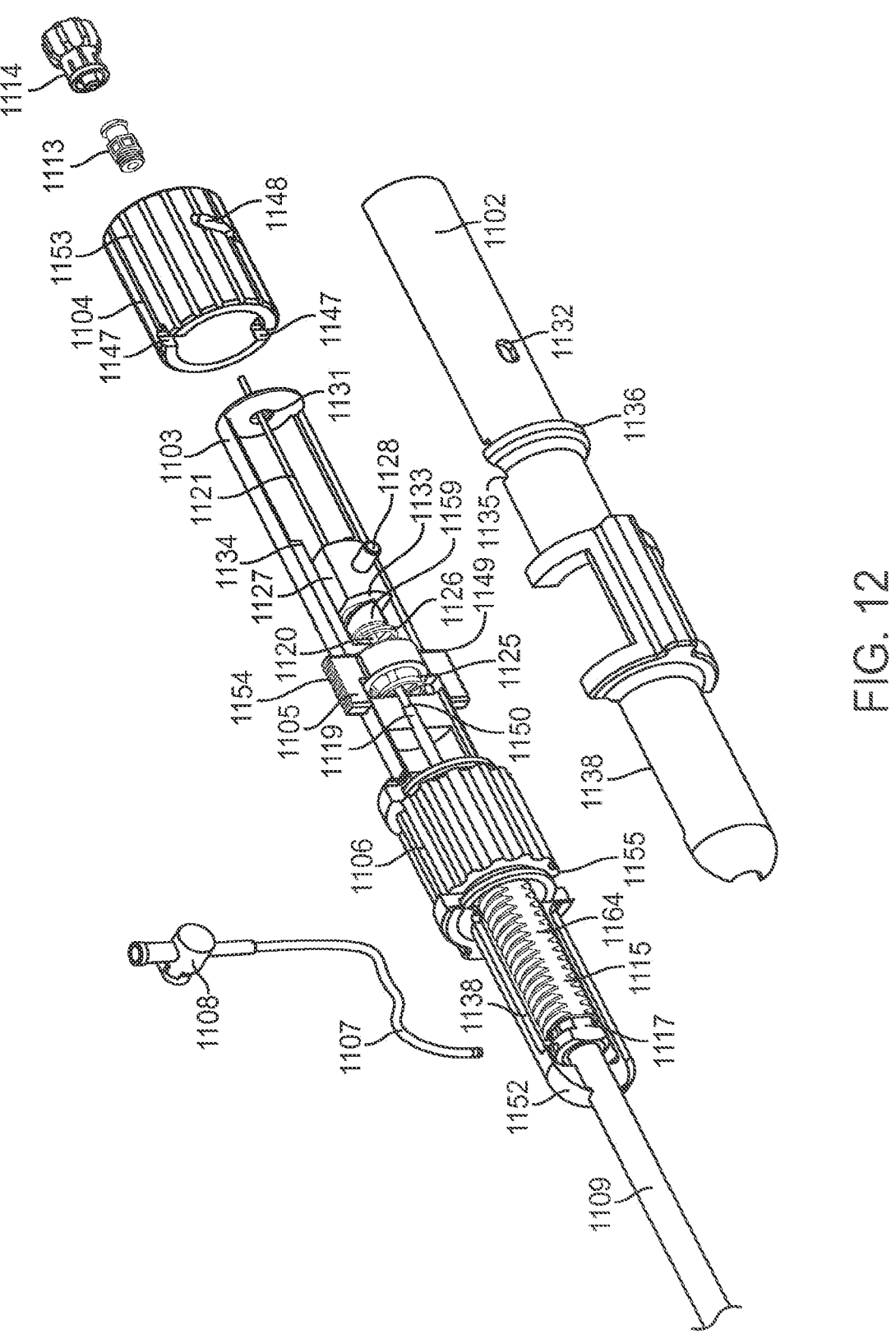
FIG. 12 is a perspective exploded view of a proximal portion of the delivery device in FIG. 11.

Internal mechanics of the delivery apparatus 1124 are illustrated in detail in FIG. 12, and the following descriptions will reveal the interactions between individual components, and the manner in which those components combine in order to achieve a prosthetic heart valve delivery apparatus.

As seen in FIG. 12, a handle section 1103 and handle section 1102 combine to create a handle 1101 that forms the basis of the delivery apparatus 1124. In order to advance the sheath catheter 1109 during valve loading, or retract the sheath catheter 1109 during deployment, a rotatable thumbwheel 1106 is in threaded contact (internal threads 1129 seen in FIG. 14) with a threaded insert 1115 (external threads 1130 of FIG. 13) that translates linearly along the axis of the delivery apparatus, from a proximal position to a distal position. The sheath catheter 1109 is in mating contact with the threaded insert 1115 and is fastened through the use of a collar 1117 that aligns and mates the collar with the insert. The collar 1117 is fastened with screws 1116 (best seen in DETAIL A in FIG. 14) to the threaded insert 1115 and contains a fluid port 1142 (best seen in DETAIL A in FIG. 14) that provides location for the fluid line 1117 so that hemostasis can be maintained between the patient and delivery apparatus. An O-ring 1118 (best seen in DETAIL A in FIG. 14) seals the stationary catheter 1119 (best seen in FIG. 14) against the sheath catheter 1109. The fluid line 1107 also provides a means of visually locating the sheath catheter 1109 with respect to position, as a slot 1138 in the handle 1101 allows the fluid line 1107 to translate with the sheath catheter 1109 (through a hole 1151 (best seen in DETAIL A in FIG. 14) during operation, and this translation is highly visible. In order to prevent rotation of the threaded insert during translation, a flat face 1164 has been machined onto both sides of the threaded insert 1115. The flat faces 1164 remain in contact with bosses 1139 and 1140 that are located on both handle section 1102 and handle section 1103 so that the bosses 1139 and 1140 act to grip the threaded insert 1115 and prevent rotation. A textured pattern 1155 allows the user to easily turn the thumbwheel 1106 in the surgical field. Detents 1141 (best seen in FIG. 14) locate flanges 63 (seen in FIG. 14) on the thumbwheel 1116 in order to allow for rotation.

The manner in which individual catheters (there are four catheters) move with respect to each other is illustrated in FIG. 12. Sheath catheter 1109 provides housing for the stationary catheter 1119, which in turn provides housing for the movable hub catheter 1120. The hub catheter 1120 translates linearly with respect to the nose catheter 1121 which can also be translated with respect to each previous catheter, and the handle 1101. The stationary catheter 1119 is mated to a handle section 1103 in an internal bore 1150 which also forms a seal between the stationary catheter 1119 and the hub catheter 1120. The distal portion of the stationary catheter 1119 is formed in the shape of a bell 1122 (see DETAIL A in FIG. 15A) which acts as a housing to retain the hub capture 1123 (seen in DETAIL A in FIG. 15A).

As previously stated a thumbwheel lock 1105 prevents rotation of the deployment thumbwheel 1104. In order to provide a seating force that keeps the thumbwheel lock 1105 in a locked position until manipulated, a spring 1125 is housed in an internal bore 62 (best seen in FIG. 14) and abuts against a shoulder 1161 (best seen in FIG. 14) that is located inside the thumbwheel lock 1105. This spring 1125 maintains the leading edge 1149 of the thumbwheel lock 1105 in a locked position within the two slots 1147 of the deployment thumbwheel 1104. Gripping texture 1154 is provided on the thumbwheel lock 1105 for ease of use. In order to locate and retain the thumbwheel lock 1105 inside of the handle 1101, a slot 1135 has been provided in both a handle section 1102 and a handle section 1103.

As shown in FIG. 12, a sliding block 1127 is housed inside of flat parallel faces 1134 which appear on the inside of the handle 1101. This sliding block 1127 is in mating contact with hub catheter 1120 and is the physical mechanism that linearly actuates the catheter. A spring 1126 is mounted on an external post 1159 and abuts against a shoulder 1133 that is located on the distal end of the sliding block 1127. This spring 1126 forces a peg 1128 (located inside a thru-hole 1156 of FIG. 14) into contact with the proximal edge of an angled slot 1148 that is cut into the deployment thumbwheel 1104. The deployment thumbwheel 1104 is contained between a shoulder 1136 and a snap ring (not shown), both of which are features of the handle 1101. Gripping texture 1153 on the deployment thumbwheel 1104 allows the user to easily rotate the thumbwheel in a clockwise direction, actuating the peg 1128 to ride distally along the slot 1148 and move the sliding block 1127, which pushes the hub catheter 1120 and hub 1123 (best seen in DETAIL A of FIG. 15A) forward and out of the bell 1122 (seen in DETAIL A of FIG. 15A). A slot 1132 appears in a handle section 1102 and a handle section 1103 and prevents the peg 1128 from translating beyond a desired range.

A nose catheter 1121 extends from a Tuohy Borst adaptor 1114 on the proximal end of the handle 1101, and internally throughout the handle and the respective catheters (sheath catheter 1109, stationary catheter 1119, and hub catheter 1120), terminating inside the rigid insert 1112 (seen in FIG. 15A) of the flexible tip 1110 (seen in FIG. 15A) that abuts with the distal end of the sheath catheter 1109.

Figure 13:
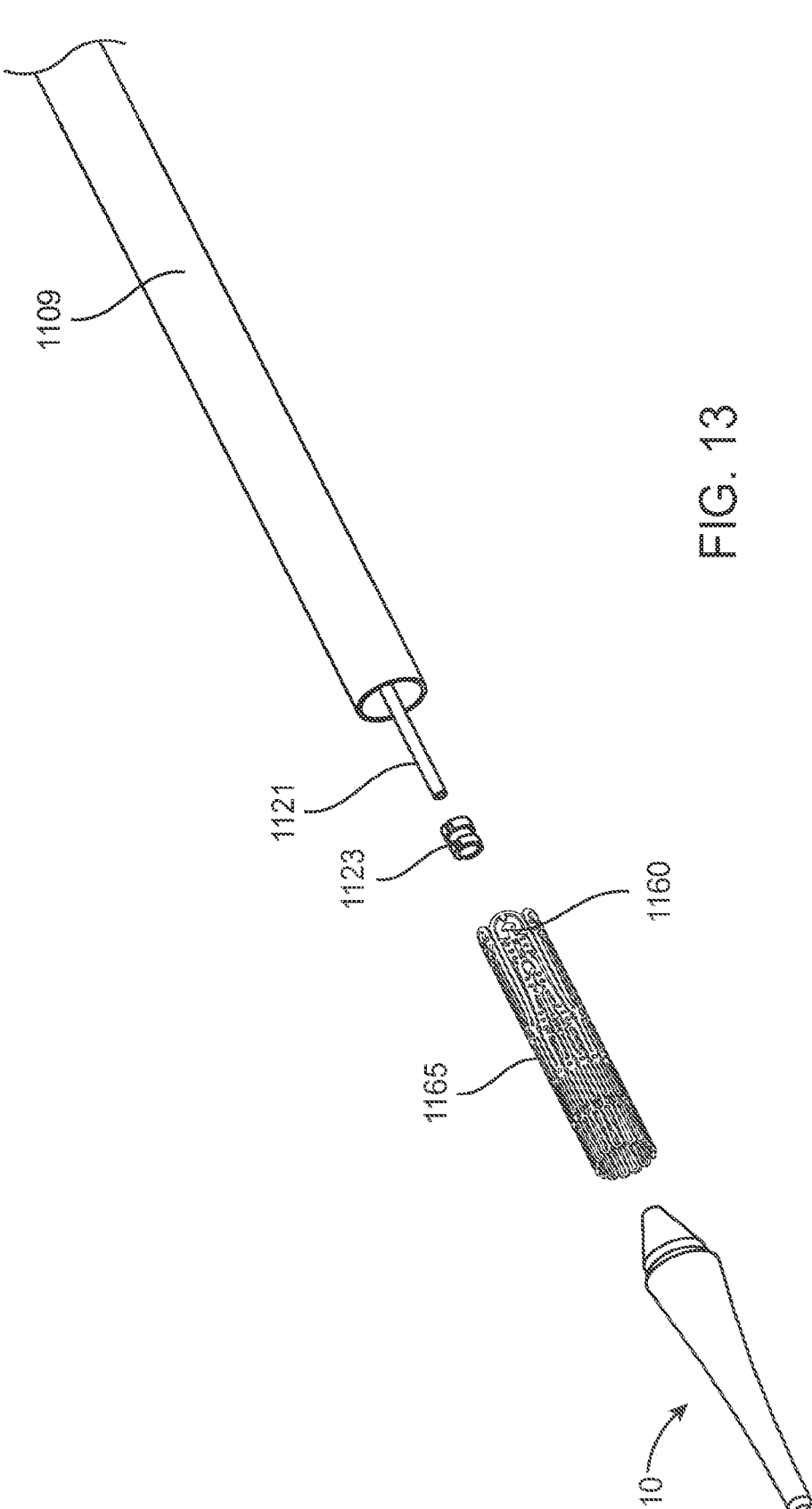
FIG. 13 is a perspective exploded view of a distal portion of the delivery device in FIG. 11.
Figure 14:
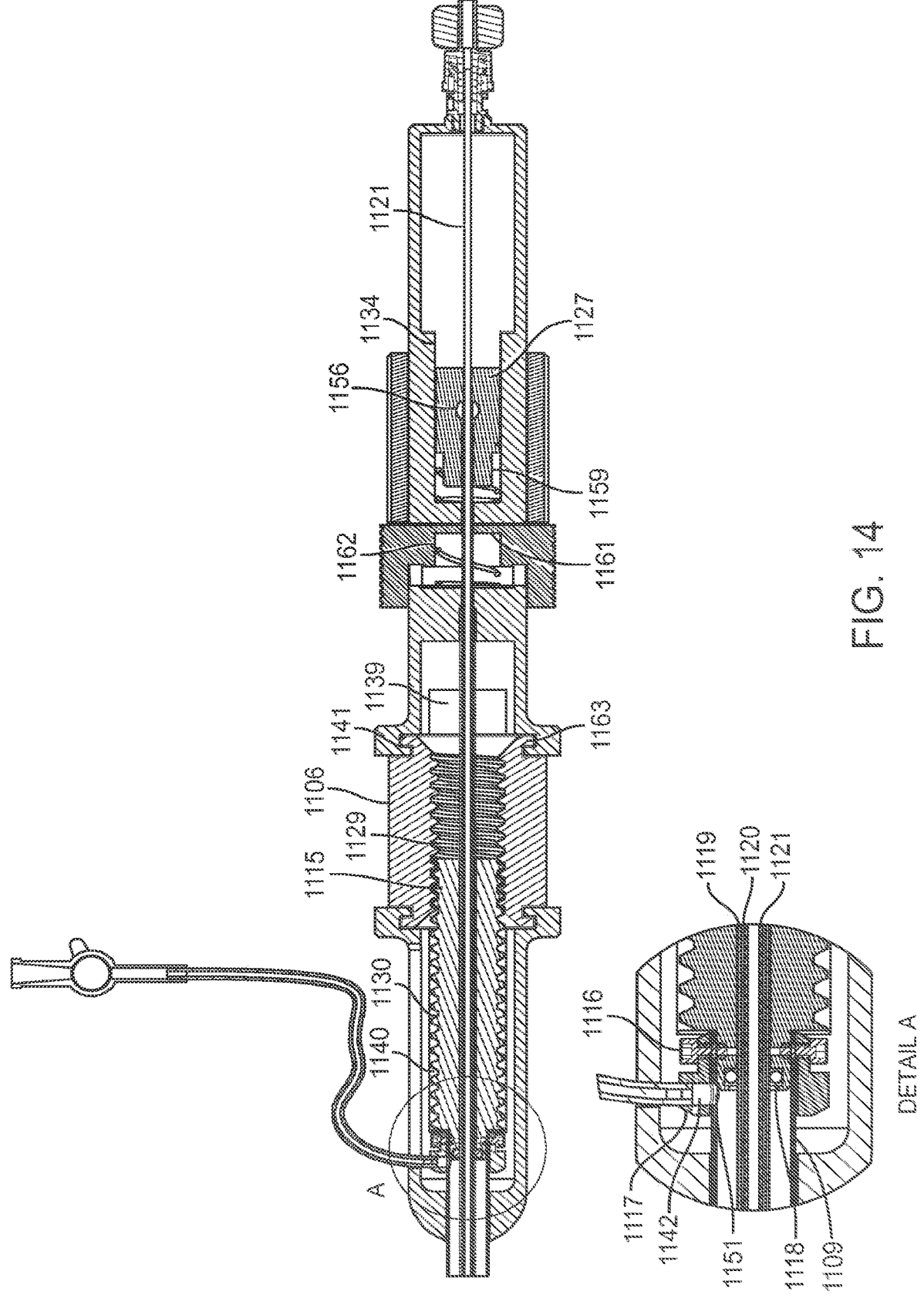
FIG. 14 is a cross-section of the a proximal portion of the delivery device in FIG. 11.

FIG. 13 displays an exploded view of the tip section of the delivery apparatus 1124, and shows the relation between prosthetic mitral valve 1165 and the internal and external catheters. When crimped and loaded, the prosthetic mitral valve 1165 is encased between the internal surface of the sheath catheter 1109 and the external surface of the nose catheter 1121. In order to capture and anchor the prosthetic mitral valve 1165 within the delivery apparatus 1124, three commissure tabs 1160 (circumferentially spaced at 120.degree. apart) appearing on the proximal end of the prosthetic mitral valve 1165 provide points of contact between the valve and three slots 1143 (seen in FIG. 15A) that are machined into the outer surface of the hub 1123 (circumferentially spaced at 120.degree. apart). After first advancing the hub catheter 1120 (FIG. 15A) by rotating the deployment thumbwheel 1104 (seen in FIG. 12) clockwise, the three commissure tabs 1160 can be captured within three slots 1143 (seen in FIG. 15A). The hub 1123 can then be retracted into the bell 1122 by releasing the deployment thumbwheel 1104 (seen in FIG. 12). In this position the prosthetic mitral valve 1165 is anchored to the delivery apparatus 1124, and further crimping of the valve will allow the sheath catheter 1109 to be advanced over the valve.

Figure 15A:
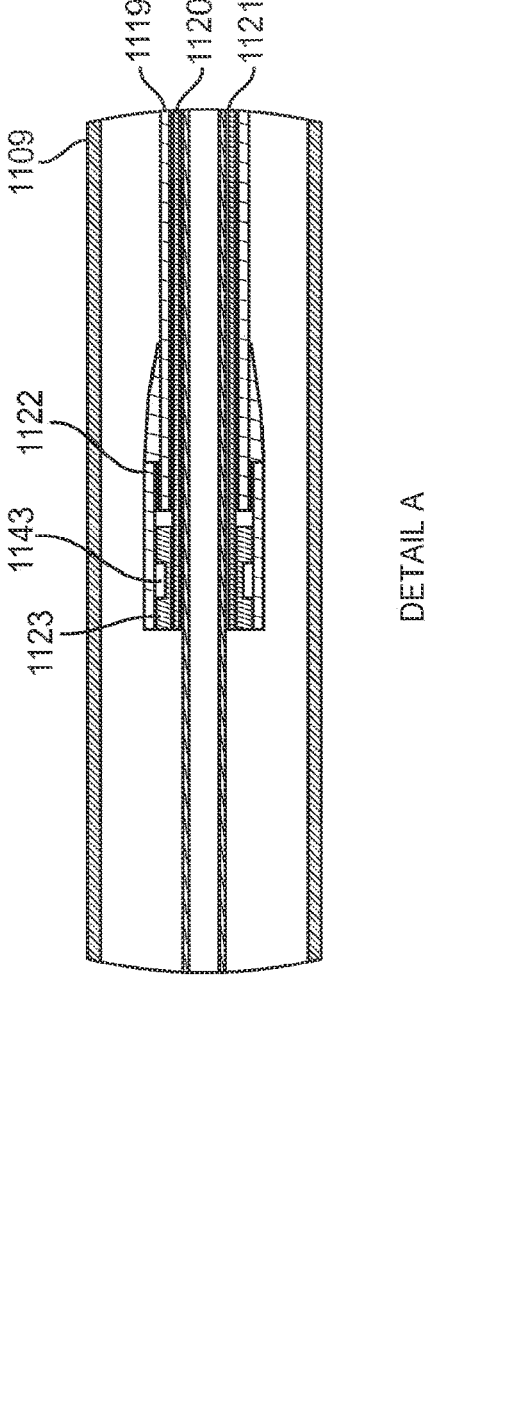
FIGS. 15A-15C are cross-sectional views of a distal portion of the delivery device in FIG. 11.
Figure 15A:
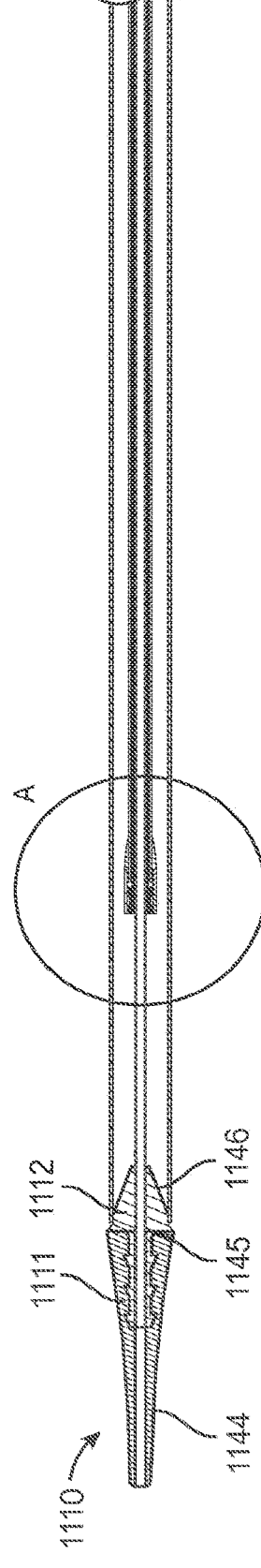
Figure 15B:
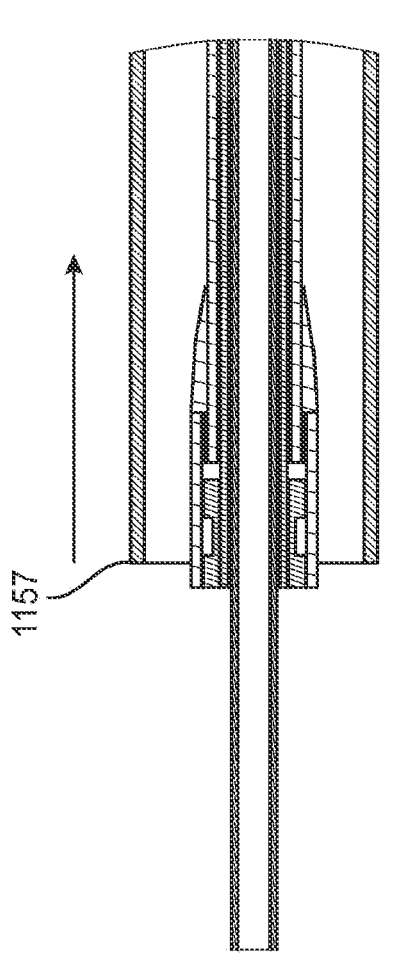
Figure 15B:
Figure 15B:
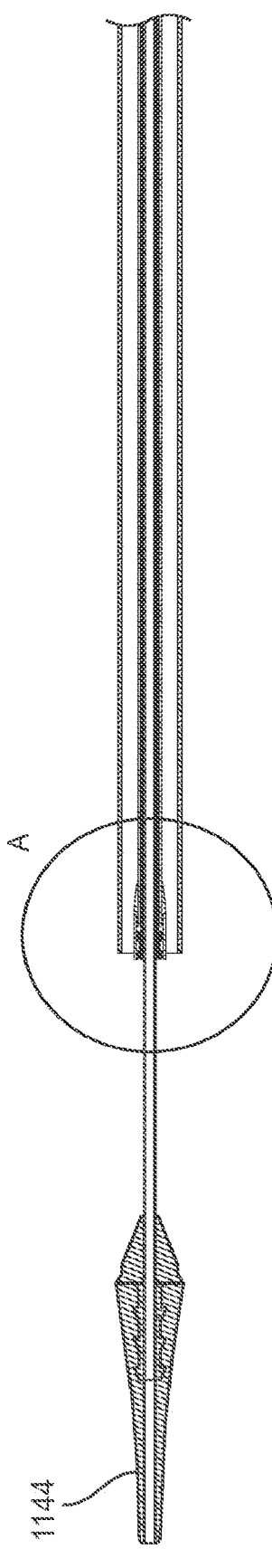
Figure 15C:
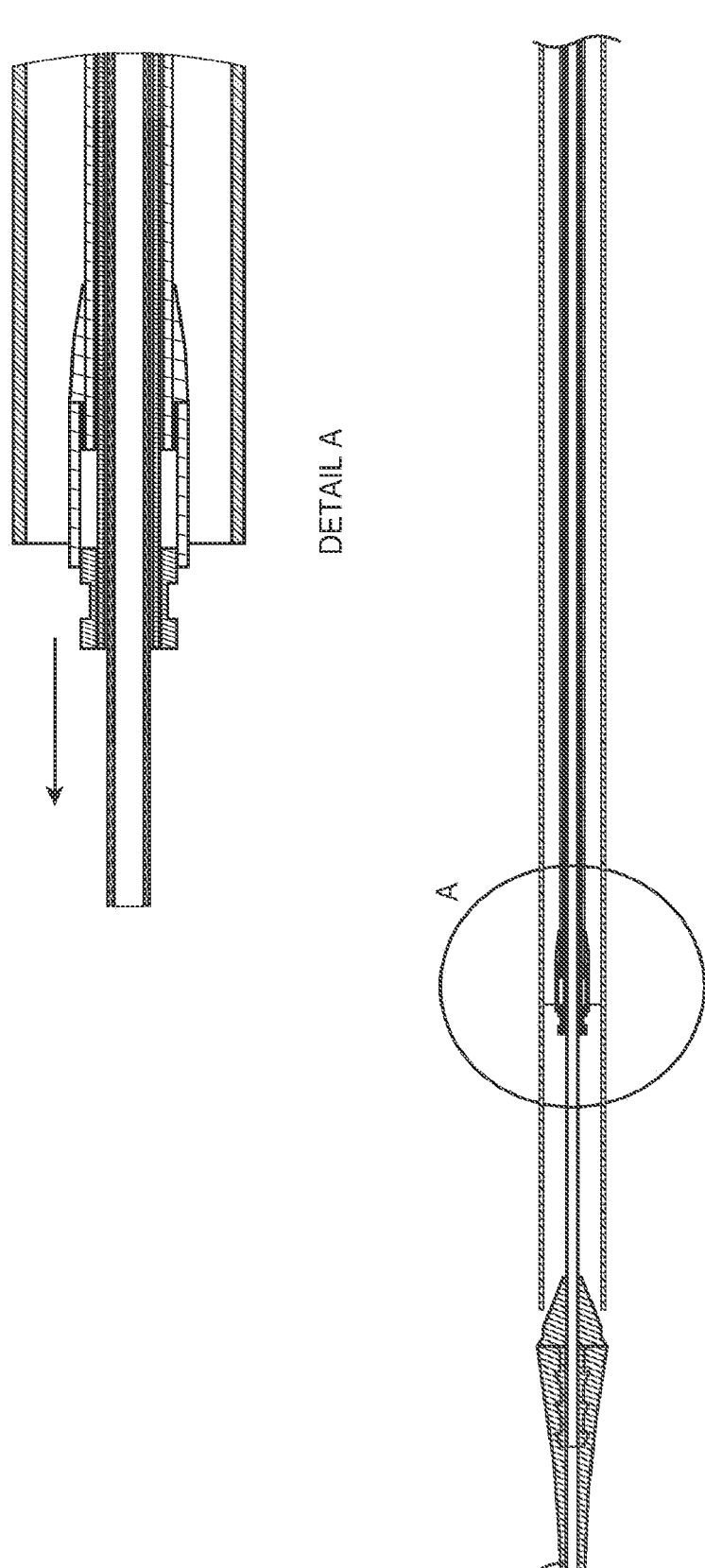

FIGS. 15A-15C further detail the manner in which loading of the prosthetic mitral valve 1165 (seen in FIG. 13) into the delivery apparatus 1124 can be achieved. Initially, the flexible tip 1110 is abutted against the distal edge 1157 of the sheath catheter 1109. The flexible tip 1110 is comprised of a rigid insert 1112, and a soft and flexible tip portion 1111 which is over-molded onto the rigid insert 1112. The shoulder 1145 and tapered face 1146 of the rigid insert 1112 act to guide and locate the distal edge 1157 of the sheath catheter 1109, so that the catheter may rest against and be stiffened by the flexible tip 1110, and be more easily introduced into the apex of the heart.

An initial position from which loading can be achieved is illustrated in FIG. 15A. As a first step in the loading of a prosthetic mitral valve 1165 (seen in FIG. 13) into the delivery apparatus 1124, the sheath catheter 1109 is withdrawn by rotation of the thumbwheel 1106 in a clockwise direction. The distal edge 1157 of the sheath catheter 1109 is retracted until it passes the distal edge of the bell 1122, as illustrated in DETAIL A of FIG. 15B. As a second step in the loading of a prosthetic mitral valve 1165 (seen in FIG. 13) into the delivery apparatus 1124, the hub 1123 is advanced from beneath the bell 1122 by clockwise turning of the deployment thumbwheel 1104 (seen in FIG. 12), as illustrated in DETAIL A of FIG. 15C. The deployment thumbwheel may only be turned once the thumbwheel lock 1105 (see FIG. 12) has been set in the forward position, disengaging it from contact with the thumbwheel. Advancement of the hub 1123 uncovers three slots 1143 into which three commissure tabs 1160 of the prosthetic mitral valve 1165 (seen in FIG. 13) will fit and be anchored. After anchoring of the commissure tabs 1160 into the slots 1143 by retraction of the hub 1123 has been achieved, a third step in the loading of a prosthetic mitral valve 1165 (seen in FIG. 13) into the delivery apparatus 1124 may be performed. The prosthetic mitral valve 1165 (seen in FIG. 13) can be crimped down to a minimum diameter by a loading mechanism (not shown), and then the sheath cannula 1109 can be advanced forward so as to cover the valve, by rotation of the thumbwheel 1106 in a counter-clockwise direction. The delivery apparatus 1124 and prosthetic mitral valve 1165 are then ready for deployment.

FIGS. 16-19B illustrate another exemplary embodiment of a delivery device for implanting a prosthetic valve in the heart transapically. However, one of skill in the art will appreciate that the delivery system may be modified and relative motion of the various components adjusted to allow the device to be used to deliver a prosthetic transseptally. The delivery apparatus is generally comprised of a handle 1601 that is the combination of two halves (1610 and 1635), as well as a tip 1603 that can smoothly penetrate the apex of the heart, and a flexible sheath 1602 which is comprised of concentric catheters that are designed to translate axially and will be described detail below.

The handle 1601 includes a handle cap 1611 which connects to a female threaded luer adaptor 1612 in order to provide a sealable exit for a 0.035" diameter guide-wire (not shown). The handle cap 1611 is attached to the handle 1601 with threaded fasteners 1613. The female threaded luer adaptor 1612 is in threaded contact with the handle cap 1611 through a tapped port, and when fully inserted squeezes against an o-ring (1636 best seen in FIG. 18) which seals against the outer diameter of a guide-wire catheter (1621 best seen in FIG. 18).

Figure 17:
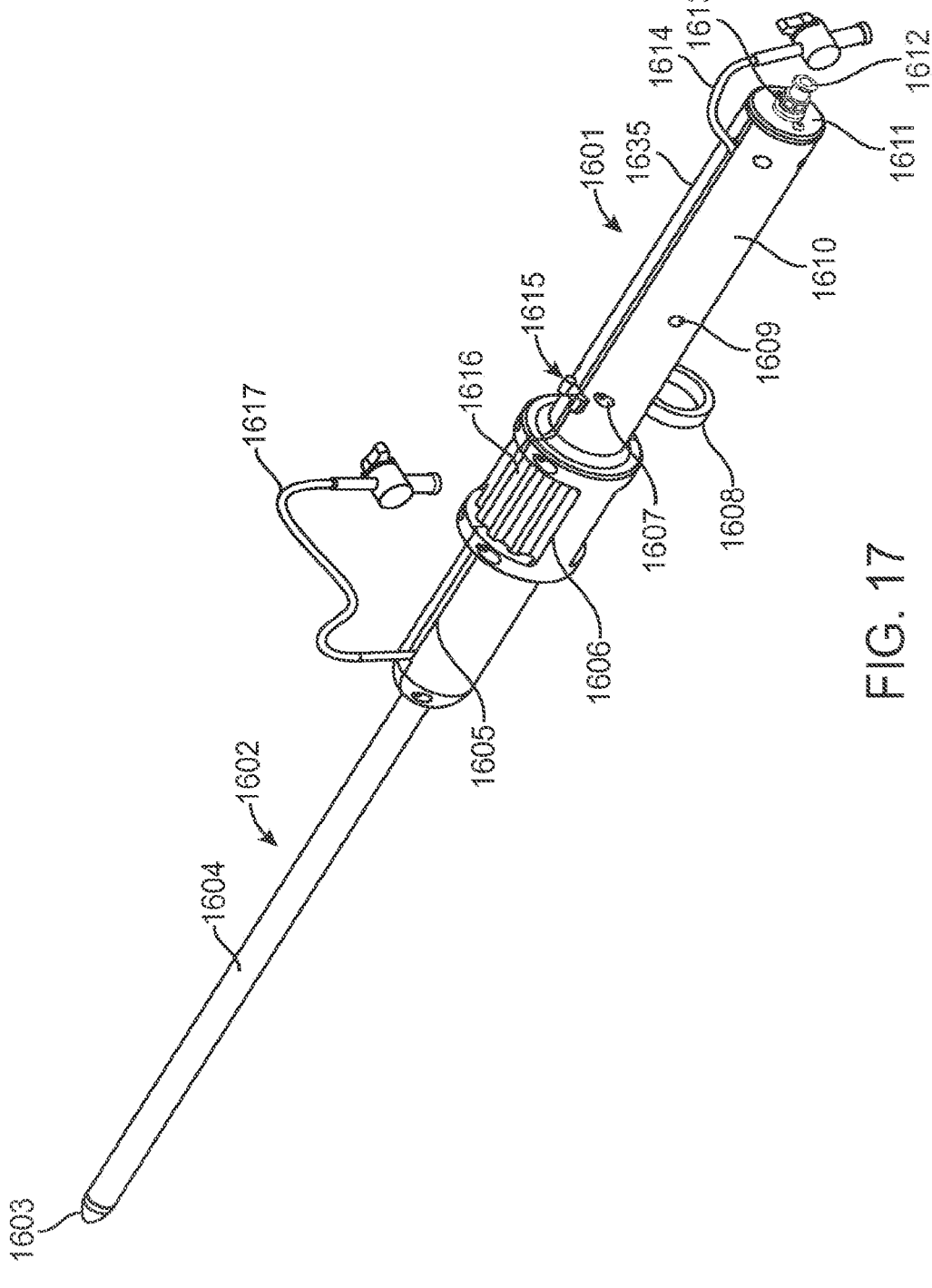
FIG. 17 is a perspective view of the delivery device in FIG. 16.

As can be seen in FIG. 17, the handle 1601 provides location for the control mechanisms used to position and deploy a prosthetic mitral valve. The handle 1601 provides housing for a thumbwheel 1616 that can be accessed through a window 1606 that appears on both the top and bottom of the handle 1601. The thumbwheel 1616 internally mates with a threaded insert (1627 in FIG. 18) that actuates the sheath catheter 1604, and the mechanics of this interaction will be explained in detail below.

Figure 18:
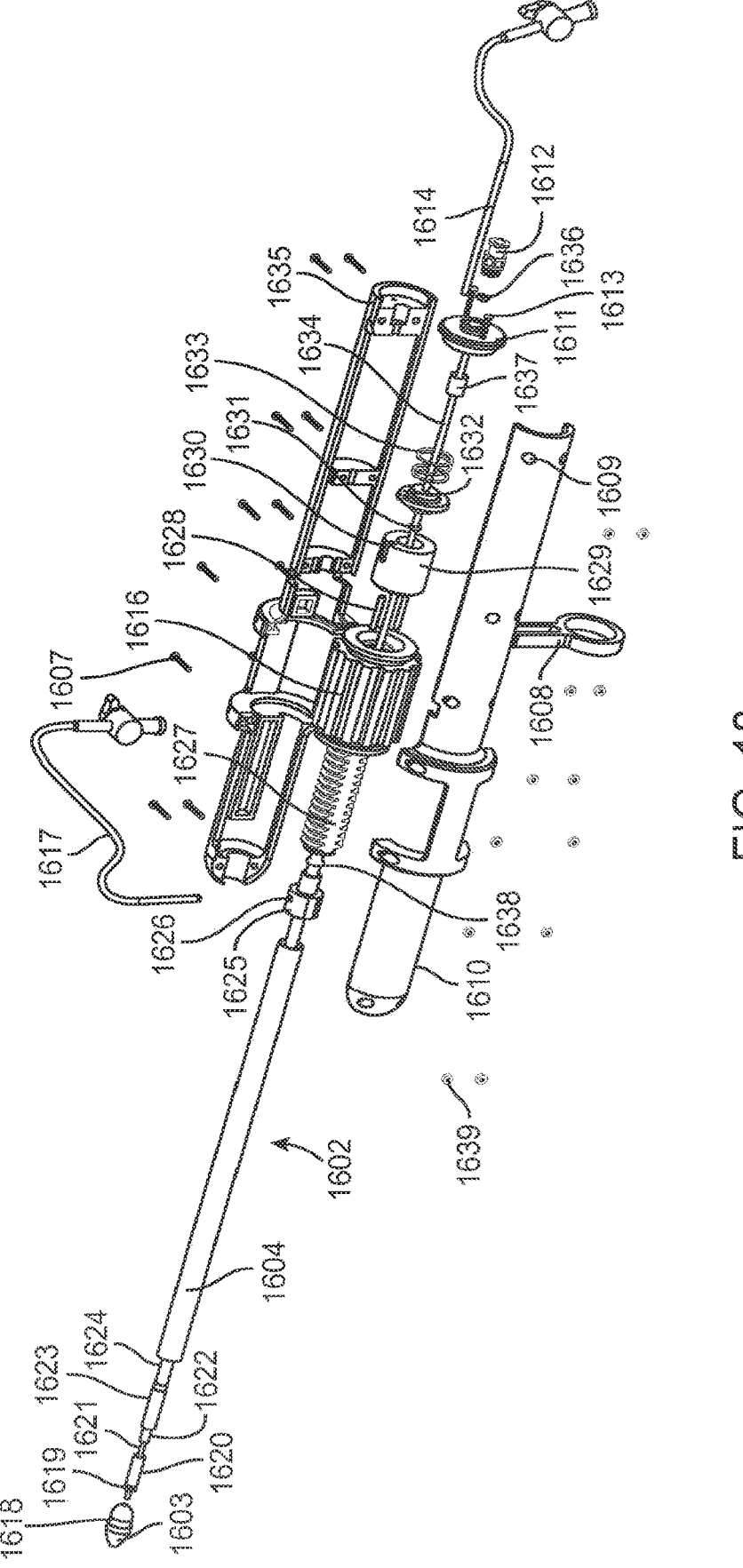
FIG. 18 is a perspective exploded view of the delivery device in FIG. 16.

FIG. 17 also shows a first hemostasis tube 1617 that is inserted internally through a slot 1605, and that mates with a first hemp-port through a hole (1625 and 1626 in FIG. 18 respectively). The first hemostasis tube 1617 allows for fluid purging between internal catheters. The position of the first hemostasis tube 1617 along the slot 1605 provides a visual cue as to the position of the sheath catheter 1604, and relative deployment phase of a prosthetic mitral valve (not shown). The relationship between the connection of the first hemostasis tube 1617 and the sheath catheter 1604 will be described below.

As can also be seen in FIG. 17, a second hemostasis tube 1614 is inserted into the handle 1601 and mated to a second hemp-port (1629 in FIG. 18) in order to allow fluid purging between internal catheters, and details of this insertion will be described below. Finally, a pin lock 1608 provides a security measure against premature release of a prosthetic mitral valve, by acting as a physical barrier to translation between internal mechanisms. Pin lock prongs 1615 rely on spring force to retain the pin lock 1608 in the handle 1601, and a user must first pull out the pin lock 1608 before final deployment of a prosthetic valve.

FIG. 17 also shows how the handle 1601 is fastened together by use of threaded fasteners and nuts (1607 and 1639 of FIG. 18 respectively), and countersunk locator holes 1609 placed throughout the handle length.

Internal mechanisms of the delivery system are illustrated in detail in FIG. 18, and the following descriptions will reveal the interactions between individual components, and the manner in which those components combine in order to create a system that is able to deliver a prosthetic mitral valve preferably transapically.

As seen in FIG. 18, the flexible sheath 1602 is comprised of four concentrically nested catheters. In order from smallest to largest in diameter, the concentrically nested catheters will be described in detail. The innermost catheter is a guide-wire catheter 1621 that runs internally throughout the entire delivery system, beginning at the tip 1603 and terminating in the female threaded luer adaptor 1612. The guide-wire catheter 1621 is composed of a lower durometer, single lumen Pebax extrusion and is stationary. It provides a channel through which a guide-wire (not shown) can communicate with the delivery system. The next catheter is the hub catheter 1622 which provides support for the hub 1620 and is generally comprised of a higher durometer, single lumen PEEK extrusion. The hub catheter 1622 is in mating connection with both the hub 1622 at the distal end, and a stainless steel support rod 1634 at the proximal end. The stainless steel support rod 1634 is held fixed by virtue of a stopper 1637 that is encased in the handle 1601. The hub catheter 1622 is stationary, and provides support and axial rigidity to the concentrically nested catheters. The next catheter is the bell catheter 1624, which provides housing to the hub 1620 and is generally comprised of a medium durometer, single lumen Pebax extrusion, including internal steel braiding and lubricious liner, as well as a radiopaque marker band (not shown). The bell catheter 1624 translates axially, and can be advanced and retracted with respect to the hub 1620. The bell catheter 1624 is in mating connection with the second Nemo-port 1629 at the proximal end, and hemostasis between the bell catheter 1624 and the stainless steel support rod 1634 can be achieved by purging the second hemostasis tube 1614. The bell catheter 1624 is bumped up to a larger diameter 1623 on the distal end in order to encapsulate the hub 1620. The outermost and final catheter is the sheath catheter 1604 which provides housing for a prosthetic mitral valve (not shown), and which is able to penetrate the apex of the heart (not shown), by supporting and directing a tip 1603 and assisting in the dilation of an incision in the heart wall muscle. The sheath catheter 1604 is generally comprised of a medium durometer, single lumen Pebax extrusion, including internal steel braiding and lubricious liner, as well as radiopaque marker band (not shown). The sheath catheter 1604 translates axially, and can be advanced and retracted with respect to the hub 1620. The sheath catheter 1604 is in mating connection with the first hemp-port 1625 at the proximal end, and hemostasis between the sheath catheter 1604 and the bell catheter 1624 can be achieved by purging the first hemostasis tube 1617.

As seen in FIG. 18, the proximal end of the sheath catheter 1604 is in mating contact with a first hemo-port 1625. The first hemo-port is in mating contact with a threaded insert 1627, and an o-ring 1638, which is entrapped between the first hemo-port 1625 and the threaded insert 1627 in order to compress against the bell catheter 1624, creating a hemostatic seal. As the thumbwheel 1616 is rotated, the screw insert 1627 will translate, and the sheath catheter 1624 can be retracted or advanced by virtue of attachment. In order to provide adequate stiffness to dilate heart wall tissue, the distal edge of the sheath catheter 1604 will abut against a shoulder 1618 located on the tip 1603. This communication allows the tip 1603 to remain secure and aligned with the sheath catheter 1604 during delivery, and creates piercing stiffness.

FIG. 18 also details the mechanism through which the bell catheter 1624 can be retracted or advanced with respect to the hub 1620. The thumbwheel 1616 can be rotated to such an extent that the screw insert 1627 will be brought into contact with two pins 1628 that are press fit into the second hemo-port 1629. As the bell catheter 1624 is in mating contact with the second hemo-port 1629, further rotation of the thumbwheel 1616 will cause the second hemo-port 1629 to translate and press against a spring 1633 by virtue of connection to a second hemo-port cap 1632. This advancement will cause the bumped larger diameter section 1623 of the bell catheter 1624 to be retracted from the hub 1620. As the thumbwheel 1616 is rotated in the opposite direction, restoring force produced by the spring 1633 will cause the second hemo-port 1629 to be pushed in the opposite direction, drawing the bumped larger diameter section 1623 of the bell catheter 1624 back over the hub 1620, an action that is necessary during the initial loading of a valve prosthesis.

FIG. 18 further details the manner in which hemostasis is achieved between the stainless steel support rod 1634 and the bell catheter 1624. An o-ring 1631 is compressed between the second hemo-port 1629 and the second hemo-port cap 1632, creating a seal against the stainless steel support rod 1634, Hemostasis between the bell catheter 1624 and the stainless steel support rod 1634 can be achieved by purging the second hemostasis tube 1614, which is in communication with the void to be purged through a slot and hole 1630.

Figure 19A:
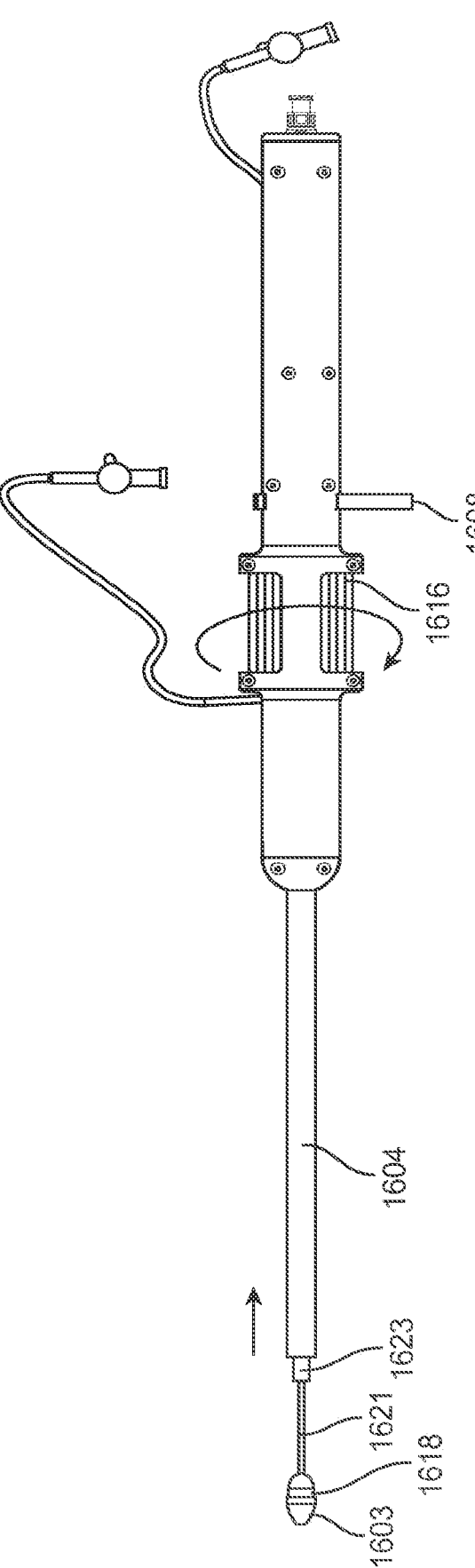
FIGS. 19A-19B are side views of the delivery device in FIG. 16 during various stages of operation.
Figure 19B:
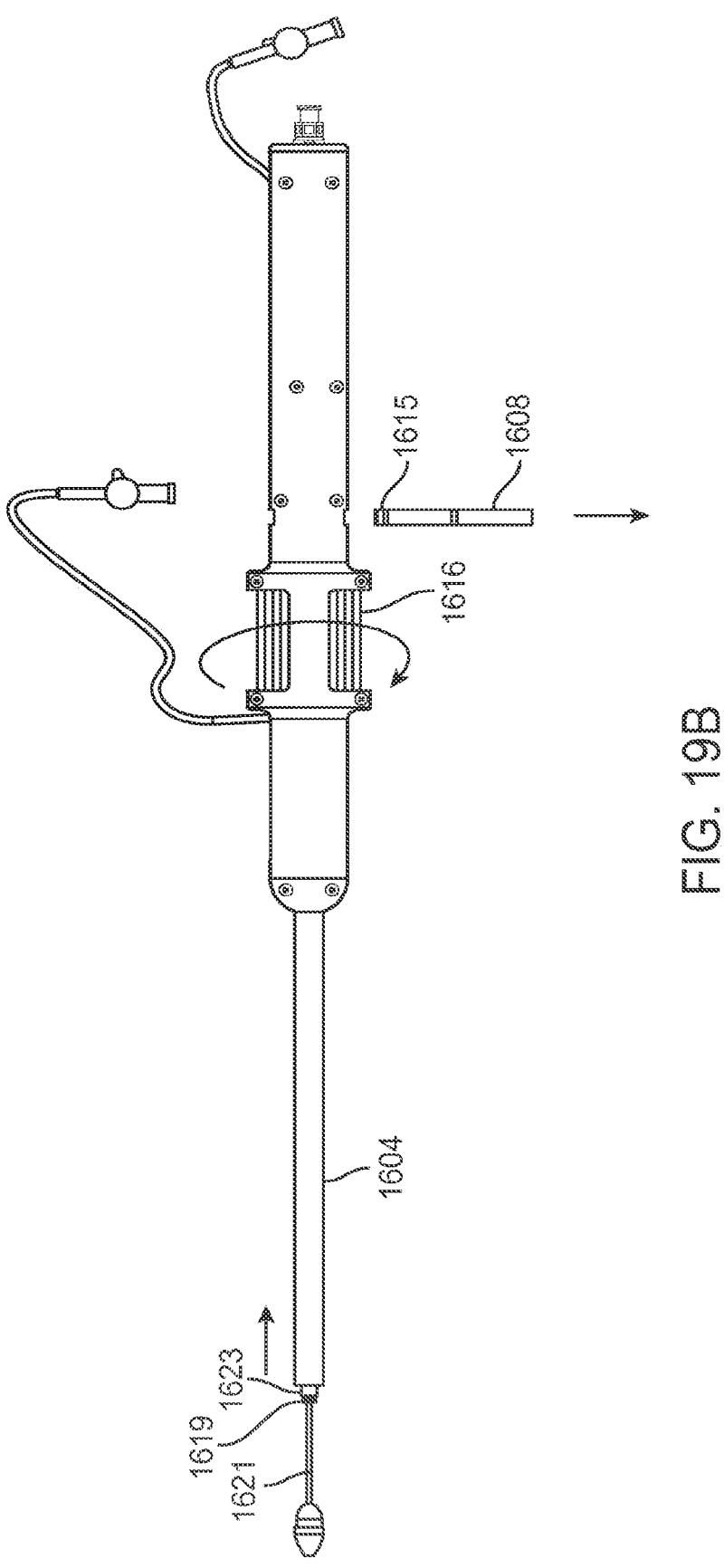

The deployment process and actions necessary to activate the mechanisms responsible for deployment are detailed in FIGS. 19A-19B. When performed in the reverse order, these actions also necessitate the first loading of a valve (not shown) prior to surgery.

As seen in FIG. 19A, manipulation of the thumbwheel 1616 will provide translational control of the sheath catheter 1604. In order to effect the deployment of a heart valve (not shown), the user must withdraw the sheath catheter 1604 from contact with the shoulder 1618 of the tip 1603 until it passes the larger diameter section 1623 of the bell catheter 1624. A heart valve (not shown) will reside concentrically above the guide-wire catheter 1621 in the position indicated by the leader for 1621 in FIG. 19A, similarly as to the embodiment illustrated in FIG. 13. The sheath catheter 1604 can be withdrawn until the screw insert 1627 comes into contact with the pin lock 1608. The pin lock 1608 must then be removed before further travel of the screw insert 1627 can be achieved.

As seen in FIG. 19B, the pin lock 1608 is removed from the handle 1601 in order to allow further translation of the sheath catheter 1604. When the sheath catheter 1604 is fully retracted, the larger diameter section 1623 of the bell catheter 1624 is also fully retracted, which completely frees the heart valve (not shown) from the delivery system. Three hub slots 1619, spaced circumferentially at 120.degree. from each other provide the anchoring mechanism and physical link between delivery system and heart valve. Once the larger diameter section 1623 of the bell catheter 1624 has been withdrawn, the hub slots 1619 become uncovered which allows the heart valve anchor (not shown) to fully expand.

Figure 16:
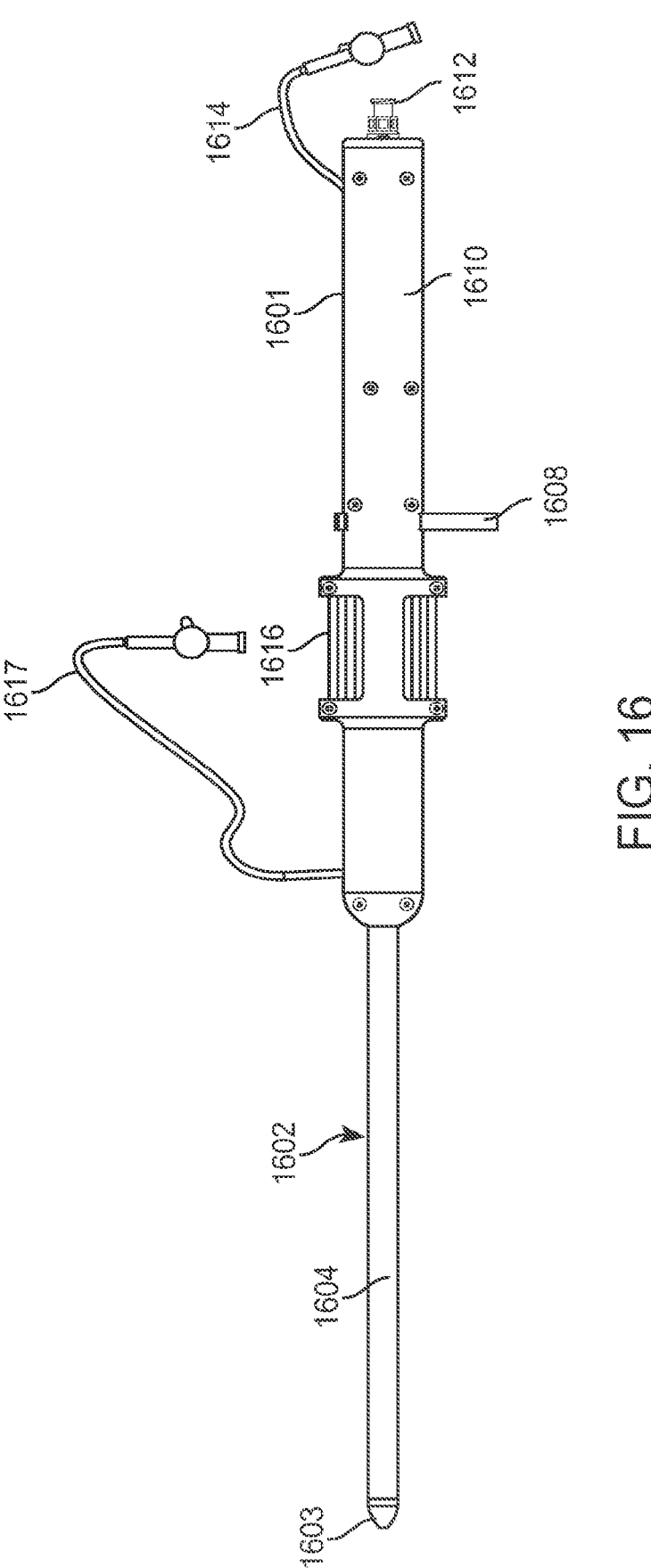
FIG. 16 is a side view of another exemplary embodiment of a delivery device for implantation of a prosthetic valve.
Figure 20:
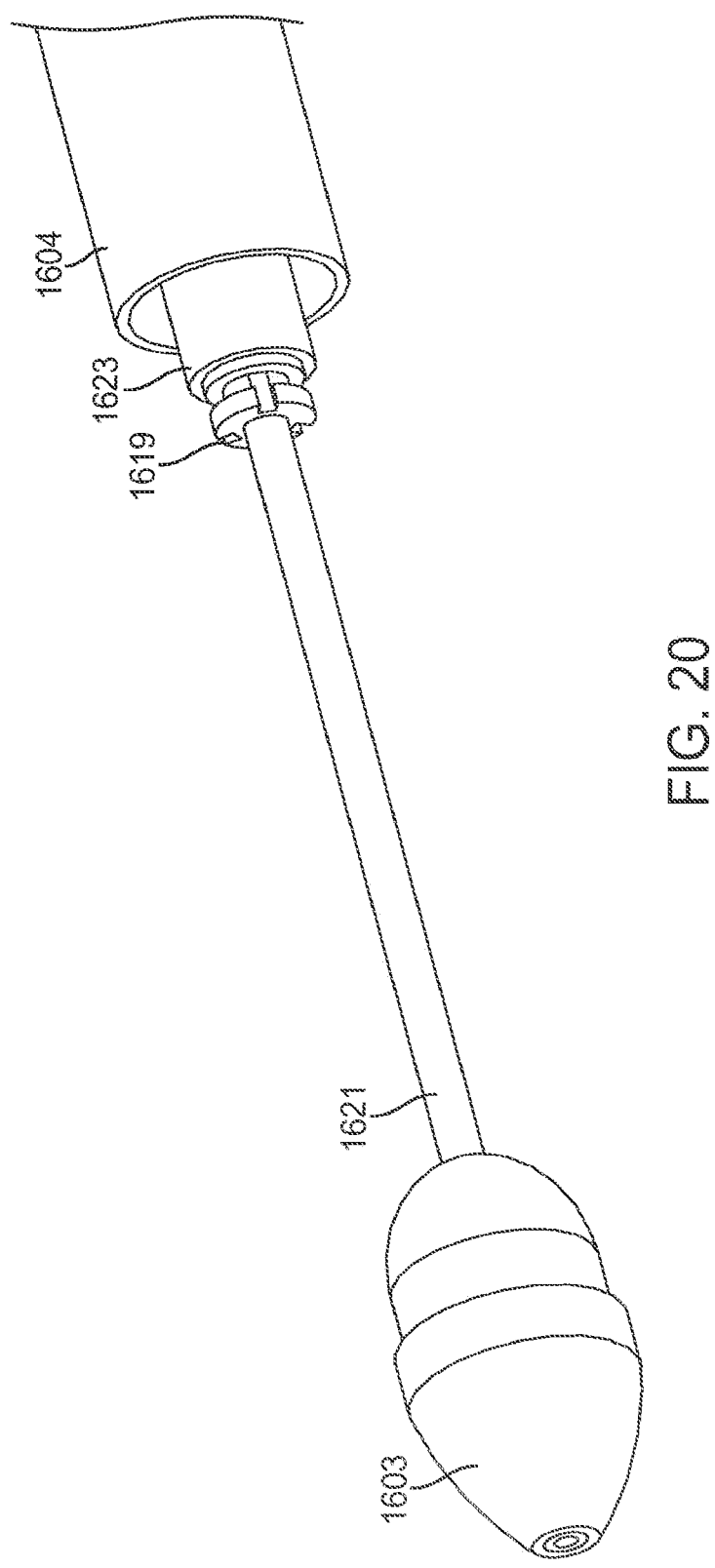
FIG. 20 illustrates a distal portion of the delivery device in FIG. 16 that is adapted to engage a portion of a prosthetic valve.

FIG. 20 illustrates a distal portion of the delivery device in FIG. 16. Three hub slots 1619 are slidably disposed distally relative to the large diameter tip 1623 of bell catheter 1624. These slots allow engagement with a prosthetic valve. The valve may be releasable held by the slots by disposing the commissure tabs or tabs 812 of the prosthetic valve into slots 1619 and then retracting the slots 1619 under tip 1623 of bell catheter 1624. The prosthetic valve may be released from the delivery catheter by advancing the slots distally relative to the bell catheter so that the loading anchors or tabs 812 may self-expand out of and away from slots 1619 when the constraint of tip 1623 on bell catheter 1624 has been removed.

Figure 21:
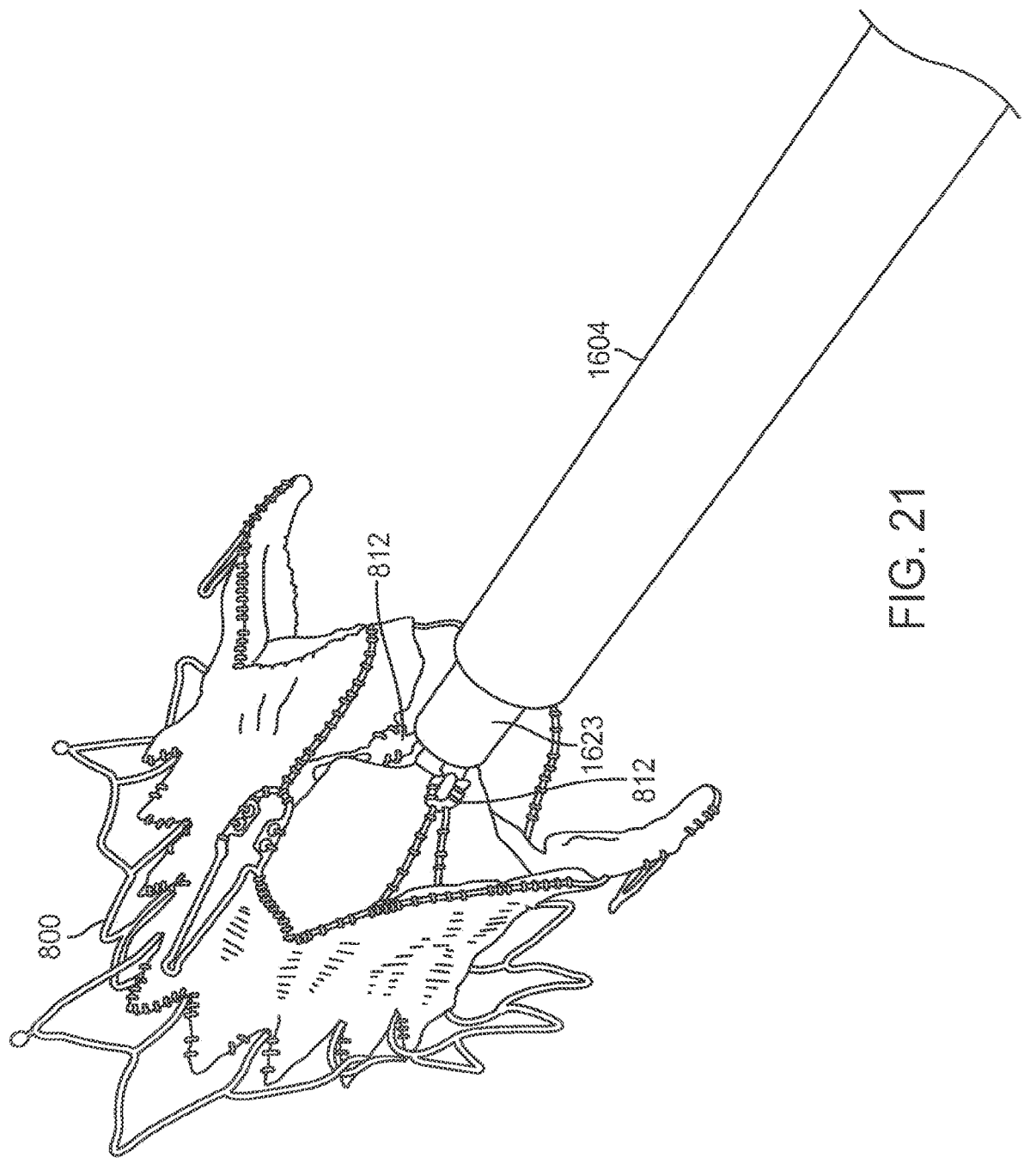
FIG. 21 illustrates engagement of the delivery device in FIG. 16 with the prosthetic valve of FIG. 8A.

FIG. 21 illustrates a prosthetic mitral valve 800 (as discussed above with reference to FIG. 8A) with the anchor tabs 812 disposed in the hub slots (not visible), and bell catheter 1623 advanced thereover. Thus, even though most of the prosthetic valve 800 has self-expanded into its expanded configuration, the valve commissures remain in a collapsed configuration with the tabs 812 captured in slots 1619. Once the constraint provided by bell catheter 1623 has been removed from the slots 1619, the tabs 812 may self-expand out of slots 1619, the commissures will open up to their unbiased position. The prosthetic valve is then disconnected and free from the delivery device.

Figure 22A:
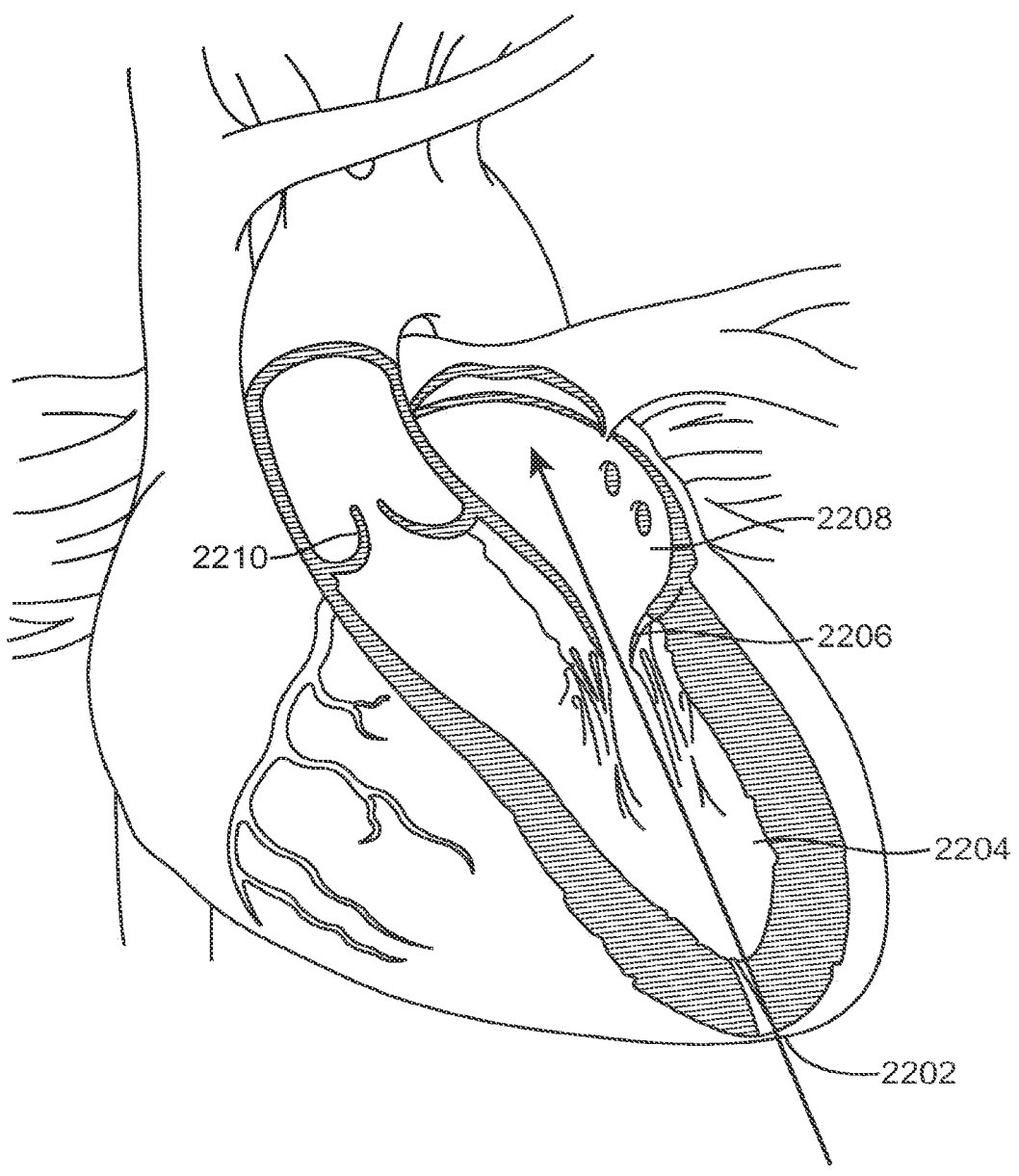
FIGS. 22A-22G illustrate an exemplary method of transapically delivering a prosthetic mitral valve.

Transapical Delivery Methods. FIGS. 22A-22G illustrate an exemplary method of transapically delivering a prosthetic mitral valve. This embodiment may use any of the prosthetic valves described herein, and may use any of the delivery devices described herein, FIG. 22A illustrates the general transapical pathway that is taken with entry into the heart at the apex 2202, through the left ventricle 2204, across the mitral valve 2206 and into the left atrium 2208. The aortic valve 2210 remains unaffected. Transapical delivery methods have been described in the patent and scientific literature, such as in International PCT Publication No. WO2009/134701, the entire contents of which are incorporated herein by reference.

Figure 22B:
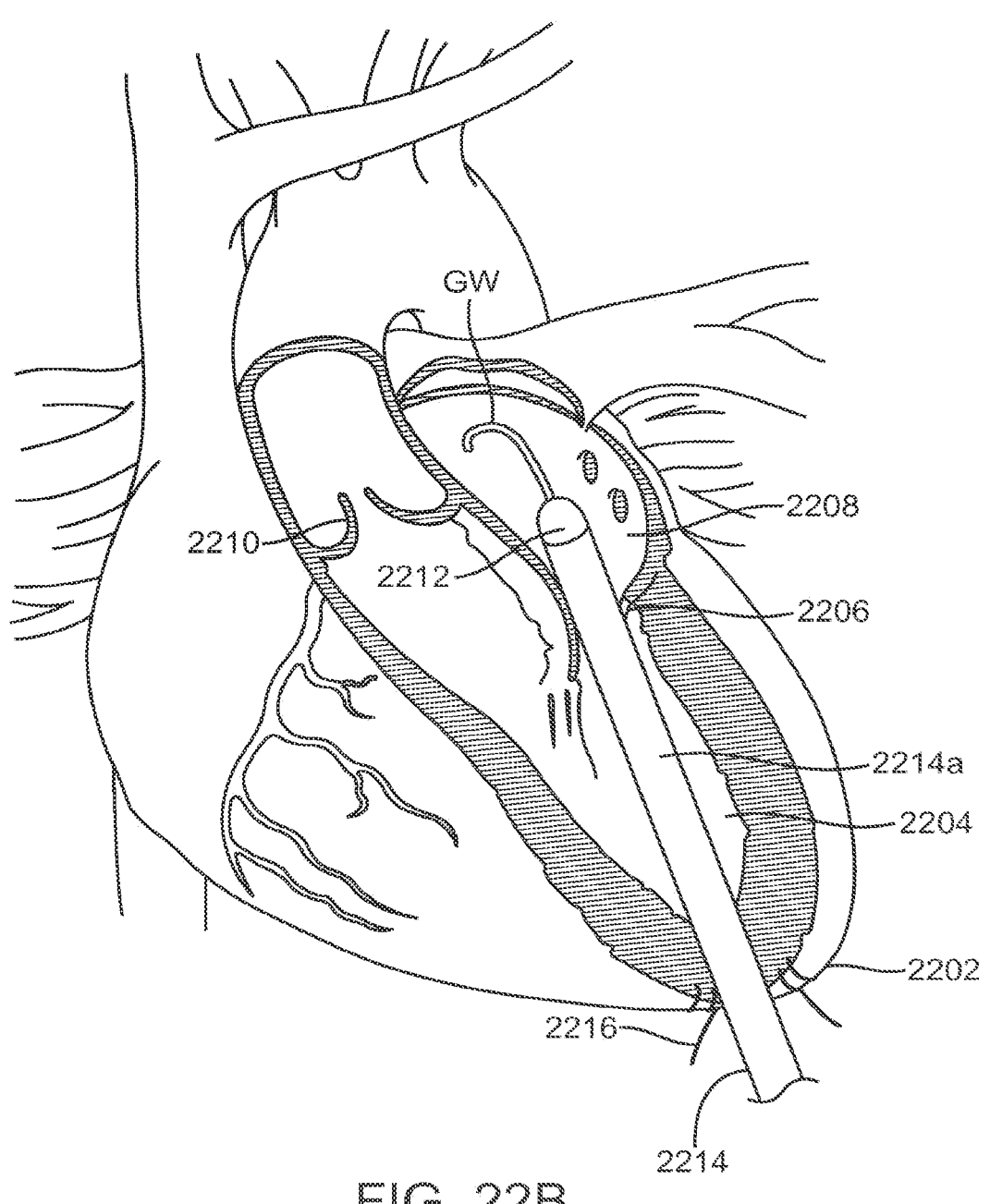

In FIG. 22B a delivery device 2214 is introduced through an incision in the apex 2202 and over a guidewire GW through the ventricle 2204, past the mitral valve 2206 with a distal portion of the delivery device 2214 disposed in the atrium 2208. The delivery device has a rounded tip 2212 that is configured to pass through and dilate the incision, and can be advanced through the heart without causing unwanted trauma to the mitral valve 2206 or adjacent tissue. Suture 2216 may be stitched around the delivery device 2214 at the apex 2202 using a purse string stitch or other patterns known in the art in order to prevent excessive bleeding and to help hold the delivery device in position.

Figure 22C:
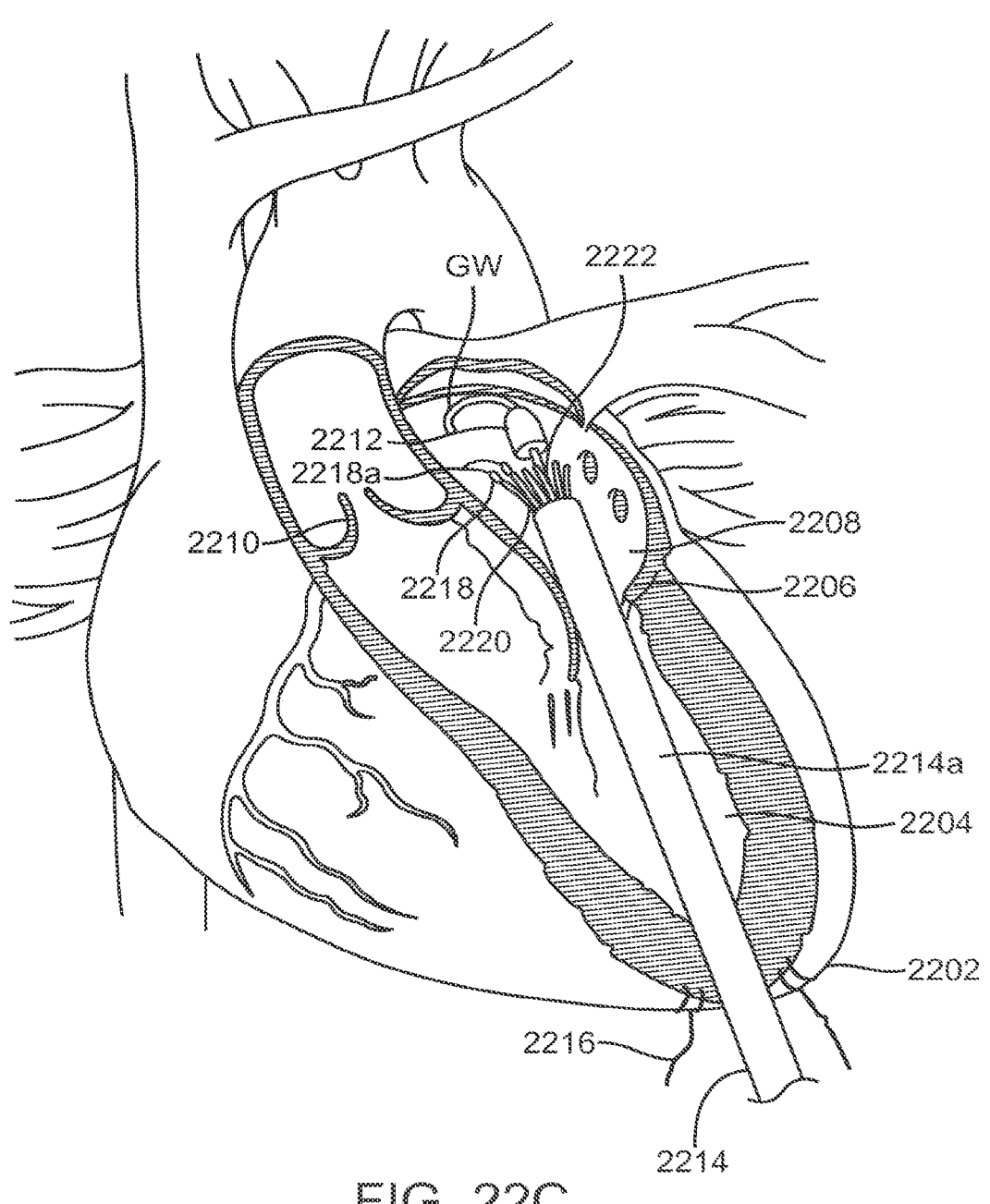

In FIG. 22C, the outer sheath 2214a of the delivery device 2214 is retracted proximally relative to the prosthetic mitral valve 2220 (or the prosthetic mitral valve is advanced distally relative to the outer sheath 2214a) to expose the alignment element 2218 and a portion of the atrial skirt region 2222 on the prosthetic mitral valve 2220 which allows the atrial skirt region 2222 to begin to partially radially expand outward and flare open. Alignment element 2218 may include a pair of radiopaque markers 2218a which facilitate visualization under fluoroscopy. The physician can then align the alignment element so that the radiopaque markers 2218a are disposed on either side of the anterior mitral valve leaflet. Delivery device 2214 may be rotated in order to help align the alignment element. The alignment element is preferably situated adjacent the aortic root and between the fibrous trigones of the native anterior leaflet.

Figure 22D:
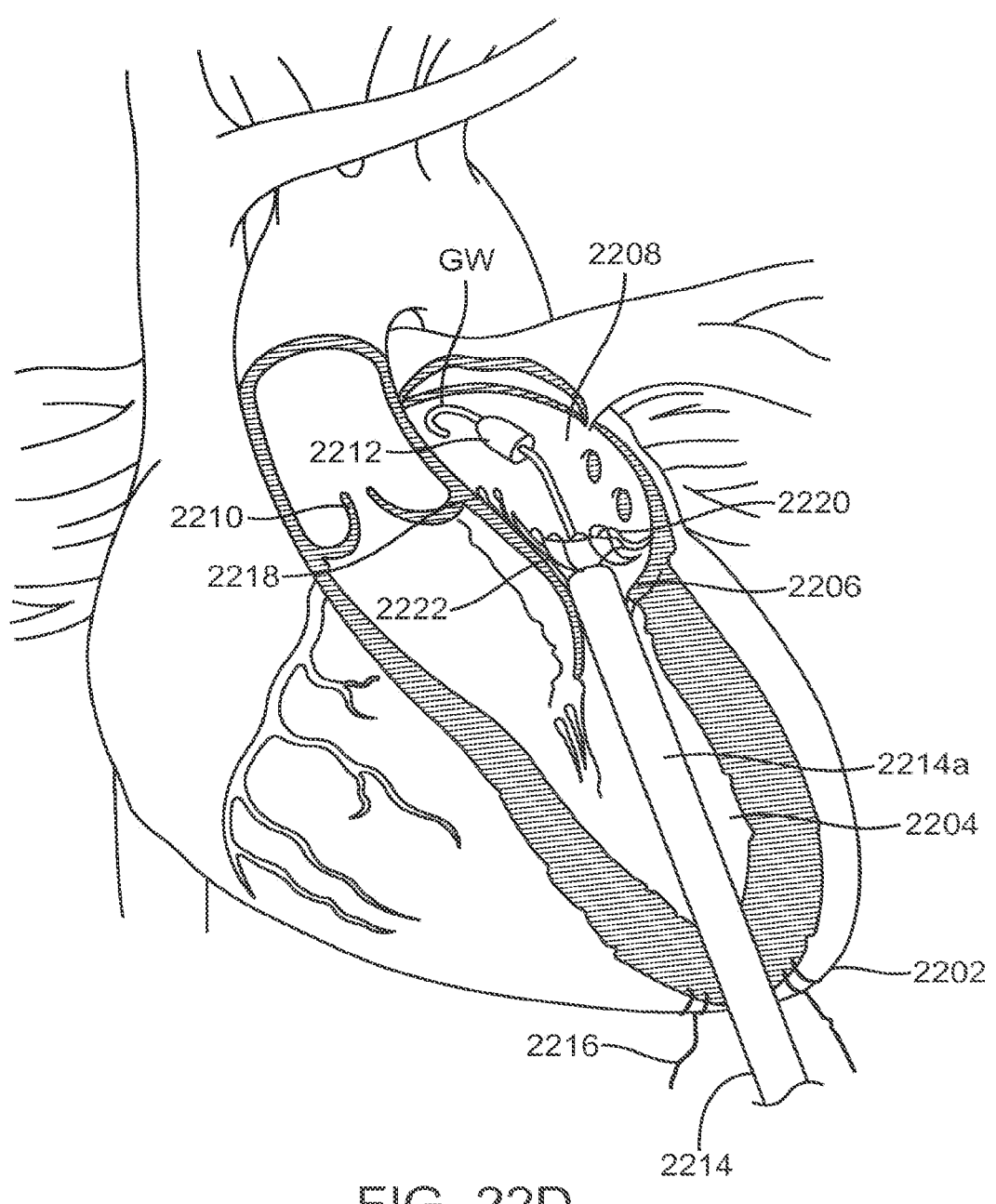

In FIG. 22D once alignment has been obtained, the sheath 2214a is further retracted proximally, allowing radial expansion of the atrial skirt 2222 which flares outward to form a flange, Proximal retraction of the delivery device 2214 and prosthetic valve 2220 seat the atrial skirt 2222 against an atrial surface adjacent the mitral valve 2206 thereby anchoring the prosthetic valve in a first position.

Figure 22E:
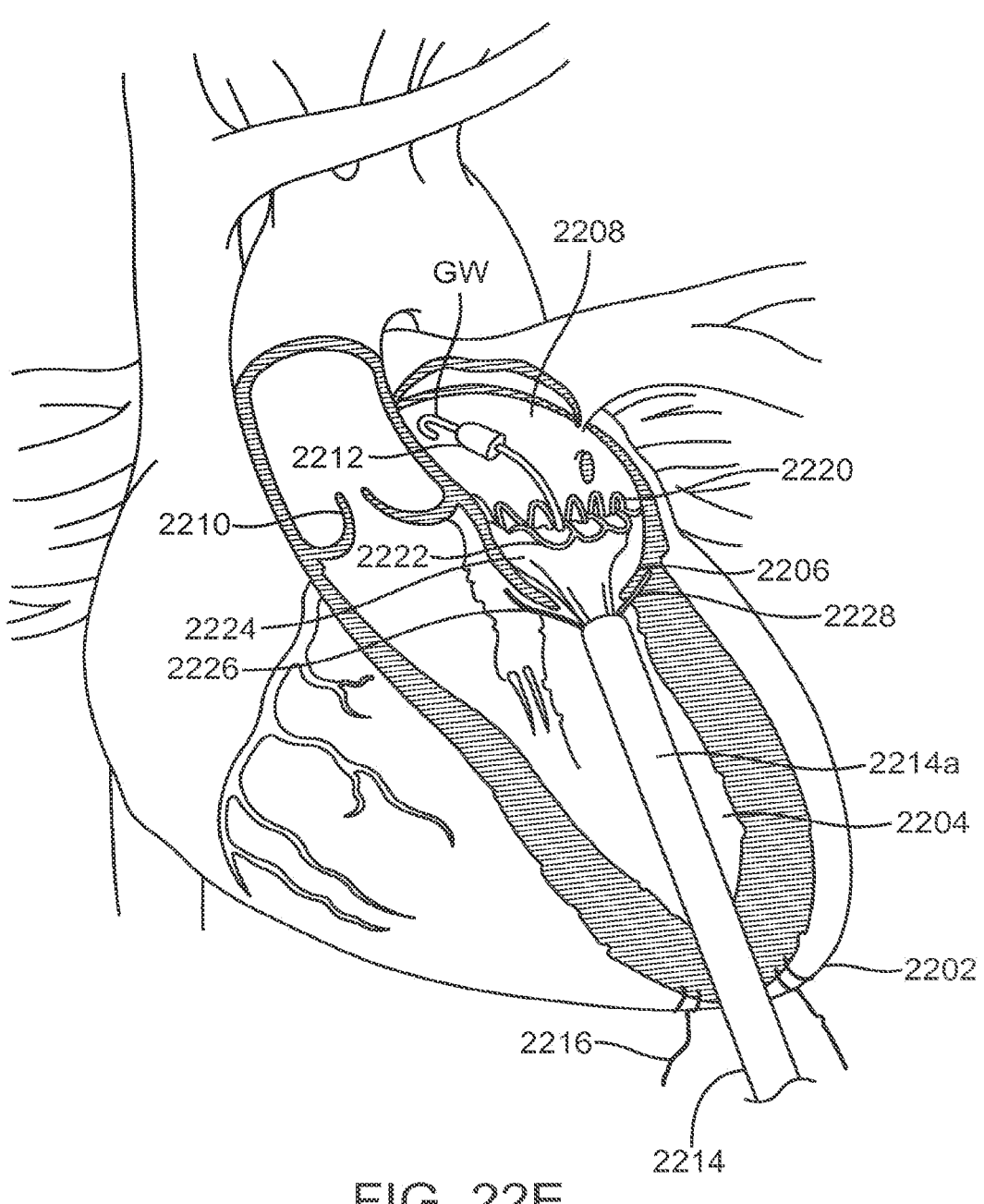

FIG. 22E shows that further proximal retraction of sheath 2214a exposes and axially removes additional constraint from the prosthetic valve 2220, thereby allowing more of the valve to self-expand. The annular region 2224 expands into engagement with the mitral valve annulus and the ventricular trigonal tabs 2226 and the posterior tab 2228 radially expand. Portions of the ventricular skirt serve as deployment control regions and prevent the entire ventricular skirt from expanding because they are still constrained. The tabs are captured between the anterior and posterior mitral valve leaflets and the ventricular wall. The posterior ventricular anchoring tab 2228 is preferably aligned in the middle of the posterior mitral valve leaflet where there is an absence of chordae attachments, and is passed over the posterior leaflet to seat between the posterior leaflet and the ventricular wall. The two ventricular trigonal anchoring tabs 2226 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 22F:
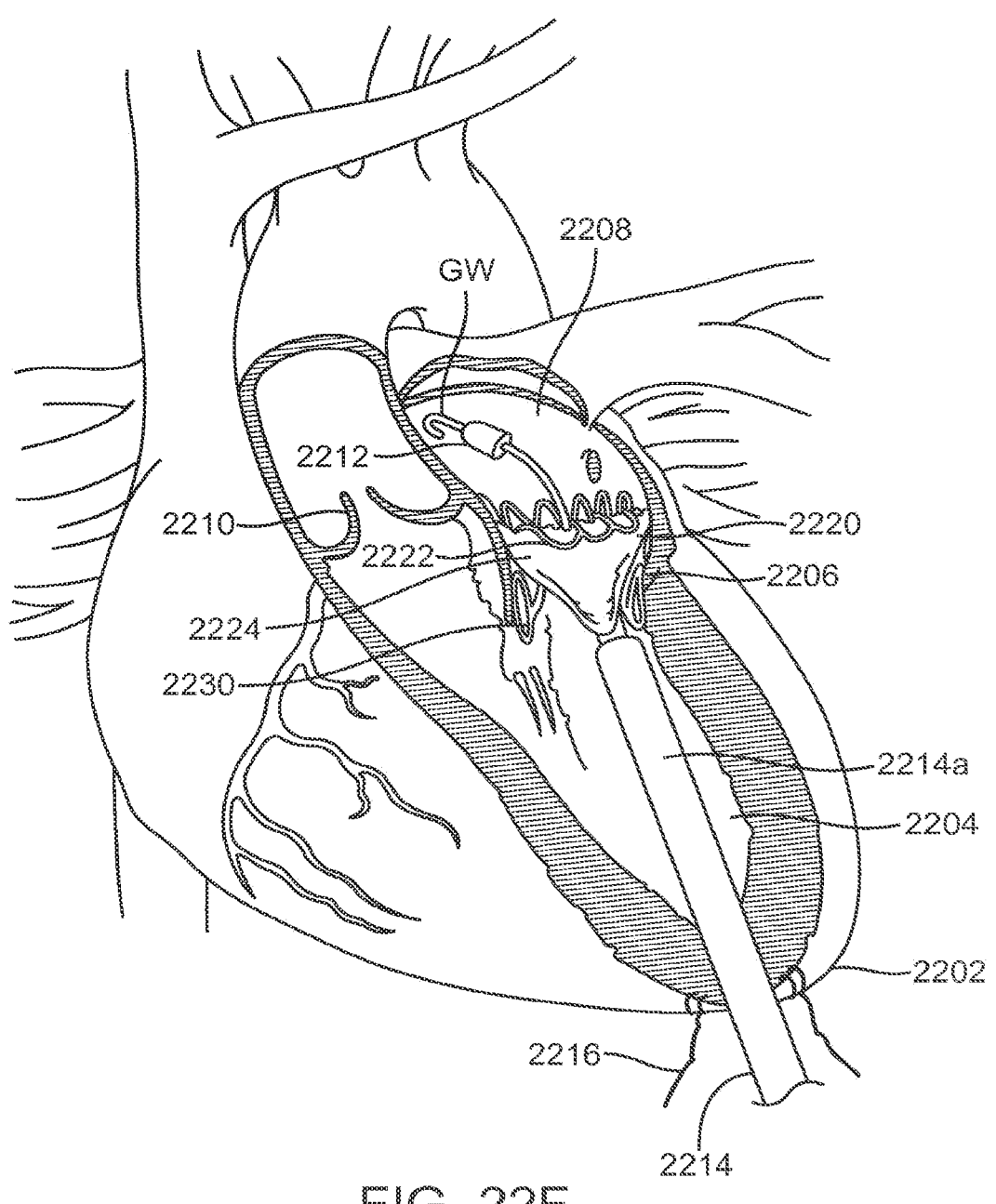
Figure 22G:
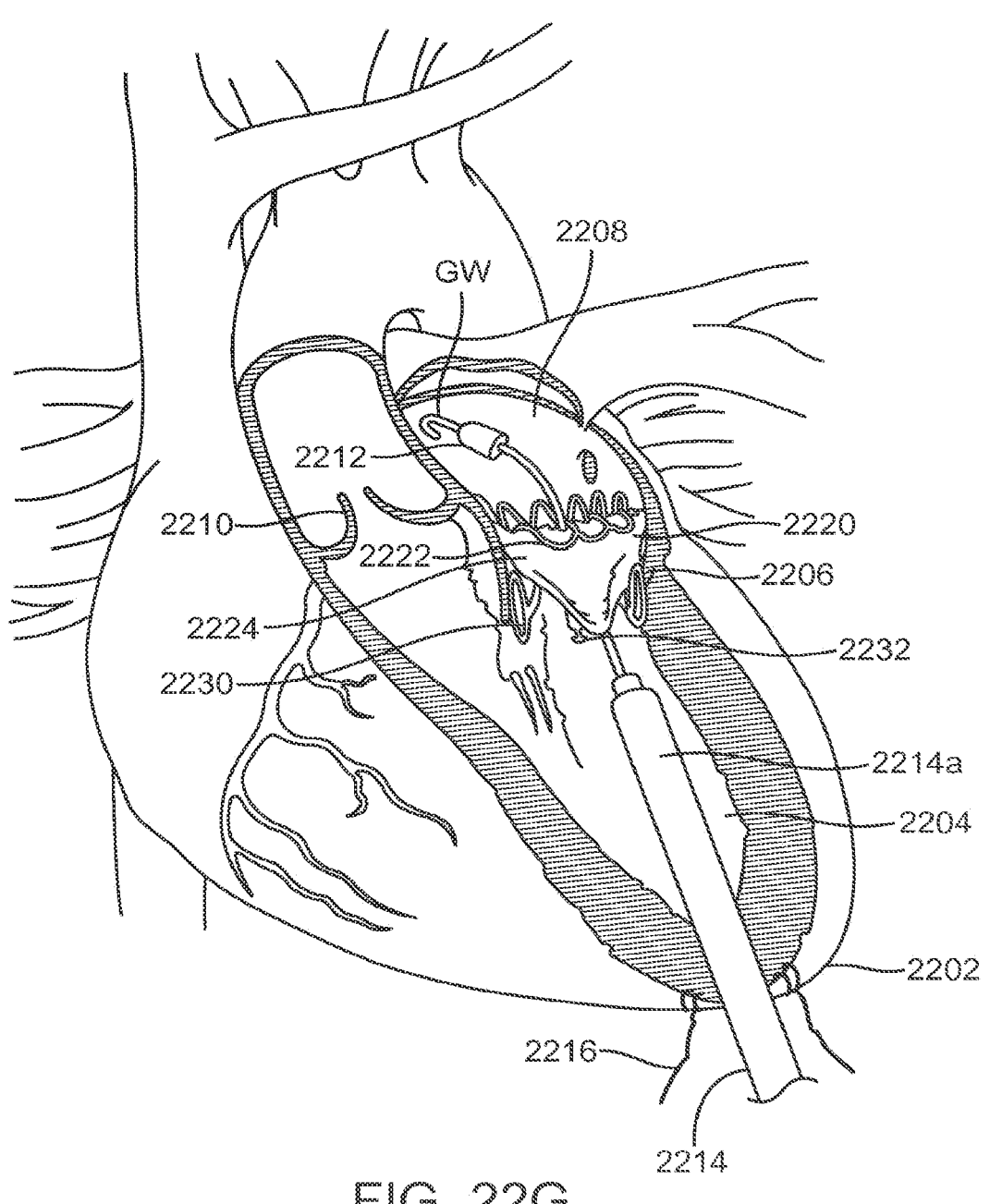

FIG. 22F shows that further retraction of sheath 2214a releases the ventricular trigonal tabs and the posterior tab and the deployment control regions of the ventricular skirt 2230 are also released and allowed to radially expand outward against the native mitral valve leaflets.

This creates a sealing funnel within the native leaflets and helps direct blood flow through the prosthetic mitral valve, With the commissures of the prosthesis still captured within the delivery system, very minor adjustments may still be made to ensure accurate positioning, anchoring and sealing. The prosthetic valve is now anchored in four positions. The anchor tabs 2232 are then released from the delivery device by retraction of an inner shaft, allowing the tabs to self-expand out of slots on the delivery catheter as previously discussed above and shown in FIG. 22G. The prosthetic valve is now implanted in the patient's heart and takes over the native mitral valve. The delivery device 2214 may then be removed from the heart by proximally retracting it and removing it from the apex incision. The suture 2216 may then be tied off, sealing the puncture site.

Figure 23A:
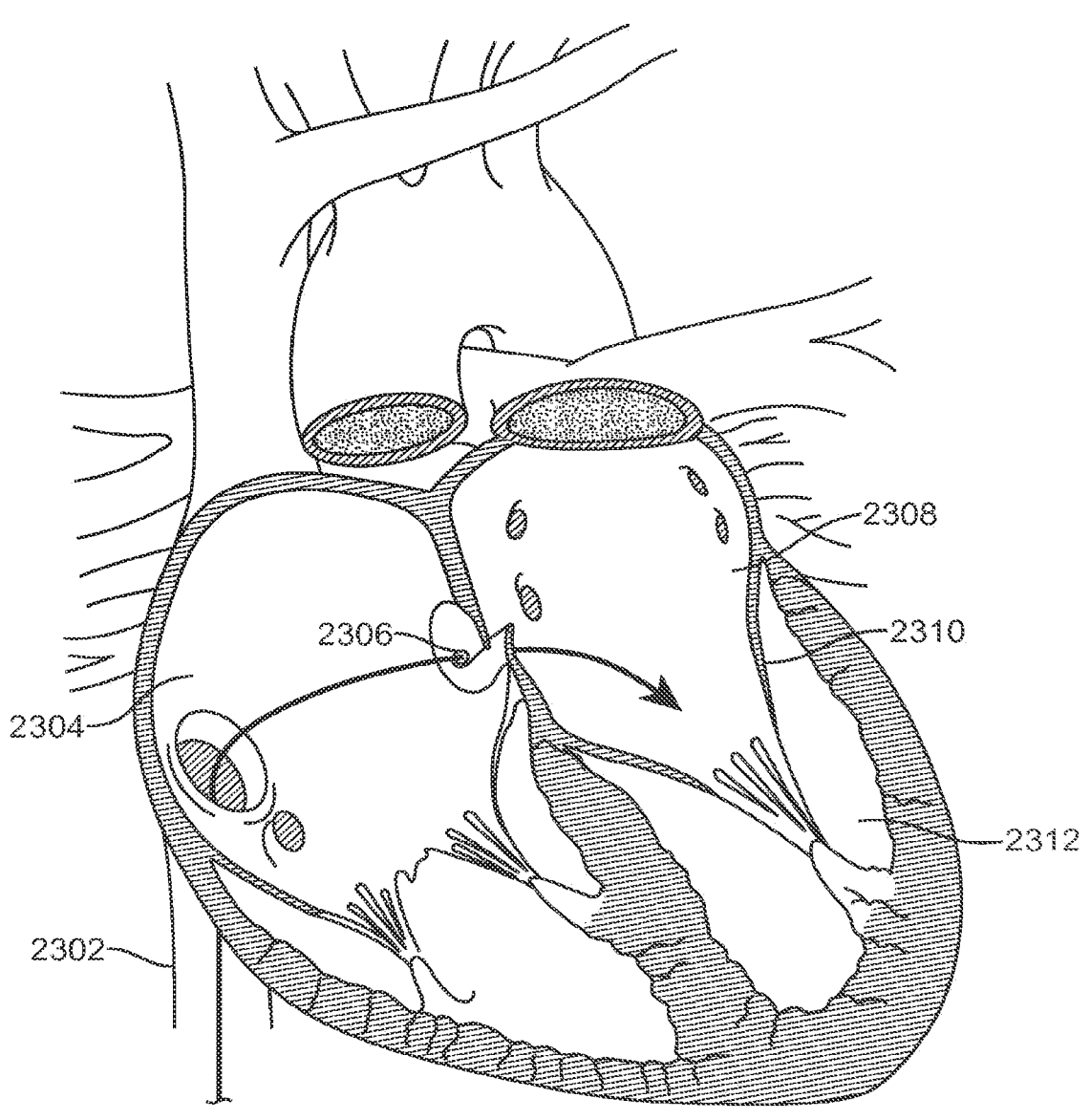
FIGS. 23A-23G illustrate an exemplary method of transseptally delivering a prosthetic mitral valve.

Transseptal Delivery Methods. FIGS. 23A-23G illustrate an exemplary method of transseptally delivering a prosthetic mitral valve. This embodiment may use any of the prosthetic valves described herein, and may use any of the delivery devices described herein if modified appropriately. One of skill in the art will appreciate that relative motion of the various shafts in the delivery system embodiments disclosed above may need to be reversed in order to accommodate a transseptal approach. FIG. 23A illustrates the general transseptal pathway that is taken with the delivery device passing up the vena cava 2302 into the right atrium 2304. A transseptal puncture 2306 is created through the atrial septum, often through the foramen ovale, so that the device may be passed into the left atrium 2308, above the mitral valve 2310 and adjacent the left ventricle 2312. Transseptal techniques have been published in the patent and scientific literature, such as in U.S. Patent Publication No. 2004/0181238 to Zarbatany et al., the entire contents of which are incorporated herein by reference.

Figure 23B:
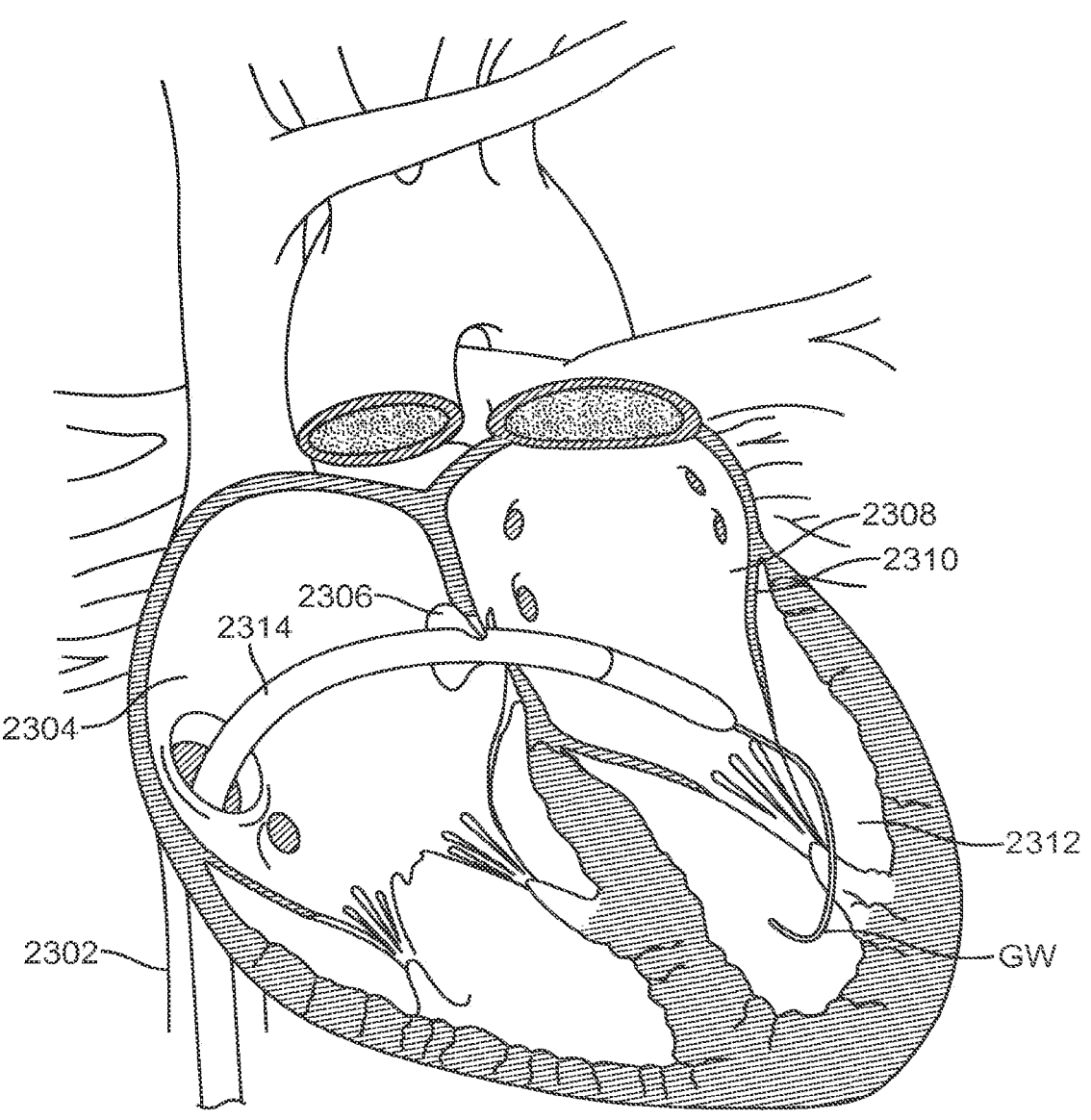

In FIG. 23B a delivery device 2314 is passed over a guidewire GW through the vena cava 2302 into the right atrium 2306. The delivery device 2314 is then transseptally passed through the atrial wall into the left atrium 2308 adjacent the mitral valve 2310. The guidewire GW may be disposed across the mitral valve 2310 in the left ventricle 2312. The distal tip of the delivery device typically includes a nose cone or other atraumatic tip to prevent damaging the mitral valve or adjacent tissue.

Figure 23C:
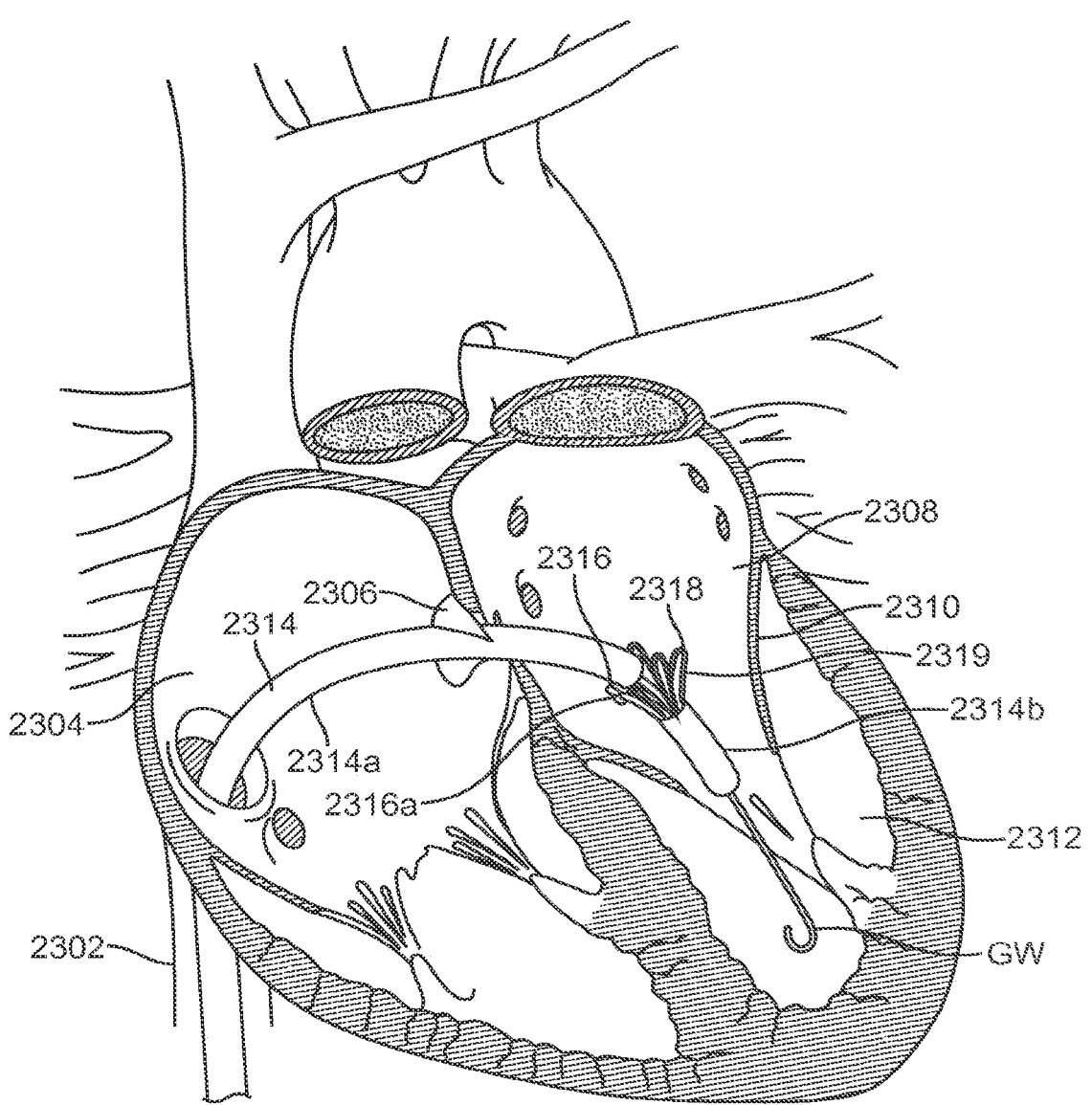

In FIG. 23C, the outer sheath 2214a of the delivery device 2214 is retracted proximally relative to the prosthetic mitral valve 2319. Alternatively, a distal portion 2314b of the delivery device 2214 may be advanced distally relative to the prosthetic valve 2319 to expose the alignment element 2316 and a portion of the atrial skirt region 2318 on the prosthetic mitral valve 2319 which allows the atrial skirt region 2318 to begin to partially radially expand outward and flare open. Alignment element 2316 may include a pair of radiopaque markers 2316a which facilitate visualization under fluoroscopy. The physician can then align the alignment element so that the radiopaque markers 2316a are disposed on either side of the anterior mitral valve leaflet. The alignment element is preferably situated adjacent the aortic root and between the fibrous trigones of the native anterior leaflet. Delivery device 2214 may be rotated in order to help align the alignment element.

Figure 23D:
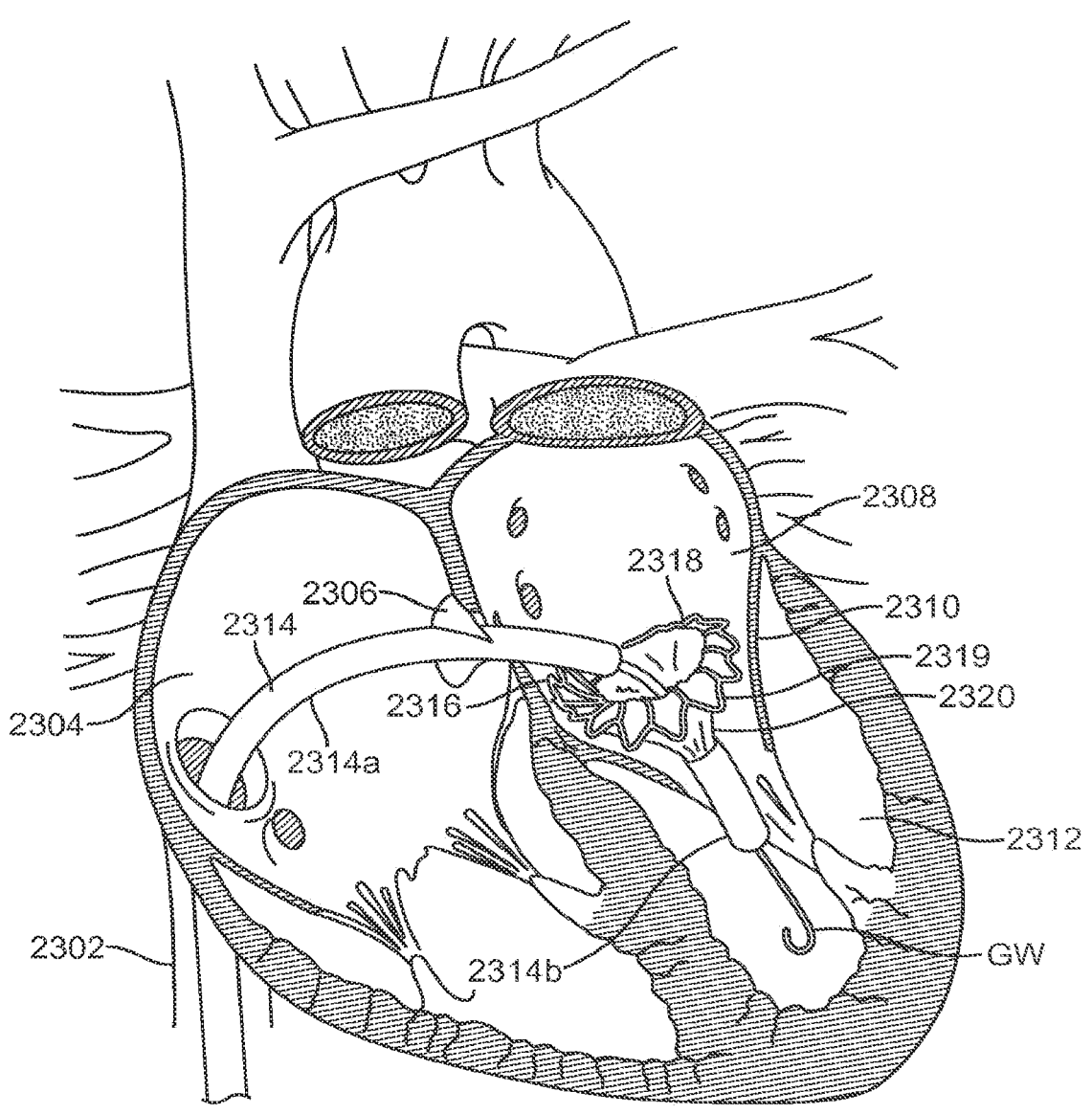

In FIG. 23D once alignment has been obtained, the distal portion 2314b is further advanced distally allowing radial expansion of the atrial skirt 2318 which flares outward to form a flange. Distally advancing the delivery device 2214 and prosthetic valve 2319 seats the atrial skirt 2318 against an atrial surface adjacent the mitral valve 2310 thereby anchoring the prosthetic valve in a first position.

Figure 23E:
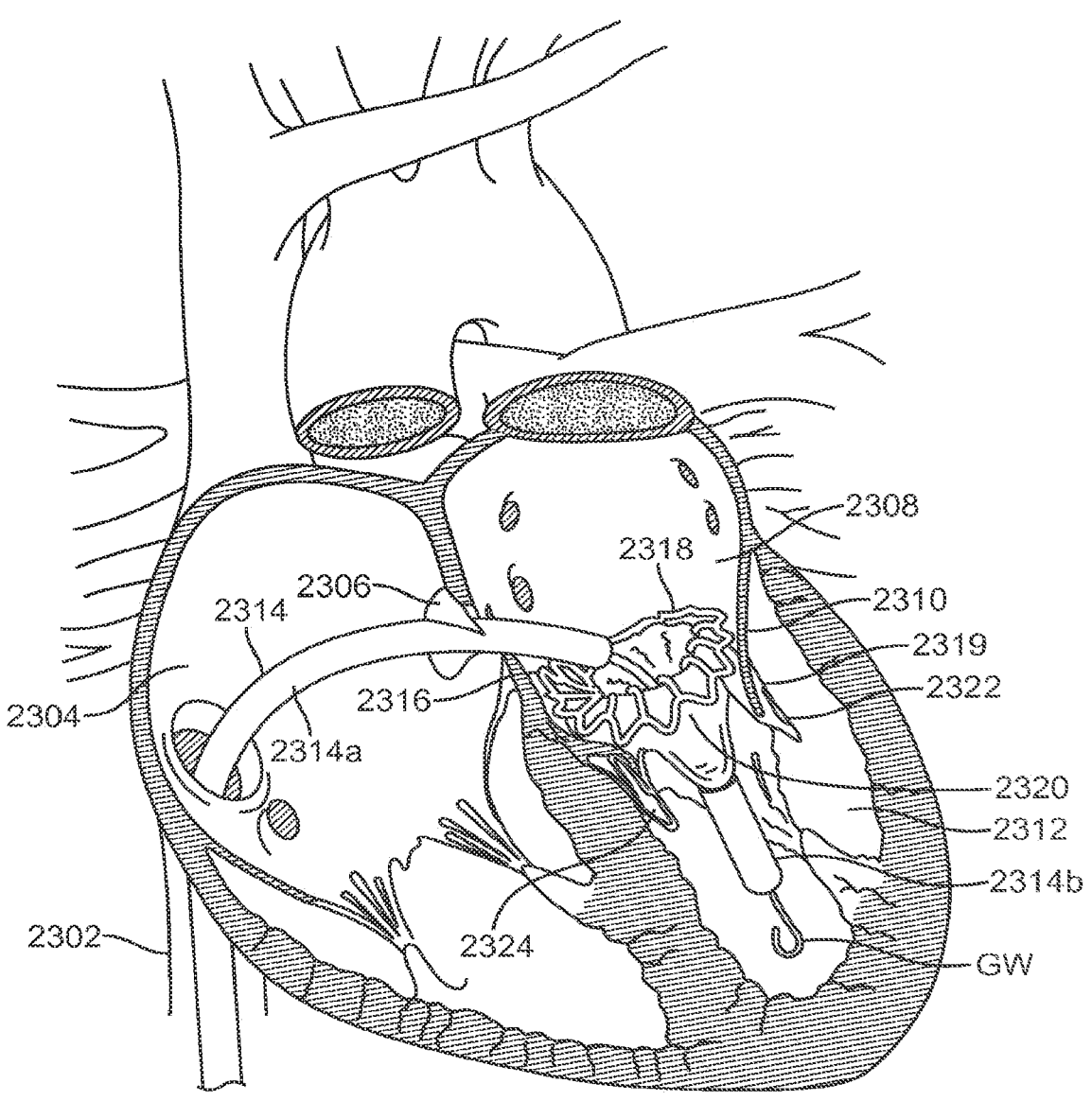

FIG. 23E shows that further distal advancement of distal portion 2314b exposes and axially removes additional constraint from the prosthetic valve 2319, thereby allowing more of the valve to self-expand. The annular region 2320 expands into engagement with the mitral valve annulus and the ventricular trigonal tabs 2324 and the posterior tab 2322 radially expand. Portions of the ventricular skirt serve as deployment control regions since they remain constrained and thus the entire ventricular skirt cannot expand. The tabs are captured between the anterior and posterior mitral valve leaflets and the ventricular wall. The posterior ventricular anchoring tab 2322 is preferably aligned in the middle of the posterior mitral valve leaflet where there is an absence of chordae attachments, and is passed over the posterior leaflet to seat between the posterior leaflet and the ventricular wall. The two ventricular trigonal anchoring tabs 2324 are positioned on either side of the anterior leaflet with their heads positioned at the fibrous trigones. Slight rotation and realignment of the prosthesis can occur at this time. As the prosthesis expands, the anterior trigonal tabs anchor against the fibrous trigones, capturing the native anterior leaflet and chordae between the tabs and the anterior surface of the prosthetic valve, and the posterior ventricular tab anchors between the ventricular wall and the posterior leaflet, capturing the posterior leaflet between the posterior anchoring tab and the posterior surface of the prosthetic valve assembly.

Figure 23F:
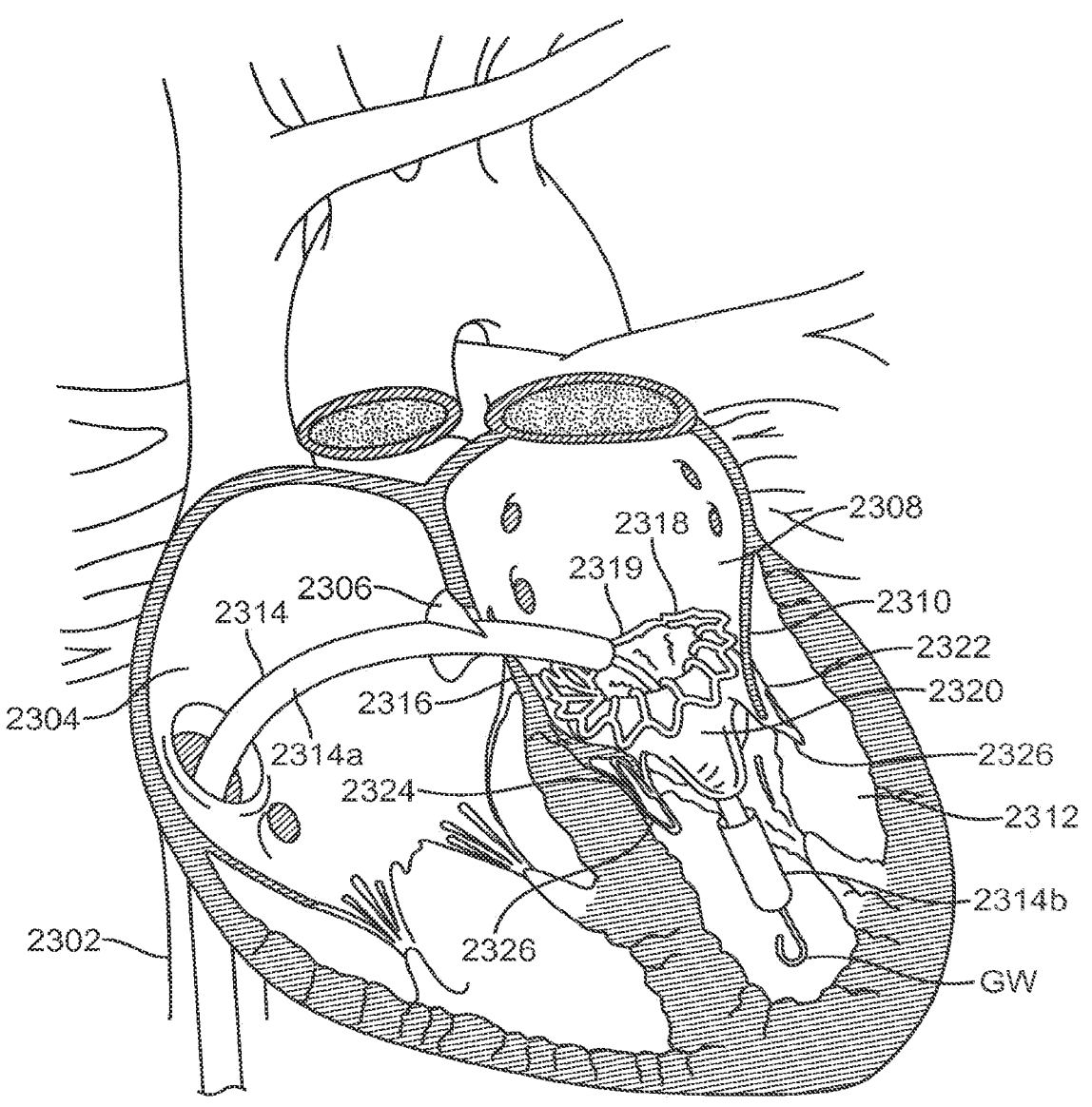
Figure 23G:
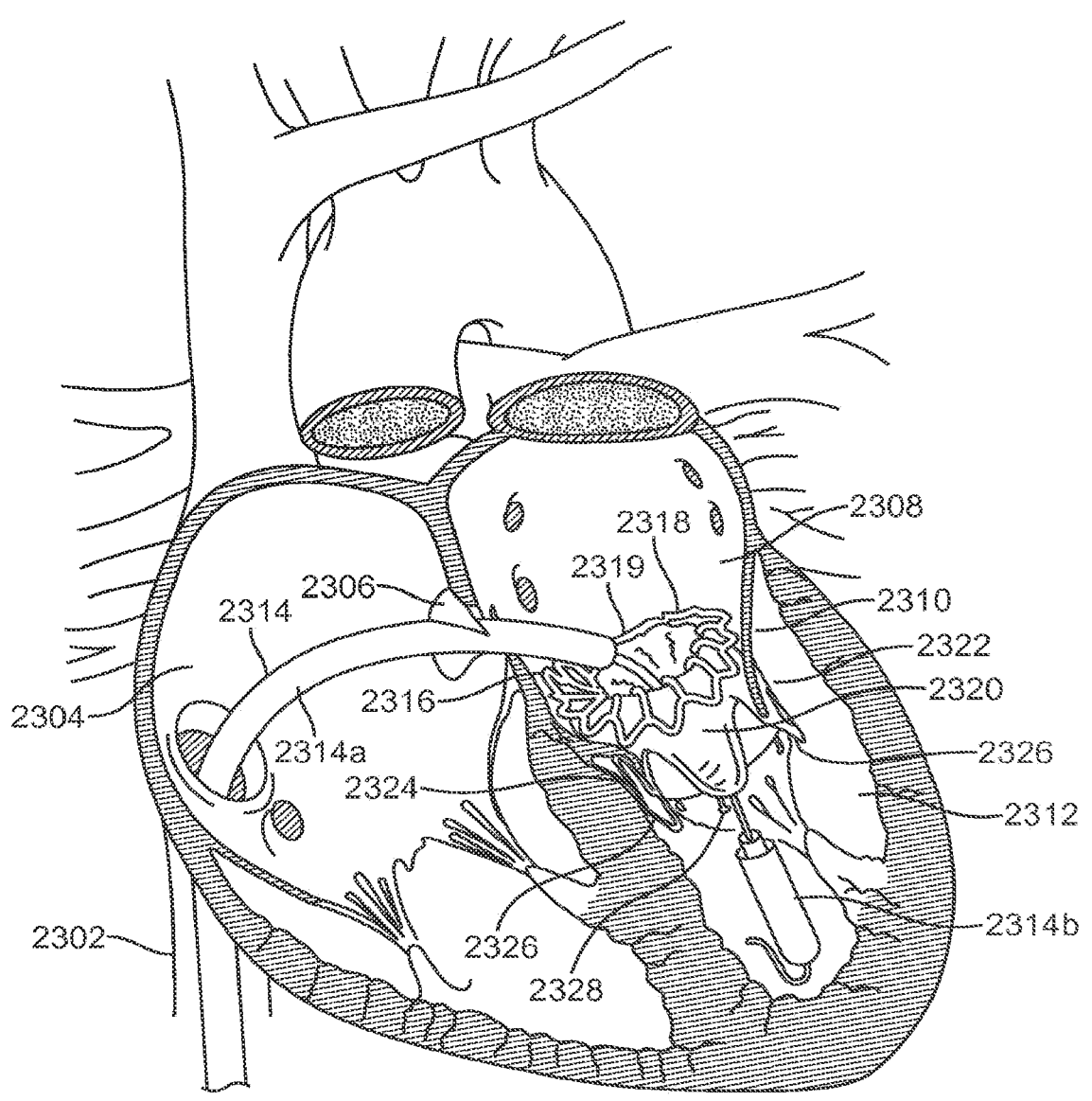

FIG. 23F shows that further distal advancement of distal portion 2314*b* releases the ventricular trigonal tabs and the posterior tab and the ventricular skirt 2326 is also released and allowed to radially expand outward against the native mitral valve leaflets without engaging the ventricular wall. This creates a sealing funnel within the native leaflets and helps funnel blood flow through the prosthetic valve. With the commissures of the prosthetic valve still captured by the delivery system, very minor adjustments may still be made to ensure accurate positioning, anchoring and sealing. The prosthetic valve is now anchored in four positions. The anchor tabs 2328 are then released from the delivery device by further advancement of an inner shaft, allowing the tabs to self-expand out of slots on the delivery catheter as previously discussed above and shown in FIG. 23G. The prosthetic valve is now implanted in the patient's heart and takes over the native mitral valve. The delivery device 2314 may then be removed from the heart by proximally retracting it back through the atrial septum, and out of the vena cava.

Figure 24:
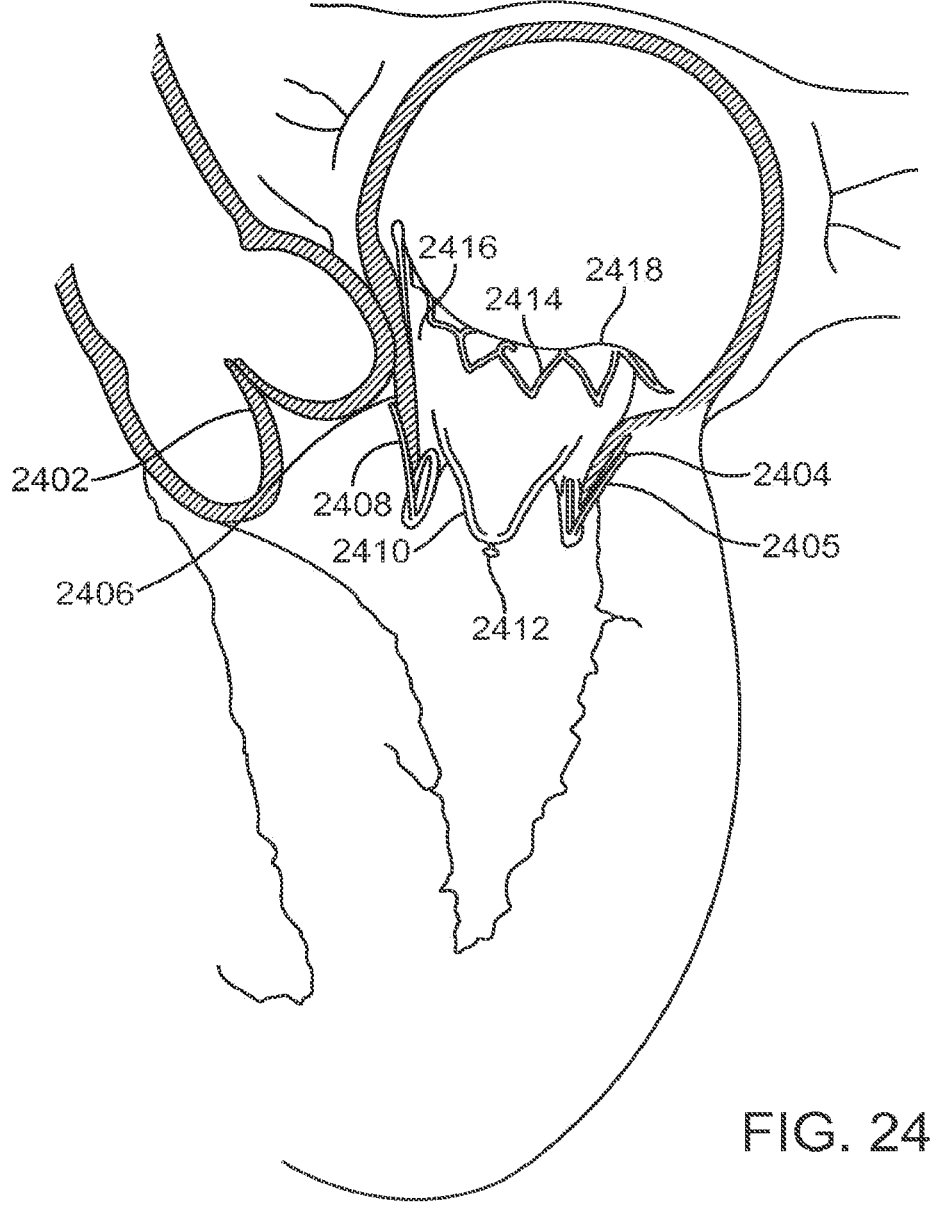
FIG. 24 illustrates a prosthetic mitral valve implanted in the mitral space.

FIG. 24 shows the prosthetic valve 2418 anchored in the mitral space after transapical or transseptal delivery. Prosthetic valve 2418 is preferably the prosthetic mitral valve illustrated in FIG. 8A, and delivered by methods shown in FIGS. 22A-22G or FIGS. 23A-23G. The prosthetic valve 2418 has radially self-expanded into engagement with the mitral valve to anchor it in position without obstructing other portions of the heart including the left ventricular outflow tract such as aortic valve 2402. The anterior trigonal tabs 2408 (only 1 seen in this view) and the posterior ventricular tab 2405 are radially expanded outward from the rest of the ventricular skirt 2410 and the anterior leaflet 2406 and posterior leaflet 2404 are captured between the respective tab and the ventricular skirt 2410 to form an anchor point. The ventricular skirt 2410 is also radially expanded outward to engage and press outwardly at least some of the chordae tendineae and papillary muscles but preferably without pressing against the ventricular wall. The annular region 2416 is expanded radially outward to engage and press against the mitral valve annulus, and the atrial skirt 2414 has also expanded outwardly to form a flange that rests on top of the mitral valve against the atrium. Thus, the prosthetic valve 2418 is anchored in four positions in the mitral space which prevents the prosthetic valve from migrating or dislodging during contraction of the heart. Moreover, using four anchor points lessens the anchoring pressure that is required to be applied in any given anchoring zone as compared to a prosthesis that is anchored in only a single anchoring zone, or in any combination of these four anchoring zones. The consequent reduction in radial force required to be exerted against the native structures in each zone minimizes the risk of obstruction or impingement of the nearby aortic valve or aortic root caused by the displacement of the native mitral valve apparatus. Valve leaflets 2420 form a tricuspid valve which opens with antegrade blood flow and closes with retrograde blood flow. Tab 2412 on a tip of the commissures 2421 (best seen in FIG. 25) remains free after disengagement from the delivery device.

Figure 25:
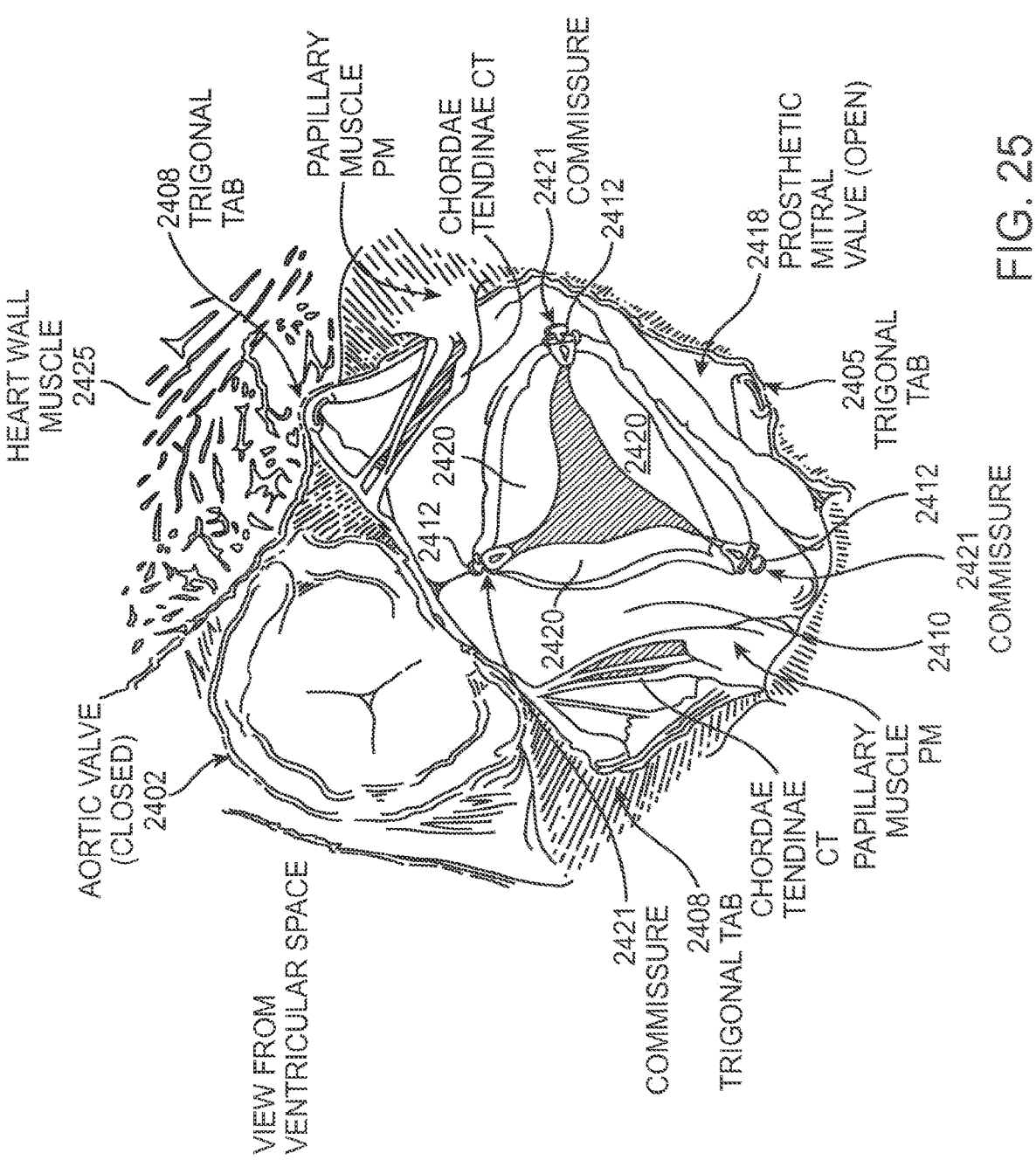
FIG. 25 illustrates a bottom view of a mitral valve implanted in the mitral space looking upward from the left ventricle.

FIG. 25 illustrates the prosthetic valve 2418 of FIG. 24 anchored in the mitral space and viewed from the left ventricle, looking upward toward the atrium. As previously mentioned, the prosthetic valve 2418 may be transapically or transseptally delivered and is preferably the prosthetic mitral valve illustrated in FIG. 8A, delivered by methods shown in FIGS. 22A-22G or FIGS. 23A-23G. This view more clearly illustrates anchoring and engagement of the prosthetic mitral valve 2418 with the adjacent tissue. For example, the three valve leaflets 2420 forming the tricuspid valve are shown in the open position, allowing blood flow therepast. Additionally, the anterior trigonal tabs 2408 and the posterior ventricular tab 2405 are shown radially expanded outward into engagement with the ventricular heart tissue 2425, The anterior portion of the prosthetic valve in between anterior trigonal tabs 2408 is approximately flat to match the corresponding flat anatomy as previously discussed above. The flat shape of the anterior portion of the prosthetic valve prevents the prosthetic valve from impinging on and obstructing adjacent anatomy such as the left ventricular outflow tract including the aortic valve. FIG. 25 also illustrates how the ventricular skirt 2410 expands radially outward against the native mitral valve leaflets.

Drug Delivery. Any of the prosthetic valves may also be used as a drug delivery device for localized drug elution. The therapeutic agent may be a coated on the prosthetic valve, on the tissue covering the anchor, on both, or otherwise carried by the prosthetic valve and controllably eluted therefrom after implantation. Exemplary drugs include anti-calcification drugs, antibiotics, anti-platelet aggregation drugs, anti-inflammatory drugs, drugs which inhibit tissue rejection, anti-restenosis drugs, anti-thrombogenic drugs, thrombolytic drugs, etc. Drugs which have these therapeutic effects are well known to those of skill in the art.

Although the exemplary embodiments have been described in some detail for clarity of understanding and by way of example, a variety of additional modifications, adaptations and changes may be clear to those of skill in the art. One of skill in the art will appreciate that the various features described herein may be combined with one another or substituted with one another. Hence, the scope of the present invention is limited solely by the appended claims.

What is claimed is:

1. A delivery system for a prosthetic heart valve, the system comprising:
   a stationary inner guidewire shaft having a lumen extending therethrough;
   a stationary hub shaft over the inner guidewire shaft and having a plurality of prosthesis engagement slots in an outer surface of and adjacent to a distal end of the hub shaft;
   a movable bell shaft over the hub shaft and configured to cover the plurality of slots on condition that the bell shaft is disposed thereover;
   a movable sheath over the bell shaft and configured to hold one or more portions of the prosthetic valve in a collapsed configuration between the sheath and the bell shaft on condition that the sheath is disposed thereover;
   a handle adjacent a proximal end of the delivery system and having an actuator configured to move the bell shaft and the sheath to modulate engagement of the prosthetic valve with the delivery system; and a pin lock coupled to the handle and configured to prevent proximal retraction of the sheath.

2. The delivery system of claim 1, wherein the inner guidewire shaft further comprises a tip configured to penetrate an apex of the patient's heart.

3. The delivery system of claim 1, wherein the inner guidewire shaft, the hub shaft, the bell shaft, and the sheath are concentric relative to one another.

4. The delivery system of claim 1, further comprising the prosthetic valve.

5. The delivery system of claim 1, wherein the actuator is a rotatable thumbwheel disposed in the handle.

6. The delivery system of claim 1, wherein actuation of the actuator in a first direction proximally retracts the sheath and the bell shaft, and wherein actuation of the actuator in a second direction opposite the first direction distally advances the sheath and the bell shaft.

7. The delivery system of claim 6, wherein actuation in the first direction proximally retracts the sheath first, followed by proximal retraction of the bell shaft, and wherein actuation in the second direction distally advances the bell shaft first, followed by distal advancement of the sheath.

8. The delivery system of 1, wherein the delivery system is configured to deliver the prosthetic heart valve transapically to the patient's heart.

9. The delivery system of 1, wherein a distal end of the bell catheter has a diameter larger than a proximal portion of the bell catheter.

10. The delivery catheter of claim 1, wherein the plurality of slots comprises three slots spaced circumferentially 120 degrees apart from one another.

11. The delivery catheter of claim 1, wherein proximal retraction of the bell catheter relative to the hub shaft removes a constraint from the plurality of slots allowing self-expansion of the portion of the prosthetic valve received in the plurality of slots, away from the plurality of slots.

12. A delivery system for a prosthetic heart valve, the system comprising:

a stationary inner guidewire shaft having a lumen extending therethrough;

a stationary hub shaft over the inner guidewire shaft and having a plurality of prosthesis engagement slots in an outer surface of and adjacent to a distal end of the hub shaft, wherein the plurality of slots comprises three slots spaced circumferentially 120 degrees apart from one another;

a movable bell shaft over the hub shaft and configured to cover the plurality of slots on condition that the bell shaft is disposed thereover;

a movable sheath over the bell shaft and configured to hold one or more portions of the prosthetic valve in a collapsed configuration between the sheath and the bell shaft on condition that the sheath is disposed thereover; and a handle adjacent a proximal end of the delivery system and having an actuator configured to move the bell shaft and the sheath to modulate engagement of the prosthetic valve with the delivery system.

13. The delivery system of claim 12, wherein the inner guidewire shaft further comprises a tip configured to penetrate an apex of the patient's heart.

14. The delivery system of claim 12, wherein the inner guidewire shaft, the hub shaft, the bell shaft, and the sheath are concentric relative to one another.

15. The delivery system of claim 12, further comprising the prosthetic valve.

16. The delivery system of claim 12, wherein the actuator is a rotatable thumbwheel disposed in the handle.

17. The delivery system of claim 12, wherein actuation of the actuator in a first direction proximally retracts the sheath and the bell shaft, and wherein actuation of the actuator in a second direction opposite the first direction distally advances the sheath and the bell shaft.

18. The delivery system of claim 17, wherein actuation in the first direction proximally retracts the sheath first, followed by proximal retraction of the bell shaft, and wherein actuation in the second direction distally advances the bell shaft first, followed by distal advancement of the sheath.

19. The delivery system of 12, wherein the delivery system is configured to deliver the prosthetic heart valve transapically to the patient's heart.

20. The delivery system of 12, wherein a distal end of the bell catheter has a diameter larger than a proximal portion of the bell catheter.

21. The delivery catheter of claim 12, wherein proximal retraction of the bell catheter relative to the hub shaft removes a constraint from the plurality of slots allowing self-expansion of the portion of the prosthetic valve received in the plurality of slots, away from the plurality of slots.

* * * * *